(12) United States Patent
Bandi et al.

(10) Patent No.: US 12,275,712 B2
(45) Date of Patent: Apr. 15, 2025

(54) TRITERPENE DERIVATIVES AS HIV INHIBITORS

(71) Applicant: HETERO LABS LIMITED, Balanagar Hyderabad (IN)

(72) Inventors: Parthasaradhi Reddy Bandi, Balanagar Hyderabad (IN); Rathnakar Reddy Kura, Balanagar Hyderabad (IN); Panduranga Reddy Adulla, Balanagar Hyderabad (IN); Bhaskar Reddy Kasireddy, Balanagar Hyderabad (IN)

(73) Assignee: HETERO LABS LIMITED, Balanagar Hyderabad (IN)

( * ) Notice: Subject to any disclaimer, the term of this patent is extended or adjusted under 35 U.S.C. 154(b) by 828 days.

(21) Appl. No.: 17/430,130

(22) PCT Filed: Feb. 11, 2020

(86) PCT No.: PCT/IB2020/051048
§ 371 (c)(1),
(2) Date: Aug. 11, 2021

(87) PCT Pub. No.: WO2020/165741
PCT Pub. Date: Aug. 20, 2020

(65) Prior Publication Data
US 2022/0177439 A1    Jun. 9, 2022

(30) Foreign Application Priority Data
Feb. 11, 2019 (IN) .............................. 201941005217

(51) Int. Cl.
| C07D 295/13 | (2006.01) |
| A61P 31/18 | (2006.01) |
| C07D 295/26 | (2006.01) |
| C07F 7/18 | (2006.01) |

(52) U.S. Cl.
CPC ............ C07D 295/13 (2013.01); A61P 31/18 (2018.01); C07D 295/26 (2013.01); C07F 7/1804 (2013.01)

(58) Field of Classification Search
CPC ..... C07D 295/13; C07D 295/26; A61P 31/18; C07F 7/1804
See application file for complete search history.

(56) References Cited

FOREIGN PATENT DOCUMENTS

| WO | 2008057420 A3 | 5/2008 | |
| WO | 2017017630 A1 | 2/2017 | |
| WO | WO 2017/149518 A1 * | 9/2017 | ............. A61K 31/00 |

OTHER PUBLICATIONS

Eliezer J. Barreiro, "The Methylation Effect in Medicinal Chemistry" Chemical Reviews 2011 111 (9), 5215-5246 (Year: 2011).*
International Search Report for Application No. PCT/IB2020/051048; International Filing Date—Feb. 11, 2020; Date of Mailing—Jul. 14, 2020, 3 pages.
Written Opinion for Application No. PCT/IB2020/051048; International Filing Date—Feb. 11, 2020; Date of Mailing—Jul. 14, 2020, 10 pages.
Ren et al., "Second Generation Inhibitors of HIV-1 Maturation," ACS Medicinal Chemistry Letters, (2019), vol. 10, (No. 3), 287-294.

* cited by examiner

*Primary Examiner* — Alexander R Pagano
*Assistant Examiner* — Derek Rhoades
(74) *Attorney, Agent, or Firm* — CANTOR COLBURN LLP

(57) ABSTRACT

The present invention relates to triterpene derivatives of formula (I); and pharmaceutically acceptable salts thereof, wherein $R_1$, $R_2$, $R_3$, $R_4$, and ring

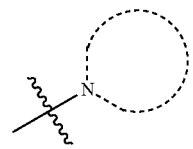

are as defined herein. The invention also relates to triterpene derivatives, related compounds, and pharmaceutical compositions useful for the therapeutic treatment of viral diseases and particularly HIV mediated diseases.

Formula (I)

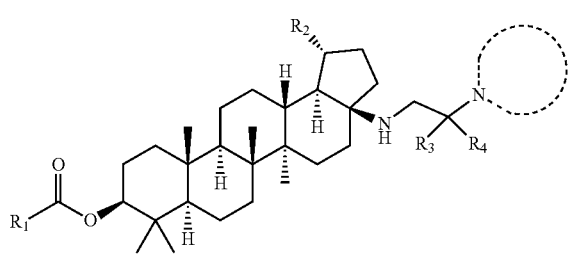

10 Claims, No Drawings

TRITERPENE DERIVATIVES AS HIV INHIBITORS

CROSS REFERENCE TO RELATED APPLICATIONS

This application is a National Stage application of PCT/IB2020/051048, filed Feb. 11, 2020 which claims the benefit of Indian provisional application No. 201941005217, filed Feb. 11, 2019, which is hereby incorporated by reference in its entirety.

FIELD OF THE INVENTION

The present invention relates to triterpene derivatives and related compounds, compositions useful for therapeutic treatment of viral diseases and particularly HIV mediated diseases.

BACKGROUND OF THE INVENTION

The Human Immunodeficiency Virus (HIV) has now been established as the causative agent of the Acquired Immunodeficiency Syndrome (AIDS) for over 20 years (Science 1983, 220, 868-871; N. Eng. J. Med. 1984, 311, 1292-1297). AIDS is characterized by the destruction of the immune system, particularly of CD4+ T-cells. HIV is a retrovirus, and the HIV life cycle encompasses several crucial steps, starting from the attachment of the virus to the host cell membrane and finishing with the release of progeny virons from the cell.

The natural compound betulinic acid, isolated from *Syzygium clavifolium* and several other plant species was found to possess anti-HIV activity. Chemical modifications were undertaken by several research groups in an attempt to identify potent anti-HIV agents by making semi-synthetic analogs of betulinic acid, leading to the discovery of bevirimat as a compound with a mechanism of action (J. Nat. Prod. 1994, 57 (2): 243-7; J. Med. Chem. 1996, 39 (5), 1016). Further studies shown that bevirimat acts by disrupting Gag processing (Proc. Natl. Acad. Sci. USA 2003, 100 (23): 13555-60; Antimicrob. Agents. Chemother. 2001, 45 (4), 1225-30; J. Virol. 2004, 78 (2): 922-9; J. Biol. Chem. 2005, 280 (51): 42149-55; J. Virol. 2006, 80 (12): 5716-22) and to be a first-in-class maturation inhibitor with a potent activity against HIV-1. Bevirimat went up to phase 2 clinical trials, in clinic despite optimal plasma concentrations, not all patients given bevirimat have a robust viral load reduction. It was reported that non-respondant patients had more frequent base line Gag polymorphisms near the capsid SP-1 cleavage site than responders. (HIV gag polymorphism determines treatment response to bevirimat. XVII international HIV drug resistance work shop Jun. 10-14, 2008, Sitges, Spain).

Encouraged by these developments, medicinal chemists started exploring betulinic acid derivatives and related compounds intensively for their therapeutic activities. For example, WO2017/149518 disclosed C-3 triterpene with C-17 amine derivatives as hiv inhibitors; WO2014/105926 disclosed betulinic acid proline derivatives as HIV inhibitors; WO2014/130810 describes preparation of C3 alkyl and alkenyl modified betulinic acid derivatives useful in the treatment of HIV; WO2014/123889 describes preparation of triterpenoid derivatives for use as HIV maturation inhibitors; WO2013/160810 disclosed betulinic acid derivatives as HIV inhibitors; WO2013/169578 describes C-17 bicyclic amines of triterpenoids with HIV maturation inhibitory activity and their preparation; WO 2013/123019 describes C-3 cycloalkenyl triterpenoids with HIV maturation inhibitory activity; WO2013/043778 describes betulinic acid derivatives with antiviral activity; WO2013/035943 describes betulinic acid and derivatives thereof having anti-aging activity; WO2012/106190 describes preparation of C17 and C3 modified triterpenoids with HIV maturation inhibitory activity; CN102399254 describes pentacyclic triterpenoid derivatives, their preparation method and application for preventing and treating diabetes, cardiovascular disease, cerebrovascular disease and tumor; WO2011/007230 describes preparation of lupeol-type triterpene derivatives as antiviral agents; WO2010/032123 describes preparation of triterpenoid compounds for pharmaceutical use; Journal of Medicinal Chemistry (2010), 53 (1), 178-190 describes structure-activity relationship study of betulinic acid, a selective TGR5 agonist, and its synthetic derivatives: potential impact in diabetes; WO 2009/100532 describes preparation of 17β-lupane derivatives for the treatment of HIV infection; CN 101367861 describes preparation method and application of 2-hydroxy-3-deoxy-pentacyclic triterpene compounds and derivatives; WO2008/138200 describes preparation of lupane derivatives as NMDA and MC receptor antagonists exhibiting neuroprotective and memory enhancing activities; WO2008/127364 describes preparation of betulinic acid derivatives for use in antiviral and anticancer pharmaceutical compositions.

Some additional references disclose betulinic acid related compounds. For example, WO2006/053255 describes preparation of betulin derivatives for use in pharmaceutical compositions which inhibit the transmission of viral infection; WO2004/089357 describes anti-fungal formulation of triterpene and essential oil; Bioorganic & Medicinal Chemistry Letters (2003), 13(20), 3549-3552 describes lupane triterpenes and derivatives with antiviral activity; Russian Journal of Bioorganic Chemistry (2003), 29(6), 594-600 describes synthesis and antiviral activity of ureides and carbamates of betulinic acid and its derivatives; Journal of Medicinal Chemistry (1996), 39(5), 1056-68 describes betulinic acid derivatives: a new class of human immunodeficiency virus type 1 specific inhibitors with a new mode of action; Oxidation Communications (1987), 10(3-4), 305-12 describes oxidative decarboxylations. II. oxidative decarboxylation of acetyl betulinic acid.

Given the fact of the world wide epidemic level of AIDS, there is a strong continued need for new effective drugs for treatment of HIV infected patients, disease conditions and/or disorders mediated by HIV by discovering new compounds with structures and/or mechanism of action(s).

SUMMARY OF THE INVENTION

The present invention relates to the compound of the formula (I)

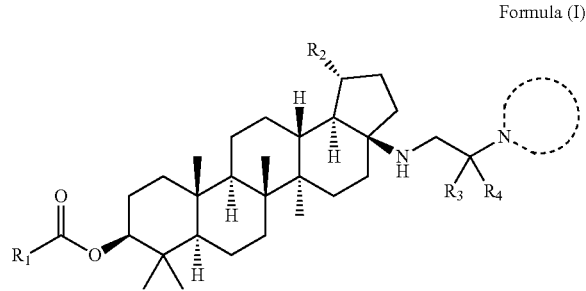

Formula (I)

wherein, $R_1$ is selected from

[structures depicted]

$R_2$ is selected from $C_1$-$C_6$ alkyl, optionally substituted $C_2$-$C_6$ alkenyl, or optionally substituted $C_3$-$C_8$ cycloalkyl; wherein the optional substituent is $C_1$-$C_6$ alkyl;

$R_3$ is hydrogen, or $C_1$-$C_6$ alkyl;

$R_4$ is selected from optionally substituted $C_1$-$C_6$ alkyl, or —C(O)O$R_a$; wherein the optional substituent is selected from halo, hydroxy, alkoxy, —OC(O)CH$_2$alkoxy, —OSi($R_a$)$_3$, —N($R_a$)($R_b$), —S($R_a$), or —O—CH$_2$—P(O)(O$R_a$)$_2$;

ring

[structures depicted] is [structures], or [structure];

$R_a$ is hydrogen, or $C_1$-$C_6$ alkyl; and $R_b$ is selected from hydrogen, alkyl, —C(O)alkoxy, or —S(O)$_2$alkyl, or pharmaceutically acceptable salts, pharmaceutically acceptable stereoisomers, prodrugs, or combination thereof.

According to one embodiment, there is provided a compound of formula (I), wherein $R_1$ is

[structure depicted].

According to another embodiment, there is provided a compound of formula (I), wherein $R_1$ is

[structure depicted].

According to yet another embodiment, there is provided a compound of formula (I), wherein $R_2$ is isopropylene.

According to yet another embodiment, there is provided a compound of formula (I), wherein $R_2$ is methylcyclopropyl.

According to yet another embodiment, there is provided a compound of formula (I), wherein $R_3$ is hydrogen.

According to yet another embodiment, there is provided a compound of formula (I), wherein $R_3$ is methyl.

According to yet another embodiment, there is provided a compound of formula (I), wherein $R_4$ is methyl, isopropyl, —C(O)OH,

[structure depicted], hydroxyethyl, hydroxymethyl, fluoromethyl, fluoroethyl,

[structures depicted], and

[structure depicted].

According to yet another embodiment, there is provided a compound of formula (I), wherein ring

[structures depicted] is [structure].

According to yet another embodiment, there is provided a compound of formula (I), wherein ring hydroxyethyl, hydroxymethyl, fluoromethyl, fluoroethyl,

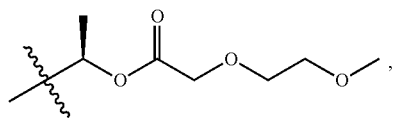

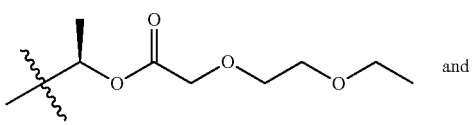
and

Accordingly, another aspect of the present invention provides compound of formula (IA):

Formula (IA)

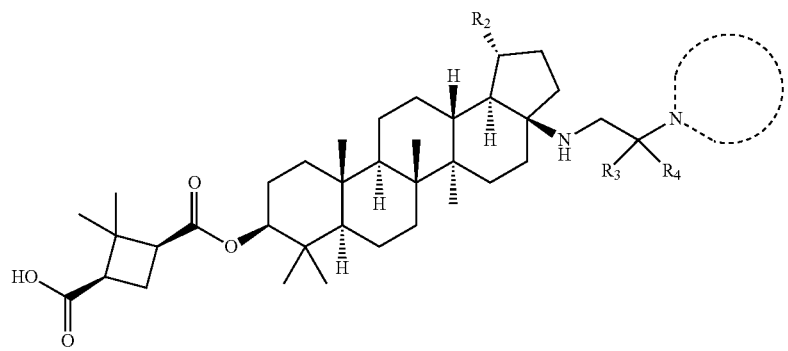

wherein,
R$_2$, R$_3$, R$_4$ and ring

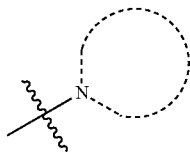

are same as defined in formula (I); or
pharmaceutically acceptable salts, pharmaceutically acceptable stereoisomers, prodrugs, or combination thereof.

According to one embodiment, there is provided a compound of formula (IA), wherein R$_2$ is isopropylene.

According to another embodiment, there is provided a compound of formula (IA), wherein R$_2$ is methylcyclopropyl.

According to yet another embodiment there is provided a compound of formula (IA), wherein R$_3$ is hydrogen.

According to yet another embodiment there is provided a compound of formula (IA), wherein R$_3$ is methyl.

According to yet another embodiment, there is provided a compound of formula (IA), wherein R$_4$ is methyl, isopropyl, —C(O)OH,

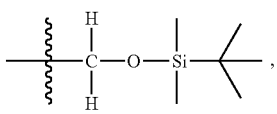

-continued

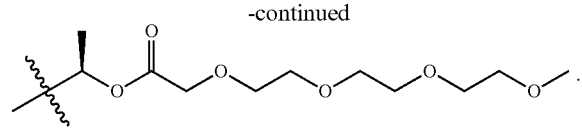

According to yet another embodiment, there is provided a compound of formula (IA), wherein ring

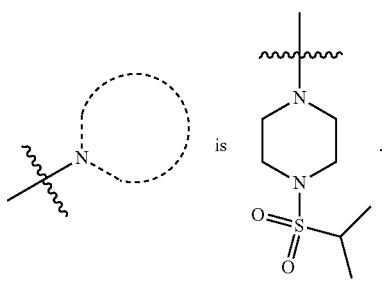 is 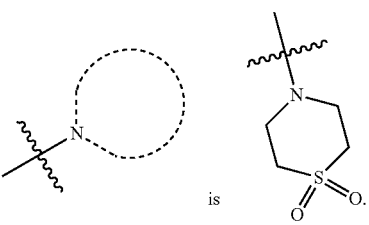

According to yet another embodiment, there is provided a compound of formula (IA), wherein ring

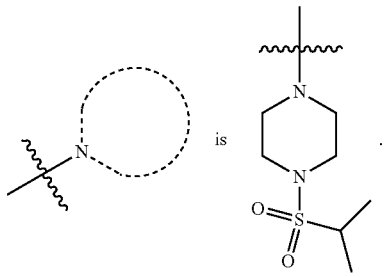 is 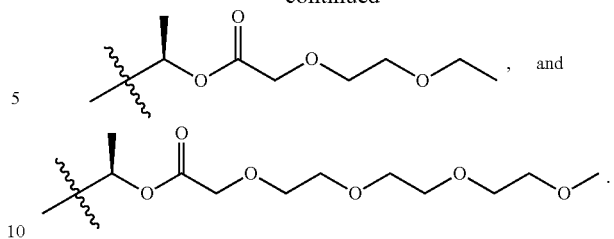

Accordingly, to yet another aspect of the present invention provides compound of formula (IB):

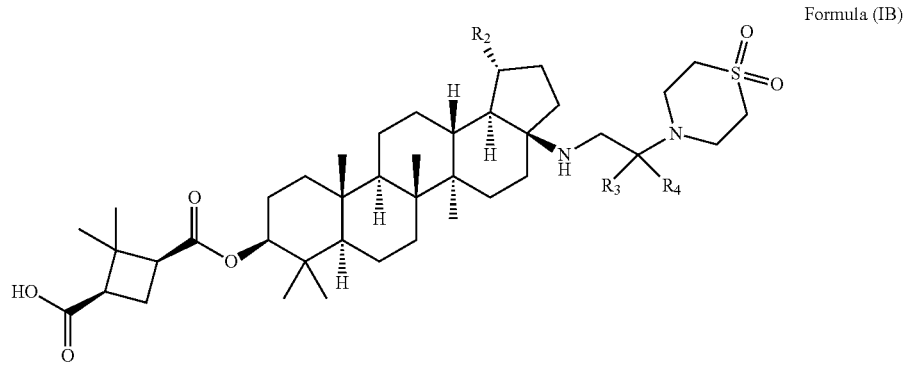

Formula (IB)

wherein, $R_2$, $R_3$, and $R_4$ are same as defined in formula (I); or pharmaceutically acceptable salts, pharmaceutically acceptable stereoisomers, prodrugs, or combination thereof.

According to one embodiment, there is provided a compound of formula (IB), wherein $R_2$ is isopropylene.

According to another embodiment, there is provided a compound of formula (IB), wherein $R_2$ is methylcyclopropyl.

According to yet another embodiment there is provided a compound of formula (IB), wherein $R_3$ is hydrogen.

According to yet another embodiment there is provided a compound of formula (IB), wherein $R_3$ is methyl.

According to yet another embodiment, there is provided a compound of formula (IB), wherein $R_4$ is methyl, isopropyl, —C(O)OH,

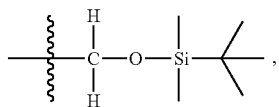 [SMILES: *CO[Si](C)(C)C(C)(C)C]

hydroxyethyl, hydroxymethyl, fluoromethyl, fluoroethyl,

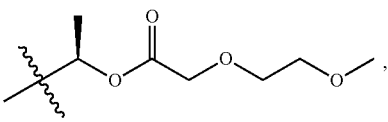

Below are the representative compounds, which are illustrative in nature only and are not intended to limit to the scope of the invention (Nomenclature has been generated from ChemBioDraw Ultra 13.0 version):

(1R,3S)-3-(((((1R,3aS,5aR,5bR,7aR,9S,11aR,11bR,13aR,13bR)-3a-((2-(1,1-dioxidothiomorpholino)-2-methylpropyl)amino)-5a,5b,8,8,11a-pentamethyl-1-(1-methylcyclopropyl)icosahydro-1H-cyclopenta[a]chrysen-9-yl)oxy)carbonyl)-2,2-dimethyl cyclobutane-1-carboxylic acid, (1R,3S)-3-(((((1R,3aS,5aR,5bR,7aR,9S,11aR,11bR,13aR,13bR)-3a-(((S)-2-(1,1-dioxidothiomorpholino)propyl)amino)-5a,5b,8,8,11a-pentamethyl-1-(1-methylcyclopropyl)icosahydro-1H-cyclopenta[a]chrysen-9-yl)oxy)carbonyl)-2,2-dimethyl cyclobutane-1-carboxylic acid, (1R,3S)-3-(((((1R,3aS,5aR,5bR,7aR,9S,11aR,11bR,13aR,13bR)-3a-(((R)-2-(1,1-dioxidothiomorpholino)-3-methylbutyl)amino)-5a,5b,8,8,11a-pentamethyl-1-(1-methylcyclopropyl)icosahydro-1H-cyclopenta[a]chrysen-9-yl)oxy)carbonyl)-2,2-dimethyl cyclobutane-1-carboxylic acid, (1R,3S)-3-(((((1R,3aS,5aR,5bR,7aR,9S,11aR,11bR,13aR,13bR)-3a-(((R)-3-((tert-butyldimethylsilyl)oxy)-2-(1,1-dioxidothiomorpholino)propyl)amino)-5a,5b,8,8,11a-pentamethyl-1-(1-methylcyclopropyl)icosahydro-1H-cyclopenta[a]chrysen-9-yl)oxy) carbonyl)-2,2-dimethylcyclobutane-1-carboxylic acid, (1R,3S)-3-(((((1R,3aS,5aR,5bR,7aR,9S,11aR,11bR,13aR,13bR)-3a-(((R)-2-(1,1-dioxidothiomorpholino)-3-hydroxypropyl)amino)-5a,5b,8,8,11a-pentamethyl-1-(1-methylcyclopropyl)icosahydro-1H-cyclopenta[a]chrysen-9-yl)oxy)carbonyl)-2,2-dimethylcyclobutane-1-carboxylic acid, (1R,3S)-3-(((((1R,3aS,5aR,5bR,7aR,9S,11aR,11bR,13aR,13bR)-3a-(((S)-2-(1,1-dioxidothiomorpholino)-3-methylbutyl)amino)-5a,5b,8,8,11a-pentamethyl-1-(1-methylcyclopropyl)icosahydro-1H-cyclopenta[a]chrysen-9-yl)
oxy)carbonyl)-2,2-dimethylcyclobutane-1-carboxylic
acid, (1R,3S)-3-(((((1R,3aS,5aR,5bR,7aR,9S,11aR,11bR,13aR,
13bR)-3a-(((2R,3R)-2-(1,1-dioxidothiomorpholino)-3-
hydroxybutyl)amino)-5a,5b,8,8,11a-pentamethyl-1-(1-
methylcyclopropyl)icosahydro-1H-cyclopenta[a]
chrysen-9-yl)oxy)carbonyl)-2,2-dimethylcyclobutane-1-
carboxylic acid, (1R,3S)-3-(((((1R,3aS,5aR,5bR,7aR,9S,11aR,11bR,13aR,
13bR)-3a-(((S)-2-(1,1-dioxidothiomorpholino)-3-hy-
droxypropyl)amino)-5a,5b,8,8,11a-pentamethyl-1-(1-
methylcyclopropyl)icosahydro-1H-cyclopenta[a]
chrysen-9-yl)oxy)carbonyl)-2,2-dimethylcyclobutane-1-
carboxylic acid, (1R,3S)-3-(((((1R,3aS,5aR,5bR,7aR,9S,11aR,11bR,13aR,
13bR)-3a-(((S)-2-(1,1-dioxidothiomorpholino)-3-fluoro-
propyl)amino)-5a,5b,8,8,11a-pentamethyl-1-(1-methyl-
cyclopropyl)icosahydro-1H-cyclopenta[a]chrysen-9-yl)
oxy)carbonyl)-2,2-dimethyl cyclobutane-1-carboxylic
acid, (1R,3S)-3-(((((1R,3aS,5aR,5bR,7aR,9S,11aR,11bR,13aR,
13bR)-3a-(((R)-2-(1,1-dioxidothiomorpholino)-3-fluoro-
propyl)amino)-5a,5b,8,8,11a-pentamethyl-1-(1-methyl-
cyclopropyl)icosahydro-1H-cyclopenta[a]chrysen-9-yl)
oxy)carbonyl)-2,2-dimethyl cyclobutane-1-carboxylic
acid, (1R,3S)-3-(((((1R,3aS,5aR,5bR,7aR,9S,11aR,11bR,13aR,
13bR)-3a-(((S)-2-(4-(isopropylsulfonyl)piperazin-1-yl)
propyl)amino)-5a,5b,8,8,11a-pentamethyl-1-(1-methyl-
cyclopropyl)icosahydro-1H-cyclopenta[a]chrysen-9-yl)
oxy)carbonyl)-2,2-dimethyl cyclobutane-1-carboxylic
acid, (1R,3S)-3-(((((1R,3aS,5aR,5bR,7aR,9S,11aR,11bR,13aR,
13bR)-3a-(((2R,3S)-2-(1,1-dioxidothiomorpholino)-3-
fluorobutyl)amino)-5a,5b,8,8,11a-pentamethyl-1-(1-
methylcyclopropyl)icosahydro-1H-cyclopenta[a]
chrysen-9-yl)oxy)carbonyl)-2,2-di
methylcyclobutane-1-carboxylic acid, (1R,3S)-3-(((((1R,3aS,5aR,5bR,7aR,9S,11aR,11bR,13aR,
13bR)-3a-(((2S,3S)-2-(1,1-dioxidothiomorpholino)-3-hy-
droxybutyl)amino)-5a,5b,8,8,11a-penta methyl-1-(1-
methylcyclopropyl)icosahydro-1H-cyclopenta[a]
chrysen-9-yl)oxy)carbonyl)-2,2-dimethylcyclobutane-1-
carboxylic acid, (1R,3S)-3-(((((1R,3aS,5aR,5bR,7aR,9S,11aR,11bR,13aR,
13bR)-3a-(((2R,3R)-3-hydroxy-2-(4-(isopropylsulfonyl)
piperazin-1-yl)butyl)amino)-5a,5b,8,8,11a-pentamethyl-
1-(1-methylcyclopropyl)icosahydro-1H-cyclopenta[a]
chrysen-9-yl)oxy)carbonyl)-2,2-dimethylcyclobutane-1-
carboxylic acid, (1R,3S)-3-(((((1R,3aS,5aR,5bR,7aR,9S,11aR,11bR,13aR,
13bR)-3a-(((2R,3R)-2-(1,1-dioxidothiomorpholino)-3-
hydroxybutyl)amino)-5a,5b,8,8,11a-penta methyl-1-
(prop-1-en-2-yl)icosahydro-1H-cyclopenta[a]chrysen-9-
yl)oxy)carbonyl)-2,2-dimethylcyclobutane-1-carboxylic
acid, (1R,3S)-3-(((((1R,3aS,5aR,5bR,7aR,9S,11aR,11bR,13aR,
13bR)-3a-(((R)-2-carboxy-2-(1,1-dioxidothiomor-
pholino)ethyl)amino)-5a,5b,8,8,11a-pentamethyl-1-(1-
methylcyclopropyl)icosahydro-1H-cyclopenta[a]
chrysen-9-yl)oxy)carbonyl)-2,2-dimethylcyclobutane-1-
carboxylic acid, (1R,3S)-3-(((((1R,3aS,5aR,5bR,7aR,9S,11aR,11bR,13aR,
13bR)-3a-(((2R,3R)-2-(1,1-dioxidothiomorpholino)-3-
(2-(2-methoxyethoxy)acetoxy)butyl)amino)-5a,5b,8,8,
11a-pentamethyl-1-(1-methylcyclopropyl)icosahydro-
1H-cyclopenta[a]chrysen-9-yl)oxy)carbonyl)-2,2-
dimethylcyclobutane-1-carboxylic acid, (1R,3S)-3-(((((1R,3aS,5aR,5bR,7aR,9S,11aR,11bR,13aR,
13bR)-3a-(((12R,13R)-13-(1,1-dioxidothiomorpholino)-
12-methyl-2,5,8,11-tetraoxatetradecan-14-yl)amino)-5a,
5b,8,8,11a-pentamethyl-1-(1-methylcyclopropyl)
icosahydro-1H-cyclopenta[a]chrysen-9-yl)oxy)
carbonyl)-2,2-dimethylcyclobutane-1-carboxylic acid, (1R,3S)-3-(((((1R,3aS,5aR,5bR,7aR,9S,11aR,11bR,13aR,
13bR)-3a-(((2R,3R)-2-(1,1-dioxidothiomorpholino)-3-
(2-(2-methoxyethoxy)acetoxy)butyl)amino)-5a,5b,8,8,
11a-pentamethyl-1-(prop-1-en-2-yl)icosahydro-1H-
cyclopenta[a]chrysen-9-yl)oxy)carbonyl)-2,2-
dimethylcyclobutane-1-carboxylic acid, 4-(((1R,3aS,5aR,5bR,7aR,9S,11aR,11bR,13aR,13bR)-3a-
(((2R,3R)-2-(1,1-dioxidothiomorpholino)-3-hydroxy-
butyl)amino)-5a,5b,8,8,11a-pentamethyl-1-(prop-1-en-2-
yl)icosahydro-1H-cyclopenta[a]chrysen-9-yl)oxy)-2,2-
dimethyl-4-oxobutanoic acid, (1R,3S)-3-(((((1R,3aS,5aR,5bR,7aR,9S,11aR,11bR,13aR,
13bR)-3a-(((15R,16R)-16-(1,1-dioxidothiomorpholino)-
15-methyl-13-oxo-2,5,8,11,14-pentaoxaheptadecan-17-
yl)amino)-5a,5b,8,8,11a-pentamethyl-1-(prop-1-en-2-yl)
icosahydro-1H-cyclopenta[a]chrysen-9-yl)oxy)
carbonyl)-2,2-dimethylcyclobutane-1-carboxylic acid, (1R,3S)-3-(((((1R,3aS,5aR,5bR,7aR,9S,11aR,11bR,13aR,
13bR)-3a-(((12R,13R)-13-(1,1-dioxidothiomorpholino)-
12-methyl-2,5,8,11-tetraoxatetradecan-14-yl)amino)-5a,
5b,8,8,11a-pentamethyl-1-(prop-1-en-2-yl)icosahydro-
1H-cyclopenta[a]chrysen-9-yl)oxy)carbonyl)-2,2-
dimethylcyclobutane-1-carboxylic acid, or pharmaceutically acceptable salts, and prodrugs of compounds are also contemplated.

The present invention also provides a pharmaceutical composition that includes at least one compound as described herein and at least one pharmaceutically acceptable excipient (such as a pharmaceutically acceptable carrier or diluent). Specifically, the pharmaceutical composition comprises a therapeutically effective amount of at least one compound described herein. The compound(s) present in the composition may be associated with a pharmaceutically acceptable excipient (such as a carrier or a diluent) or may be diluted by a carrier, or enclosed within a carrier which may be in the form of a capsule, sachet, or other container.

The compounds and pharmaceutical compositions described herein are useful in the treatment of diseases, conditions and/or disorders mediated by viral infections.

The present invention further provides a method of treating a disease, condition and/or disorder mediated by viral infections in a subject in need thereof by administering to the subject one or more compounds described herein in a therapeutically effective amount to cure that infection, specifically in the form of a pharmaceutical composition.

Also provided herein are processes for preparing compounds described herein.

The invention provides a method for preventing; ameliorating or treating a HIV mediated disease, disorder or syndrome in a subject in need thereof comprising administering to the subject a therapeutically effective amount of a compound of the invention. The invention further provides a method, wherein the HIV mediated disease, disorder or syndrome is like AIDS, AIDS related complex, or a syndrome characterized by symptoms such as persistent generalized lymphadenopathy, fever and weight loss, or a retroviral infection genetically related to AIDS.

Anti HIV inhibitory potential of the compounds of present invention may be demonstrated by any one or more methodologies known in the art, such as by using the assays described in Mossman T, December 1983, Journal of immunological methods, 65 (1-2), 55-63 and SPC Cole, cancer chemotherapy and Pharmacology, 1986, 17, 259-263.

DETAILED DESCRIPTION OF THE INVENTION

The present invention provides triterpene derivatives and related compounds, which may be used as antiviral particularly as anti-HIV compounds and processes for the synthesis of these compounds and their pharmaceutically acceptable salts thereof, together with pharmaceutically acceptable carriers, excipients or diluents, which can be used for the treatment of diseases, condition and/or disorders mediated by viral infections, are also provided.

The Following Definitions Apply to the Terms as Used Herein

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term "alkenyl" refers to a hydrocarbon chain that may be a straight chain or branched chain, containing the indicated number of carbon atoms having at least one —C=C—, for example, a $C_2$-$C_6$ alkenyl group may have from 2 to 6 (inclusive) —C=C— atoms in it. Examples of $C_2$-$C_6$ alkenyl groups include, but are not limited to ethylene, prop-1-ene, but-1-ene, but-2-ene, pent-1-ene, pent-2-ene, hex-1-ene, hex-2-ene and the like.

The term "alkoxy" refers to a straight or branched hydrocarbon chain with oxygen radical consisting carbon and hydrogen atoms, containing saturation or unsaturation, having from one to eight carbon atoms, and which is attached through oxygen atom to the rest of the molecule by a single bond. One of the hydrogen atoms in the alkoxy group may be further substituted by one or more alkoxy groups to further increase the alkoxy chain length. e.g., methyloxy, ethyloxy, isopropoxy, n-propyloxy, t-butyloxy, 1-methylethyloxy (isopropyloxy), n-butyloxy, n-pentyloxy, 1,1-dimethylethyloxy (t-butyloxy),

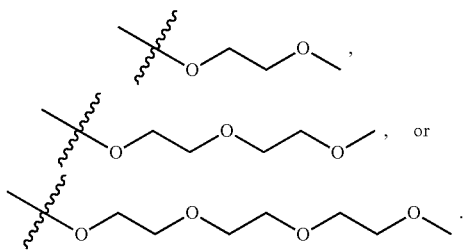

The term "cycloalkyl" denotes a non-aromatic mono or multicyclic ring system of from 3 to about 12 carbon atoms, such as but are not limited to, cyclopropyl, cyclobutyl, cyclopentyl, and cyclohexyl. Examples of multicyclic cycloalkyl groups include, but are not limited to, perhydronapthyl, adamantyl and norbornyl groups, bridged cyclic groups and spirobicyclic groups, e.g., spiro (4,4) non-2-yl.

The terms "halogen" or "halo" includes fluorine, chlorine, bromine, or iodine.

The term "hydroxy" refers to —OH.

The term "optionally substituted" refers to replacement of one or more hydrogen radicals in a given structure with a radical of a specified substituent including, but are not limited to: hydroxy, halo, carboxyl, cyano (CN), nitro, oxo (=O), thio (=S), alkyl, methyl sulfonyl, haloalkyl, alkoxy, alkenyl, aryl, aralkyl, cycloalkyl, cycloalkylalkyl, amino, —C(O)O-alkyl, heterocyclyl, heteroaryl, heterocyclylalkyl, heteroarylalkyl, alkylthio, arylthio, aryloxy, amino carbonyl, alkoxycarbonyl, alkylamino, arylamino, acyl, carboxylic acid, sulfonic acid, sulfonyl, phosphonic acid, and aliphatic. It is understood that the substituent may be further substituted.

The term "prodrug" denotes a derivative of a compound, which derivative, when administered to warm blooded animals, e.g. humans, is converted into the compound (drug). The enzymatic and/or chemical hydrolytic cleavage of the compounds of the present invention occurs in such a manner that the proven drug form (parent carboxylic acid drug) is released, and the moiety or moieties split off remain nontoxic or are metabolized so that nontoxic metabolic products are produced. For example, a carboxylic acid group can be esterified, e.g., with a methyl group or ethyl group to yield an ester. When an ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed Edward B. Roche, American Pharmaceutical Association and Pergamon Press, 1987.

The term "treating" or "treatment" of a state, disease, disorder or condition includes:

(1) preventing or delaying the appearance of clinical symptoms of the state, disease, disorder or condition developing in a subject that may be afflicted with or predisposed to the state, disease, disorder or condition but does not yet experience or display clinical or subclinical symptoms of the state, disease, disorder or condition;

(2) inhibiting the state, disease, disorder or condition, i.e., arresting or reducing the development of the state, disease, disorder or condition or at least one clinical or subclinical symptom thereof; or (3) relieving the state, disease, disorder or condition, i.e., causing regression of the state, disease, disorder or condition or at least one of its clinical or subclinical symptoms.

The benefit to a subject receiving treatment is either statistically significant or at least perceptible to the subject or to the physician.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disease, disorder or condition, is sufficient to effect such treatment. The "therapeutically effective amount" will vary depending on the compound, the state, disease, disorder or condition and its severity and the age, weight, physical condition and responsiveness of the subject receiving treatment.

The compounds of the present invention may form salts. Non-limiting examples of pharmaceutically acceptable salts forming part of this invention include salts derived from inorganic bases salts of organic bases salts of chiral bases, salts of natural amino acids and salts of non-natural amino acids. Certain compounds of the present invention are capable of existing in stereoisomeric forms (e.g., diastereomers, enantiomers, racemates, and combinations thereof). With respect to the overall compounds described by the formula (I), the present invention extends to these stereoisomeric forms and to mixtures thereof. To the extent prior art teaches synthesis or separation of particular stereoisomers, the different stereo isomeric forms of the present invention may be separated from one another by the methods known in the art, or a given isomer may be obtained by stereospecific or asymmetric synthesis. Tautomeric forms and mixtures of compounds described herein are also contemplated.

Pharmaceutical Compositions

The pharmaceutical compositions provided in the present invention include at least one compound described herein and at least one pharmaceutically acceptable excipient (such as a pharmaceutically acceptable carrier or diluent). Specifically, the contemplated pharmaceutical compositions include a compound(s) described herein in an amount sufficient to treat viral infection in a subject.

The subjects contemplated include, for example, a living cell and a mammal, including human. The compound of the present invention may be associated with a pharmaceutically acceptable excipient (such as a carrier or a diluent) or be diluted by a carrier, or enclosed within a carrier which can be in the form of a capsule, sachet, or other container.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters, and polyoxyethylene.

The carrier or diluent may include a sustained release material, such as, for example, glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick-, sustained-, or delayed-release of the active ingredient after administration to the subject by employing procedures known in the art.

The pharmaceutical compositions described herein may be prepared, e.g., as described in *Remington: The Science and Practice of Pharmacy,* 20$^{th}$ Ed., 2003 (Lippincott Williams & Wilkins). For example, the active compound can be mixed with a carrier, or diluted by a carrier, or enclosed within a carrier, which may be in the form of an ampule, capsule, or sachet. When the carrier serves as a diluent, it may be a solid, semi-solid, or liquid material that acts as a vehicle, excipient, or medium for the active compound.

The pharmaceutical compositions may be in conventional forms, for example, capsules, tablets, solutions, suspensions, injectables or products for topical application. Further, the pharmaceutical composition of the present invention may be formulated so as to provide desired release profile.

The route of administration may be any route which effectively transports the active compound to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is specifically suitable.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Exemplary carriers for tablets, dragees, or capsules include lactose, cornstarch, and/or potato starch. A syrup or elixir can be used in cases where a sweetened vehicle can be employed.

A typical tablet that may be prepared by conventional tableting techniques.

Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, specifically aqueous solutions with the active compound dissolved in polyhydroxylated castor oil.

Methods of Screening

Antiviral HIV activity and cytotoxicity of compounds present invention can be measured in parallel by following the methods published in the literature.

The cytotoxic effect of compounds can be analyzed by measuring the proliferation of cells using the 3-(4,5-Dimethylthiazol-2-yl)-2,5-diphenyl tetrazlium bromide (MTT) staining. Cells ($5 \times 10^3$ cells/well) will be incubated in in 96 well plates in the presence or absence of compounds. At the end of treatment, 20!J·l of MTT (5 mg/ml in PBS) will be added to each well and incubated for an additional 4 hours at 37° C. The purple-blue MTT formazan precipitate will be dissolved in a triplex reagent containing 10% SDS, 5% isobutanol and 10 mmol/lit HCl. The activity of mitochondria, reflecting cellular growth and viability, will be evaluated by measuring the optical density at 570 nm on micro titer plate.

Action of compounds on replication of HIV in Sup-T1 cells can be determined by the method published by Roda Rani et al., 2006 (Archives of Biochemistry and Biophysics, Volume 456, Issue 1, 1 Dec. 2006, Pages 79-92).

Briefly, $1 \times 10^6$ Sup-T1 cells with 100% cell viability will be seeded in RPMI 1640, 0.1% FBS four 12 well plates. Increasing concentrations of Epap-1 peptides will be added to the cells and will be infected with $HIV1_{93\ IN\ 101}$ each at final concentration of virus equivalent to 2 ng of p24 per ml. The infected cells will be incubated at 37° C. and 5% $CO_2$ incubator for 2 hours. After 2 hours the cells will be pelleted at 350 g for 10 minutes, supernatant will be discarded and cell will be held with RPMI 1640 containing 10% FBS. The cells will be resuspended in the same medium with increasing concentrations of Epap-1 peptides and will be incubated for 96 hours. The cells will be supplemented with peptides at every 24 hours. The supernatants will be collected after 96 hours and analyzed using P24 antigen capture assay kit (SAIC Fredrick). The infection in the absence of Epap-1 will be considered to be 0% inhibition Azidothymidine (AZT) will be taken as positive control.

Action of compound on virus entry and quantification of virus entered can be done in terms of GFP expression by the following the methods published J. Virol. 72, 6988 (1998) by in Cecilia et al., and Analytical Biochemistry Volume 360, Issue 2, 15 Jan. 2007, Pages 315-317 (Dyavar S. Ravi and Debashis Mitra).

Briefly, cells will be seeded in to wells of 24 well plates 1 day prior to the experiment. The cells will be transfected with Tat-reporter. The virus inoculum will be adjusted to 1,000-4,000 TCID 50/ml in assay medium (DMEM, 10% FCS, glutamine and antibiotics), 50 µl aliquots will be incubated with serial dilutions of compounds (50 µl) for 1 hour at 37° C. The reporter expression will be quantified at appropriate time calculated inhibitory doses referrers to the concentration of these agents in this preincubation mixture.

Other relevant references useful for screening antiviral HIV activity are: Averett, D. R. 1989. Anti-HIV compound assessment by two novel high capacity assays. J. Virol. Methods 23: 263-276; Schwartz, O., et al. 1998; A rapid and simple colorimeric test for the study of anti HIV agents. AIDS Res. and Human Retroviruses, 4(6):441-447; Daluge, S. M., et al. 1994. 5-Chloro-2',3'-deoxy-3'fluorouridine (935U83), a selective anti human immunodeficiency virus agent with an improved metabolic and toxicological profile; Antimicro. Agents and Chemotherapy, 38(7): 1590-1603; H. Mitsuya and S. Border, Inhibition of the in vitro infectivity and cytopathic effect of human T-lymphotropic virus type lymphadenopathy-associated virus (HLTV-111/LAV) by 2,3'-dideoxynucleo side s, Proc. Natl. Acad. Sci. USA, 83,1911-15(1986); Pennington et al., Peptides 1990; Meek T. D et al., Inhibition of HIV-1 protease in infected T-limphocytes by synthetic peptide analogues, Nature, 343, p 90 (1990); Weislow et al., J. Natl. Cancer Inst. 81, 577-586, 1989; T. Mimoto et al., J. Med. Chern., 42, 1789-1802, 1999; Uckun et al 1998, Antimicrobial Agents and Chemotherapy 42:383; for P24 antigen assay Erice et al., 1993, Antimicrob. Ag. Chemotherapy 37: 385-383; Koyanagi et al., Int. J. Cancer, 36, 445-451, 1985; Balzarini et al. AIDS (1991), 5, 21-28; Connor et al., Journal of virology, 1996, 70, 5306-5311; Popik et al., Journal of virology, 2002, 76, 4709-4722; Harrigton et al., Journal of Virology Methods, 2000, 88, 111-115; Roos et al., Virology 2000, 273, 307-315; Fedyuk N. V. et al; Problems of Virology 1992, (3)P135; Mosmann T, December 1983, Journal of immunological methods, 65 (1-2), 55-63; SPC Cole, cancer chemotherapy and Pharmacology, 1986, 17, 259-263, Antiviral methods and protocols (Eds: D Kinchington and R. F. Schinazi) Humana Press Inc., 2000, HIV protocols (Eds: N. L. Michael and J. H. Kim) Humana Press Inc, 1999, DAIDS Virology manual from HIV laboratories, Publication NIH-97-3838, 1997, 4. HIV-1 p24 antigen capture assay, enzyme immunoassay for detection of Human immunodeficiency Virus Type 1 (HIV-1) p24 in tissue culture media—Advanced bio science laboratories, Inc kit procedure.

Methods of Treatment

The present invention provides compounds and pharmaceutical formulations thereof that are useful in the treatment of diseases, conditions and/or disorders mediated by viral infections. The connection between therapeutic effect and antiviral is illustrated. For example, PCT publication Nos. WO 01/07646, WO 01/65957, or WO 03/037908; US publication Nos. U.S. Pat. No. 4,598,095 or US 2002/0068757; EP publication Nos. EP 0989862 or EP 0724650; *Bioorganic & Medicinal Chemistry Letters,* 16, (6), 1712-1715, 2006; and references cited therein, all of which are incorporated herein by reference in their entirety and for the purpose stated.

The present invention further provides a method of treating a disease, condition and/or disorder mediated by viral infections in a subject in need thereof by administering to the subject a therapeutically effective amount of a compound or a pharmaceutical composition of the present invention.

Diseases, conditions, and/or disorders that are mediated by viral infections are believed to include, but are not limited to, HIV infection, HBV infection, HCV infection, a retroviral infection genetically related to HIV, AIDS, inflammatory disease, respiratory disorders (including adult respiratory distress syndrome (ARDS), bronchitis, chronic bronchitis, chronic obstructive pulmonary disease, cystic fibrosis, asthma, emphysema, rhinitis and chronic sinusitis), inflammatory bowel disease (including Crohn's disease and ulcerative colitis), multiple sclerosis, rheumatoid arthritis, graft rejection (in particular but not limited to kidney and lung allografts), endometriosis, type I diabetes, renal diseases, chronic pancreatitis, inflammatory lung conditions, chronic heart failure and bacterial infections (in particular but not limited to tuberculosis).

The compounds of the present invention can obtain more advantageous effects than additive effects in the prevention or treatment of the above diseases when using suitably in combination with the available drugs. Also, the administration dose can be decreased in comparison with administration of either drug alone, or adverse effects of co administrated drugs other than antiviral can be avoided or declined.

Methods of Preparation

The compounds described herein may be prepared by techniques known in the art. In addition, the compounds described herein may be prepared by following the reaction sequence as depicted in below schemes. Further, in the following schemes, where specific bases, acids, reagents, solvents, coupling agents, etc., are mentioned, it is understood that other bases, acids, reagents, solvents, coupling agents etc., known in the art may also be used and are therefore included within the present invention. Variations in reaction conditions, for example, temperature and/or duration of the reaction, which may be used as known in the art, are also within the scope of the present invention. All the stereoisomers of the compounds in these schemes, unless otherwise specified, are also encompassed within the scope of this invention.

Compounds of the present invention can be synthesized from naturally occurring Betulinic acid. Key intermediates required for synthesizing analogues are either commercially available or can be prepared by the methods published in the literature. For example, the key intermediates in the present invention were prepared by modifying the procedures published in *Journal of organic chemistry* 2010, 75, 1285-1288; *Journal of organic chemistry* 2000, 65, 3934-3940; *Tetrahedron: asymmetry* 2008, 19, 302-308; or *Tetrahedron: asymmetry* 2003, 14, 217-223.

Another embodiment of the present invention provides process for preparation of the compounds of general formula (I) are set forth in the below generalized schemes. One of skilled in the art will recognize that below generalised schemes can be adapted to produce the compounds of general formula (I) and pharmaceutically acceptable salts according to the present invention. Wherein all symbols/variables are as defined earlier unless otherwise stated.

General Synthetic Procedures of the formula (ii) can be converted to the ester compounds of the formula (iii) by using the reagent such as benzyl bromide and the bases such as potassium carbonate or sodium carbonate in solvents such as acetonitrile or THF under reflux conditions. The C-3 acetyl and C-28 ester compounds of formula (iii) can be converted to the C-20 cyclopropyl compounds of the formula (iv) in the presence

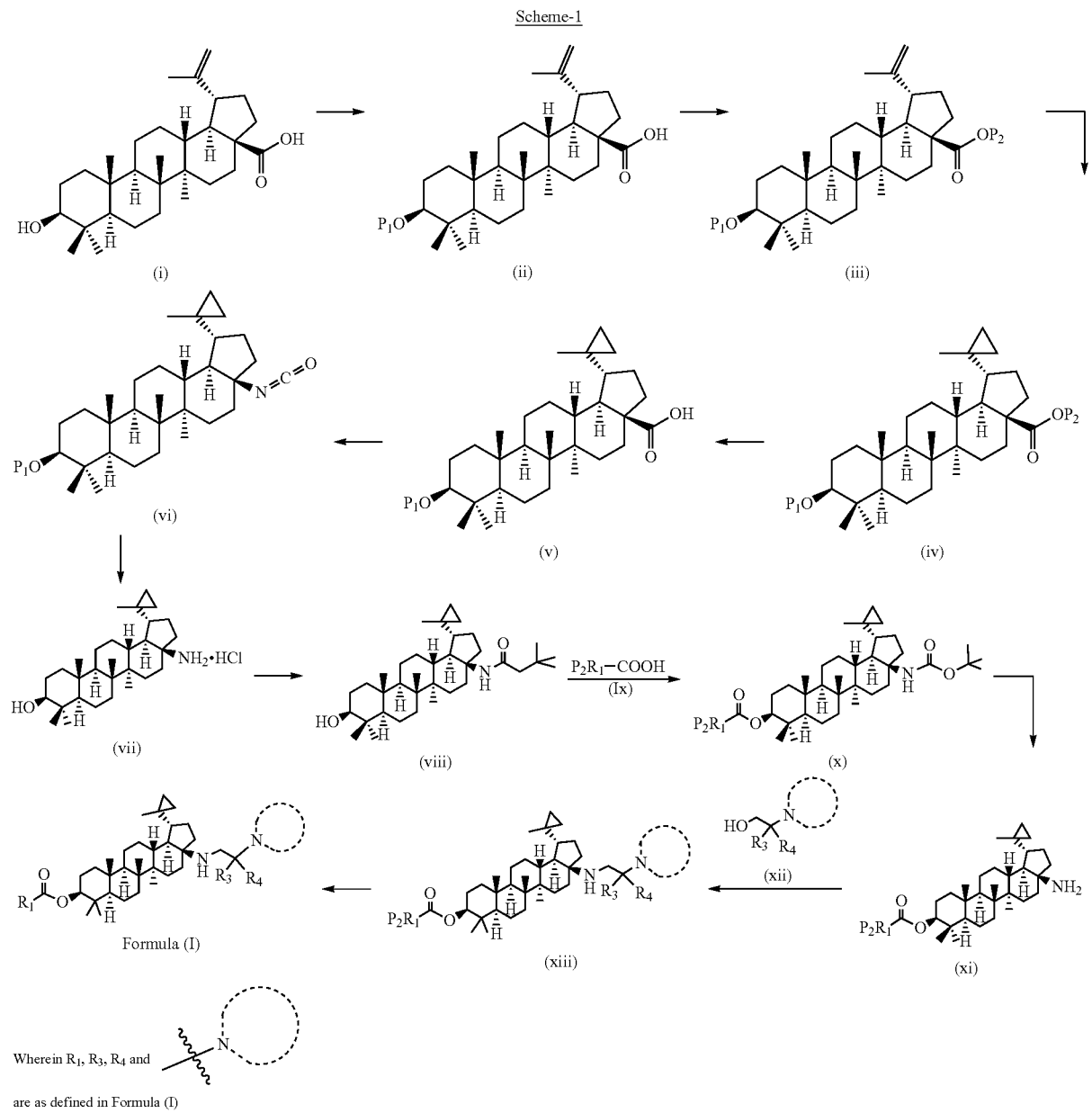

The compounds of formula (I) (wherein, $R_1$, $R_3$ and $R_4$ are same as defined above; $P_1$ and $P_2$ are protecting groups such as acetyl, benzyl or the like) can be prepared as described in Scheme 1. The C-3 hydroxy compounds of formula (i) can be protected by using the reagent such as acetic anhydride with acetic acid under reflux conditions (or) with acetic anhydride under basic conditions by using the reagent such as triethylamine or N,N-diisopropylethylamine and catalyst such as 4-Dimethylaminopyridine under reflux conditions in solvents such as THF or the like. The C-28 acid compounds of formula (ii) can be converted to the ester compounds of the formula (iii) by using the reagent such as benzyl bromide and the bases such as potassium carbonate or sodium carbonate in solvents such as acetonitrile or THF under reflux conditions. The C-3 acetyl and C-28 ester compounds of formula (iii) can be converted to the C-20 cyclopropyl compounds of the formula (iv) in the presence of cyclopropanating agents such as Diethylzinc or Dimethylzinc with Diiodomethane in solvents such as Dichloromethane or Toluene or the like. The C-28 ester compounds of formula (iv) can be deprotected to the C-28 acid compounds of the formula (v) by using (i) the catalyst like Pd/C in solvents like ethyl acetate and methanol or the like under hydrogen pressure (or) (ii) the catalyst like Pd/C and the reagent like ammonium formate in solvents like ethanol and THF. The C-28 acid compounds of formula (v) can be converted to the C-17 isocyanato compounds of formula (vi)

in the presence of reagent such as diphenylphosphoryl azide (DPPA) or the like in the presence of bases such as triethylamine (TEA) or N,N-Diisopropylethylamine or the like in the solvents such as Toluene or 1,4-dioxane or the like. The C-17 isocyanato compounds of formula (vi) can be converted to the C-17 amine hydrochloride compounds of formula (vii) in the presence of reagents such as conc. HCl or the like in the solvents such as 1,4-dioxane or the like. The C-17 amine hydrochloride compounds of formula (vii) can be converted to the C-17 amine protected compounds of formula (viii) in the presence of reagents such as di-tert-butyl dicarbonate [(Boc)$_2$O] or the like in the presence of bases such as sodium bicarbonate (NaHCO$_3$) or sodium carbonate or the like in the solvents such as 1,4-dioxane: H$_2$O or the like. The C-3 hydroxy compounds of formula (viii) can be coupled with the compounds of formula (ix) to give the C-3 ester compounds of formula (x) with reagent such as EDC.HCl or the like and the catalyst such as 4-Dimethylaminopyridine (DMAP) or the like, in the solvents such as dichloromethane (DCM) or THF or the like. The C-17 amine protected compounds of formula (x) can be converted to the C-17 amine compounds of formula (xi) in the presence of reagents such as 4N HCl in 1,4-dioxane or the like in the solvents such as 1,4-dioxane or the like. The C-17 amine compounds of formula (xi) can be coupled with the hydroxy compounds of formula (xii) in situ conditions to give the corresponding C-17 substituted amine compounds of formula (xiii) in the presence of reagents such as triflic anhydride, 2,6-Lutidine and bases such as triethylamine or N,N-diisopropylethylamine or the like in the solvents such as Dichloromethane or the like. The C-3 protected compounds of formula (xiii) can be deprotected to give the corresponding acid compounds of the present invention of formula (I) in the presence of reagents such as KOH or NaOH in the combination of solvents such as methanol, THF, H$_2$O or the like.

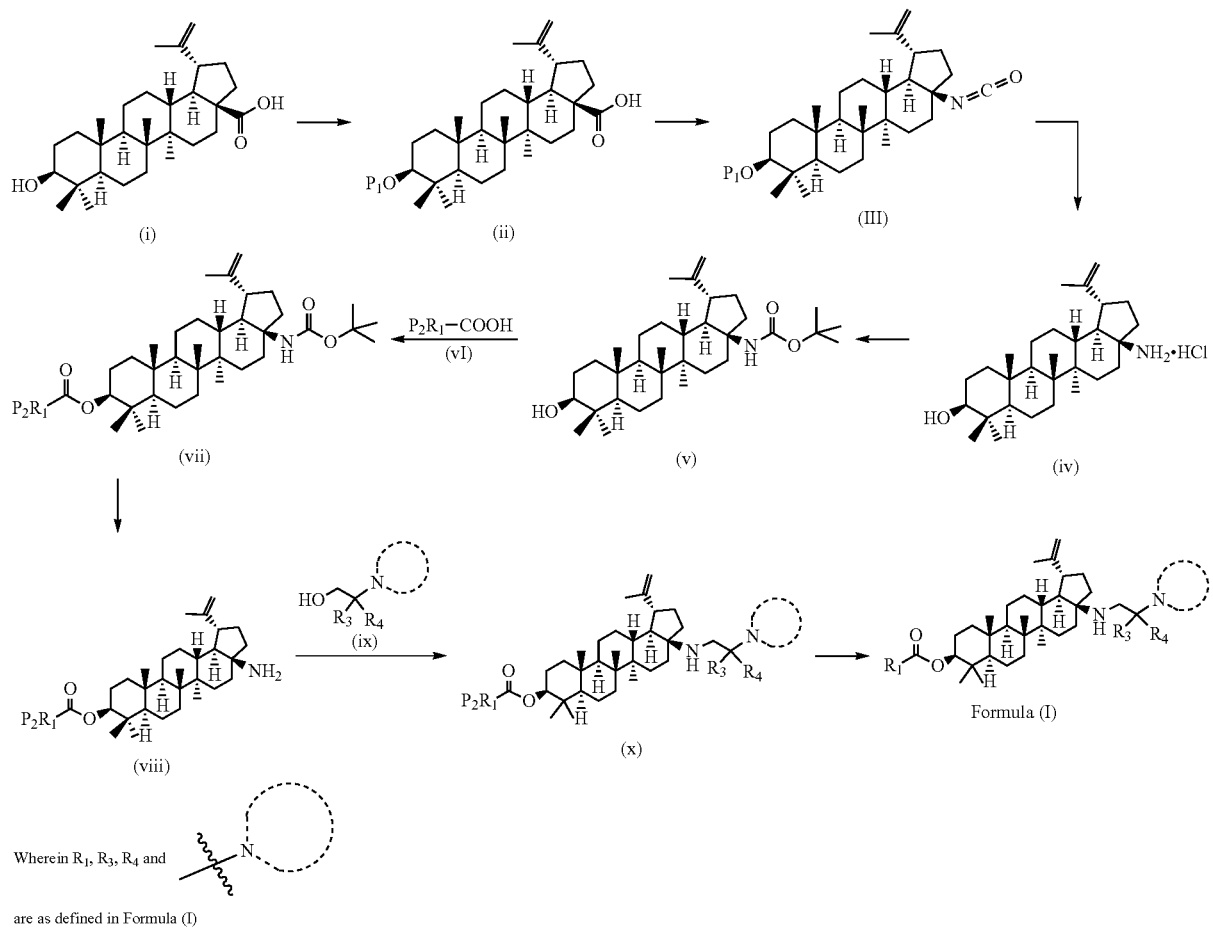

The compounds of formula (I) (wherein, R$_1$, R$_3$ and R$_4$ are same as defined above; P$_1$ and P$_2$ are protecting groups such as acetyl, benzyl or the like) can be prepared as described in Scheme 2. The C-3 Hydroxy compounds of formula (i) can be protected by using the reagent such as acetic anhydride with acetic acid under reflux conditions (or) with acetic anhydride under basic conditions by using the reagent such as triethylamine or N,N-diisopropylethyl amine and catalyst such as 4-Dimethylaminopyridine under reflux conditions in solvents such as THF or the like. The C-28 acid compounds of formula (ii) can be converted to the C-17 isocyanato compounds of formula (iii) in the presence of reagent such as diphenylphosphoryl azide (DPPA) or the like in the presence of bases such as triethylamine (TEA) or N,N-Diisopropylethylamine or the like in the solvents such as Toluene or 1,4-dioxane or the like. The C-17 isocyanato compounds of formula (iii) can be converted to the C-17 amine hydrochloride compounds of formula (iv) in the presence of reagents such as conc. HCl or the like in the solvents such as 1,4-dioxane or the like. The C-17 amine hydrochloride compounds of formula (iv) can be converted to the C-17 amine protected compounds of formula (v) in the presence of reagents such as di-tert-butyl dicarbonate [(Boc)$_2$O] or the like in the presence of bases such as sodium bicarbonate (NaHCO$_3$) or sodium carbonate or the like in the solvents such as 1,4-dioxane:H$_2$O or the like. The C-3 hydroxy compounds of formula (v) can be coupled with the compounds of formula (vi) to give the C-3 ester compounds of formula (vii) with reagent such as EDC.HCl or the like and the catalyst such as 4-Dimethylaminopyridine (DMAP) or the like in the solvents such as dichloromethane (DCM) or THF or the like. The C-17 amine protected compounds of formula (vii) can be converted to the C-17 amine compounds of formula (viii) in the presence of reagents such as 4N HCl in 1,4-dioxane or the like in the solvents such as 1,4-dioxane or the like. The C-17 amine compounds of formula (xiii) can be coupled with the hydroxyl compounds of formula (ix) in situ conditions to give the corresponding C-17 substituted amine compounds of formula (x) in the presence of reagents such as triflic anhydride, 2,6-Lutidine and bases such as triethylamine or N,N-diisopropylethylamine or the like in the solvents such as Dichloromethane or the like. The C-3 protected compounds of formula (x) can be deprotected to give the corresponding acid compounds of the present invention of formula (I) in the presence of reagents such as KOH or NaOH in the combination of solvents such as methanol, THF, H$_2$O or the like.

Scheme-3

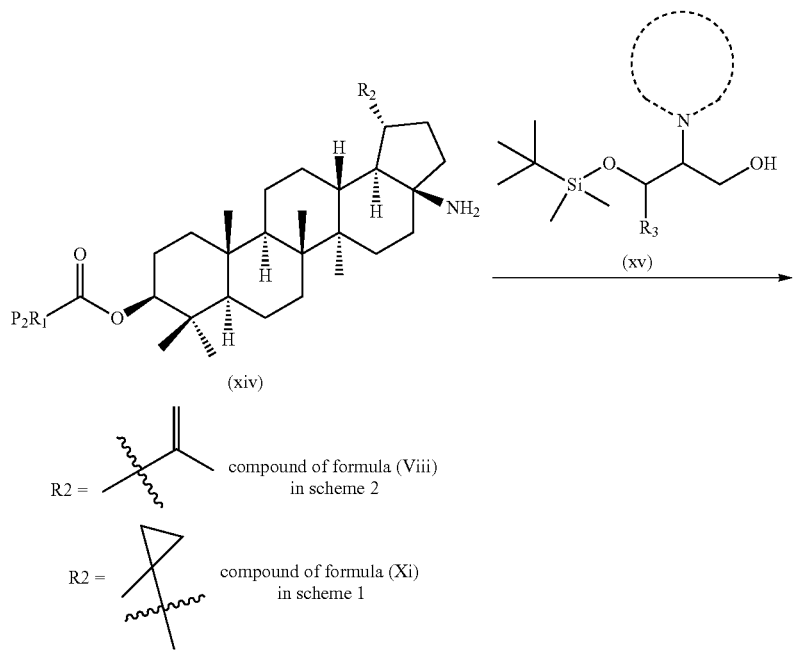

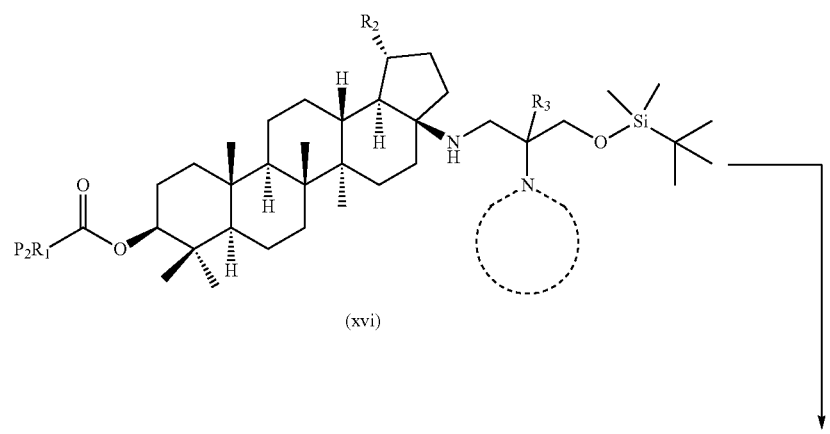

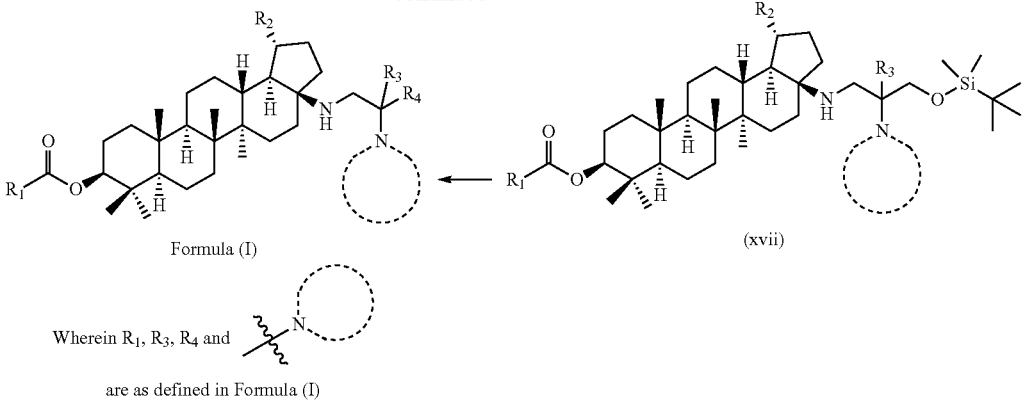

Formula (I) ← (xvii)

Wherein R₁, R₃, R₄ and [structure] are as defined in Formula (I)

The C-17 amine compounds of formula (xiv) can be coupled with the hydroxy compounds of formula (xv) in situ conditions to give the corresponding C-17 substituted amine compounds of formula (xvi) in the presence of reagents such as triflic anhydride, 2,6-Lutidine and bases such as triethylamine or N,N-diisopropylethylamine or the like in the solvents such as Dichloromethane or the like. The C-3 protected compounds of formula (xvi) can be deprotected to give the corresponding acid compounds of the formula (xvii) in the presence of reagents such as KOH or NaOH in the combination of solvents such as methanol, THF, H₂O or the like. The silyl ether group in compounds of formula (xvii) can be deprotected to give the corresponding acid compounds of the present invention of the formula (I) with reagent like TBAF in THF or the like and in solvents like THF or the like.

In a further aspect, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2$H ("D"), $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Particular isotopes are —CD₃ or —C(D₂)-. Isotopically-labeled compounds of the present inventions can generally be prepared by following procedures analogous to those disclosed in the Schemes and/or in the Examples herein below, by substituting an isotopically-labeled reagent for a non-isotopically-labeled reagent.

Abbreviations: The abbreviations used in the entire specification may be summarized herein below with their particular meaning: 1H NMR (Proton Nuclear Magnetic Resonance); Hz (hertz); MHz (megahertz); DMSO-d6 (Deuterated Dimethylsulfoxide); δ (delta); ppm (parts per million); s (singlet); d (doublet); dd (doublet of doublet(s)); t (triplet); m (multiplet); J (coupling constant); JAB (coupling constant); ABq (AB quartet); brs (broad singlet); ml (millilitre); ° C. (degree Celsius); mol (mole(s)); mmol (millimole(s)); N (Normal solution); g (gram(s)); pH (Pouvoir hydrogen); Pd/C (palladium on activated carbon); eq (equivalent(s)); psi (pounds per square inch); ESI-MS (Electrospray ionization mass spectrometry); ES-MS (Electrospray mass spectrometry); m/z (mass to charge ratio); M−H− (parent mass spectrum peak minus hydrogen−); M+Na+ (parent mass spectrum peak plus sodium+); M+H+ (parent mass spectrum peak plus hydrogen+); DCM (Dichloromethane); DMF (N,N-dimethylformamide); THF (Tetrahydrofuran); Na₂SO₄ (sodium sulfate); HCl (Hydrochloric acid); TLC (Thin Layer Chromatography); % (percentage); TEMPO (2,2,6,6-Tetramethylpiperidin-1-yl)oxyl); KBr (potassium bromide); DIBAL-H (Diisobutylaluminium Hydride); DAST (Diethylaminosulfur trifluoride); TBAF (Tetra-n-butylammonium fluoride); NaOH (sodium hydroxide); KOH (potassium hydroxide); EDC.HCl (1-(3-Dimethylaminopropyl)-3-ethylcarbodiimide Hydrochloride); MTBE (Methyl tert-butyl ether); HBTU (N,N,N',N'-Tetramethyl-O-(1H-benzotriazol-1-yl)uronium hexafluorophosphate); h (or) hrs (hour(s)); H (Hydrogen); APCI-MS (Atmospheric-pressure Chemical ionization mass spectroscopy); DMAP (4-Dimethylaminopyridine); TBDMSCl (tert-butyldimethylsilyl chloride).

EXPERIMENTAL

The present invention is further illustrated by the following examples, which are not to be construed in any way as imposing limitations upon the scope of this disclosure, but rather are intended to be illustrative only. On the contrary, it is to be clearly understood that resort may be had to various other embodiments, modifications, and equivalents thereof which, after reading the description herein, may suggest one of ordinary skill in the art without departing from the spirit of the present invention. Thus, the skilled artisan will appreciate how the experiments and examples may be further implemented as disclosed by variously altering the following examples, substituents, reagents, or conditions.

Intermediates

Intermediate 1: Preparation of 1-((1R,3aS,5aR,5bR,7aR,9S,11aR,11bR,13aR,13bR)-3a-amino-5a,5b,8,8,11a-pentamethyl-1-(1-methylcyclopropyl)icosahydro-1H-cyclopenta[a]chrysen-9-yl) 3-benzyl (1S,3R)-2,2-dimethylcyclobutane-1,3-dicarboxylate

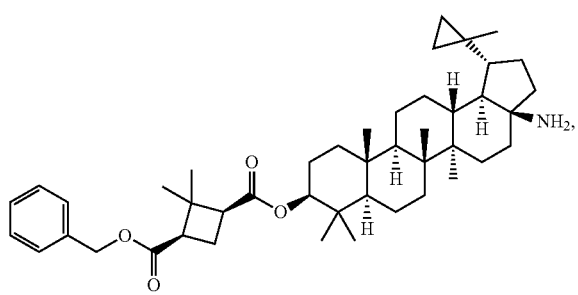

Step 1: Synthesis of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-3aH-cyclopenta[a]chrysene-3a-carboxylic acid

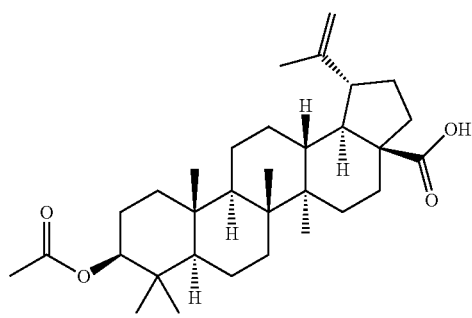

To Betulinic acid (200 g, 0.438 moles, 1.0 eq) in RB flask, acetic acid (1600 ml) and acetic anhydride (173 g, 1.696 moles, 3.87 eq) were added. The reaction mixture was stirred and heated to 130-140° C. for around 4 hours. The progress of the reaction monitored by TLC, indicated starting material was completed. Acetic acid was distilled out approximately 1100 ml under vacuum. The flask was cooled to room temperature, methanol (1400 ml) was slowly added and stir at room temperature for 12-16 hours. The solid was filtered, washed with methanol (200 ml) and dried under vacuum (50-55° C.) to obtain the title compound as a white solid (182 g, 83.32% yield).

Step 2: Synthesis of benzyl (1R,3aS,5aR,5bR,7aR,9S,11aR,11bR,13aR,13bR)-9-acetoxy-5a,5b,8,8,11a-pentamethyl-1-(prop-1-en-2-yl)icosahydro-3aH-cyclopenta[a]chrysene-3a-carboxylate

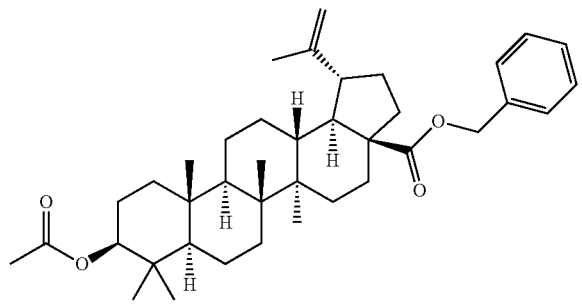

To a stirred solution of (1R,3aS,5aR,5bR,7aR,9S,11aR,13bR,13aR,13bR)-9-acetoxy-5a,5b,8,8,11a-pentamethyl-1-(prop-1-en-2-yl)icosahydro-3aH-cyclopenta[a]chrysene-3a-carboxylic acid (step 1, 180 g, 0.361 moles, 1.0 eq) in acetonitrile (1800 ml) was added potassium carbonate (99.75 g, 0.721 moles, 2.0 eq). The reaction mixture was stirred at room temperature, Benzyl bromide (42.5 ml, 0.361 moles, 1.0 eq) was added drop wise for 30 minutes. The reaction mixture was stirred and heated to reflux for around 6 hours. The progress of the reaction monitored by TLC, indicated starting material was completed. The reaction mixture was cooled to room temperature, water (2700 ml) was added and stirred for 2 hours. Ethyl acetate (2700 ml) was added and stirred for 30 minutes. Organic layer was separated and aqueous layer was again extracted twice with ethyl acetate (2×900 ml). The combined organic layers were washed with water (1800 ml) and brine solution (1800 ml). The organic layer was dried over sodium sulphate, filtered and concentrated under reduced pressure. The crude compound was purified by treating with methanol (720 ml), stirred and heated to 60-65° C. for 30 minutes. Cool the reaction mixture to room temperature and stirred for 2 hours. The mixture was filtered, washed with methanol (180 ml) and dried under vacuum (55-60° C.) to obtain the title compound (180 g, 84.7% yield) as a solid.

Step 3: Synthesis of benzyl (1R,3aS,5aR,5bR,7aR,9S,11aR,11bR,13aR,13bR)-9-acetoxy-5a,5b,8,8,11a-pentamethyl-1-(1-methylcyclopropyl)icosahydro-3aH-cyclopenta[a]chrysene-3a-carboxylate

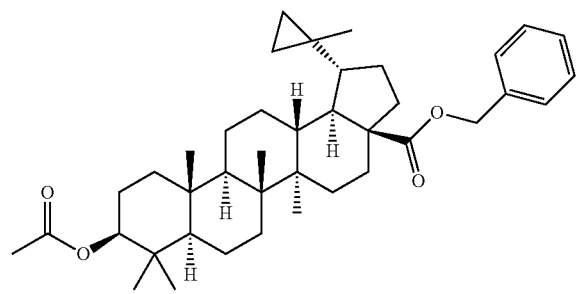

To a stirred solution of benzyl (1R,3aS,5aR,5bR,7aR,9S,11aR,11bR,13aR,13bR)-9-acetoxy-5a,5b,8,8,11a-pentamethyl-1-(prop-1-en-2-yl)icosahydro-3aH-cyclopenta[a] chrysene-3a-carboxylate (step 2, 120 g, 0.204 moles, 1.0 eq) in DCM (1200 ml) at −25 to −35° C. under nitrogen atmosphere was added Diethyl Zinc (75.61 g, 408 ml, 0.612 mol, 3.0 eq, 1.5M in Toluene). The reaction mixture was stirred at −25 to −35° C. for 1 hour. Diiodomethane (81.5 ml, 1.02 moles, 5.0 eq) was slowly added drop wise at −25 to −35° C. for around 45 minutes. The reaction mixture was stirred at −25 to −35° C. for around 3 hours. The reaction mixture was slowly warmed to room temperature and stirred for around 14 hours. TLC indicated starting material was completed and the desired product was observed. The reaction mixture was cooled to 0-5° C., quenched with saturated ammonium chloride solution (600 ml), 1N HCl (240 ml) was slowly added to adjust the pH (3 to 4) and stirred for 30 minutes. The organic layer was separated and the aqueous layer was extracted with DCM (600 ml). The combined organic layers were washed with 10% sodium bicarbonate solution, water (1800 ml) and brine solution (1800 ml). The organic layer was dried over sodium sulphate, filtered and concentrated under reduced pressure. To this obtained solid, Diisopropyl ether (360 ml) was added and stirred at room temperature for 3 hours. The solid was filtered, washed with diisopropyl ether (120 ml) and dried under vacuum (55-60° C.) to obtain the title compound (100 g, 81.4% yield) as a white solid.

Step 4: Synthesis of (1R,3aS,5aR,5bR,7aR,9S,11aR, 11bR,13aR,13bR)-9-acetoxy-5a,5b,8,8,11a-pentamethyl-1-(1-methylcyclopropyl)icosahydro-3aH-cyclopenta[a]chrysene-3a-carboxylic acid

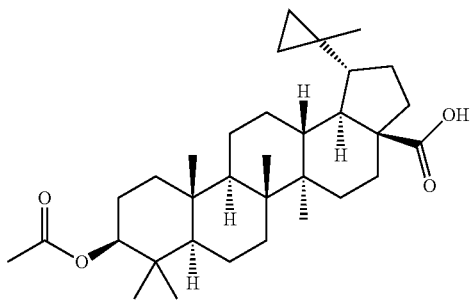

To a suspension of 10% Pd/C (15 g, 50% wet) in ethyl acetate (350 ml) was added benzyl (1R,3aS,5aR,5bR,7aR, 9S,11aR,11bR,13aR,13bR)-9-acetoxy-5a,5b,8,8,11a pentamethyl-1-(1-methylcyclopropyl)icosahydro-3aH-cyclopenta[a]chrysene-3a-carboxylate (step 3, 35 g, 58.13 mmol, 1.0 eq) dissolved in methanol (200 ml). The reaction mixture was hydrogenated in parr shaker apparatus at 50 psi pressure for 3 hours. TLC indicates consumption of starting material. The reaction mixture was filtered through celite pad and the filtrate was evaporated under reduced pressure to obtain the title compound (30 g) as a solid. $^1$H NMR (300 MHz, CDCl$_3$): δ ppm 4.51-4.46 (m, 1H), 2.25-2.21 (m, 1H), 2.13-0.78 (m, 24H), 2.04 (s, 3H), 0.98 (s, 3H), 0.91 (s, 6H), 0.86 (s, 3H), 0.85 (s, 3H), 0.84 (s, 3H), 0.38-0.34 (m, 2H), 0.27-0.24 (m, 2H); ESI-MS: m/z 511.45 (M−H)$^-$.

Step 5: Synthesis of (1R,3aS,5aR,5bR,7aR,9S,11aR, 11bR,13aR,13bR)-3a-isocyanato-5a,5b,8,8,11a-pentamethyl-1-(1-methylcyclopropyl)icosahydro-1H-cyclopenta[a]chrysen-9-yl acetate

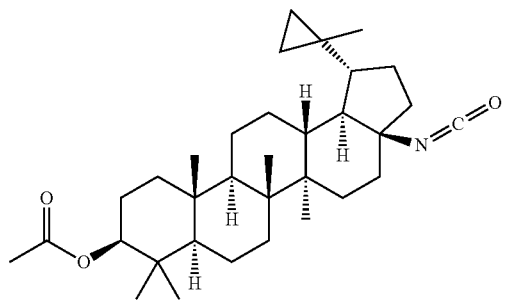

To a stirred solution of (1R,3aS,5aR,5bR,7aR,9S,11aR, 11bR,13aR,13bR)-9-acetoxy-5a,5b,8,8,11a-pentamethyl-1-(1-methylcyclopropyl)icosahydro-3aH-cyclopenta[a] chrysene-3a-carboxylic acid (step 4, 20 g, 39.00 mmol, 1.0 eq) in Toluene (200 ml) was added Diphenylphosphoryl azide (22.36 ml, 97.50 mmol, 2.5 eq) and triethylamine (13.70 ml, 97.50 mmol, 2.5 eq). The reaction mixture was refluxed for 1 hour. TLC indicated starting material was consumed and the desired product was observed. The reaction mixture was evaporated under reduced pressure, diluted with water (250 ml) and extracted with DCM (2×200 ml). The combined organic layer was dried over Na$_2$SO$_4$, filtered and concentrated under reduced pressure. The residue was triturated with methanol (100 ml), filtered and dried under vacuum to obtain the title compound (19 g, 95.5% yield) as an off-white solid. $^1$H NMR (300 MHz, CDCl$_3$): δ ppm 4.45 (m, 1H), 2.04 (s, 3H), 2.03-0.78 (m, 25H), 1.04 (s, 3H), 0.94 (s, 3H), 0.91 (s, 3H), 0.88 (s, 3H), 0.85 (s, 3H), 0.84 (s, 3H), 0.38-0.26 (m, 4H).

Step 6: Synthesis of (1R,3aS,5aR,5bR,7aR,9S,11aR, 11bR,13aR,13bR)-3a-amino-5a,5b,8,8,11a-pentamethyl-1-(1-methylcyclopropyl)icosahydro-1H-cyclopenta[a]chrysen-9-ol hydrochloride

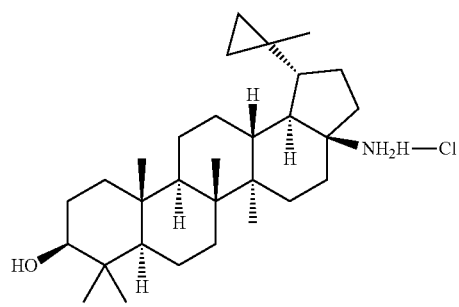

To a stirred solution of (1R,3aS,5aR,5bR,7aR,9S,11aR, 11bR,13aR,13bR)-3a-isocyanato-5a,5b,8,8,11a-pentamethyl-1-(1-methylcyclopropyl)icosahydro-1H-cyclopenta[a]chrysen-9-yl acetate (step 5, 19 g, 37.27 mmol, 1.0 eq) in 1,4-dioxane (190 ml) at 0° C. was added concentrated HCl (57 ml). The reaction mixture was stirred at 50-60° C. for overnight. TLC indicated starting material was consumed and the desired product was observed. The reaction mixture was evaporated under reduced pressure and co-distilled with acetonitrile (100 ml) to obtain the title compound (20 g) as a solid, which is used as such for next step without further purification. ES-MS: m/z 442.20 (M+H)$^+$.

Step 7. Synthesis of tert-butyl ((1R,3aS,5aR,5bR, 7aR,9S,11aR,11bR,13aR,13bR)-9-hydroxy-5a,5b,8, 8,11a-pentamethyl-1-(1-methylcyclopropyl)icosahydro-3aH-cyclopenta[a]chrysen-3a-yl)carbamate

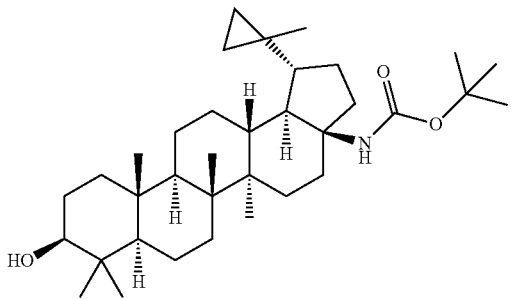

To a stirred solution of (1R,3aS,5aR,5bR,7aR,9S,11aR, 11bR,13aR,13bR)-3a-amino-5a,5b,8,8,11a-pentamethyl-1-(1-methylcyclopropyl)icosahydro-1H-cyclopenta[a]chrysen-9-ol hydrochloride (step 6, 20 g, 41.823 mmol, 1.0 eq) in 1,4-dioxane (200 ml) at 0° C. was added saturated sodium bicarbonate solution (100 ml) and di-tert-butyldicarbonate (14.41 ml, 62.734 mmol, 1.5 eq). The reaction mixture was stirred at room temperature for overnight. TLC indicated starting material was consumed and the desired product was observed. The reaction mixture was evaporated under reduced pressure, diluted with water and extracted with DCM (2×200 ml). The combined organic layer was dried over Na$_2$SO$_4$, filtered and concentrated under reduced pressure. The residue was purified by silica gel column chromatography using 10% Ethyl acetate in hexane as an eluent to obtain the title compound (9 g, 44.57% yield over two steps) as an off-white solid. $^1$H NMR (300 MHz, CDCl$_3$): δ ppm 3.23-3.16 (m, 1H), 2.54-2.51 (m, 1H), 2.42-2.25 (m, 2H), 2.0-1.80 (m, 2H), 1.73-0.67 (m, 20H), 1.42 (s, 9H), 1.01 (s, 3H), 0.97 (s, 6H), 0.91 (s, 3H), 0.85 (s, 3H), 0.77 (s, 3H), 0.40-0.25 (m, 4H); ES-MS: m/z 564.17 (M+Na)$^+$.

Step 8: Synthesis of 1-benzyl 3-((1R,3aS,5aR,5bR, 7aR,9S,11aR,11bR,13aR,13bR)-3a-((tert-butoxycarbonyl)amino)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate

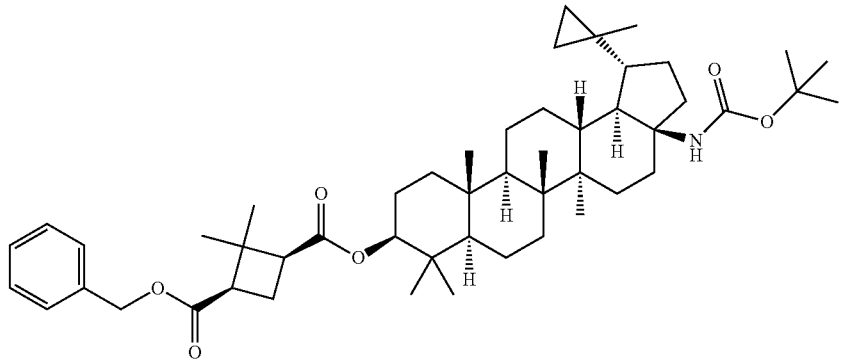

To a stirred solution of tert-butyl ((1R,3aS,5aR,5bR,7aR, 9S,11aR,11bR,13aR,13bR)-9-hydroxy-5a,5b,8,8,11a-pentamethyl-1-(1-methylcyclopropyl)icosahydro-3aH-cyclopenta[a]chrysen-3a-yl)carbamate (step 7, 9 g, 16.609 mmol, 1.0 eq) in Dichloromethane (90 ml) was added (1S,3R)-3-((benzyloxy)carbonyl)-2,2-dimethylcyclobutane-1-carboxylic acid (prepared according to the procedure described in WO2011/007230A2, 8.71 g, 33.21 mmol, 2.0 eq), 1-(3-Dimethylaminopropyl)-3-ethylcarbodiimide Hydrochloride (EDC.HCl) (9.55 g, 49.82 mmol, 3.0 eq) and 4-(Dimethylamino)pyridine (0.81 g, 6.643 mmol, 0.4 eq). The reaction mixture was stirred at room temperature for overnight. TLC indicated starting material was consumed and the desired product was observed. The reaction mixture was diluted with water (100 ml) and extracted with dichloromethane (2×100 ml). The combined organic layer was dried over Na$_2$SO$_4$, filtered and concentrated under reduced pressure. The crude compound was purified by silica gel column chromatography using 10% ethyl acetate:hexane as an eluent to obtain the title compound (11 g, 84.29% yield) as an off-white solid. $^1$H NMR (300 MHz, CDCl$_3$): δ ppm 7.34 (m, 5H), 5.15, 5.09 (ABq, J$_{AB}$=12.3 Hz, 2H), 4.44 (dd, J=11.1, 4.5 Hz, 1H), 4.17 (s, 1H), 2.84-2.73 (m, 2H), 2.69-2.58 (m, 1H), 2.57-2.51 (m, 1H), 2.42-2.23 (m, 2H), 2.07-1.81 (m, 3H), 1.72-0.76 (m, 20H), 1.42 (s, 9H), 1.34 (s, 3H), 1.0 (s, 3H), 0.96 (s, 6H), 0.91 (s, 3H), 0.89 (s, 3H), 0.87 (s, 3H), 0.85 (s, 3H), 0.40-0.25 (m, 4H); ES-MS: m/z 786.47 (M+H)$^+$.

Step 9: Synthesis of 1-((1R,3aR,5aR,5bR,7aR,9S,11aR,11bR,13aR,13bR)-3a-amino-5a,5b,8,8,11a-pentamethyl-1-(1-methylcyclopropyl)icosahydro-1H-cyclopenta[a]chrysen-9-yl) 3-benzyl (1S,3R)-2,2-dimethylcyclobutane-1,3-dicarboxylate

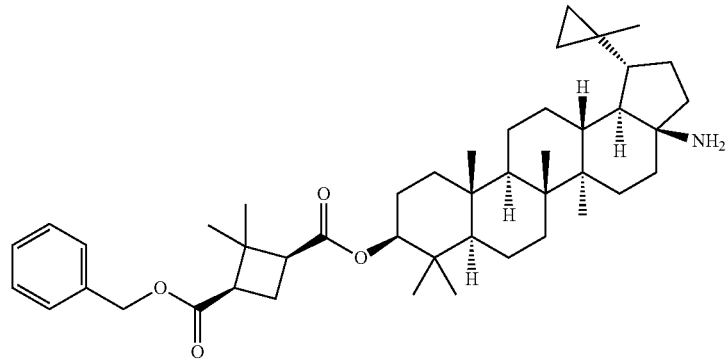

To a stirred solution of 1-benzyl 3-((1R,3aS,5aR,5bR,7aR,9S,11aR,11bR,13aR,13bR)-3a-((tert-butoxycarbonyl)amino)-5a,5b,8,8,11a-pentamethyl-1-(1-methylcyclopropyl) icosahydro-1H-cyclopenta[a]chrysen-9-yl) (1R,3S)-2,2-dimethylcyclobutane-1,3-dicarboxylate (step 8, 11 g, 13.99 mmol, 1.0 eq) in 1,4-dioxane (11 ml) at 0° C. was added 4N HCl in 1,4-dioxane (33 ml). The reaction mixture was stirred at room temperature for overnight. TLC indicated starting material was consumed and the desired product was observed. The reaction mixture was evaporated under reduced pressure, residue was basified with saturated sodium bicarbonate solution and extracted with dichloromethane (3×100 ml). The combined organic layer was washed with water, dried over Na$_2$SO$_4$, filtered and evaporated under reduced pressure to obtain the title compound (9 g, 93.84% yield) as an off-white solid. $^1$H NMR (300 MHz, CDCl$_3$): δ ppm 7.34 (m, 5H), 5.15, 5.09 (ABq, J$_{AB}$=12.3 Hz, 2H), 4.45 (m, 1H), 2.81-2.73 (m, 2H), 2.65-2.62 (m, 1H), 2.08-1.88 (m, 3H), 1.74-0.78 (m, 23H), 1.34 (s, 3H), 1.03 (s, 3H), 0.96 (s, 6H), 0.91 (s, 3H), 0.87 (s, 3H), 0.85 (s, 3H), 0.84 (s, 3H), 0.37-0.22 (m, 4H); ES-MS: m/z 686.45 (M+H)$^+$.

Intermediate 2: Preparation of tert-butyl (2-methyl-1-oxopropan-2-yl)carbamate

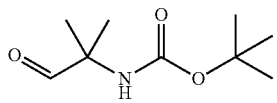

Step 1: Synthesis of tert-butyl (1-hydroxy-2-methylpropan-2-yl)carbamate

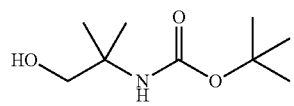

To a stirred solution of 2-amino-2-methylpropan-1-ol (10 g, 112.17 mmol, 1.0 eq) in dichloromethane (120 ml) and methanol (100 ml) was added triethylamine (1.57 ml, 11.217 mmol, 0.1 eq) and di-tert-butyl dicarbonate (30.92 ml, 134.60 mmol, 1.2 eq). The reaction mixture was stirred at room temperature for overnight. TLC indicated starting material was consumed and the desired product was observed. The reaction mixture was evaporated under reduced pressure, water (100 ml) was added and the compound was extracted with DCM (2×50 ml). The organic layer was separated, dried over sodium sulfate, filtered and concentrated under reduced pressure. The residue was triturated with n-hexane, solid was filtered and dried under vacuum to obtain the title compound (14.0 g, 66% yield) as an off-white solid. $^1$H NMR (300 MHz, CDCl$_3$): δ ppm 4.66 (s, 1H), 4.04 (s, 1H), 3.58 (d, J=6.3 Hz, 2H), 1.43 (s, 9H), 1.25 (s, 6H); ES-MS: m/z 189.80 (M+H)$^+$.

Step 2: Synthesis of tert-butyl (2-methyl-1-oxopropan-2-yl)carbamate

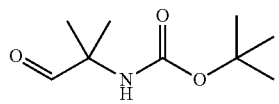

To a stirred solution of tert-butyl (1-hydroxy-2-methylpropan-2-yl)carbamate (step 1, 4 g, 21.134 mmol, 1.0 eq) in dichloromethane (50 ml) was added TEMPO (0.098 g, 0.634 mmol, 0.03 eq), KBr (0.251 g, 2.1134 mmol, 0.1 eq), sodium bicarbonate (10.82 g, 128.91 mmol, 6.1 eq), 10% NaOCl (26 ml) and followed by water (1.05 ml). The reaction mixture was stirred at room temperature for about 30 minutes. TLC indicated starting material was consumed and the desired product was observed. The reaction mixture was diluted with dichloromethane (2×50 ml) and washed with water (50 ml). The organic layer was dried over sodium sulfate, filtered and concentrated under reduced pressure to obtain the title compound (7.0 g) as a colorless liquid. The obtained compound was used as such for next step without further purification; $^1$H NMR (300 MHz, CDCl$_3$): δ ppm 9.43 (s, 1H), 4.98 (s, 1H), 1.44 (s, 9H), 1.33 (s, 6H); ES-MS: m/z 187.78 (M+H)$^+$.

Intermediate 3: Preparation of (S)-4-(1-chloropropan-2-yl)thiomorpholine 1,1-dioxide

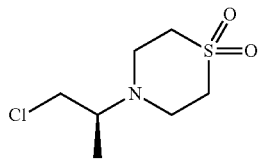

Step 1: Synthesis of (S)-4-(1-hydroxypropan-2-yl)thiomorpholine 1,1-dioxide

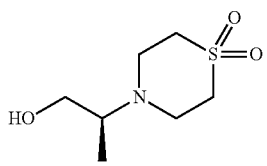

To a stirred solution of (S)-2-aminopropan-1-ol (1.0 g, 13.31 mmol, 1.0 eq) in 1,4-dioxane (5 ml) and ethanol (5 ml) were added divinyl sulfone (2.67 ml, 26.62 mmol, 2.0 eq) and triethylamine (5.61 ml, 39.93 mmol, 3.0 eq). The reaction mixture was heated to 85° C. for about 3 hours. TLC indicated starting material was consumed and the desired product was observed. The reaction mixture was evaporated under reduced pressure and the crude compound was purified by silica gel column chromatography using 5% methanol in DCM as an eluent to obtain the title compound (2.0 g, 80% yield) as an off-white solid. $^1$H NMR (300 MHz, CDCl$_3$): δ ppm 3.51-3.34 (m, 2H), 3.22-3.16 (m, 2H), 3.13-3.06 (m, 4H), 3.03-2.90 (m, 3H), 2.60 (s, 1H), 0.97 (d, J=6.9 Hz, 3H); ES-MS: m/z 193.97 (M+H)$^+$.

Step 2: Synthesis of (S)-4-(1-chloropropan-2-yl)thiomorpholine 1,1-dioxide

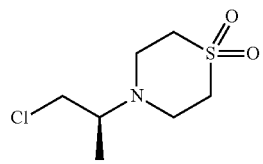

To a stirred solution of (S)-4-(1-hydroxypropan-2-yl) thiomorpholine 1,1-dioxide (step 1, 1.3 g, 6.72 mmol, 1.0 eq) in 1,2-dichloroethane (13 ml) was added thionyl chloride (1.47 ml, 20.18 mmol, 3.0 eq). The reaction mixture was heated to reflux for about 3 hours. TLC indicated starting material was consumed and the desired product was observed. The reaction mixture was evaporated under reduced pressure, diluted with dichloromethane (20 ml), washed with saturated sodium bicarbonate solution and water. The organic layer was dried over Na$_2$SO$_4$, filtered and concentrated under reduced pressure. The residue was purified by silica gel column chromatography using 3% methanol in dichloromethane as an eluent to obtain the title compound (0.925 g, 64.91% yield) as a colourless liquid. $^1$H NMR (300 MHz, CDCl$_3$): δ ppm 4.06-3.99 (m, 1H), 3.12-3.05 (m, 8H), 2.84-2.77 (m, 1H), 2.72-2.66 (m, 1H), 1.51 (d, J=6.6 Hz, 3H); ES-MS: m/z 212.34 (M+H)$^+$.

Intermediate 4: Preparation of (R)-4-(1-hydroxy-3-methylbutan-2-yl)thiomorpholine 1,1-dioxide

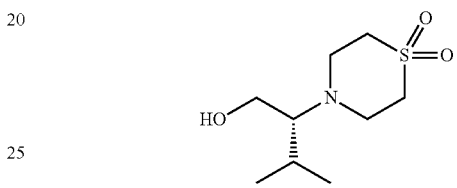

To a stirred solution of (R)-2-amino-3-methylbutan-1-ol (3 g, 29.069 mmol, 1.0 eq) in ethanol (10 ml) and 1,4-dioxane (10 ml) was added triethylamine (12.25 ml, 87.207 mmol, 3.0 eq) followed by divinyl sulfone (6.869 g, 58.139 mmol, 2.0 eq). The reaction mixture was refluxed for about 3 hours. TLC indicated starting material was consumed and the desired product was observed. The reaction mixture was evaporated under reduced pressure. The crude compound was purified by silica gel column chromatography using 2% methanol in dichloromethane as an eluent to obtain the title compound (3.6 g, 55.9% yield) as an off-white solid. $^1$H NMR (300 MHz, CDCl$_3$): δ ppm 3.69 (m, 1H), 3.46-3.39 (m, 1H), 3.32-3.14 (m, 4H), 3.05-3.03 (m, 4H), 2.45-2.38 (m, 1H), 1.85-1.73 (m, 1H), 1.02 (d, J=6.6 Hz, 3H), 0.89 (d, J=6.6 Hz, 3H).

Intermediate 5: Preparation of methyl (R)-2-(1,1-dioxidothiomorpholino)-3-hydroxy propanoate

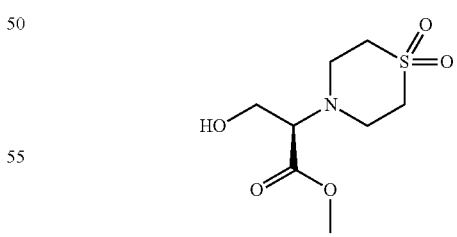

To a stirred solution of methyl D-serinate hydrochloride (4.0 g, 25.70 mmol, 1.0 eq) in 1,4-dioxane (20 ml) and ethanol (20 ml) were added triethylamine (14.34 ml, 102.8 mmol, 4.0 eq) followed by divinyl sulfone (5.15 ml, 51.4 mmol, 2.0 eq). The reaction mixture was heated to 85° C. for 3 hours. TLC indicated starting material was completed and the desired product was observed. The reaction mixture was cooled to room temperature and concentrated under reduced pressure. The crude compound was purified by silica gel column chromatography using 5-10% methanol in dichloromethane gradient to obtain the title compound (5.8 g, 95% yield) as a white solid. $^1$H NMR (300 MHz, CDCl$_3$): δ ppm 3.90-3.84 (m, 1H), 3.81-3.73 (m, 1H), 3.76 (s, 3H), 3.54 (dd, J=8.1, 6.0 Hz, 1H), 3.40-3.30 (m, 2H), 3.17-3.13 (m, 1H), 3.09-3.06 (m, 5H), 2.48 (s, 1H).

Intermediate 6: Preparation of (R)-4-(1-((tert-butyldimethylsilyl)oxy)-3-hydroxypropan-2-yl)thiomorpholine 1,1-dioxide

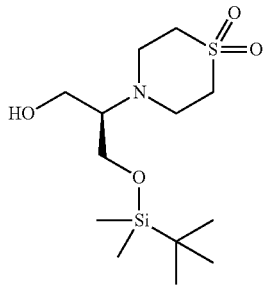 [SMILES: CC(C)(C)[Si](C)(C)OC[C@@H](CO)N1CCS(=O)(=O)CC1]

Step 1: Synthesis of methyl (5)-2-(1,1-dioxidothiomorpholino)-3-hydroxypropanoate

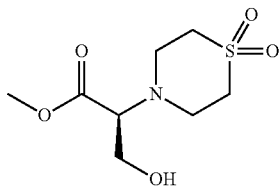

To a stirred solution of methyl L-serinate hydrochloride (4 g, 25.707 mmol, 1.0 eq) in 1,4-dioxane (40 ml) and ethanol (40 ml) was added triethylamine (14.3 ml, 102.828 mmol, 4.0 eq) and divinyl sulfone (6 g, 51.414 mmol, 2.0 eq). The reaction mixture was stirred at 85° C. for about 3 hours. TLC indicated starting material was completed and the desired product was observed. The reaction mixture was concentrated under reduced pressure. The crude compound was purified by silica gel column chromatography using 40-80% ethyl acetate in hexanes gradient to obtain the title compound (5 g, 81.96% yield) as an off-white solid. $^1$H NMR (300 MHz, CDCl$_3$): δ ppm 3.91-3.83 (m, 1H), 3.81-3.73 (m, 1H), 3.76 (s, 3H), 3.54 (dd, J=8.1, 6.0 Hz, 1H), 3.40-3.31 (m, 2H), 3.19-3.02 (m, 6H), 2.42 (s, 1H); ES-MS: m/z 238.04 (M+H)$^+$.

Step 2: Synthesis of methyl (5)-3-((tert-butyldimethylsilyl)oxy)-2-(1,1-dioxidothiomorpholino) propanoate

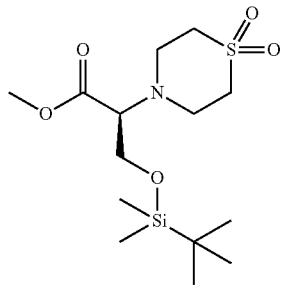 [SMILES: COC(=O)[C@H](CO[Si](C)(C)C(C)(C)C)N1CCS(=O)(=O)CC1]

To a stirred solution of methyl (S)-2-(1,1-dioxidothiomorpholino)-3-hydroxy propanoate (step 1, 2.5 g, 10.536 mmol, 1.0 eq) in DCM (37.5 ml) at 0° C. was added triethylamine (4.4 ml, 31.609 mmol, 3.0 eq), 4-(Dimethylamino)pyridine (0.064 g, 0.525 mmol, 0.05 eq) followed by tert-Butyldimethylsilyl chloride (2.5 g, 16.858 mmol, 1.6 eq). The reaction mixture was stirred at room temperature for overnight. The reaction mixture was diluted with water and aqueous layer was separated. The organic layer was washed with saturated ammonium chloride solution, 5% sodium bicarbonate solution, water and brine solution. The organic layer was dried over sodium sulfate, filtered and concentrated under reduced pressure. The residue was purified by silica gel column chromatography using 0-40% ethyl acetate in hexanes gradient to obtain the title compound (3 g, 81% yield) as an off-white solid. $^1$H NMR (300 MHz, CDCl$_3$): δ ppm 3.93-3.90 (m, 2H), 3.72 (s, 3H), 3.53-3.49 (m, 1H), 3.29-3.24 (m, 4H), 3.08-3.02 (m, 4H), 0.87 (s, 9H), 0.05 (s, 6H).

Step 3: Synthesis of (R)-4-(1-((tert-butyldimethylsilyl)oxy)-3-hydroxypropan-2-yl) thiomorpholine 1,1-dioxide

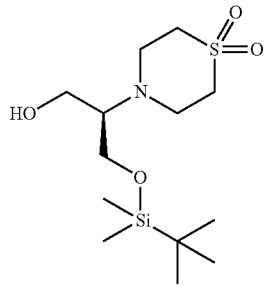 [SMILES: CC(C)(C)[Si](C)(C)OC[C@@H](CO)N1CCS(=O)(=O)CC1]

To a stirred solution of methyl (S)-3-((tert-butyldimethylsilyl)oxy)-2-(1,1-dioxidothiomorpholino)propanoate (step 2, 3.5 g, 9.956 mmol, 1.0 eq) in methanol (70 ml) at 0° C. was added sodium borohydride (7.53 g, 199.129 mmol, 20 eq) portion wise. The reaction mixture was stirred at room temperature for about 2 hours. TLC indicated starting material was consumed and the desired product was observed. The reaction mixture was neutralized with 1N HCl, organic phase was evaporated under reduced pressure and aqueous layer was extracted with ethyl acetate (2×100 ml). The combined organic layer was washed with water (100 ml), brine solution (100 ml), dried over sodium sulfate, filtered and concentrated under reduced pressure. The crude compound was purified by silica gel column chromatography using 0-10% methanol in dichloromethane gradient to obtain the title compound (3 g, 93.7% yield) as an off-white solid. $^1$H NMR (300 MHz, CDCl$_3$): δ ppm 3.73-3.68 (m, 1H), 3.67-3.57 (m, 1H), 3.56-3.47 (m, 1H), 3.46-3.33 (m, 2H), 3.18-3.01 (m, 7H), 2.99-2.89 (m, 1H), 0.89 (s, 9H), 0.06 (s, 6H); ES-MS: m/z 323.64 (M+H)$^+$.

Intermediate 7: Preparation of (S)-4-(1-hydroxy-3-methylbutan-2-yl)thiomorpholine 1,1-dioxide

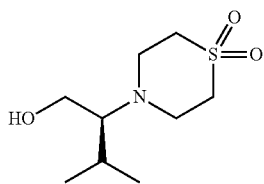

To a stirred solution of (S)-2-amino-3-methylbutan-1-ol (2.0 g, 19.398 mmol, 1.0 eq) in ethanol (10 ml) and 1,4-dioxane (10 ml) were added divinyl sulfone (3.89 ml, 38.797 mmol, 2.0 eq) and triethylamine (8.178 ml, 58.19 mmol, 3.0 eq). The reaction mixture was heated to reflux for about 5 hours. TLC indicated starting material was consumed and the desired product was observed. The reaction mixture was evaporated under reduced pressure. The residue was purified by silica gel column chromatography using 2% methanol in DCM as an eluent to obtain the title compound (4.0 g, 95.2% yield) as an off-white solid. $^1$H NMR (300 MHz, CDCl$_3$): δ ppm 3.74-3.68 (m, 1H), 3.45-3.38 (m, 1H), 3.32-3.14 (m, 4H), 3.05-3.02 (m, 4H), 2.47-2.36 (m, 2H), 1.83-1.75 (m, 1H), 1.02 (d, J=6.6 Hz, 3H), 0.89 (d, J=6.6 Hz, 3H); ES-MS: m/z 221.85 (M+H)$^+$.

Intermediate 8: Preparation of 4-((2R,3R)-3-((tert-butyldimethylsilyl)oxy)-1-hydroxybutan-2-yl)thiomorpholine 1,1-dioxide

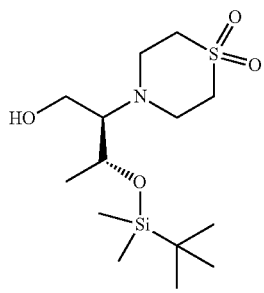 [SMILES: C[C@@H](O[Si](C)(C)C(C)(C)C)[C@@H](CO)N1CCS(=O)(=O)CC1]

Step 1: Synthesis of methyl L-threoninate

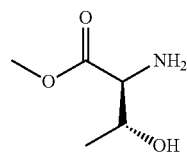

To a stirred solution of L-threonine (10 g, 83.94 mmol, 1.0 eq) in methanol (100 ml) at 0° C. was added thionyl chloride (18.38 ml, 251.84 mmol, 3.0 eq). The reaction mixture was heated to reflux for about 3 hours. TLC indicated starting material was completed and the desired product was observed. The reaction mixture was evaporated under reduced pressure, ethyl acetate (100 ml) and triethylamine (35.39 ml, 251.84 mmol, 3.0 eq) were added to the reaction mixture, precipitate was formed. The precipitates formed were collected by filtration and the filtrate was evaporated under reduced pressure to obtain the title compound (8 g) as oil. The obtained compound was used as such for next step without further purification. $^1$H NMR (300 MHz, DMSO-d6): δ ppm 4.62 (s, 1H), 3.85-3.82 (m, 1H), 3.61 (s, 3H), 3.16 (d, J=3.9 Hz, 1H), 1.08 (d, J=6.3 Hz, 3H); ES-MS: m/z 134.07 (M+H)$^+$.

Step 2: Synthesis of methyl (2S,3R)-2-(1,1-dioxido-thiomorpholino)-3-hydroxybutanoate

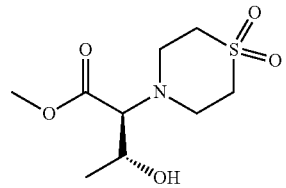 [SMILES: COC(=O)[C@H]([C@@H](C)O)N1CCS(=O)(=O)CC1]

To a stirred solution of methyl L-threoninate (step 1, 2.5 g, 18.77 mmol, 1.0 eq) in ethanol (25 ml) and 1,4-dioxane (25 ml) was added triethylamine (7.91 ml, 56.31 mmol, 3.0 eq) and divinyl sulfone (5.61 ml, 37.55 mmol, 2.0 eq). The reaction mixture was heated to reflux for about 3 hours. TLC indicated starting material was consumed and the desired product was observed. The reaction mixture was evaporated under reduced pressure. The residue was purified by silica gel column chromatography using 2% methanol in DCM as an eluent to obtain the title compound (4 g, 85.1% yield) as a solid. $^1$H NMR (300 MHz, CDCl$_3$): δ ppm 4.13-3.96 (m, 1H), 3.76 (s, 3H), 3.42-2.90 (m, 9H), 1.21 (d, J=6.0 Hz, 3H); ES-MS: m/z 252.26 (M+H)$^+$.

Step 3: Synthesis of methyl (2S,3R)-3-((tert-butyldimethylsilyl)oxy)-2-(1,1-dioxido thiomorpholino)butanoate

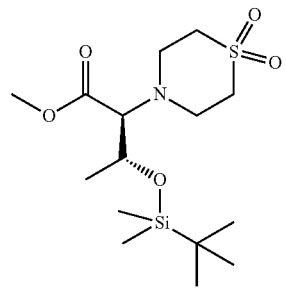 [SMILES: COC(=O)[C@H]([C@@H](C)O[Si](C)(C)C(C)(C)C)N1CCS(=O)(=O)CC1]

To a stirred solution of methyl (2S,3R)-2-(1,1-dioxidothiomorpholino)-3-hydroxybutanoate (step 2, 1.5 g, 5.976 mmol, 1.0 eq) in DCM (15 ml) and DMF (10 ml) was added imidazole (0.813 g, 11.952 mmol, 2.0 eq) and tert-Butyldimethylsilyl chloride (1.35 g, 8.964 mmol, 1.5 eq). The reaction mixture was stirred at room temperature for overnight. TLC indicated starting material was consumed and the desired product was observed. The reaction mixture was diluted with water (20 ml) and extracted with DCM (2×30 ml). The combined organic layer was separated, dried over Na$_2$SO$_4$, filtered and concentrated under reduced pressure. The residue was purified by silica gel column chromatography using 1% methanol in DCM as an eluent to obtain the title compound (0.6 g, 27.52% yield) as an off-white solid. $^1$H NMR (300 MHz, CDCl$_3$): δ ppm 4.39 (m, 1H), 3.73 (s, 3H), 3.64-3.56 (m, 2H), 3.30-3.24 (m, 3H), 3.06-3.03 (m, 4H), 1.26 (d, J=6.3 Hz, 3H), 0.86 (s, 9H), 0.08 (s, 3H), 0.04 (s, 3H); ES-MS: m/z 388.10 (M+Na)$^+$.

Step 4: Synthesis of 4-((2R,3R)-3-((tert-butyldimethylsilyl)oxy)-1-hydroxybutan-2-yl) thiomorpholine 1,1-dioxide

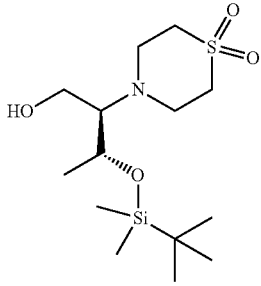 [SMILES: C[C@@H](O[Si](C)(C)C(C)(C)C)[C@@H](CO)N1CCS(=O)(=O)CC1]

To a stirred solution of methyl (2S,3R)-3-((tert-butyldimethylsilyl)oxy)-2-(1,1-dioxidothiomorpholino)butanoate (step 3, 0.6 g, 1.641 mmol, 1.0 eq) in DCM (12 ml) at −78° C. was added DIBAL-H (6.5 ml, 9.847 mmol, 6.0 eq, 1.5M in toluene). The reaction mixture was stirred at same temperature for about 4 hours. TLC indicated starting material was consumed and the desired product was observed. The reaction mixture was quenched with saturated ammonium chloride solution and extracted with ethyl acetate (2×30 ml). The organic layer was washed with water, dried over Na$_2$SO$_4$, filtered and concentrated under reduced pressure. The residue was purified by silica gel column chromatography using 2% methanol in DCM as an eluent to obtain the title compound (0.442 g, 79.92% yield) as an off-white solid. $^1$H NMR (300 MHz, CDCl$_3$): δ ppm 4.11-4.03 (m, 1H), 3.71-3.64 (m, 2H), 3.55-3.39 (m, 4H), 3.19-3.08 (m, 4H), 2.81-2.74 (m, 1H), 2.49 (s, 1H), 1.30 (d, J=6.0 Hz, 3H), 1.0 (s, 9H), 0.20 (s, 6H); ESI-MS: m/z 360.05 (M+Na)$^+$.

Intermediate 9: Preparation of (S)-4-(1-((tert-butyldimethylsilyl)oxy)-3-hydroxypropan-2-yl) thiomorpholine 1,1-dioxide

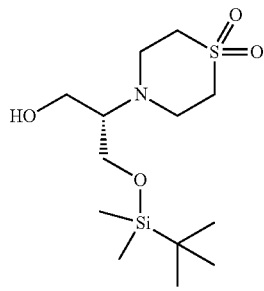 [SMILES: CC(C)(C)[Si](C)(C)OC[C@H](CO)N1CCS(=O)(=O)CC1]

Step 1: Synthesis of methyl (R)-3-((tert-butyldimethylsilyl)oxy)-2-(1,1-dioxidothiomorpholino) propanoate

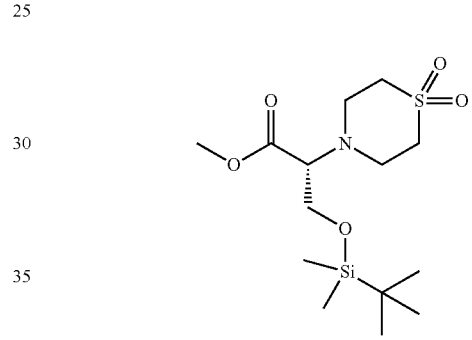

To a stirred solution of methyl (R)-2-(1,1-dioxidothiomorpholino)-3-hydroxy propanoate (Intermediate 5, 4.4 g, 18.54 mmol, 1.0 eq) in DCM (45 ml) at 0° C. was added triethylamine (7.7 ml, 55.63 mmol, 3.0 eq), 4-(Dimethylamino)pyridine (0.113 g, 0.92 mmol, 0.05 eq) and tert-Butyldimethylsilyl chloride (4.4 g, 29.67 mmol, 1.6 eq). The reaction mixture was stirred at room temperature for overnight. TLC indicated starting material was completed and the desired product was observed. The reaction mixture was diluted with DCM (150 ml), washed with water (100 ml) and brine solution (100 ml). The organic layer was dried over sodium sulfate, filtered and evaporated under reduced pressure. The crude compound was purified by silica gel column chromatography using 0-40% ethyl acetate in hexanes gradient to obtain the title compound (5 g, 77% yield) as an off-white solid. $^1$H NMR (300 MHz, CDCl$_3$): δ ppm 3.93-3.90 (m, 2H), 3.72 (s, 3H), 3.51 (t, J=5.7 Hz, 1H), 3.26-3.24 (m, 4H), 3.06-3.02 (m, 4H), 0.87 (s, 9H), 0.05 (s, 6H); ES-MS: m/z 352.55 (M+H)$^+$.

Step 2: Synthesis of (S)-4-(1-((tert-butyldimethylsi-lyl)oxy)-3-hydroxypropan-2-yl) thiomorpholine 1,1-dioxide

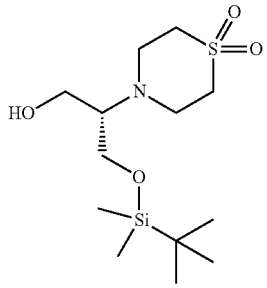 [SMILES: CC(C)(C)[Si](C)(C)OC[C@H](CO)N1CCS(=O)(=O)CC1]

To a stirred solution of methyl (R)-3-((tert-butyldimethylsilyl)oxy)-2-(1,1-dioxido thiomorpholino)propanoate (step 1, 5 g, 14.223 mmol, 1.0 eq) in Methanol (100 ml) at 0° C. was added sodium borohydride (10.76 g, 284.47 mmol, 20.0 eq) portion wise. The reaction mixture was stirred at room temperature for about 2 hours. TLC indicated starting material was consumed and the desired product was observed. The reaction mixture was cooled to 0° C., neutralized with 1N HCl and the organic phase was evaporated under reduced pressure. The aqueous layer was extracted with ethyl acetate (2×150 ml). The combined organic layer was washed with water (150 ml) and brine solution (150 ml). The organic layer was dried over sodium sulfate, filtered and concentrated under reduced pressure. The crude compound was purified by silica gel column chromatography using 0-10% methanol in dichloromethane gradient to obtain the title compound (4 g, 87% yield) as an off-white solid. $^1$H NMR (300 MHz, CDCl$_3$): δ ppm 3.75-3.62 (m, 1H), 3.61-3.55 (m, 1H), 3.54-3.46 (m, 1H), 3.42-3.33 (m, 2H), 3.17-3.10 (m, 2H), 3.10-3.02 (m, 5H), 3.0-2.90 (m, 1H), 2.50 (s, 1H), 0.90 (s, 9H), 0.06 (s, 6H); ES-MS: m/z 324.56 (M+H)$^+$.

Intermediate 10: Preparation of (S)-4-(1-fluoro-3-hydroxypropan-2-yl)thiomorpholine 1,1-dioxide

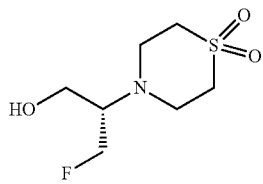 [SMILES: O=S1(=O)CCN([C@@H](CO)CF)CC1]

Step 1: Synthesis of (S)-4-(1-((tert-butyldimethylsi-lyl)oxy)-3-fluoropropan-2-yl) thiomorpholine 1,1-dioxide

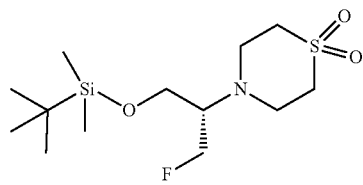 [SMILES: CC(C)(C)[Si](C)(C)OC[C@@H](CF)N1CCS(=O)(=O)CC1]

To a stirred solution of (R)-4-(1-((tert-butyldimethylsilyl)oxy)-3-hydroxypropan-2-yl)thiomorpholine 1,1-dioxide (Intermediate 6, 7.5 g, 23.291 mmol, 1.0 eq) in DCM (150 ml) at 0° C. was added DAST (3 ml, 23.291 mmol, 1.0 eq). The reaction mixture was stirred at room temperature for about 1 hour. TLC indicated starting material was consumed and the desired product was observed. The reaction mixture was quenched with saturated sodium carbonate solution and extracted with DCM. The organic layer was washed with water, dried over sodium sulfate, filtered and concentrated under reduced pressure. The residue was purified by silica gel column chromatography using 0-20% ethyl acetate in hexanes gradient to obtain the title compound (1.8 g, 23.8% yield) as a colourless liquid. $^1$H NMR (300 MHz, CDCl$_3$): δ ppm 4.67-4.64 (m, 1H), 4.51-4.49 (m, 1H), 3.79-3.71 (m, 2H), 3.25-3.22 (m, 3H), 3.14-2.87 (m, 6H), 0.90 (s, 9H), 0.07 (s, 6H); ES-MS: m/z 326.46 (M+H)$^+$.

Step 2: Synthesis of (S)-4-(1-fluoro-3-hydroxypropan-2-yl)thiomorpholine 1,1-dioxide

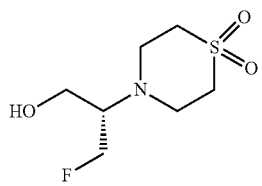

To a stirred solution of (S)-4-(1-((tert-butyldimethylsilyl)oxy)-3-fluoropropan-2-yl)thiomorpholine 1,1-dioxide (step 1, 1.8 g, 5.538 mmol, 1.0 eq) in THF (36 ml) at 0° C. was added 1.0M TBAF in THF (6.64 ml, 6.646 mmol, 1.2 eq). The reaction mixture was stirred at room temperature for about 4 hours. TLC indicated starting material was consumed and the desired product was observed. The reaction mixture was diluted with DCM, washed with saturated sodium bicarbonate solution and water. The organic layer was dried over sodium sulfate, filtered and concentrated under reduced pressure. The crude compound was purified by silica gel column chromatography using 0-4% methanol in dichloromethane gradient to obtain the title compound (0.950 g, 81.9% yield) as a colour less liquid. $^1$H NMR (300 MHz, CDCl$_3$): δ ppm 4.65-4.63 (m, 1H), 4.49-4.47 (m, 1H), 3.66-3.64 (m, 2H), 3.39-3.30 (m, 2H), 3.21-3.12 (m, 3H), 3.11-3.05 (m, 4H), 2.20 (s, 1H); ES-MS: m/z 212.34 (M+H)$^+$.

Intermediate 11: Preparation of (R)-4-(1-fluoro-3-hydroxypropan-2-yl)thiomorpholine 1,1-dioxide

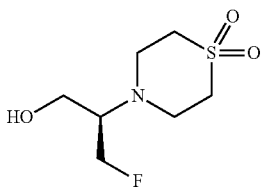 [SMILES: O=S1(=O)CCN([C@H](CO)CF)CC1]

Step 1: Synthesis of (R)-4-(1-((tert-butyldimethylsilyl)oxy)-3-fluoropropan-2-yl) thiomorpholine 1,1-dioxide

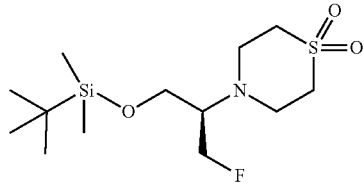 [SMILES: CC(C)(C)[Si](C)(C)OC[C@H](CF)N1CCS(=O)(=O)CC1]

To a stirred solution of (S)-4-(1-((tert-butyldimethylsilyl)oxy)-3-hydroxypropan-2-yl)thiomorpholine 1,1-dioxide (Intermediate 9, 6 g, 18.633 mmol, 1.0 eq) in DCM (120 ml) at 0° C. was added DAST (1.83 ml, 18.633 mmol, 1.0 eq). The reaction mixture was stirred at 0° C. for about 1 hour, changed to room temperature and stirred for about 1 hour. TLC indicated starting material was consumed and the desired product was observed. The reaction mixture was cooled to 0° C., quenched with saturated sodium carbonate solution and extracted with DCM (100 ml). The organic layer was washed with water, brine solution (100 ml), dried over sodium sulfate, filtered and concentrated under reduced pressure. The crude compound was purified by silica gel column chromatography using 0-20% ethyl acetate in hexanes gradient to obtain the title compound (1.3 g, 21.5% yield) as a colourless liquid. $^1$H NMR (300 MHz, CDCl$_3$): δ ppm 4.67-4.64 (m, 1H), 4.51-4.49 (m, 1H), 3.75 (dd, J=6.0, 1.2 Hz, 2H), 3.25-3.22 (m, 4H), 3.04-2.90 (m, 5H), 0.89 (s, 9H), 0.06 (s, 6H); ES-MS: m/z 326.53 (M+H)$^+$.

Step 2: Synthesis of (R)-4-(1-fluoro-3-hydroxypropan-2-yl)thiomorpholine 1,1-dioxide

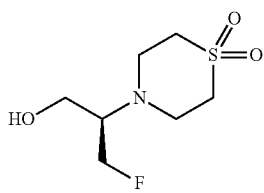 [SMILES: O=S1(=O)CCN([C@H](CO)CF)CC1]

To a stirred solution of (R)-4-(1-((tert-butyldimethylsilyl)oxy)-3-fluoropropan-2-yl)thiomorpholine 1,1-dioxide (step 1, 1.3 g, 4.0 mmol, 1.0 eq) in THF (26 ml) at 0° C. was added TBAF (4.8 ml, 4.80 mmol, 1.2 eq, 1.0M in THF). The reaction mixture was stirred at room temperature for about 4 hours. TLC indicated starting material was consumed and the desired product was observed. The reaction mixture was diluted with DCM (100 ml), washed with saturated sodium bicarbonate solution and water. The organic layer was separated, dried over sodium sulfate, filtered and concentrated under reduced pressure. The crude compound was purified by silica gel column chromatography using 0-3% methanol in dichloromethane gradient to obtain the title compound (0.650 g. 77% yield) as a colourless liquid. $^1$H NMR (300 MHz, CDCl$_3$): δ ppm 4.65-4.63 (m, 1H), 4.49-4.47 (m, 1H), 3.66-3.64 (m, 2H), 3.39-3.30 (m, 2H), 3.22-3.12 (m, 3H), 3.11-3.03 (m, 4H), 2.19 (s, 1H); ES-MS: m/z 212.34 (M+H)$^+$.

Intermediate 12: Preparation of (S)-2-(4-(isopropylsulfonyl)piperazin-1-yl)propan-1-ol

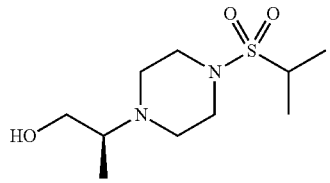 [SMILES: CC(C)S(=O)(=O)N1CCN([C@@H](C)CO)CC1]

Step 1: Synthesis of tert-butyl 4-(isopropylsulfonyl)piperazine-1-carboxylate

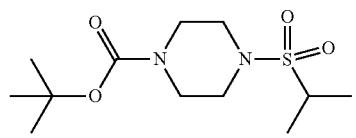 [SMILES: CC(C)S(=O)(=O)N1CCN(C(=O)OC(C)(C)C)CC1]

A mixture of tert-butyl piperazine-1-carboxylate (5 g, 26.84 mmol, 1.0 eq) and DCM (100 ml) was cooled to −25° C., triethylamine (3.25 g, 32.21 mmol, 1.2 eq) followed by Isopropylsulfonyl chloride (4.4 g, 30.87 mmol, 1.15 eq) were slowly added drop wise. The reaction mixture was slowly warmed up to room temperature and stirred overnight. TLC indicated starting material was consumed and the desired product was observed. The reaction mixture was cooled to 0° C., neutralized with 1N HCl solution and extracted with DCM (3×400 ml). The combined organic layer was washed with water (100 ml), dried over sodium sulfate, filtered and concentrated under reduced pressure to obtain the title compound (6.9 g, 87.92% yield) as a yellow solid. $^1$H NMR (300 MHz, CDCl$_3$): δ ppm 3.48-3.46 (m, 4H), 3.33-3.30 (m, 4H), 3.23-3.14 (m, 1H), 1.46 (s, 9H), 1.34 (d, J=6.9 Hz, 6H); ES-MS: m/z 315.45 (M+Na)$^+$.

Step 2: Synthesis of 1-(isopropylsulfonyl)piperazine

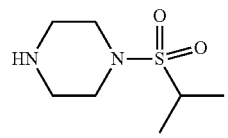

To a stirred solution of tert-butyl 4-(isopropylsulfonyl)piperazine-1-carboxylate (step 1, 6.9 g, 23.60 mmol, 1.0 eq) in 1,4-dioxane (30 ml) at 0° C. was added 4N HCl/1,4-dioxane (30 ml). The reaction mixture was stirred at room temperature for about 3 hours. TLC indicated starting material was consumed and the desired product was observed. The reaction mixture was evaporated under reduced pressure, cooled to 0° C., saturated sodium bicarbonate solution was added and extracted with DCM (3×400 ml). The combined organic layers were washed with water (150 ml), dried over sodium sulfate, filtered and concentrated under reduced pressure. The crude compound was purified by silica gel column chromatography using 0-10% methanol in dichloromethane gradient. The fractions containing the expected product were combined and concentrated under reduced pressure to obtain the title compound (2.8 g, 62.2% yield) as yellow semi solid. $^1$H NMR (300 MHz, CDCl$_3$): δ ppm 3.35-3.32 (m, 4H), 3.23-3.14 (m, 1H), 2.92-2.89 (m, 4H), 1.34 (d, J=6.9 Hz, 6H); ES-MS: m/z 193.42 (M+H)$^+$.

Step 3: Synthesis of methyl (5)-2-(4-(isopropylsulfonyl)piperazin-1-yl)propanoate

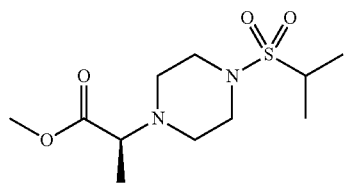 [SMILES: COC(=O)[C@H](C)N1CCN(S(=O)(=O)C(C)C)CC1]

To a stirred solution of methyl (R)-2-hydroxypropanoate (1.461 g, 14.042 mmol, 1.5 eq) in DCM (40 ml) at −78° C. was added trifluoromethanesulfonic anhydride (2.67 ml, 15.915 mmol, 1.7 eq). The reaction mixture was stirred at −78° C. for about 45 minutes, at which time, 2,6-lutidine (1.85 ml, 15.915 mmol, 1.7 eq) was added and stirred at same temperature for about 45 minutes. A solution of 1-(isopropylsulfonyl)piperazine (step 2, 1.8 g, 9.361 mmol, 1.0 eq) in DCM (10 ml) followed by triethylamine (3.9 ml, 28.085 mmol, 3.0 eq) were added to the reaction mixture at −78° C. The reaction mixture was allowed to stir at 0° C. for about 1 hour and stir at room temperature for about 3 hours. TLC indicated starting material was consumed and the desired product was observed. The reaction mixture was cooled to 0° C., quenched with saturated sodium bicarbonate solution and extracted with DCM (3×250 ml). The combined organic layers were washed with water (100 ml), dried over sodium sulfate, filtered and concentrated under reduced pressure to obtain the title compound (1.8 g, 69.2% yield) as a pale yellow oil. $^1$H NMR (300 MHz, CDCl$_3$): δ ppm 3.71 (s, 3H), 3.43-3.31 (m, 5H), 3.23-3.14 (m, 1H), 2.71-2.59 (m, 4H), 1.34 (d, J=6.9 Hz, 6H), 1.30 (d, J=7.2 Hz, 3H); ES-MS: m/z 279.40 (M+H)$^+$.

Step 4: Synthesis of (S)-2-(4-(isopropylsulfonyl)piperazin-1-yl)propan-1-ol

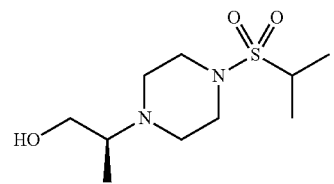 [SMILES: CC(C)S(=O)(=O)N1CCN([C@@H](C)CO)CC1]

To a stirred solution of methyl (S)-2-(4-(isopropylsulfonyl)piperazin-1-yl)propanoate (step 3, 1.8 g, 6.466 mmol, 1.0 eq) in methanol (100 ml) at 0° C. was added sodium borohydride (6.11 g, 161.65 mmol, 25.0 eq) portion wise. The reaction mixture was stirred at room temperature for overnight. TLC indicated starting material was consumed and the desired product was observed. The reaction mixture was cooled to 0° C., pH adjusted to 6.0 with 1N HCl and evaporated under reduced pressure. The reaction mixture was cooled to 0° C., saturated sodium bicarbonate solution was added and extracted with DCM (3×250 ml). The combined organic layers were washed with water (100 ml), dried over sodium sulfate, filtered and concentrated under reduced pressure to obtain the title compound (1.0 g, 61.8% yield) as a liquid. $^1$H NMR (300 MHz, CDCl$_3$): δ ppm 3.55-3.39 (m, 6H), 3.24-3.13 (m, 1H), 3.01-2.90 (m, 1H), 2.87-2.78 (m, 2H), 2.65-2.57 (m, 2H), 1.35 (d, J=6.6 Hz, 6H), 0.99 (d, J=6.9 Hz, 3H); ES-MS: m/z 251.58 (M+H)$^+$.

Intermediate 13: Preparation of 4-((2R,3S)-3-fluoro-1-hydroxybutan-2-yl)thiomorpholine 1,1-dioxide

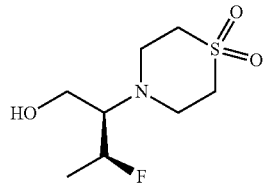

Step 1: Synthesis of methyl (2R,3S)-2-(1,1-dioxidothiomorpholino)-3-fluorobutanoate

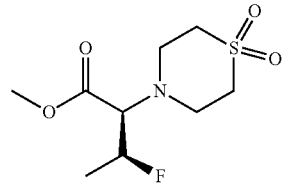

To a stirred solution of methyl (2S,3R)-2-(1,1-dioxidothiomorpholino)-3-hydroxy butanoate (Intermediate 8-step 2, 15 g, 59.76 mmol, 1.0 eq) in DCM (150 ml) at 0° C. was added DAST (8.68 ml, 65.73 mmol, 1.1 eq). The reaction mixture was stirred at same temperature for about 30 minutes and stirred at room temperature for about 1 hour. TLC indicated starting material was consumed and the desired product was observed. The reaction mixture was cooled to 0° C., saturated sodium bicarbonate solution was added and extracted with DCM (2×200 ml). The organic layer was washed with water, dried over sodium sulfate, filtered and concentrated under reduced pressure. The crude compound was purified by silica gel column chromatography using 1% methanol in dichloromethane as an eluent to obtain the title compound (8 g, 52.94% yield) as a liquid. $^1$H NMR (300 MHz, CDCl$_3$): δ ppm 5.22-5.13 (m, 0.5H), 5.06-4.98 (m, 0.5H), 3.77 (s, 3H), 3.44-3.22 (m, 5H), 3.10-2.96 (m, 4H), 1.45 (d, J=6.3 Hz, 1.5H), 1.37 (d, J=6.3 Hz, 1.5H); ES-MS: m/z 254.46 (M+H)$^+$.

Step 2: Synthesis of 4-((2R,3S)-3-fluoro-1-hydroxybutan-2-yl)thiomorpholine 1,1-dioxide

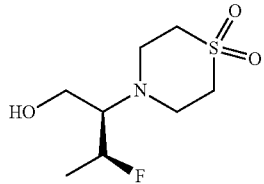

To a stirred suspension of Lithium aluminium hydride (3.59 g, 94.86 mmol, 3.0 eq) in THF (160 ml) at 0° C. was added methyl (2R,3S)-2-(1,1-dioxidothiomorpholino)-3-fluorobutanoate (step 1, 8 g, 31.62 mmol, 1.0 eq). The reaction mixture was stirred at 0° C. for about 1 hour and then stirred at room temperature for about 2 hours. TLC indicated starting material was consumed and the desired product was observed. The reaction mixture was cooled to 0° C., slowly quenched with water (3.59 ml), 10% NaOH solution (3.59 ml) followed by water (10.59 ml) and stirred for about 2 hours. The precipitates formed were filtered and the filtrate was concentrated under reduced pressure. The residue was purified by silica gel column chromatography using 0-2% methanol in dichloromethane gradient to obtain the title compound (1 g, 14.06% yield) as an off-white solid. $^1$H NMR (300 MHz, CDCl$_3$): δ ppm 4.57-4.51 (m, 0.5H), 4.40-4.33 (m, 0.5H), 3.94-3.83 (m, 2H), 3.30-3.22 (m, 3H), 3.18-3.0 (m, 6H), 1.17 (d, J=6.9 Hz, 3H); ES-MS: m/z 226.48 (M+H)$^+$.

Intermediate 14: Preparation of 4-((2S,3S)-3-((tert-butyldimethylsilyl)oxy)-1-hydroxybutan-2-yl)thiomorpholine 1,1-dioxide

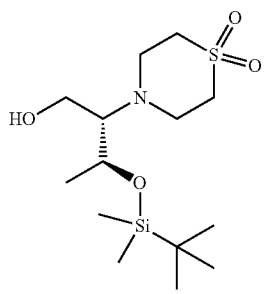 [SMILES: C[C@H](O[Si](C)(C)C(C)(C)C)[C@H](CO)N1CCS(=O)(=O)CC1]

Step 1: Synthesis of methyl (2R,3S)-2-(1,1-dioxido-thiomorpholino)-3-hydroxybutanoate

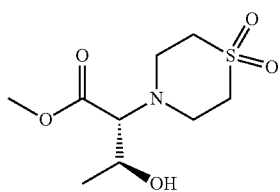 [SMILES: COC(=O)[C@@H]([C@H](C)O)N1CCS(=O)(=O)CC1]

To a stirred solution of D-Threonine methyl ester hydrochloride (13 g, 76.65 mmol, 1.0 eq) in 1,4-dioxane (78 ml) and ethanol (78 ml) was added divinyl sulfone (19.18 ml, 191.62 mmol, 2.5 eq) followed by triethylamine (53.4 ml, 383.25 mmol, 5.0 eq). The reaction mixture was heated to reflux for about 6 hours. TLC indicated starting material was completed and the desired product was observed. The reaction mixture was evaporated under reduced pressure. The crude compound was purified by silica gel column chromatography using 0-6% methanol in dichloromethane gradient to obtain the title compound (10 g, 51.9% yield) as an off-white solid. $^1$H NMR (300 MHz, CDCl$_3$): δ ppm 4.0-3.96 (m, 1H), 3.76 (s, 3H), 3.40-3.33 (m, 2H), 3.18-2.99 (m, 7H), 1.20 (d, J=6.0 Hz, 3H); ES-MS: m/z 252.45 (M+H)$^+$.

Step 2: Synthesis of methyl (2R,3S)-3-((tert-butyldimethylsilyl)oxy)-2-(1,1-dioxido thiomorpholino)butanoate

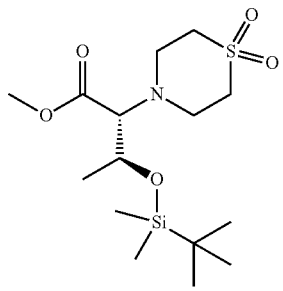 [SMILES: COC(=O)[C@@H]([C@H](C)O[Si](C)(C)C(C)(C)C)N1CCS(=O)(=O)CC1]

To a stirred solution of methyl (2R,3S)-2-(1,1-dioxidothiomorpholino)-3-hydroxybutanoate (step 1, 5.0 g, 19.89 mmol, 1.0 eq) in DCM (40 ml) and DMF (20 ml) at 0° C. was added imidazole (2.7 g, 39.78 mmol, 2.0 eq) and tert-Butyldimethylsilyl chloride (3.29 g, 21.88 mmol, 1.1 eq). The reaction mixture was stirred at room temperature for about 72 hours. TLC indicated starting material was completed and the desired product was observed. The reaction mixture was evaporated under reduced pressure, diluted with water (200 ml) and extracted with ethyl acetate (3×100 ml). The combined organic layer was washed with water (2×200 ml), dried over Na$_2$SO$_4$, filtered and concentrated under reduced pressure. The crude compound was purified by silica gel column chromatography using 0-5% methanol in dichloromethane gradient to obtain the title compound (4.5 g, 61.89% yield) as an off-white solid. $^1$H NMR (300 MHz, CDCl$_3$): δ ppm 4.41-4.37 (m, 1H), 3.69 (s, 3H), 3.62-3.52 (m, 2H), 3.29-3.20 (m, 3H), 3.11-2.99 (m, 4H), 1.22 (d, J=6.3 Hz, 3H), 0.82 (s, 9H), 0.04 (s, 3H), 0.01 (s, 3H); ES-MS: m/z 366.50 (M+H)$^+$.

Step 3: Synthesis of 4-((2S,3S)-3-((tert-butyldimethylsilyl)oxy)-1-hydroxybutan-2-yl) thiomorpholine 1,1-dioxide

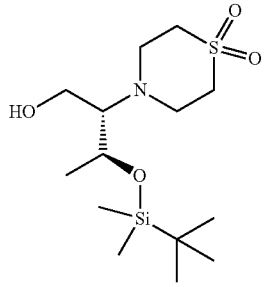 [SMILES: C[C@H](O[Si](C)(C)C(C)(C)C)[C@H](CO)N1CCS(=O)(=O)CC1]

To a stirred solution of methyl (2R,3S)-3-((tert-butyldimethylsilyl)oxy)-2-(1,1-dioxidothiomorpholino)butanoate (step 2, 2.8 g, 7.65 mmol, 1.0 eq) in DCM (56 ml) at −78° C. was slowly added DIBAL-H (15.3 ml, 22.97 mmol, 3.0 eq, 1.5M in toluene). The reaction mixture was stirred at −78° C. for about 30 minutes and allowed to stir at room temperature for about 1 hour. TLC indicated starting material was completed and the desired product was observed. The reaction mixture was quenched with aqueous ammonium chloride solution and extracted with DCM (3×80 ml). The combined organic layer was washed with water (80 ml), dried over sodium sulfate, filtered and concentrated under reduced pressure. The crude compound was purified by silica gel column chromatography using 0-3% methanol in dichloromethane gradient to obtain the title compound (1.8 g, 69.7% yield) as a solid. $^1$H NMR (300 MHz, CDCl$_3$): δ ppm 4.02-3.92 (m, 1H), 3.57-3.48 (m, 2H), 3.44-3.32 (m, 3H), 3.14-3.0 (m, 6H), 2.43 (s, 1H), 1.19 (d, J=6.0 Hz, 3H), 0.88 (s, 9H), 0.1 (s, 6H); ES-MS: m/z 338.57 (M+H)$^+$.

Intermediate 15: Preparation of (2R,3R)-3-((tert-butyldimethylsilyl)oxy)-2-(4-(isopropyl sulfonyl) piperazin-1-yl)butan-1-ol

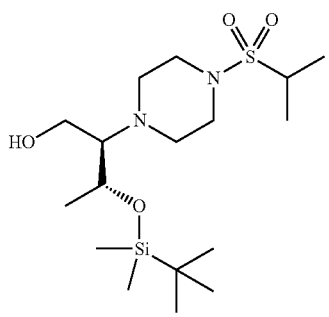 [SMILES: CC(C)S(=O)(=O)N1CCN([C@H](CO)[C@@H](C)O[Si](C)(C)C(C)(C)C)CC1]

Step 1: Synthesis of methyl 0-(tert-butyldimethylsilyl)-L-threoninate

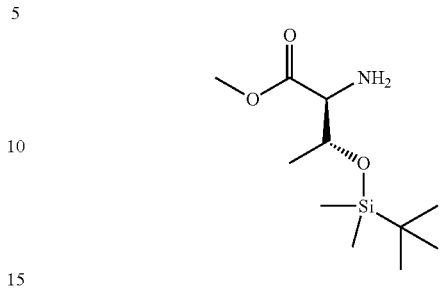

To a stirred solution of methyl L-threoninate hydrochloride (21.5 g, 126.76 mmol, 1.0 q) in DCM (400 ml) at 0° C. was added triethylamine (124.7 ml, 887.32 mmol, 7.0 eq), 4-(Dimethylamino)pyridine (1.54 g, 12.676 mmol, 0.1 eq) and tert-butyldimethylsilyl chloride (38.21 g, 253.53 mmol, 2.0 eq). The reaction mixture was stirred at room temperature for overnight. TLC indicated starting material was consumed and the desired product was observed. The reaction mixture was diluted with water (200 ml) and extracted with DCM (2×200 ml). The organic layer was separated, dried over sodium sulfate, filtered and concentrated under reduced pressure. The crude compound was purified by silica gel column chromatography using 0-1% methanol in dichloromethane gradient to obtain the title compound (20 g, 63.77% yield) as a colourless liquid. $^1$H NMR (300 MHz, CDCl$_3$): δ ppm 4.34-4.27 (m, 1H), 3.72 (s, 3H), 3.29 (d, J=2.7 Hz, 1H), 1.62 (brs, 2H), 1.26 (d, J=6.3 Hz, 3H), 0.86 (s, 9H), 0.04 (s, 6H); ES-MS: m/z 248.37 (M+H)$^+$.

Step 2: Synthesis of methyl (2S,3R)-2-(4-benzylpiperazin-1-yl)-3-((tert-butyldimethylsilyl) oxy) butanoate

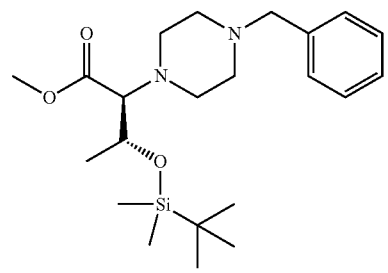 [SMILES: COC(=O)[C@H]([C@@H](C)O[Si](C)(C)C(C)(C)C)N1CCN(Cc2ccccc2)CC1]

To a stirred solution of methyl O-(tert-butyldimethylsilyl)-L-threoninate (step 1, 20 g, 80.83 mmol, 1.0 eq) and N-benzyl-2-chloro-N-(2-chloroethyl)ethan-1-amine hydrochloride (prepared as described in E. J. M. C, 2014, 75, pp: 11-20) (32.56 g, 121.24 mmol, 1.5 eq) in methanol (20 ml) was added N,N-Diisopropylethylamine (100 ml). The reaction mixture was heated at 90-100° C. for overnight. The reaction mixture was evaporated under reduced pressure, diluted with water (200 ml) and extracted with DCM (2×200 ml). The organic layer was separated, dried over sodium sulfate, filtered and concentrated under reduced pressure. The crude compound was purified by silica gel column chromatography using 2% methanol in dichloromethane eluent to obtain the title compound (18 g, 54.86% yield) as a colourless liquid. $^1$H NMR (300 MHz, CDCl$_3$): δ ppm 7.32-7.30 (m, 5H), 4.23-4.14 (m, 1H), 3.67 (s, 3H), 3.49 (s, 2H), 3.07 (d, J=6.6 Hz, 1H), 2.83-2.76 (m, 2H), 2.64-2.58 (m, 2H), 2.45 (m, 4H), 1.19 (d, J=6.3 Hz, 3H), 0.85 (s, 9H), 0.04 (s, 6H); APCI-MS: m/z 407.3 (M+H)⁺.

Step 3: Synthesis of methyl (2S,3R)-3-((tert-butyldimethylsilyl)oxy)-2-(piperazin-1-yl) butanoate

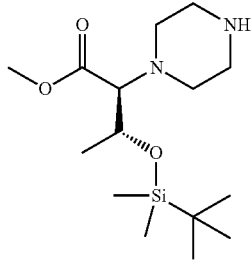 [SMILES: COC(=O)[C@H]([C@@H](C)O[Si](C)(C)C(C)(C)C)N1CCNCC1]

To a stirred suspension of 10% Pd/C (9 g, 50% wet) in methanol (360 ml) was added methyl (2S,3R)-2-(4-benzylpiperazin-1-yl)-3-((tert-butyldimethylsilyl)oxy)butanoate (step 2, 18 g, 44.33 mmol, 1.0 eq) and ammoniumformate (55.90 g, 886.6 mmol, 20 eq). The reaction mixture was stirred at room temperature for overnight. TLC indicated starting material was consumed and the desired product was observed. The reaction mixture was filtered through celite pad and washed with methanol. The filtrate was evaporated under reduced pressure, diluted with DCM, washed with water, dried over sodium sulphate, filtered and evaporated under reduced pressure to obtain the title compound (12 g, 85.7% yield), which was used as such for next step without further purification. ¹H NMR (300 MHz, CDCl₃): δ ppm 4.36-4.30 (m, 1H), 3.71 (s, 3H), 3.37-3.29 (m, 2H), 3.23-3.11 (m, 5H), 3.05-2.97 (m, 2H), 1.21 (d, J=6.3 Hz, 3H), 0.83 (s, 9H), 0.04 (s, 6H); APCI-MS: m/z 317.3 (M+H)⁺.

Step 4: Synthesis of methyl (2S,3R)-3-((tert-butyldimethylsilyl)oxy)-2-(4-(isopropylsulfonyl)piperazin-1-yl)butanoate

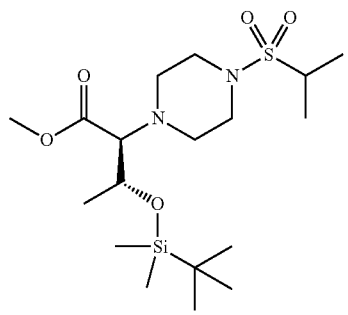 [SMILES: COC(=O)[C@H]([C@@H](C)O[Si](C)(C)C(C)(C)C)N1CCN(S(=O)(=O)C(C)C)CC1]

To a stirred solution of methyl (2S,3R)-3-((tert-butyldimethylsilyl)oxy)-2-(piperazin-1-yl)butanoate (step 3, 12.0 g, 37.97 mmol, 1.0 eq) in DCM (180 ml) at 0° C. was added triethylamine (21.18 ml, 151.88 mmol, 4.0 eq) followed by isopropylsulfonyl chloride (8.12 g, 56.96 mmol, 1.5 eq). The reaction mixture was changed to room temperature and stirred for overnight. TLC indicated starting material was completed and the desired product was observed. The reaction mixture was diluted with water (100 ml) and extracted with DCM (3×100 ml). The combined organic layer was washed with water (100 ml), dried over sodium sulfate, filtered and concentrated under reduced pressure. The crude compound was purified by silica gel column chromatography using 0-3% methanol in dichloromethane gradient to obtain the title compound (8.0 g, 50% yield) as a liquid. ¹H NMR (300 MHz, CDCl₃): δ ppm 4.30-4.26 (m, 1H), 3.69 (s, 3H), 3.34-3.31 (m, 4H), 3.20-3.12 (m, 2H), 3.03-2.96 (m, 2H), 2.77-2.70 (m, 2H), 1.34 (d, J=6.9 Hz, 6H), 1.22 (d, J=6.3 Hz, 3H), 0.85 (s, 9H), 0.05 (s, 3H), 0.02 (s, 3H); ES-MS: m/z 423.1 (M+H)⁺.

Step 5: Synthesis of (2R,3R)-3-((tert-butyldimethylsilyl)oxy)-2-(4-(isopropylsulfonyl) piperazin-1-yl) butan-1-ol

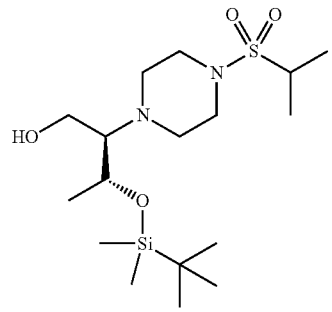 [SMILES: CC(C)S(=O)(=O)N1CCN([C@H](CO)[C@@H](C)O[Si](C)(C)C(C)(C)C)CC1]

To a stirred solution of methyl (2S,3R)-3-((tert-butyldimethylsilyl)oxy)-2-(4-(isopropylsulfonyl)piperazin-1-yl)butanoate (step 4, 5.0 g, 11.82 mmol, 1.0 eq) in DCM (75 ml) at −78° C. was added DIBAL-H (19.7 ml, 29.57 mmol, 2.5 eq, 1.5M in Toluene). The reaction mixture was stirred at −78° C. for about 4 hours. TLC indicated starting material was completed and the desired product was observed. The reaction mixture was quenched with saturated ammonium chloride solution and stirred for about 10 minutes. The mixture was filtered and the filtrate was extracted with DCM (3×100 ml). The combined organic layer was washed with water (100 ml), dried over sodium sulfate, filtered and concentrated under reduced pressure. The residue was purified by silica gel column chromatography using 0-3% methanol in dichloromethane gradient to obtain the title compound (3.7 g, 80% yield) as an off-white solid. ¹H NMR (300 MHz, CDCl₃): δ ppm 3.99-3.95 (m, 1H), 3.54-3.26 (m, 6H), 3.22-3.13 (m, 1H), 3.04-2.96 (m, 2H), 2.82-2.75 (m, 2H), 2.63-2.56 (m, 1H), 1.34 (d, J=6.9 Hz, 6H), 1.15 (d, J=6.3 Hz, 3H), 0.89 (s, 9H), 0.086 (s, 3H), 0.081 (s, 3H); ES-MS: m/z 395.46 (M+H)⁺.

Intermediate 16: Preparation of 1-((1R,3aS,5aR, 5bR,7aR,9S,11aR,11bR,13aR,13bR)-3a-amino-5a, 5b,8,8,11a-pentamethyl-1-(prop-1-en-2-yl)icosa- hydro-1H-cyclopenta chrysen-9-yl) 3-benzyl (1S, 3R)-2,2-dimethylcyclobutane-1,3-dicarboxylate

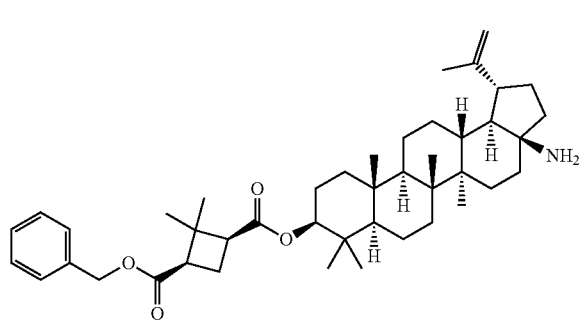

Step 1: Synthesis of (1R,3aS,5aR,5bR,7aR,9S,11aR, 11bR,13aR,13bR)-3a-isocyanato-5a,5b,8,8,11a-pen- tamethyl-1-(prop-1-en-2-yl)icosahydro-1H-cyclo- penta[a]chrysen-9-yl acetate

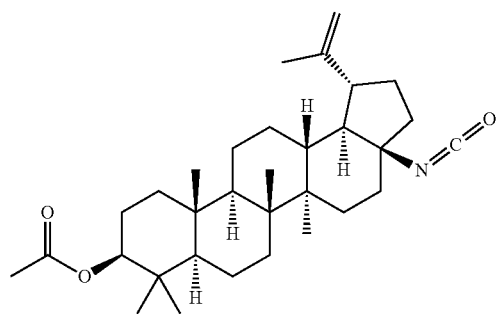

To a stirred solution of (1R,3aS,5aR,5bR,7aR,9S,11aR, 11bR,13aR,13bR)-9-acetoxy-5a,5b,8,8,11a-pentamethyl-1-(prop-1-en-2-yl)icosahydro-3aH-cyclopenta[a]chrysene-3a-carboxylic acid (Intermediate 1-step 1, 26 g, 52.13 mmol, 1.0 eq) in toluene at 0° C. was added diphenylphosphory- lazide (28.684 g, 104.26 mmol, 2.0 eq) and triethylamine (15.82 g, 156.39 mmol, 3.0 eq). The reaction mixture was heated to 80° C. for 1.5 hours. TLC indicated starting material was consumed and the desired product was observed. The reaction mixture was evaporated under reduced pressure, diluted with water (500 ml) and extracted with DCM (3×500 ml). The combined organic layer was washed with water (200 ml) and brine solution (200 ml). The organic layer was dried over sodium sulfate, filtered and evaporated under reduced pressure. The crude compound was treated with methanol (78 ml), stirred at room tempera- ture for 15 minutes, filtered and dried under vacuum to obtain the title compound (23 g, 89.1% yield) as an off-white solid. $^1$H NMR (300 MHz, CDCl$_3$): δ ppm 4.74 (d, J=1.5 Hz, 1H), 4.63 (t, J=1.5 Hz, 1H), 4.45 (m, 1H), 2.57-2.50 (m, 1H), 2.15-2.02 (m, 1H), 2.04 (s, 3H), 1.88-0.77 (m, 23H), 1.68 (s, 3H), 1.05 (s, 3H), 0.93 (s, 3H), 0.86 (s, 3H), 0.84 (s, 3H), 0.84 (s, 3H).

Step 2: Synthesis of (1R,3aS,5aR,5bR,7aR,9S,11aR, 11bR,13aR,13bR)-3a-amino-5a,5b,8,8,11a-pentam- ethyl-1-(prop-1-en-2-yl)icosahydro-1H-cyclopenta [a]chrysen-9-ol hydrochloride

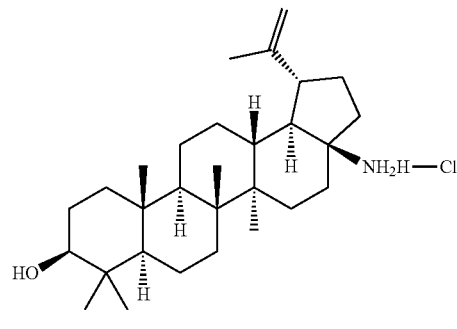

To a stirred solution of (1R,3aS,5aR,5bR,7aR,9S,11aR, 11bR,13aR,13bR)-3a-isocyanato-5a,5b,8,8,11a-pentam- ethyl-1-(prop-1-en-2-yl)icosahydro-1H-cyclopenta[a]chry- sen-9-yl acetate (step 1, 23 g, 46.394 mmol, 1.0 eq) in 1,4-dioxane (230 ml) at 0° C. was added concentrated hydrochloric acid (69 ml). The reaction mixture was heated at 60° C. for overnight. TLC indicated starting material was consumed and the desired product was observed. The reac- tion mixture was concentrated under reduced pressure. The obtained compound was treated with heptane (69 ml), stirred for 15 minutes, solid was filtered and dried under vacuum to obtain the title compound (20 g, 93% yield) as an off-white solid. $^1$H NMR (300 MHz, CDCl$_3$): δ ppm 7.67 (s, 3H), 4.72 (s, 1H), 4.62 (s, 1H), 3.09-2.94 (m, 1H), 2.60 (m, 1H), 2.11-1.99 (m, 1H), 1.91-1.79 (m, 2H), 1.76-0.62 (m, 21H), 1.66 (s, 3H), 1.03 (s, 3H), 0.93 (s, 3H), 0.87 (s, 3H), 0.78 (s, 3H), 0.65 (s, 3H).

Step 3: Synthesis of tert-butyl ((1R,3aS,5aR,5bR, 7aR,9S,11aR,11bR,13aR,13bR)-9-hydroxy-5a,5b,8, 8,11a-pentamethyl-1-(prop-1-en-2-yl)icosahydro- 3aH-cyclopenta[a]chrysen-3a-yl)carbamate

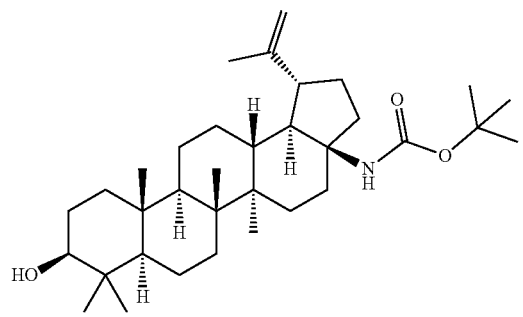

To a stirred solution of (1R,3aS,5aR,5bR,7aR,9S,11aR, 11bR,13aR,13bR)-3a-amino-5a,5b,8,8,11a-pentamethyl-1-(prop-1-en-2-yl)icosahydro-1H-cyclopenta[a]chrysen-9-ol hydrochloride (step 2, 20 g, 43.087 mmol, 1.0 eq) in 1,4-dioxane (200 ml) at 0° C. was added saturated sodium bicarbonate solution (200 ml) and di-tert-butyl dicarbonate (14.1 g, 64.631 mmol, 1.5 eq). The reaction mixture was stirred at room temperature for 6 hours. TLC indicated starting material was consumed and the desired product was observed. The reaction mixture was diluted with water (400 ml) and extracted with DCM (3×500 ml). The combined organic layer was washed with water (400 ml) and brine solution (200 ml). The organic layer was dried over sodium sulfate, filtered and concentrated under reduced pressure. The crude compound was purified by silica gel column chromatography using 0-3% ethyl acetate in hexane gradient. The fractions containing the expected product were combined and concentrated under reduced pressure to obtain the title compound (16 g, 70.48% yield) as an off-white solid. $^1$H NMR (300 MHz, CDCl$_3$): δ ppm 4.732 (d, J=1.5 Hz, 1H), 4.628 (d, J=1.5 Hz, 1H), 4.33 (s, 1H), 3.22-3.17 (m, 1H), 2.58-2.54 (m, 1H), 2.50-2.35 (m, 2H), 2.06-1.92 (m, 1H), 1.70 (s, 3H), 1.66-0.69 (m, 21H), 1.46 (s, 9H), 1.03 (s, 3H), 0.99 (s, 3H), 0.97 (s, 3H), 0.85 (s, 3H), 0.78 (s, 3H); ESI-MS: m/z 550.45 (M+Na)$^+$.

Step 4: Synthesis of 1-benzyl 3-((1R,3aS,5aR,5bR,7aR,9S,11aR,11bR,13aR,13bR)-3a-((tert-butoxycarbonyl)amino)-5a,5b,8,8,11a-pentamethyl-1-(prop-1-en-2-yl)icosahydro-1H-cyclopenta[a]chrysen-9-yl) (1R,3S)-2,2-dimethylcyclobutane-1,3-dicarboxylate

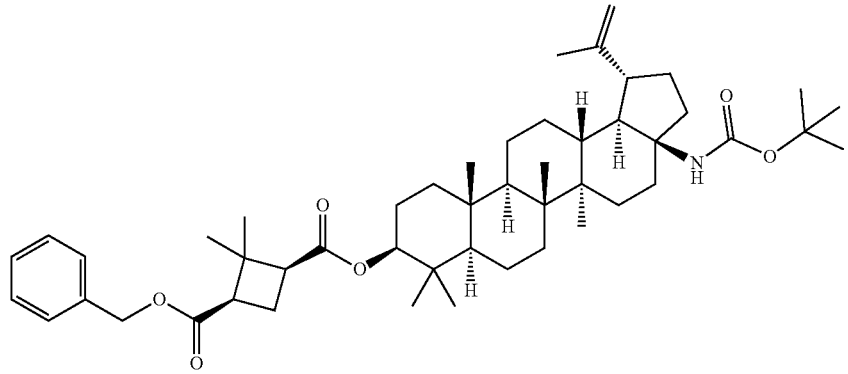

To a stirred solution of tert-butyl ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)carbamate (step 3, 16 g, 30.312 mmol, 1.0 eq) in DCM (240 ml) at 0° C. was added (1S,3R)-3-((benzyloxy)carbonyl)-2,2-dimethylcyclobutane-1-carboxylic acid (prepared as described in WO 2011/007230 A2, 11.92 g, 45.469 mmol, 1.5 eq), 1-(3-Dimethylaminopropyl)-3-ethylcarbodiimide Hydrochloride (EDC.HCl) (14.52 g, 75.781 mmol, 2.5 eq) and 4-(Dimethylamino)pyridine (1.11 g, 9.093 mmol, 0.3 eq). The reaction mixture was stirred at room temperature for overnight. TLC indicated starting material was completed and the desired product was observed. The reaction mixture was diluted with water (500 ml) and extracted with DCM (3×500 ml). The combined organic layer was washed with water (200 ml) and brine solution (100 ml). The organic layer was dried over sodium sulfate, filtered and concentrated under reduced pressure. The crude compound was purified by silica gel column chromatography using 0-3% ethyl acetate in hexane gradient. The fractions containing the expected product were combined and concentrated under reduced pressure to obtain the title compound (16 g, 68.37% yield) as an off-white solid. $^1$H NMR (300 MHz, CDCl$_3$): δ ppm 7.36-7.32 (m, 5H), 5.14, 5.09 (ABq, J$_{AB}$=12.3 Hz, 2H), 4.70 (s, 1H), 4.60 (s, 1H), 4.43 (dd, J=11.4, 4.5 Hz, 1H), 4.30 (s, 1H), 2.84-2.51 (m, 4H), 2.48-2.31 (m, 2H), 2.07-0.76 (m, 23H), 1.68 (s, 3H), 1.43 (s, 9H), 1.34 (s, 3H), 1.01 (s, 3H), 0.96 (s, 3H), 0.95 (s, 3H), 0.85 (s, 6H), 0.84 (s, 3H); ESI-MS: m/z 794.55 (M+Na)$^+$.

Step 5: Synthesis of 1-((1R,3aS,5aR,5bR,7aR,9S,11aR,11bR,13aR,13bR)-3a-amino-5a,5b, 8,8,11a-pentamethyl-1-(prop-1-en-2-yl)icosahydro-1H-cyclopenta[a]chrysen-9-yl) 3-benzyl (1S,3R)-2,2-dimethylcyclobutane-1,3-dicarboxylate

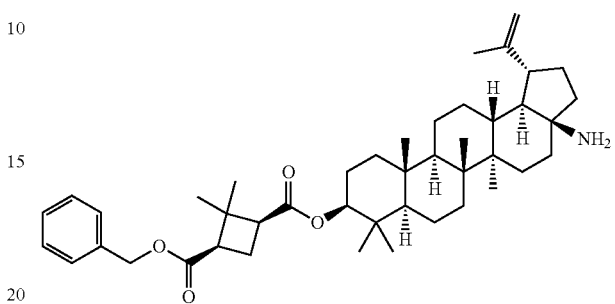

To a stirred solution of 1-benzyl 3-((1R,3aS,5aR,5bR,7aR,9S,11aR,11bR,13aR,13bR)-3a-((tert-butoxycarbonyl)amino)-5a,5b,8,8,11a-pentamethyl-1-(prop-1-en-2-yl)icosahydro-1H-cyclopenta[a]chrysen-9-yl) (1R,3S)-2,2-dimethylcyclobutane-1,3-dicarboxylate (step 4, 11.0 g, 14.24 mmol, 1.0 eq) in 1,4-dioxane (55 ml) at 0° C. was added 4N HCl in 1,4-dioxane (55 ml). The reaction mixture was changed to room temperature and stirred for about 3 hours. TLC indicated starting material was completed and the desired product was observed. The reaction mixture was evaporated under reduced pressure, diluted with water (50 ml), basified with aqueous sodium bicarbonate solution and extracted with DCM (3×100 ml). The combined organic layer was washed with water (100 ml), dried over sodium sulfate, filtered and concentrated under reduced pressure. The crude compound was treated with hexane (50 ml), stirred, filtered and dried under vacuum to obtain the title compound (7.0 g, 73.1% yield) as a solid. $^1$H NMR (300 MHz, CDCl$_3$): δ ppm 7.36-7.32 (m, 5H), 5.14, 5.09 (ABq, J$_{AB}$=12.3 Hz, 2H), 4.72 (s, 1H), 4.59 (s, 1H), 4.43 (dd, J=11.4, 4.5 Hz, 1H), 2.84-2.48 (m, 4H), 2.07-1.98 (m, 2H), 1.68 (s, 3H), 1.63-0.76 (m, 23H), 1.34 (s, 3H), 1.04 (s, 3H), 0.96 (s, 3H), 0.95 (s, 3H), 0.85 (s, 6H), 0.83 (s, 3H); ES-MS: m/z 672.49 (M+H)$^+$.

Intermediate 17: Preparation of 2-(2-methoxyethoxy)acetic acid

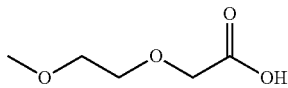

Step 1: Synthesis of ethyl 2-(2-methoxyethoxy)acetate

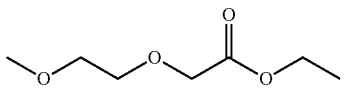

To a stirred solution of sodium hydride (6.6 g, 275.98 mmol, 3.0 eq) in THF (140 ml) at 0° C. was added 2-methoxyethan-1-ol (7.0 g, 91.996 mmol, 1.0 eq). The reaction mixture was stirred at 0° C. for about 30 minutes. Ethyl bromoacetate (19.97 g, 119.59 mmol, 1.3 eq) and potassium iodide (3.054 g, 18.399 mmol, 0.2 eq) were added to the reaction mixture and stirred at room temperature for about 2 hours. TLC indicated starting material was consumed and the desired product was observed. The reaction mixture was cooled to 0° C., quenched with saturated sodium chloride solution and extracted with DCM (3×350 ml). The combined organic layer was washed with water (150 ml), dried over sodium sulfate, filtered and concentrated under reduced pressure to obtain the title compound (10 g, 67% yield) as an oil, which is used as such for next step without further purification.

Step 2: Synthesis of 2-(2-methoxyethoxy)acetic acid

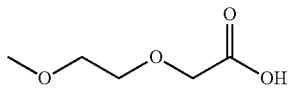

To a stirred solution of ethyl 2-(2-methoxyethoxy)acetate (step 1, 10 g, 61.656 mmol, 1.0 eq) in methanol (100 ml) and THF (100 ml) at 0° C. was added aqueous 2.5N KOH solution (184.96 ml, 462.42 mmol, 7.5 eq). The reaction mixture was stirred at room temperature for overnight. TLC indicated starting material was consumed and the desired product was observed. The reaction mixture was evaporated under reduced pressure, cooled to 0° C., pH adjusted to 2.0 with 1N HCl and evaporated under reduced pressure. The obtained solid was stirred with DCM (4×150 ml), filtered and the filtrate was evaporated under reduced pressure to obtain the title compound (5.0 g, 60.97% yield) as an oil. $^1$H NMR (300 MHz, CDCl$_3$): δ ppm 4.19 (s, 2H), 3.77-3.74 (m, 2H), 3.64-3.59 (m, 2H), 3.42 (s, 3H); ES-MS: m/z 135.17 (M+H)$^+$.

Intermediate 18: Preparation of 4-((12R,13R)-14-hydroxy-12-methyl-2,5,8,11-tetraoxatetradecan-13-yl)thiomorpholine 1,1-dioxide

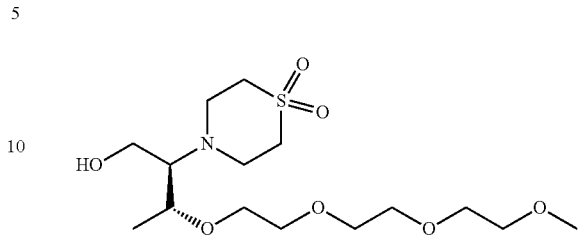

Step 1: Synthesis of 2-(2-(2-methoxyethoxy)ethoxy)ethyl methanesulfonate

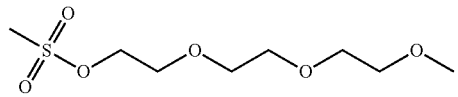

To a stirred solution of 2-(2-(2-methoxyethoxy)ethan-1-ol (3.29 g, 20.03 mmol, 1.0 eq) in DCM (40 ml) at 0° C. was added triethylamine (8.4 ml, 60.09 mmol, 3.0 eq) followed by methanesulfonyl chloride (2.01 ml, 26.04 mmol, 1.3 eq). The reaction mixture was stirred at room temperature for overnight. TLC indicated starting material was consumed and the desired product was observed. Water was added to the reaction mixture and extracted with DCM (2×30 ml). The combined organic layer was dried over sodium sulfate, filtered and concentrated under reduced pressure to obtain the title compound (4.3 g) as a liquid, used for next step without further purification. $^1$H NMR (300 MHz, CDCl$_3$): δ ppm 4.40-4.36 (m, 2H), 3.78-3.75 (m, 2H), 3.70-3.61 (m, 6H), 3.56-3.52 (m, 2H), 3.37 (s, 3H), 3.07 (s, 3H); ES-MS: m/z 243.37 (M+H)$^+$.

Step 2: Synthesis of 4-((2R,3R)-1,3-dihydroxybutan-2-yl)thiomorpholine 1,1-dioxide

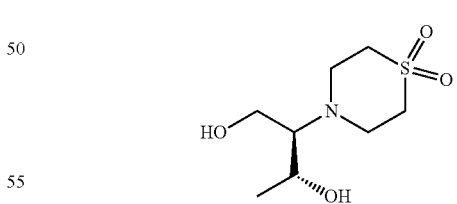

To a stirred solution of methyl (2S,3R)-2-(1,1-dioxidothiomorpholino)-3-hydroxybutanoate (Intermediate 8-step 2, 15 g, 59.713 mmol, 1.0 eq) in methanol (300 ml) at 0° C. was added sodium borohydride (22.5 g, 597.13 mmol, 10.0 eq) portion wise. The reaction mixture was stirred at room temperature for overnight. TLC indicated starting material was consumed and the desired product was observed. The reaction mixture was neutralized with 4N HCl/1,4-dioxane (120 ml) and concentrated under reduced pressure. The residue was stirred with DCM, filtered and the filtrate was evaporated under reduced pressure. The crude product was purified by silica gel column chromatography using 0-5% methanol in dichloromethane gradient to obtain the title compound (6.5 g, 48.8% yield) as an off-white solid. $^1$H NMR (300 MHz, DMSO-$d_6$): δ ppm 4.38 (t, J=4.8 Hz, 1H), 4.26 (d, J=3.0 Hz, 1H), 4.09-4.04 (m, 1H), 3.61-3.44 (m, 2H), 3.25-3.16 (m, 2H), 3.08-3.02 (m, 6H), 2.40-2.33 (m, 1H), 1.04 (d, J=6.0 Hz, 3H); ES-MS: m/z 224.16 (M+H)$^+$.

Step 3: Synthesis of 4-((2R,3R)-1-((tert-butyldimethylsilyl)oxy)-3-hydroxybutan-2-yl)thiomorpholine 1,1-dioxide

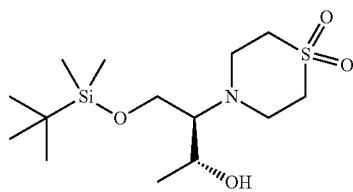 [SMILES: C[C@@H](O)[C@@H](CO[Si](C)(C)C(C)(C)C)N1CCS(=O)(=O)CC1]

To a stirred solution of 4-((2R,3R)-1,3-dihydroxybutan-2-yl)thiomorpholine 1,1-dioxide (step 2, 4.5 g, 20.153 mmol, 1.0 eq) in DCM (90 ml) at 0° C. was added triethylamine (14 ml, 100.76 mmol, 5.0 eq), DMAP (0.492 g, 4.030 mmol, 0.2 eq) and TBDMSCl (7.59 g, 50.383 mmol, 2.5 eq). The reaction mixture was stirred at room temperature for overnight. TLC indicated starting material was consumed and the desired product was observed. The reaction mixture was diluted with DCM (200 ml), washed with water (200 ml) and brine solution (250 ml). The organic layer was dried over sodium sulfate, filtered and concentrated under reduced pressure. The crude product was purified by silica gel column chromatography using 0-60% ethyl acetate in hexanes gradient to obtain the title compound (4 g, 58.8% yield) as a white solid. $^1$H NMR (300 MHz, CDCl$_3$): δ ppm 3.80 (dd, J=11.1, 3.0 Hz, 1H), 3.72-3.61 (m, 2H), 3.52-3.39 (m, 3H), 3.12-3.02 (m, 6H), 2.50-2.43 (m, 1H), 1.20 (d, J=6.0 Hz, 3H), 0.89 (s, 9H), 0.07 (s, 6H); ES-MS: m/z 338.32 (M+H)$^+$.

Step 4: Synthesis of 4-((12R,13R)-12,16,16,17,17-pentamethyl-2,5,8,11,15-pentaoxa-16-silaoctadecan-13-yl)thiomorpholine 1,1-dioxide

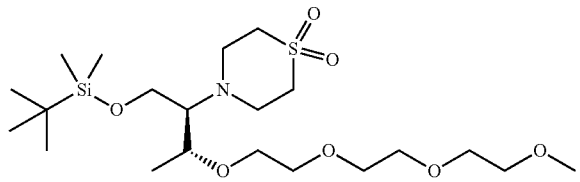 [SMILES: COCCOCCOCCO[C@H](C)[C@@H](CO[Si](C)(C)C(C)(C)C)N1CCS(=O)(=O)CC1]

To a suspension of sodium hydride (1.77 g, 74.05 mmol, 5.0 eq) in THF (50 ml) at 0° C. was added 4-((2R,3R)-1-((tert-butyldimethylsilyl)oxy)-3-hydroxybutan-2-yl)thiomorpholine 1,1-dioxide (step 3, 5 g, 14.81 mmol, 1.0 eq). The reaction mixture was stirred at 40-50° C. for about 30 minutes. 2-(2-(2-methoxyethoxy)ethoxy)ethyl methanesulfonate (step 1, 4.3 g, 17.77 mmol, 1.2 eq) and potassium iodide (0.245 g, 1.48 mmol, 0.1 eq) were added to the reaction mixture and stirred at 50-60° C. for overnight. The reaction mixture was cooled to 0° C., quenched with ice cold water and extracted with DCM (2×50 ml). The combined organic layer was dried over sodium sulfate, filtered and concentrated under reduced pressure. The product was purified by silica gel column chromatography using 0-40% ethyl acetate in hexanes gradient to obtain the title compound (2.0 g, 27.93% yield) as a colorless liquid. $^1$H NMR (300 MHz, CDCl$_3$): δ ppm 4.0-3.93 (m, 1H), 3.84-3.70 (m, 2H), 3.68-3.63 (m, 10H), 3.62-3.50 (m, 4H), 3.38 (s, 3H), 3.14-2.95 (m, 6H), 2.66-2.61 (m, 1H), 1.20 (d, J=6.6 Hz, 3H), 0.89 (s, 9H), 0.07 (s, 3H), 0.05 (s, 3H); ES-MS: m/z 484.65 (M+H)$^+$.

Step 5: Synthesis of 4-((12R,13R)-14-hydroxy-12-methyl-2,5,8,11-tetraoxatetradecan-13-yl)thiomorpholine 1,1-dioxide

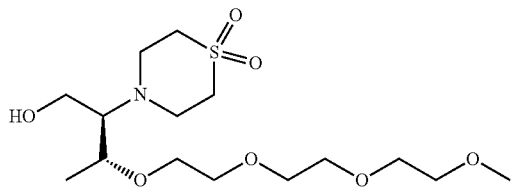 [SMILES: COCCOCCOCCO[C@H](C)[C@@H](CO)N1CCS(=O)(=O)CC1]

To a stirred solution of 4-((12R,13R)-12,16,16,17,17-pentamethyl-2,5,8,11,15-pentaoxa-16-silaoctadecan-13-yl) thiomorpholine 1,1-dioxide (step 4, 2.0 g, 4.134 mmol, 1.0 eq) in THF (20 ml) was added TBAF (8.26 ml, 8.269 mmol, 2.0 eq, 1.0M in THF). The reaction mixture was stirred at room temperature for overnight. TLC indicated starting material was completed and the desired product was observed. The reaction mixture was diluted with DCM (100 ml) and washed with water (100 ml). The organic layer was dried over sodium sulfate, filtered and concentrated under reduced pressure. The crude product was purified by silica gel column chromatography using 0-9% methanol in dichloromethane gradient to obtain the title compound (0.8 g, 52.6% yield) as a colorless liquid. $^1$H NMR (300 MHz, CDCl$_3$): δ ppm 3.67-3.59 (m, 9H), 3.58-3.53 (m, 4H), 3.47-3.41 (m, 2H), 3.38 (s, 3H), 3.35-3.20 (m, 2H), 3.13-3.0 (m, 6H), 2.63-2.56 (m, 1H), 1.20 (d, J=6.0 Hz, 3H); ES-MS: m/z 370.20 (M+H)$^+$.

Intermediate 19: Preparation of 2,5,8,11-tetraoxatridecan-13-oic acid

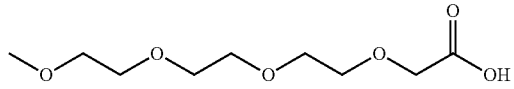

Step 1: Synthesis of ethyl 2,5,8,11-tetraoxatridecan-13-oate

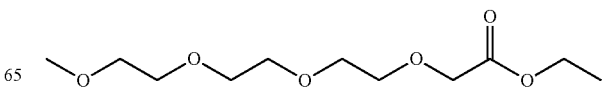

To a stirred suspension of sodium hydride (3.65 g, 152.25 mmol, 5.0 eq) in THF (125 ml) at 0° C. was added 2-(2-(2-methoxyethoxy)ethoxy)ethan-1-ol (5.0 g, 30.45 mmol, 1.0 eq) and Tetrabutylammoniumiodide (2.24 g, 6.09 mmol, 0.2 eq). The reaction mixture was stirred at 0° C. for about 30 minutes, ethyl 2-bromoacetate (6.611 g, 39.58 mmol, 1.3 eq) was added, stirred at 0° C. for about 1 hour and stirred at room temperature for overnight. TLC indicated starting material was consumed and the desired product was observed. The reaction mixture was cooled to 0° C., quenched with ice and extracted with DCM (3×250 ml). The combined organic layer was washed with water (150 ml) and brine solution (150 ml). The organic layer was dried over sodium sulfate, filtered and concentrated under reduced pressure to obtain the title compound (6 g, 78.74% yield) as a solid, which was used as such for next step without further purification.

Step 2: Synthesis of 2,5,8,11-tetraoxatridecan-13-oic acid

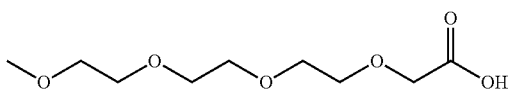

To a stirred solution of ethyl 2,5,8,11-tetraoxatridecan-13-oate (step 1, 6.0 g, 23.97 mmol, 1.0 eq) in methanol (60 ml) and THF (60 ml) at 0° C. was added aqueous 2.5N KOH solution (71.85 ml, 179.79 mmol, 7.5 eq). The reaction mixture was stirred at room temperature for overnight. TLC indicated starting material was consumed and the desired product was observed. The reaction mixture was evaporated under reduced pressure, water (50 ml) was added, cooled to 0° C., acidified to pH 2.0 with 1N HCl and extracted with DCM (3×250 ml). The combined organic layer was washed with water (100 ml), dried over sodium sulfate, filtered and concentrated under reduced pressure. The residue (5.3 g) was used as such for next step without further purification. $^1$H NMR (300 MHz, CDCl$_3$): δ ppm 4.17 (s, 2H), 3.75-3.57 (m, 12H), 3.39 (s, 3H); ES-MS: m/z 223.63 (M+H)$^+$.

EXAMPLES

Example 1: Preparation of (1R,3S)-3-((((1R,3aS,5aR,5bR,7aR,9S,11aR,11bR,13aR,13bR)-3a-((2-(1,1-dioxidothiomorpholino)-2-methylpropyl)amino)-5a,5b,8,8,11a-pentamethyl-1-(1-methylcyclopropyl) icosahydro-1H-cyclopenta chrysen-9-yl)oxy) carbonyl)-2,2-dimethyl cyclobutane-1-carboxylic acid

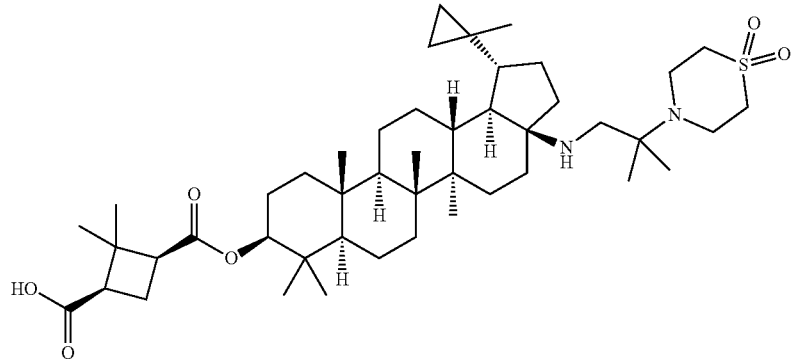

Step 1: Synthesis of 1-benzyl 3-((1R,3aS,5aR,5bR,7aR,9S,11 aR,11bR,13aR,13bR)-3a-((2-((tert-butoxycarbonyl)amino)-2-methylpropyl)amino)-5a,5b,8,8,11a-pentamethyl-1-(1-methyl cyclopropyl) icosahydro-1H-cyclopenta[a]chrysen-9-yl) (1R,3S)-2,2-dimethylcyclobutane-1,3-dicarboxylate

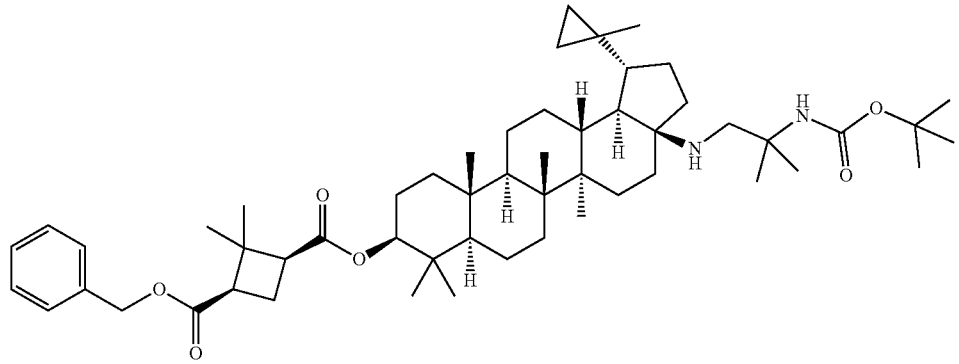

To a stirred solution of 1-((1R,3aS,5aR,5bR,7aR,9S,11aR,11bR,13aR,13bR)-3a-amino-5a,5b,8,8,11a-pentamethyl-1-(1-methylcyclopropyl)icosahydro-1H-cyclopenta[a]chrysen-9-yl) 3-benzyl (1S,3R)-2,2-dimethylcyclobutane-1,3-dicarboxylate (Intermediate 1, 4 g, 5.83 mmol, 1.0 eq) in 1,2-dichloroethane (40 ml) was added tert-butyl (2-methyl-1-oxopropan-2-yl)carbamate (Intermediate 2, 3.27 g, 17.49 mmol, 3.0 eq) and Titanium tetraisopropoxide (3.4 ml, 11.66 mmol, 2.0 eq). The reaction mixture was stirred at room temperature for about 1 hour and then sodium triacetoxyborohydride (3.7 g, 17.49 mmol, 3.0 eq) was added and stirred at room temperature for overnight. TLC indicated starting material was consumed and the desired product was observed. Saturated sodium bicarbonate solution was added to the reaction mixture, organic layer was separated and aqueous layer was extracted with dichloromethane (2×40 ml). The combined organic layer was washed with water, dried over $Na_2SO_4$, filtered and concentrated under reduced pressure. The residue was purified by silica gel column chromatography using 1% methanol in dichloromethane as an eluent to obtain the title compound (4 g, 80% yield) as an off-white solid. $^1$H NMR (300 MHz, $CDCl_3$): δ ppm 7.34 (m, 5H), 5.15, 5.09 (ABq, $J_{AB}$=12.3 Hz, 2H), 4.45 (m, 1H), 2.90-2.46 (m, 3H), 2.40-2.30 (m, 2H), 2.10-2.0 (m, 2H), 1.97-1.13 (m, 32H), 1.42 (s, 9H), 1.03-0.76 (m, 22H), 0.40-0.20 (m, 4H); ESI-MS: m/z 857.75 (M+H)$^+$.

Step 2: Synthesis of 1-((1R,3aS,5aR,5bR,7aR,9S,11aR,11bR,13aR,13bR)-3a-((2-amino-2-methylpropyl)amino)-5a,5b,8,8,11a-pentamethyl-1-(1-methylcyclopropyl)icosahydro-1H-cyclopenta[a]chrysen-9-yl) 3-benzyl (1S,3R)-2,2-dimethylcyclobutane-1,3-dicarboxylate

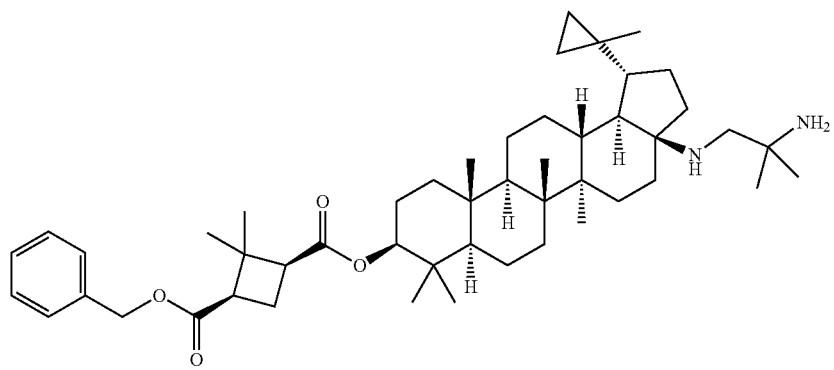

To a stirred solution of 1-benzyl 3-((1R,3aS,5aR,5bR,7aR,9S,11aR,11bR,13aR,13bR)-3a-((2-((tert-butoxycarbonyl)amino)-2-methylpropyl)amino)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate (step 1, 4 g, 4.66 mmol, 1.0 eq) in 1,4-dioxane (10 ml) at 0° C. was added 4N HCl/1,4-dioxane (30 ml). The reaction mixture was stirred at room temperature for overnight. TLC indicated starting material was consumed and the desired product was observed. The reaction mixture was evaporated under reduced pressure, basified with saturated sodium bicarbonate solution and extracted with dichloromethane (2×40 ml). The organic layer was washed with water, dried over $Na_2SO_4$, filtered and concentrated under reduced pressure to obtain the title compound (3 g, 85.2% yield) as an off-white solid. $^1$H NMR (300 MHz, $CDCl_3$): δ ppm 7.34 (m, 5H), 5.14, 5.09 (ABq, $J_{AB}$=12.3 Hz, 2H), 4.45 (m, 1H), 2.84-2.61 (m, 3H), 2.27-2.13 (m, 2H), 2.07-1.17 (m, 34H), 1.13-0.78 (m, 22H), 0.36-0.22 (m, 4H); ESI-MS: m/z 757.50 (M+H)$^+$.

Step 3: Synthesis of 1-benzyl 3-((1R,3aS,5aR,5bR, 7aR,9S,11aR,11bR,13aR,13bR)-3a-((2-(1,1-dioxido-thiomorpholino)-2-methylpropyl)amino)-5a,5b,8,8, 11a-pentamethyl-1-(1-methylcyclopropyl) icosahydro-1H-cyclopenta[a]chrysen-9-yl) (1R,3S)-2,2-dimethylcyclobutane-1,3-dicarboxylate

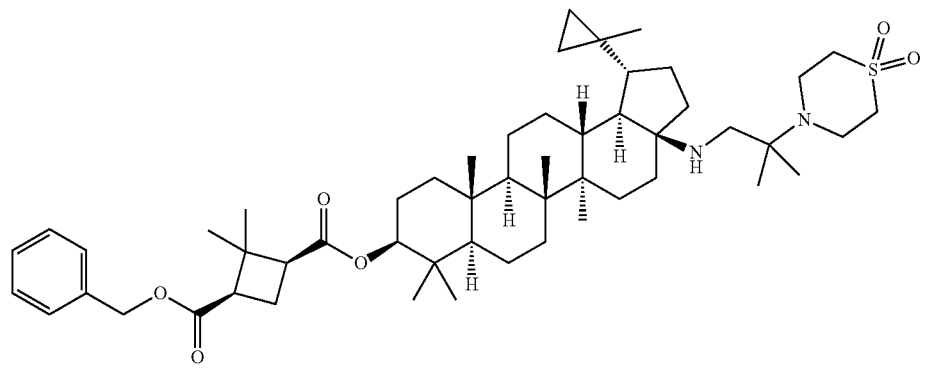

To a stirred solution of 1-((1R,3aS,5aR,5bR,7aR,9S, 11aR,11bR,13aR,13bR)-3a-((2-amino-2-methylpropyl) amino)-5a,5b,8,8,11a-pentamethyl-1-(1-methylcyclopropyl) icosahydro-1H-cyclopenta[a]chrysen-9-yl) 3-benzyl (1S,3R)-2,2-dimethylcyclobutane-1,3-dicarboxylate (step 2, 0.4 g, 0.52 mmol, 1.0 eq) in 1,4-dioxane (4 ml) and ethanol (4 ml) was added triethylamine (0.21 ml, 1.56 mmol, 3.0 eq) followed by divinyl sulfone (0.12 g, 1.056 mmol, 2.0 eq). The reaction mixture was heated to 85° C. for about 3 hours. TLC indicated starting material was completed and the desired product was observed. The reaction mixture was evaporated under reduced pressure, diluted with water (100 ml) and extracted with ethyl acetate (3×30 ml). The combined organic layer was washed with water (100 ml), dried over $Na_2SO_4$, filtered and concentrated under reduced pressure. The residue was purified by silica gel column chromatography using 20-40% ethyl acetate in hexane gradient to obtain the title compound (0.4 g, 88.8% yield) as a solid. $^1$H NMR (300 MHz, $CDCl_3$): δ ppm 7.35 (m, 5H), 5.14, 5.09 (ABq, $J_{AB}$=12.3 Hz, 2H), 4.49-4.40 (m, 1H), 3.05 (m, 8H), 2.86-2.73 (m, 2H), 2.71-2.60 (m, 1H), 2.50-2.28 (m, 2H), 2.10-1.13 (m, 34H), 1.08-0.78 (m, 22H), 0.42-0.22 (m, 4H).

Step 4: Synthesis of (1R,3S)-3-((a 1R,3aS,5aR,5bR, 7aR,9S,11 aR,11bR,13aR,13bR)-3a-((2-(1,1-dioxidothiomorpholino)-2-methylpropyl)amino)-5a,5b,8, 8,11a-pentamethyl-1-(1-methyl cyclopropyl) icosahydro-1H-cyclopenta[a]chrysen-9-yl)oxy) carbonyl)-2,2-dimethylcyclobutane-1-carboxylic acid

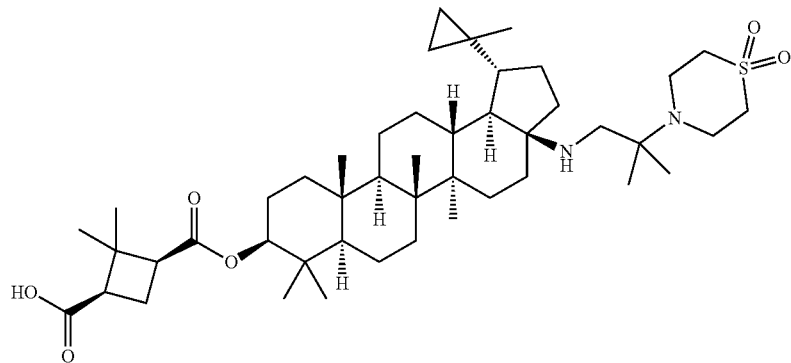

To a stirred solution of 1-benzyl 3-((1R,3aS,5aR,5bR, 7aR,9S,11aR,11bR,13aR,13bR)-3a-((2-(1,1-dioxidothiomorpholino)-2-methylpropyl)amino)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate (step 3, 0.4 g, 0.456 mmol, 1.0 eq) in THF (4 ml) and methanol (4 ml) was added aqueous 2.5N KOH solution (1.35 ml, 3.427 mmol, 7.5 eq). The reaction mixture was stirred at room temperature for overnight. TLC indicated starting material was completed and the desired product was observed. The reaction mixture was evaporated under reduced pressure and diluted with water (5 ml). The reaction mixture was cooled to 0° C., pH adjusted to 5 with 1N HCl and extracted with dichloromethane (3×30 ml). The combined organic layers were washed with water (20 ml) and brine solution (10 ml). The organic layer was dried over Na$_2$SO$_4$, filtered and concentrated under reduced pressure. The crude compound was purified by silica gel column chromatography using 30 to 45% ethyl acetate in hexanes gradient to obtain the title compound (0.15 g, 41.8% yield) as a white solid. $^1$H NMR (300 MHz, CDCl$_3$): δ ppm 4.46 (dd, J=10.8, 4.8 Hz, 1H), 3.10-2.92 (m, 8H), 2.86-2.74 (m, 2H), 2.65-2.53 (m, 1H), 2.39-2.28 (m, 2H), 2.10-2.0 (m, 2H), 1.98-1.05 (m, 32H), 1.03-0.78 (m, 22H), 0.40-0.20 (m, 4H). ESI-MS: m/z 785.65 (M+H)$^+$.

Example 2: Preparation of (1R,3S)-3-((((1R,3aS, 5aR,5bR,7aR,9S,11aR,11bR,13aR,13bR)-3a-(((S)-2-(1,1-dioxidothiomorpholino)propyl)amino)-5a,5b,8, 8,11a-pentamethyl-1-(1-methylcyclopropyl) icosahydro-1H-cyclopenta chrysen-9-yl)oxy) carbonyl)-2,2-dimethyl cyclobutane-1-carboxylic acid

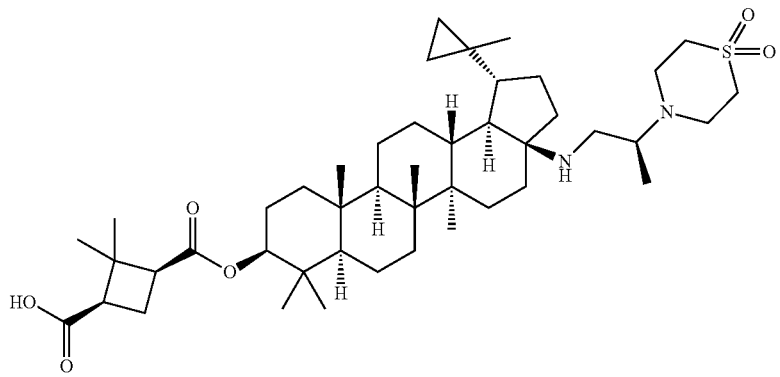

Step 1: Synthesis of 1-benzyl 3-((1R,3aS,5aR,5bR, 7aR,9S,11aR,11bR,13aR,13bR)-3a-(((S)-2-(1,1-dioxidothiomorpholino)propyl)amino)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate

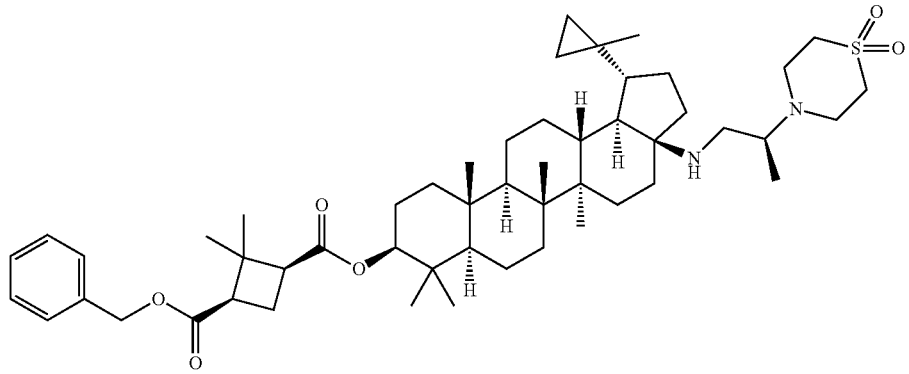

To a stirred solution of 1-((1R,3aS,5aR,5bR,7aR,9S, 11aR,11bR,13aR,13bR)-3a-amino-5a,5b,8,8,11a-pentamethyl-1-(1-methylcyclopropyl)icosahydro-1H-cyclopenta[a]chrysen-9-yl) 3-benzyl (1S,3R)-2,2-dimethylcyclobutane-1,3-dicarboxylate (Intermediate 1, 1 g, 1.457 mmol, 1.0 eq) in acetonitrile (20 ml) was added (S)-4-(1-chloropropan-2-yl)thiomorpholine 1,1-dioxide (Intermediate 3, 0.925 g, 4.372 mmol, 3.0 eq), potassium phosphate tribasic (1.36 g, 6.4108 mmol, 4.4 eq) and potassium iodide (0.653 g, 3.934 mmol, 2.7 eq). The reaction mixture was heated to reflux for overnight. TLC indicated starting material was consumed and the desired product was observed. The reaction mixture was filtered through celite pad and washed with acetonitrile (25 ml). The filtrate was evaporated under reduced pressure and the residue was purified by silica gel column chromatography using 2% methanol in dichloromethane as an eluent to obtain the title compound (0.35 g, 27.88% yield) as an off-white solid. $^1$H NMR (300 MHz, CDCl$_3$): δ ppm 7.35 (m, 5H), 5.15, 5.09 (ABq, J$_{AB}$=12.3 Hz, 2H), 4.44 (dd, J=10.5, 4.8 Hz, 1H), 3.32 (m, 1H), 3.12-3.06 (m, 8H), 2.88-2.72 (m, 2H), 2.70-2.52 (m, 2H), 2.50-2.48 (m, 1H), 2.18-2.0 (m, 3H), 1.92-1.17 (m, 25H), 1.17-0.78 (m, 25H), 0.68 (m, 1H), 0.50-0.36 (m, 2H), 0.28 (m, 1H); ES-MS: m/z 861.79 (M+H)$^+$.

Step 2: Synthesis of (1R,3S)-3-((((1R,3aS,5aR,5bR, 7aR,9S,11aR,11bR,13aR,13bR)-3a-(((S)-2-(1,1-dioxidothiomorpholino)propyl)amino)-5a,5b,8,8,11a-pentamethyl-1-(1-methylcyclopropyl)icosahydro-1H-cyclopenta[a]chrysen-9-yl)oxy)carbonyl)-2,2-dimethylcyclobutane-1-carboxylic acid

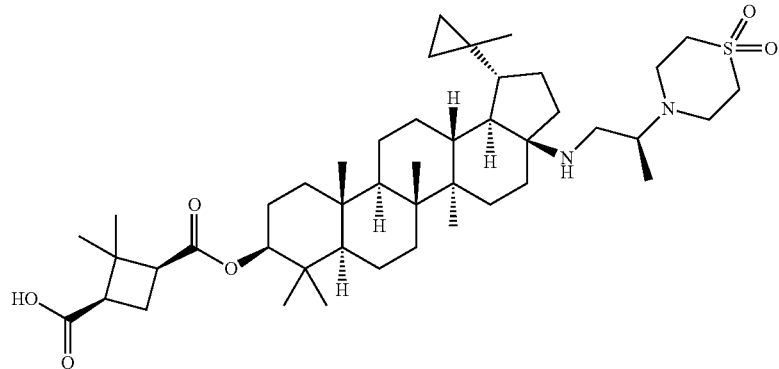

To a stirred solution of 1-benzyl 3-((1R,3aS,5aR,5bR, 7aR,9S,11aR,11bR,13aR,13bR)-3a-(((S)-2-(1,1-dioxidothiomorpholino)propyl)amino)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate (step 1, 0.35 g, 0.406 mmol, 1.0 eq) in THF (3.5 ml) and methanol (3.5 ml) at 0° C. was added aqueous 2.5N KOH solution (1.22 ml, 3.047 mmol, 7.5 eq). The reaction mixture was stirred at room temperature for overnight. TLC indicated starting material was consumed and the desired product was observed. The reaction mixture was evaporated under reduced pressure, diluted with water (10 ml), cooled to 0° C. and pH adjusted to 5.0 with 1N HCl. The aqueous layer was extracted with dichloromethane (2×20 ml). The combined organic layer was washed with water, dried over Na$_2$SO$_4$, filtered and concentrated under reduced pressure. The crude compound was purified by silica gel column chromatography using 0-5% methanol in DCM gradient. The obtained compound was further purified by recrystallization over MTBE (10 ml) to obtain the title compound (0.1 g, 32% yield) as an off-white solid. $^1$H NMR (300 MHz, CDCl$_3$): δ ppm 4.46 (m, 1H), 3.30-2.90 (m, 9H), 2.88-2.72 (m, 2H), 2.68-2.50 (m, 2H), 2.28-2.0 (m, 3H), 2.0-1.17 (m, 26H), 1.14-0.78 (m, 25H), 0.62-0.52 (m, 1H), 0.50-0.36 (m, 2H), 0.32-0.25 (m, 1H); ES-MS: m/z 771.87 (M+H)$^+$.

Example 3: Preparation of (1R,3S)-3-((((1R,3aS, 5aR,5bR,7aR,9S,11aR,11bR,13aR,13bR)-3a-(((R)-2-(1,1-dioxidothiomorpholino)-3-methylbutyl)amino)-5a,5b,8,8,11a-pentamethyl-1-(1-methylcyclopropyl) icosahydro-1H-cyclopenta[a]chrysen-9-yl)oxy) carbonyl)-2,2-dimethyl cyclobutane-1-carboxylic acid

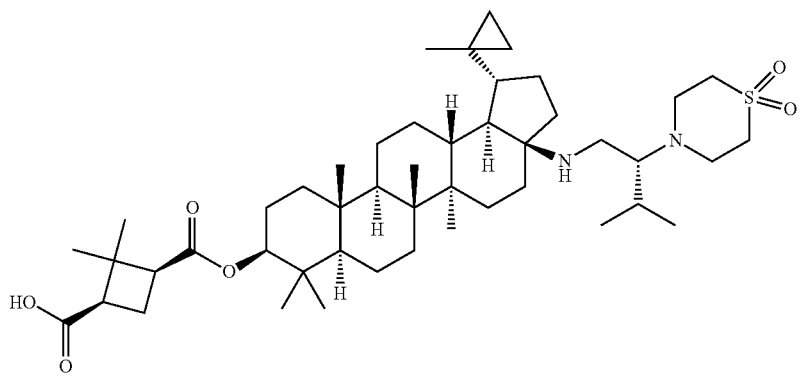

Step 1: Synthesis of 1-benzyl 3-((1R,3aS,5aR,5bR, 7aR,9S,11aR,11bR,13aR,13bR)-3a-(((R)-2-(1,1-dioxidothiomorpholino)-3-methylbutyl)amino)-5a, 5b,8,8,11a-pentamethyl-1-(1-methyl cyclopropyl) icosahydro-1H-cyclopenta[a]chrysen-9-yl) (1R,3S)-2,2-dimethylcyclobutane-1,3-dicarboxylate

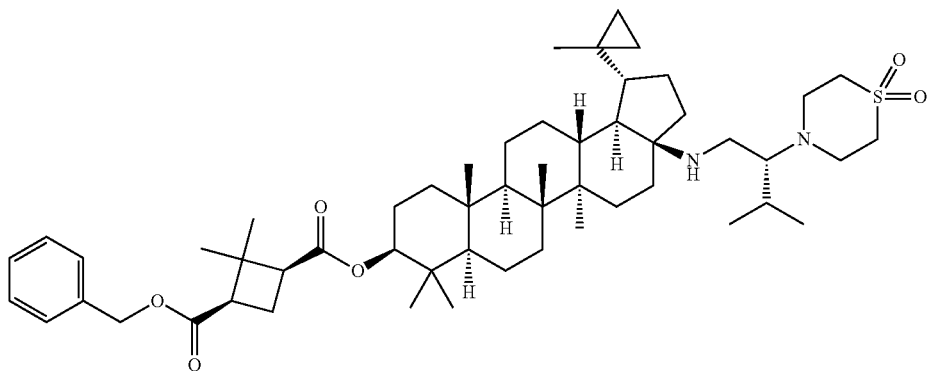

To a stirred solution of (R)-4-(1-hydroxy-3-methylbutan-2-yl)thiomorpholine 1,1-dioxide (Intermediate 4, 0.241 g, 1.093 mmol, 1.25 eq) in dichloromethane (12 ml) at 0° C. was added trifluoromethanesulfonic anhydride (0.20 ml, 1.224 mmol, 1.4 eq). The reaction mixture was stirred at same temperature for about 10 minutes. 2,6-Lutidine (0.145 ml, 1.25 mmol, 1.43 eq) was added and stirred at 0° C. for 10 minutes. 1-((1R,3aS,5aR,5bR,7aR,9S,11aR,11bR,13aR, 13bR)-3a-amino-5a,5b,8,8,11a-pentamethyl-1-(1-methylcyclopropyl) icosahydro-1H-cyclopenta[a]chrysen-9-yl) 3-benzyl (1S,3R)-2,2-dimethylcyclobutane-1,3-dicarboxylate (Intermediate 1, 0.6 g, 0.874 mmol, 1.0) followed by triethylamine (0.175 ml, 1.25 mmol, 1.43 eq) were added to the reaction mixture and stirred at 0° C. for about 1 hour. The cooling bath was removed and stirred at room temperature for about 4 hours. TLC indicated starting material was consumed and the desired product was observed. The reaction mixture was diluted with dichloromethane (2×20 ml), organic layer was washed with water, dried over sodium sulfate, filtered and evaporated under reduced pressure. The crude compound was purified by silica gel column chromatography using 30% ethyl acetate in hexane as an eluent to obtain the title compound (0.3 g, 38.96% yield) as an off-white solid. $^1$H NMR (300 MHz, CDCl$_3$): δ ppm 7.35 (m, 5H), 5.15, 5.09 (ABq, J$_{AB}$=12.3 Hz, 2H), 4.45 (dd, J=11.1, 4.5 Hz, 1H), 3.22-3.06 (m, 6H), 3.02-2.94 (m, 2H), 2.88-2.58 (m, 3H), 2.52-2.18 (m, 3H), 2.10-1.90 (m, 2H), 1.88-1.10 (m, 27H), 1.06-0.78 (m, 28H), 0.40-0.20 (m, 4H); ES-MS: m/z 889.81 (M+H)$^+$.

Step 2: Synthesis of (1R,3S)-3-((((1R,3aS,5aR,5bR,7aR,9S,11aR,11bR,13aR,13bR)-3a-(((R)-2-(1,1-dioxidothiomorpholino)-3-methylbutyl)amino)-5a,5b,8,8,11a-pentamethyl-1-(1-methyl cyclopropyl)icosahydro-1H-cyclopenta[a]chrysen-9-yl)oxy)carbonyl)-2,2-dimethylcyclobutane-1-carboxylic acid

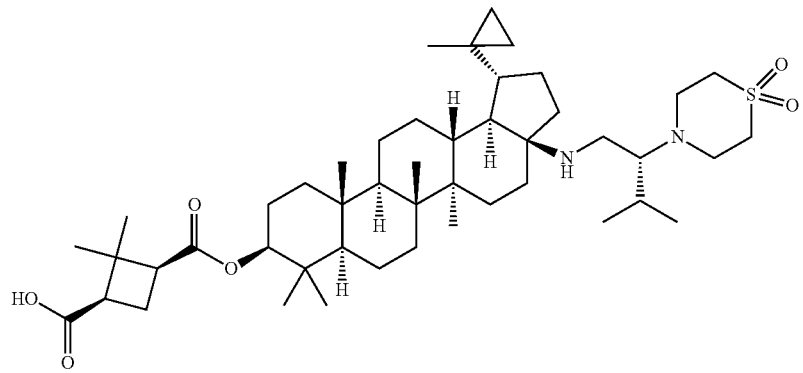

To a stirred solution of 1-benzyl 3-((1R,3aS,5aR,5bR,7aR,9S,11aR,11bR,13aR,13bR)-3a-(((R)-2-(1,1-dioxidothiomorpholino)-3-methylbutyl)amino)-5a,5b,8,8,11a-pentamethyl-1-(1-methylcyclopropyl)icosahydro-1H-cyclopenta[a]chrysen-9-yl) (1R,3S)-2,2-dimethyl cyclobutane-1,3-dicarboxylate (step 1, 0.3 g, 0.337 mmol, 1.0 eq) in methanol (3 ml) and THF (3 ml) was added aqueous 2.5N KOH solution (1.01 ml, 2.527 mmol, 7.5 eq). The reaction mixture was stirred at room temperature for overnight. TLC indicated starting material was consumed and the desired product was observed. The reaction mixture was evaporated under reduced pressure, cooled to 0° C., acidified with 1N HCl to pH 5.0 and extracted with dichloromethane (2×30 ml). The combined organic layer was washed with water, dried over Na$_2$SO$_4$, filtered and concentrated under reduced pressure. The crude compound was purified by silica gel column chromatography using 5% methanol in dichloromethane as an eluent to obtain the title compound (0.100 g, 37.3% yield) as an off-white solid. $^1$H NMR (300 MHz, CDCl$_3$): δ ppm 4.45 (m, 1H), 3.25-2.95 (m, 8H), 2.80-2.70 (m, 3H), 2.62-2.42 (m, 2H), 2.38-2.20 (m, 1H), 2.20-1.20 (m, 29H), 1.18-0.78 (m, 28H), 0.42-0.20 (m, 4H); ES-MS: m/z 799.89 (M+H)$^+$.

Example 4: Preparation of (1R,3S)-3-((((1R,3aS,5aR,5bR,7aR,9S,11aR,11bR,13aR,13bR)-3a-(((R)-3-((tert-butyldimethylsilyl)oxy)-2-(1,1-dioxidothiomorpholino)propyl)amino)-5a,5b, 8,8,11a-pentamethyl-1-(1-methylcyclopropyl)icosahydro-1H-cyclopenta[a]chrysen-9-yl)oxy) carbonyl)-2,2-dimethylcyclobutane-1-carboxylic acid

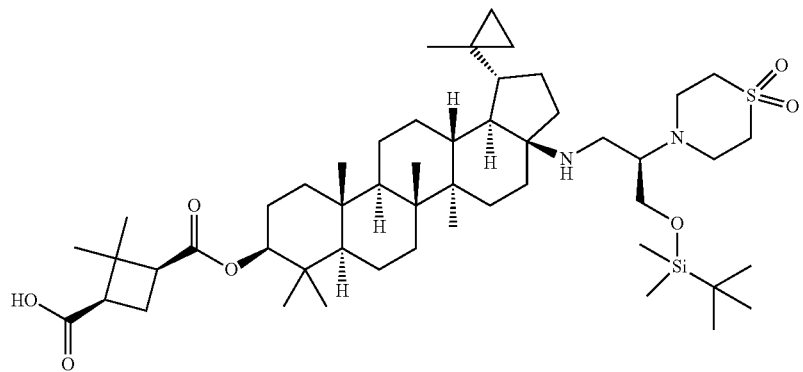

Step 1: Synthesis of 1-benzyl 3-((1R,3aS,5aR,5bR, 7aR,9S,11aR,11bR,13aR,13bR)-3a-(((R)-3-((tert-butyldimethylsilyl)oxy)-2-(1,1-dioxidothiomorpholino)propyl)amino)-5a,5b,8,8,11a-pentamethyl-1-(1-methylcyclopropyl)icosahydro-1H-cyclopenta[a]chrysen-9-yl) (1R,3 S)-2,2-dimethylcyclobutane-1,3-dicarboxylate was purified by silica gel column chromatography using 0-15% ethyl acetate in hexane gradient to obtain the title compound (1 g, 69.4% yield) as an off-white solid. $^1$H NMR (300 MHz, CDCl$_3$): δ ppm 7.34 (m, 5H), 5.14, 5.09 (ABq, J$_{AB}$=12.3 Hz, 2H), 4.44 (dd, J=11.1, 4.8 Hz, 1H), 3.71-3.65 (m, 2H), 3.40-3.20 (m, 3H), 3.19-2.98 (m, 8H), 2.85-2.57

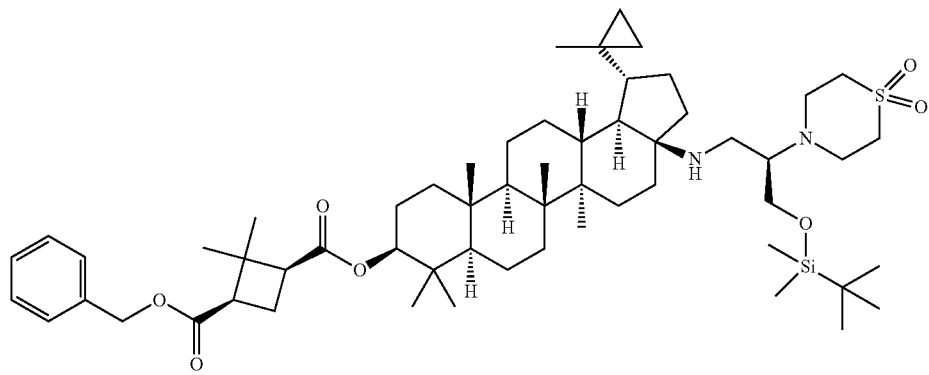

To a stirred solution of (R)-4-(1-((tert-butyldimethylsilyl)oxy)-3-hydroxypropan-2-yl)thiomorpholine 1,1-dioxide (Intermediate 6, 0.742 g, 2.186 mmol, 1.5 eq) in DCM (20 ml) at 0° C. was added trifluoromethanesulfonic anhydride (0.39 ml, 2.332 mmol, 1.6 eq). The reaction mixture was stirred at 0° C. for about 10 minutes, then 2,6-Lutidine (0.21 ml, 2.332 mmol, 1.6 eq) was added, stirred at 0° C. for about 10 minutes. 1-((1R,3aS,5aR,5bR,7aR,9S,11aR,11bR,13aR,13bR)-3a-amino-5a,5b,8,8,11a-pentamethyl-1-(1-methylcyclopropyl) icosahydro-1H-cyclopenta[a]chrysen-9-yl) 3-benzyl (1S,3R)-2,2-dimethylcyclobutane-1,3-dicarboxylate (Intermediate 1, 1 g, 1.457 mmol, 1.0 eq) and triethylamine (0.32 ml, 2.332 mmol, 1.6 eq) were added sequentially at 0° C. and stirred at same temperature for about 1 hour. The reaction mixture was stirred at room temperature for overnight. TLC indicated starting material was consumed and the desired product was observed. The reaction mixture was diluted with DCM (100 ml), washed with saturated sodium bicarbonate solution, water and brine solution. The organic layer was dried over Na$_2$SO$_4$, filtered and evaporated under reduced pressure. The crude compound (m, 3H), 2.46-2.40 (m, 2H), 2.08-2.0 (m, 1H), 1.95-0.70 (m, 26H), 1.34 (s, 3H), 1.05 (s, 3H), 0.96 (s, 3H), 0.898 (s, 6H), 0.891 (s, 6H), 0.84 (s, 9H), 0.36-0.21 (m, 4H), 0.07 (s, 3H), 0.05 (s, 3H); ESI-MS: m/z 992.16 (M+H)$^+$.

Step 2: Synthesis of (1R,3S)-3-((((1R,3aS,5aR,5bR, 7aR,9S,11aR,11bR,13aR,13bR)-3a-(((R)-3-((tert-butyldimethylsilyl)oxy)-2-(1,1-dioxidothiomorpholino)propyl)amino)-5a,5b,8,8,11a-pentamethyl-1-(1-methylcyclopropyl)icosahydro-1H-cyclopenta[a]chrysen-9-yl)oxy) carbonyl)-2,2-dimethylcyclobutane-1-carboxylic acid

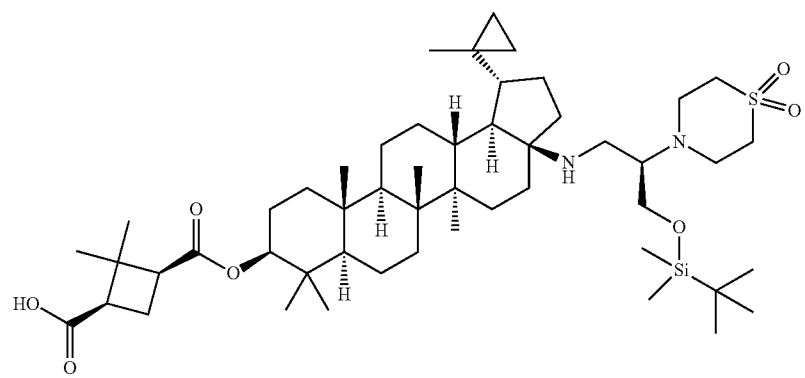

To a stirred solution of 1-benzyl 3-((1R,3aS,5aR,5bR, 7aR,9S,11aR,11bR,13aR,13bR)-3a-(((R)-3-((tert-butyldimethylsilyl)oxy)-2-(1,1-dioxidothiomorpholino)propyl)amino)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate (step 1, 1 g, 1.008 mmol, 1.0 eq) in methanol (10 ml) and THF (10 ml) was added aqueous 2.5N KOH solution (3 ml, 7.56 mmol, 7.5 eq). The reaction mixture was stirred at room temperature for overnight. TLC indicated starting material was consumed and the desired product was observed. The reaction mixture was evaporated under reduced pressure, cooled to 0° C., pH adjusted to 5.0 with 1N HCl and extracted with DCM (2×100 ml). The combined organic layer was washed with water (100 ml) and brine solution (100 ml). The organic layer was dried over $Na_2SO_4$, filtered and evaporated under reduced pressure. The crude compound was purified by silica gel column chromatography using 0 to 6% methanol in dichloromethane gradient to obtain the title compound (0.350 g, 38.5% yield) as an off-white solid. $^1$H NMR (300 MHz, $CDCl_3$): δ ppm 4.53-4.45 (m, 1H), 3.76-3.62 (m, 2H), 3.40-3.23 (m, 3H), 3.20-2.93 (m, 8H), 2.80-2.52 (m, 5H), 2.02-0.78 (m, 24H), 1.35 (s, 3H), 1.05 (s, 3H), 1.0 (s, 3H), 0.98 (s, 3H), 0.89 (s, 3H), 0.88 (s, 3H), 0.87 (s, 3H), 0.85 (s, 3H), 0.83 (s, 9H), 0.40-0.24 (m, 4H), 0.05 (s, 3H), 0.04 (s, 3H); ESI-MS: m/z 901.91 $(M+H)^+$.

Example 5: Preparation of (1R,3S)-3-((((1R,3aS,5aR,5bR,7aR,9S,11aR,11bR,13aR,13bR)-3a-(((R)-2-(1,1-dioxidothiomorpholino)-3-hydroxypropyl)amino)-5a,5b,8,8,11a-pentamethyl-1-(1-methylcyclopropyl)icosahydro-1H-cyclopenta[a]chrysen-9-yl)oxy)carbonyl)-2,2-dimethylcyclobutane-1-carboxylic acid

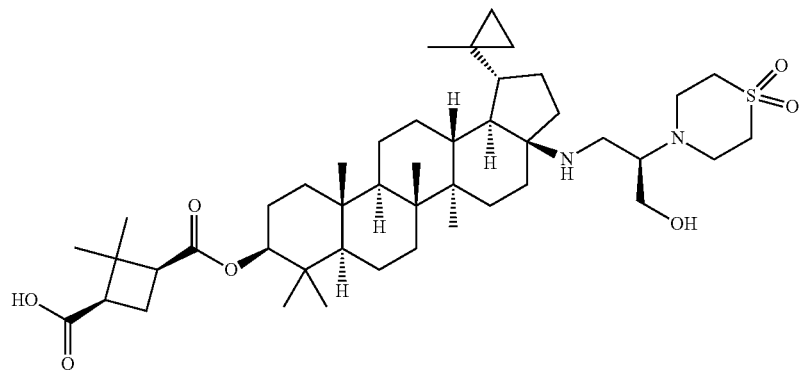

To a stirred solution of (1R,3S)-3-((((1R,3aS,5aR,5bR,7aR,9S,11aR,11bR,13aR, 13bR)-3a-(((R)-3-((tert-butyldimethylsilyl)oxy)-2-(1,1-dioxidothiomorpholino)propyl)amino)-5a,5b,8,8,11a-pentamethyl-1-(1-methylcyclopropyl)icosahydro-1H-cyclopenta[a]chrysen-9-yl)oxy)carbonyl)-2,2-dimethylcyclobutane-1-carboxylic acid (Example 4, 0.500 g, 0.554 mmol, 1.0 eq) in THF (15 ml) at 0° C. was added TBAF (0.66 ml, 0.6659 mmol, 1.2 eq, 1.0M in THF). The reaction mixture was stirred at room temperature for about 4 hours. TLC indicated starting material was consumed and the desired product was observed. The reaction mixture was evaporated under reduced pressure. The residue was dissolved in ethyl acetate (100 ml), washed with water (2×100 ml) and brine solution. The organic layer was dried over $Na_2SO_4$, filtered and concentrated under reduced pressure. The crude compound was purified by silica gel column chromatography using 0-10% methanol in dichloromethane gradient to obtain the title compound (0.110 g, 25.2% yield) as an off-white solid. $^1$H NMR (300 MHz, DMSO-d6): δ ppm 4.35 (m, 1H), 3.55-3.45 (m, 1H), 3.44-3.38 (m, 1H), 3.20-3.10 (m, 2H), 3.09-2.92 (m, 6H), 2.82-2.70 (m, 3H), 2.35-2.22 (m, 4H), 1.98-0.78 (m, 25H), 1.33 (s, 3H), 1.02 (s, 3H), 0.95 (s, 3H), 0.91 (s, 3H), 0.89 (s, 3H), 0.83 (s, 6H), 0.82 (s, 3H), 0.35-0.20 (m, 4H); ESI-MS: m/z 787.55 $(M+H)^+$.

Example 6: Preparation of (1R,3S)-3-((((1R,3aS,5aR,5bR,7aR,9S,11aR,11bR,13aR,13bR)-3a-(((S)-2-(1,1-dioxidothiomorpholino)-3-methylbutyl)amino)-5a,5b,8,8,11a-pentamethyl-1-(1-methylcyclopropyl)icosahydro-1H-cyclopenta chrysen-9-yl)oxy)carbonyl)-2,2-dimethylcyclobutane-1-carboxylic acid

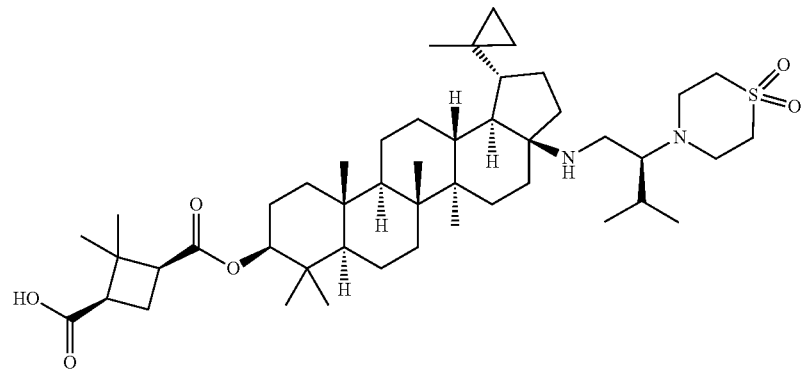

Step 1: Synthesis of 1-benzyl 3-((1R,3aS,5aR,5bR, 7aR,9S,11aR,11bR,13aR,13bR)-3a-(((S)-2-(1,1-dioxidothiomorpholino)-3-methylbutyl)amino)-5a,5b, 8,8,11a-pentamethyl-1-(1-methyl cyclopropyl) icosahydro-1H-cyclopenta[a]chrysen-9-yl) (1R,3S)-2,2-dimethylcyclobutane-1,3-dicarboxylate

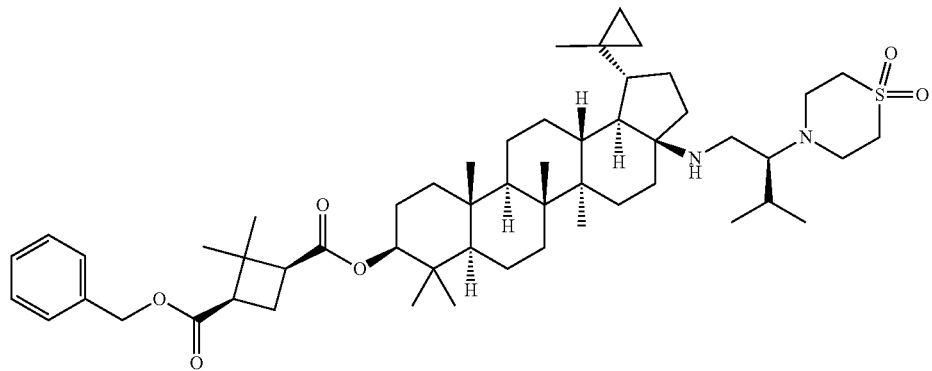

To a stirred solution of (S)-4-(1-hydroxy-3-methylbutan-2-yl)thiomorpholine 1,1-dioxide (Intermediate 7, 0.290 g, 1.311 mmol, 1.5 eq) in DCM (10 ml) at 0° C. was added Trifluoromethanesulfonic anhydride (0.234 ml, 1.399 mmol, 1.6 eq). The reaction mixture was stirred at 0° C. for about 10 minutes. 2,6-Lutidine (0.161 ml, 1.399 mmol, 1.6 eq) was added and stirred at 0° C. for 10 minutes. 1-((1R,3aS,5aR, 5bR,7aR,9S,11aR,11bR,13aR, 13bR)-3a-amino-5a,5b,8,8, 11a-pentamethyl-1-(1-methylcyclopropyl)icosahydro-1H-cyclo penta[a]chrysen-9-yl) 3-benzyl (1S,3R)-2,2-dimethylcyclobutane-1,3-dicarboxylate (Intermediate 1, 0.6 g, 0.8745 mmol, 1.0 eq) and triethylamine (0.36 ml, 2.623 mmol, 3.0 eq) were added sequentially at 0° C. and allowed to stir at room temperature for about 4 hours. TLC indicated starting material was consumed and the desired product was observed. The reaction mixture was quenched with saturated sodium bicarbonate solution and extracted with DCM (2×20 ml). The combined organic layer was washed with water, dried over Na$_2$SO$_4$, filtered and concentrated under reduced pressure. The crude compound was purified by silica gel column chromatography using 2% methanol in DCM as an eluent to obtain the title compound (0.4 g, 51.48% yield) as an off-white solid. $^1$H NMR (300 MHz, CDCl$_3$): δ ppm 7.36-7.31 (m, 5H), 5.15, 5.09 (ABq, J$_{AB}$=12.3 Hz, 2H), 4.44 (dd, J=11.1, 4.8 Hz, 1H), 3.15-3.13 (m, 4H), 3.03-2.98 (m, 4H), 2.84-2.73 (m, 2H), 2.70-2.59 (m, 1H), 2.50-2.37 (m, 2H), 2.32-2.24 (m, 1H), 2.14-0.77 (m, 33H), 1.34 (s, 3H), 1.04 (s, 3H), 0.96 (s, 6H), 0.91 (s, 3H), 0.87 (s, 3H), 0.85 (s, 3H), 0.84 (s, 3H), 0.39-0.20 (m, 4H); ESI-MS: m/z 889.65 (M+H)$^+$.

Step 2: Synthesis of (1R,3S)-3-(((((1R,3aS,5aR,5bR, 7aR,9S,11aR,11bR,13aR,13bR)-3a-(((S)-2-(1,1-dioxidothiomorpholino)-3-methylbutyl)amino)-5a,5b, 8,8,11a-pentamethyl-1-(1-methyl cyclopropyl) icosahydro-1H-cyclopenta[a]chrysen-9-yl)oxy) carbonyl)-2,2-dimethylcyclobutane-1-carboxylic acid

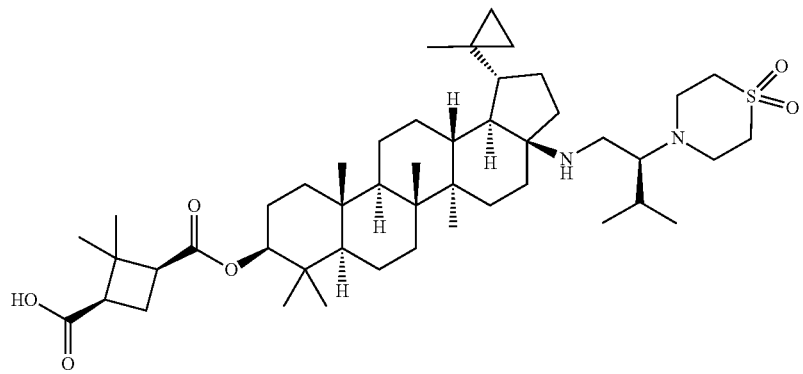

To a stirred solution of 1-benzyl 3-((1R,3aS,5aR,5bR, 7aR,9S,11aR,11bR,13aR,13bR)-3a-(((S)-2-(1,1-dioxidothiomorpholino)-3-methylbutyl)amino)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate (step 1, 0.4 g, 0.449 mmol, 1.0 eq) in methanol (4 ml) and THF (4 ml) was added aqueous 2.5N KOH solution (1.35 ml, 3.373 mmol, 7.5 eq). The reaction mixture was stirred at room temperature for overnight. TLC indicated starting material was consumed and the desired product was observed. The reaction mixture was evaporated under reduced pressure, cooled to 0° C., pH adjusted to 5.0 with 1N HCl and extracted with DCM (2×25 ml). The combined organic layer was washed with water, dried over Na₂SO₄, filtered and concentrated under reduced pressure. The crude compound was purified by silica gel column chromatography using 5% methanol in DCM as an eluent to obtain the title compound (0.120 g, 33.5% yield) as an off-white solid. ¹H NMR (300 MHz, DMSO-d6): δ ppm 4.44 (m, 1H), 3.06-2.95 (m, 8H), 2.84-2.71 (m, 3H), 2.45-2.24 (m, 5H), 1.95-0.78 (m, 31H), 1.26 (s, 3H), 1.02 (s, 3H), 0.95 (s, 3H), 0.91 (s, 3H), 0.89 (s, 3H), 0.86 (s, 6H), 0.83 (s, 3H), 0.38-0.18 (m, 4H); ESI-MS: m/z 799.60 (M+H)⁺.

Example 7: Preparation of (1R,3S)-3-((((1R,3aS, 5aR,5bR,7aR,9S,11aR,11bR,13aR,13bR)-3a-(((2R, 3R)-2-(1,1-dioxidothiomorpholino)-3-hydroxybutyl) amino)-5a,5b,8,8,11a-pentamethyl-1-(1-methylcyclopropyl)icosahydro-1H-cyclopenta chrysen-9-yl)oxy) carbonyl)-2,2-dimethylcyclobutane-1-carboxylic acid minutes. 1-((1R,3aS,5aR,5bR,7aR,9S,11aR, 11bR,13aR, 13bR)-3a-amino-5a,5b,8,8,11a-pentamethyl-1-(1-methylcyclopropyl)icosahydro-1H-cyclopenta[a]chrysen-9-yl) 3-benzyl (1S,3R)-2,2-dimethylcyclobutane-1,3-dicarboxylate (Intermediate 1, 0.6 g, 0.8745 mmol, 1.0 eq) and triethylamine (0.36 ml, 2.623 mmol, 3.0 eq) were added sequentially at 0° C. and stirred at same temperature for about 1 hour. The reaction mixture was changed to room temperature and stirred for about 4 hours. TLC indicated starting material was consumed and the desired product was observed. The reaction mixture was quenched with saturated sodium bicarbonate solution and extracted with DCM (2×30 ml). The combined organic layer was washed with water,

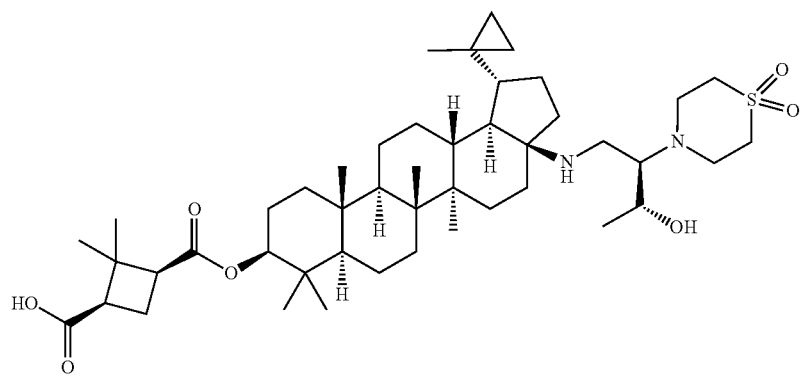

Step 1: Synthesis of 1-benzyl 3-((1R,3aS,5aR,5bR, 7aR,9S,11aR,11bR,13aR,13bR)-3a-(((2R,3R)-3-((tert-butyldimethylsilyl)oxy)-2-(1,1-dioxidothiomorpholino)butyl)amino)-5a,5b, 8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate dried over Na₂SO₄, filtered and concentrated under reduced pressure. The crude compound was purified by silica gel column chromatography using 20% ethyl acetate in hexane as an eluent to obtain the title compound (0.4 g, 45.5% yield) as an off-white solid. ¹H NMR (300 MHz, CDCl₃): δ ppm 7.36-7.33 (m, 5H), 5.15, 5.09 (ABq, $J_{AB}$=12.3 Hz, 2H), 4.44

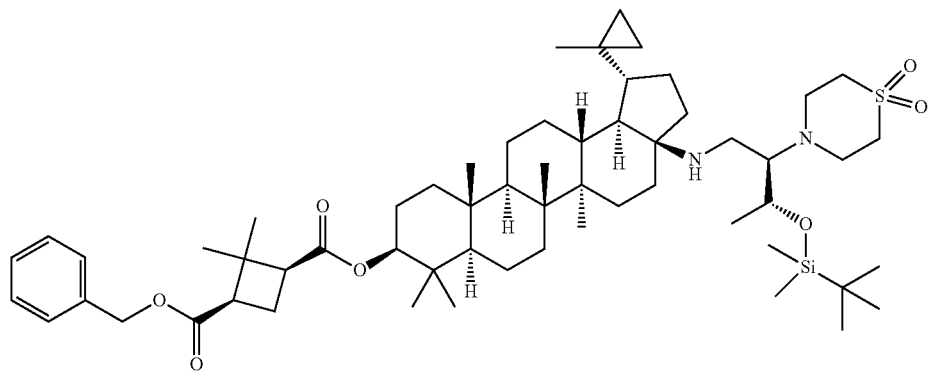

To a stirred solution of 4-((2R,3R)-3-((tert-butyldimethylsilyl)oxy)-1-hydroxybutan-2-yl)thiomorpholine 1,1-dioxide (Intermediate 8, 0.442 g, 1.311 mmol, 1.5 eq) in DCM (10 ml) at 0° C. was added trifluoromethanesulfonic anhydride (0.234 ml, 1.399 mmol, 1.6 eq). The reaction mixture was stirred at 0° C. for 10 minutes. 2,6-Lutidine (0.166 ml, 1.399 mmol, 1.6 eq) was added, stirred at 0° C. for about 10

(dd, J=11.1, 4.5 Hz, 1H), 4.0-3.97 (m, 1H), 3.46-3.35 (m, 2H), 3.28-3.20 (m, 2H), 2.98 (m, 4H), 2.84-2.72 (m, 2H), 2.70-2.60 (m, 1H), 2.60-2.50 (m, 2H), 2.42 (m, 2H), 2.15-0.78 (m, 28H), 1.34 (s, 3H), 1.04 (s, 3H), 0.96 (s, 6H), 0.91 (s, 3H), 0.87 (brs, 12H), 0.85 (s, 3H), 0.84 (s, 3H), 0.38-0.20 (m, 4H), 0.06 (s, 3H), 0.05 (s, 3H); ESI-MS: m/z 1005.85 (M+H)⁺.

Step 2: Synthesis of (1R,3 S)-3-(((((1R,3aS,5aR, 5bR,7 aR,9S,11aR,11bR,13aR,13bR)-3a-(((2R,3R)-3-((tert-butyldimethylsilyl)oxy)-2-(1,1-dioxidothiomorpholino)butyl)amino)-5a, 5b, 8,8,11a-pentamethyl-1-(1-methylcyclopropyl)icosahydro-1H-cyclopenta[a]chrysen-9-yl)oxy) carbonyl)-2,2-dimethylcyclobutane-1-carboxylic acid

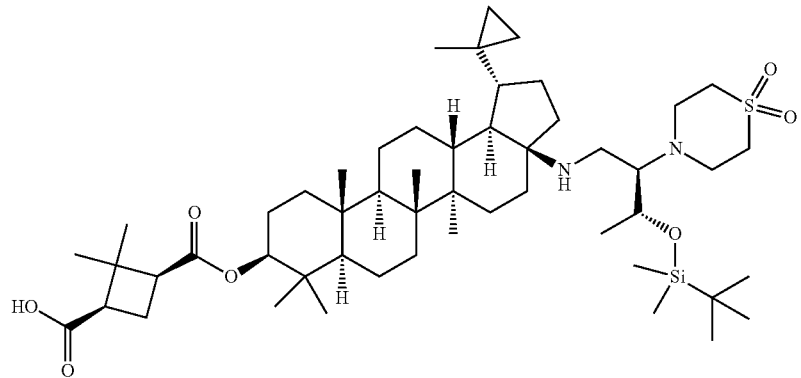

To a stirred solution of 1-benzyl 3-((1R,3aS,5aR,5bR,7aR,9S,11aR,11bR,13aR,13bR)-3a-(((2R,3R)-3-((tert-butyldimethylsilyl)oxy)-2-(1,1-dioxidothiomorpholino)butyl)amino)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate (step 1, 0.4 g, 0.3977 mmol, 1.0 eq) in methanol (5 ml) and THF (5 ml) was added aqueous 2.5N KOH solution (1.19 ml, 2.983 mmol, 7.5 eq). The reaction mixture was stirred at room temperature for overnight. TLC indicated starting material was consumed and the desired product was observed. The reaction mixture was evaporated under reduced pressure, cooled to 0° C., pH adjusted to 5.0 with 1N HCl and extracted with DCM (2×20 ml). The combined organic layer was washed with water, dried over Na$_2$SO$_4$, filtered and concentrated under reduced pressure. The crude compound was purified by silica gel column chromatography using 3% methanol in DCM as an eluent to obtain the title compound (0.3 g, 82.41% yield) as an off-white solid. $^1$H NMR (300 MHz, CDCl$_3$): δ ppm 4.56-4.50 (m, 1H), 3.99-3.96 (m, 1H), 3.43-3.29 (m, 4H), 3.17-3.03 (m, 2H), 3.0-2.82 (m, 3H), 2.78-2.63 (m, 2H), 2.60-2.47 (m, 3H), 2.02-0.78 (m, 29H), 1.33 (s, 3H), 1.03 (s, 3H), 0.99 (s, 3H), 0.94 (s, 3H), 0.92 (s, 3H), 0.89 (s, 3H), 0.88 (s, 3H), 0.87 (s, 9H), 0.85 (s, 3H), 0.40-0.22 (m, 4H), 0.06 (s, 3H), 0.04 (s, 3H); ES-MS: m/z 915.60 (M+H)$^+$.

Step 3: Synthesis of (1R,3S)-3-(((((1R,3aS,5aR,5bR,7aR,9S,11aR,11bR,13aR,13bR)-3a-(((2R,3R)-2-(1,1-dioxidothiomorpholino)-3-hydroxybutyl)amino)-5a,5b,8,8,11a-pentamethyl-1-(1-methylcyclopropyl)icosahydro-1H-cyclopenta[a]chrysen-9-yl)oxy)carbonyl)-2,2-dimethylcyclobutane-1-carboxylic acid

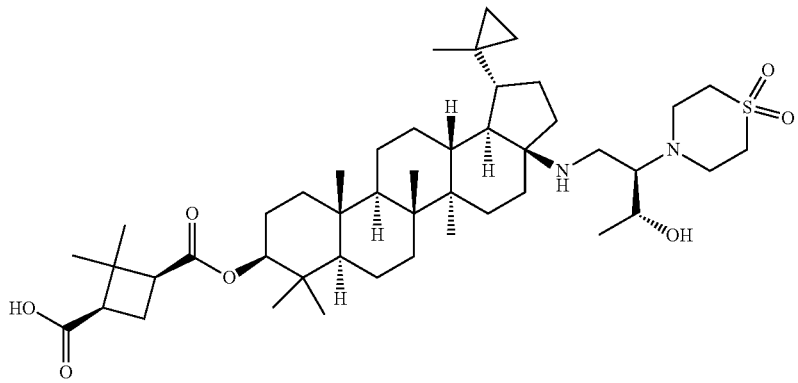

To a stirred solution of (1R,3S)-3-(((((1R,3aS,5aR,5bR,7aR,9S,11aR,11bR,13aR, 13bR)-3a-(((2R,3R)-3-((tert-butyldimethylsilyl)oxy)-2-(1,1-dioxidothiomorpholino)butyl) amino)-5a,5b,8,8,11a-pentamethyl-1-(1-methylcyclopropyl)icosahydro-1H-cyclopenta[a]chrysen-9-yl)oxy)carbonyl)-2,2-dimethylcyclobutane-1-carboxylic acid (step 2, 0.3 g, 0.327 mmol, 1.0 eq) in THF (6 ml) at 0° C. was added Tetra-n-butylammonium fluoride (10 ml, 10.0 mmol, 31.0 eq, 1.0M in THF). The reaction mixture was stirred at room temperature for overnight. TLC indicated starting material was consumed and the desired product was observed. The reaction mixture was diluted with water (20 ml) and extracted with DCM (2×20 ml). The combined organic layer was washed with water, dried over Na$_2$SO$_4$, filtered and evaporated under reduced pressure. The crude compound was purified by silica gel column chromatography using 5% methanol in DCM as an eluent to obtain the title compound (65 mg, 24.8% yield) as an off-white solid. $^1$H NMR (300 MHz, CDCl$_3$): δ ppm 4.48-4.45 (m, 1H), 3.75 (m, 1H), 3.33 (m, 2H), 3.20-3.05 (m, 6H), 2.82-2.74 (m, 2H), 2.63-2.53 (m, 5H), 2.10-2.0 (m, 2H), 1.97-0.78 (m, 26H), 1.33 (s, 3H), 1.07 (s, 6H), 0.98 (s, 3H), 0.91 (s, 3H), 0.89 (s, 3H), 0.86 (s, 6H), 0.42-0.20 (m, 4H); ES-MS: m/z 802.2 (M+H)$^+$.

Example 8: Preparation of (1R,3S)-3-((((1R,3aS, 5aR,5bR,7aR,9S,11aR,11bR,13aR,13bR)-3a-(((S)-2-(1,1-dioxidothiomorpholino)-3-hydroxypropyl) amino)-5a,5b,8,8,11a-pentamethyl-1-(1-methylcyclopropyl)icosahydro-1H-cyclopenta[a] chrysen-9-yl)oxy)carbonyl)-2,2-dimethylcyclobutane-1-carboxylic acid (0.47 ml, 2.798 mmol, 1.6 eq). The reaction mixture was stirred at 0° C. for about 10 minutes. 2,6-Lutidine (0.32 ml, 2.798 mmol, 1.6 eq) was added and stirred at 0° C. for about 10 minutes. 1-((1R,3aS,5aR,5bR,7aR,9S,11aR,11bR,13aR, 13bR)-3a-amino-5a,5b,8,8,11a-pentamethyl-1-(1-methylcyclopropyl) icosahydro-1H-cyclopenta[a]chrysen-9-yl) 3-benzyl (1S,3R)-2,2-dimethylcyclobutane-1,3-dicarboxylate (Intermediate 1, 1.2 g, 1.749 mmol, 1.0 eq) and triethylamine (0.39 ml, 2.798 mmol, 1.6 eq) were added sequentially at 0° C., stirred at same temperature for about 1 hour. The reaction mixture was changed to room temperature and stirred for overnight. TLC indicated starting material was consumed and the desired product was observed. The reaction mixture was diluted with DCM (150 ml), washed with saturated sodium bicarbonate solution, water and brine solution. The organic layer was dried over Na$_2$SO$_4$, filtered and

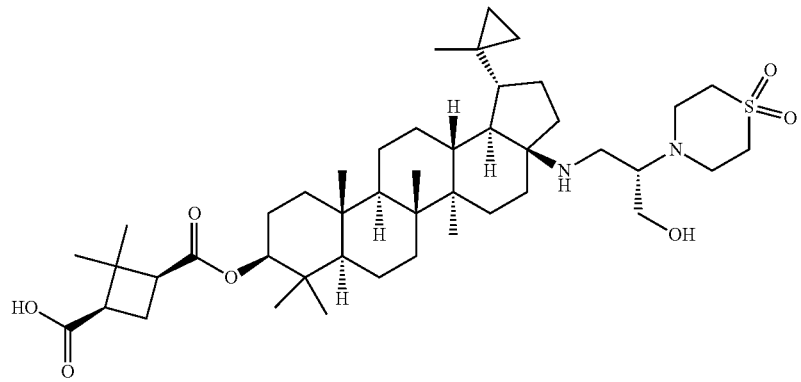

Step 1: Synthesis of 1-benzyl 3-((1R,3aS,5aR,5bR, 7aR,9S,11aR,11bR,13aR,13bR)-3a-(((S)-3-((tert-butyldimethylsilyl)oxy)-2-(1,1-dioxidothiomorpholino)propyl)amino)-5a,5b,8,8,11a-pentamethyl-1-(1-methylcyclopropyl)icosahydro-1H-cyclopenta[a] chrysen-9-yl) (1R,3S)-2,2-dimethylcyclobutane-1,3-dicarboxylate concentrated under reduced pressure. The crude compound was purified by silica gel column chromatography using 0-15% ethyl acetate in hexane gradient to obtain the title compound (1 g, 57.8% yield) as an off-white solid. $^1$H NMR (300 MHz, CDCl$_3$): δ ppm 7.36-7.33 (m, 5H), 5.15, 5.09 (ABq, J$_{AB}$=12.3 Hz, 2H), 4.44 (dd, J=11.1, 4.8 Hz, 1H), 3.71-3.67 (m, 2H), 3.30-3.22 (m, 2H), 3.18-3.06 (m, 2H),

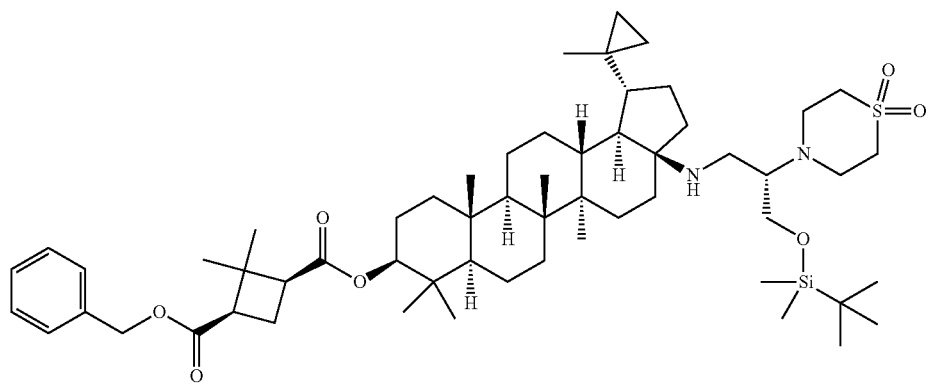

To a stirred solution of (S)-4-(1-((tert-butyldimethylsilyl) oxy)-3-hydroxypropan-2-yl)thiomorpholine 1,1-dioxide (Intermediate 9, 0.844 g, 2.623 mmol, 1.5 eq) in DCM (24 ml) at 0° C. was added Trifluoromethanesulfonic anhydride 3.05-2.90 (m, 5H), 2.83-2.72 (m, 3H), 2.70-2.59 (m, 2H), 2.46-2.32 (m, 2H), 2.10-1.20 (m, 26H), 1.0-0.78 (m, 31H), 0.39-0.23 (m, 4H), 0.05 (s, 6H); ES-MS: m/z 992.09 (M+H)$^+$.

Step 2: Synthesis of (1R,3S)-3-((((1R,3aS,5aR,5bR,7aR,9S,11aR,11bR,13aR,13bR)-3a-(((S)-3-((tert-butyldimethylsilyl)oxy)-2-(1,1-dioxidothiomorpholino)propyl)amino)-5a,5b,8,8,11a-pentamethyl-1-(1-methylcyclopropyl)icosahydro-1H-cyclopenta[a]chrysen-9-yl)oxy) carbonyl)-2,2-dimethylcyclobutane-1-carboxylic acid

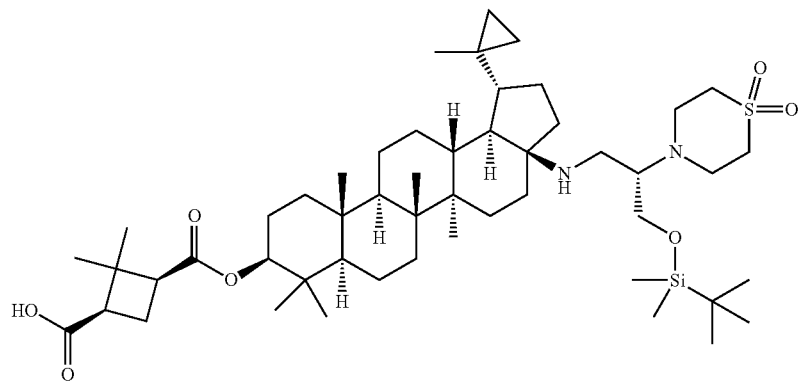

To a stirred solution of 1-benzyl 3-((1R,3aS,5aR,5bR,7aR,9S,11aR,11bR,13aR,13bR)-3a-(((S)-3-((tert-butyldimethylsilyl)oxy)-2-(1,1-dioxidothiomorpholino)propyl)amino)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate (step 1, 1.0 g, 1.008 mmol, 1.0 eq) in methanol (12 ml) and THF (12 ml) was added aqueous 2.5N KOH solution (3.0 ml, 7.564 mmol, 7.5 eq). The reaction mixture was stirred at room temperature for overnight. TLC indicated starting material was consumed and the desired product was observed. The reaction mixture was evaporated under reduced pressure, cooled to 0° C., pH adjusted to 5.0 with 1N HCl and extracted with DCM (2×100 ml). The combined organic layer was washed with water (100 ml) and brine solution (100 ml). The organic layer was dried over Na$_2$SO$_4$, filtered and concentrated under reduced pressure. The crude compound was purified by silica gel column chromatography using 0-6% methanol in DCM as an eluent to obtain the title compound (0.4 g, 44.4% yield) as an off-white solid. $^1$H NMR (300 MHz, CDCl$_3$): δ ppm 4.45 (m, 1H), 3.69-3.65 (m, 2H), 3.30 (m, 2H), 3.10-2.96 (m, 7H), 2.80-2.72 (m, 3H), 2.60-2.50 (m, 2H), 2.10-0.78 (m, 38H), 1.36 (s, 3H), 0.91 (s, 3H), 0.88 (s, 9H), 0.86 (s, 6H), 0.35-0.27 (m, 4H), 0.05 (s, 6H); ES-MS: m/z 902.18 (M+H)$^+$.

Step 3: Synthesis of (1R,3S)-3-((((1R,3aS,5aR,5bR,7aR,9S,11aR,11bR,13aR,13bR)-3a-(((S)-2-(1,1-dioxidothiomorpholino)-3-hydroxypropyl)amino)-5a,5b,8,8,11a-pentamethyl-1-(1-methylcyclopropyl)icosahydro-1H-cyclopenta[a]chrysen-9-yl)oxy)carbonyl)-2,2-dimethyl cyclobutane-1-carboxylic acid

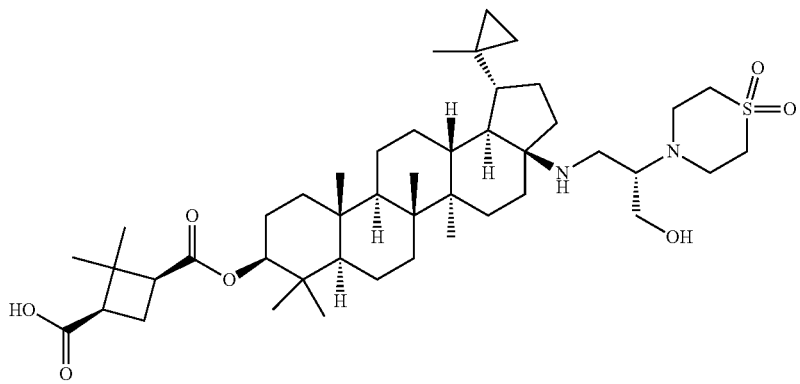

To a stirred solution of (1R,3S)-3-((((1R,3aS,5aR,5bR,7aR,9S,11aR,11bR,13aR, 13bR)-3a-(((S)-3-((tert-butyldimethylsilyl)oxy)-2-(1,1-dioxidothiomorpholino)propyl)amino)-5a,5b,8,8,11a-pentamethyl-1-(1-methylcyclopropyl)icosahydro-1H-cyclopenta[a]chrysen-9-yl)oxy)carbonyl)-2,2-dimethylcyclobutane-1-carboxylic acid (step 2, 0.4 g, 0.444 mmol, 1.0 eq) in THF (10 ml) at 0° C. was added TBAF (0.532 ml, 0.532 mmol, 1.2 eq, 1.0 M in THF). The reaction mixture was stirred at room temperature for about 4 hours. TLC indicated starting material was consumed and the desired product was observed. The reaction mixture was evaporated under reduced pressure, diluted with water and extracted with DCM. The organic layer was dried over Na$_2$SO$_4$, filtered and evaporated under reduced pressure. The residue was purified by silica gel column chromatography using 0-10% methanol in DCM gradient to obtain the title compound (90 mg, 25.7% yield) as an off-white solid.

¹H NMR (300 MHz, DMSO-d6): δ ppm 4.40-4.32 (m, 1H), 3.62-3.58 (m, 1H), 3.50-3.45 (m, 1H), 3.10-2.92 (m, 8H), 2.82-2.70 (m, 3H), 2.38-2.23 (m, 5H), 1.92-0.78 (m, 24H), 1.26 (s, 3H), 0.99 (s, 3H), 0.94 (s, 3H), 0.91 (s, 3H), 0.89 (s, 3H), 0.83 (s, 6H), 0.81 (s, 3H), 0.33-0.22 (m, 4H); ESI-MS: m/z 788.27 (M+H)⁺.

Example 9: Preparation of (1R,3S)-3-((((1R,3aS, 5aR,5bR,7aR,9S,11aR,11bR,13aR,13bR)-3a-(((S)-2-(1,1-dioxidothiomorpholino)-3-fluoropropyl)amino)-5a,5b,8,8,11a-pentamethyl-1-(1-methylcyclopropyl) icosahydro-1H-cyclopenta chrysen-9-yl)oxy) carbonyl)-2,2-dimethyl cyclobutane-1-carboxylic acid

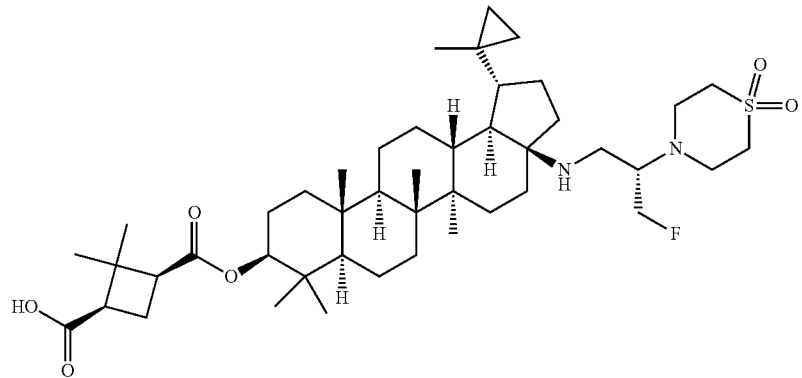

Step 1: Synthesis of 1-benzyl 3-((1R,3aS,5aR,5bR, 7aR,9S,11aR,11bR,13aR,13bR)-3a-(((S)-2-(1,1-dioxidothiomorpholino)-3-fluoropropyl)amino)-5a,5b, 8,8,11a-pentamethyl-1-(1-methyl cyclopropyl) icosahydro-1H-cyclopenta[a]chrysen-9-yl) (1R,3 S)-2,2-dimethylcyclobutane-1,3-dicarboxylate

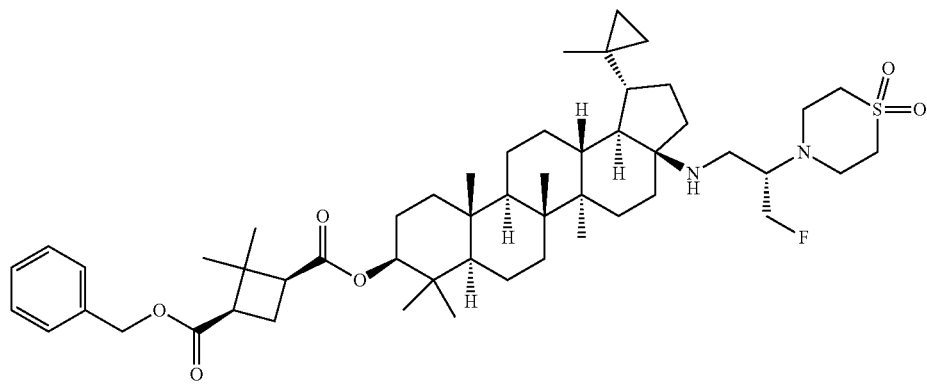

To a stirred solution of (S)-4-(1-fluoro-3-hydroxypropan-2-yl)thiomorpholine 1,1-dioxide (Intermediate 10, 0.922 g, 4.372 mmol, 3.0 eq) in DCM (10 ml) at 0° C. was added Trifluoromethanesulfonic anhydride (0.78 ml, 4.664 mmol, 3.2 eq). The reaction mixture was stirred at 0° C. for about 10 minutes. 2,6-Lutidine (0.54 ml, 4.664 mmol, 3.2 eq) was added, stirred at 0° C. for about 10 minutes. 1-((1R,3aS, 5aR,5bR,7aR,9S,11aR,11bR,13aR,13bR)-3a-amino-5a,5b, 8,8,11a-pentamethyl-1-(1-methylcyclopropyl)icosahydro-1H-cyclopenta[a]chrysen-9-yl) 3-benzyl (1S,3R)-2,2-dimethylcyclobutane-1,3-dicarboxylate (Intermediate 1, 1.0 g, 1.457 mmol, 1.0 eq) and triethylamine (0.65 ml, 4.664 mmol, 3.2 eq) were added sequentially at 0° C., stirred at same temperature for about 1 hour. The reaction mixture was stirred at room temperature for overnight. TLC indicated starting material was consumed and the desired product was observed. The reaction mixture was diluted with DCM (100 ml), washed with saturated sodium bicarbonate solution (100 ml) and brine solution (100 ml). The organic layer was dried over Na₂SO₄, filtered and concentrated under reduced pressure. The crude compound was purified by silica gel column chromatography using 0-20% ethyl acetate in hexanes gradient to obtain the title compound (0.300 g, 23.4% yield) as an off-white solid. ¹H NMR (300 MHz, CDCl₃): δ ppm 7.36-7.33 (m, 5H), 5.15, 5.09 (ABq, J$_{AB}$=12.3 Hz, 2H), 4.67 (d, J=4.5 Hz, 1H), 4.51 (d, J=4.8 Hz, 1H), 4.44 (dd, J=11.1, 4.5 Hz, 1H), 3.28-3.14 (m, 4H), 3.11-3.07 (m, 1H), 3.05-2.98 (m, 4H), 2.85-2.73 (m, 3H), 2.69-2.62 (m, 1H), 2.53-2.47 (m, 3H), 2.08-0.78 (m, 24H), 1.34 (s, 3H), 1.0 (s, 3H), 0.96 (s, 3H), 0.95 (s, 3H), 0.91 (s, 3H), 0.86 (s, 3H), 0.85 (s, 3H), 0.84 (s, 3H), 0.40-0.20 (m, 4H); ES-MS: m/z 880.01 (M+H)⁺.

Step 2: Synthesis of (1R,3S)-3-((((1R,3aS,5aR,5bR,7aR,9S,11aR,11bR,13aR,13bR)-3a-(((S)-2-(1,1-dioxidothiomorpholino)-3-fluoropropyl)amino)-5a,5b,8,8,11a-pentamethyl-1-(1-methylcyclopropyl)icosahydro-1H-cyclopenta[a]chrysen-9-yl)oxy)carbonyl)-2,2-dimethyl cyclobutane-1-carboxylic acid

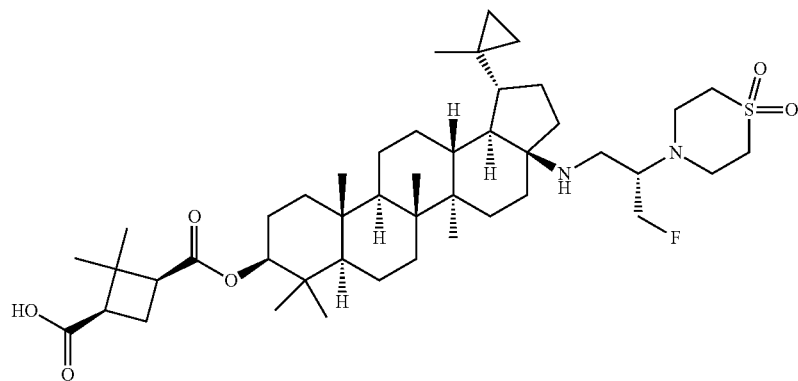

To a stirred solution of 1-benzyl 3-((1R,3aS,5aR,5bR,7aR,9S,11aR,11bR,13aR,13bR)-3a-(((S)-2-(1,1-dioxidothiomorpholino)-3-fluoropropyl)amino)-5a,5b,8,8,11a-pentamethyl-1-(1-methylcyclopropyl)icosahydro-1H-cyclopenta[a]chrysen-9-yl) (1R,3S)-2,2-dimethyl cyclobutane-1,3-dicarboxylate (step 1, 0.300 g, 0.341 mmol, 1.0 eq) in methanol (3 ml) and THF (3 ml) was added aqueous 2.5N KOH solution (1 ml, 2.559 mmol, 7.5 eq). The reaction mixture was stirred at room temperature for overnight. TLC indicated starting material was consumed and the desired product was observed. The reaction mixture was evaporated under reduced pressure, cooled to 0° C., pH adjusted to 4.0 with 1N HCl and extracted with DCM (2×100 ml). The combined organic layer was washed with water (100 ml), dried over sodium sulfate, filtered and concentrated under reduced pressure. The crude compound was purified by silica gel column chromatography using 0-5% methanol in dichloromethane gradient. The obtained compound was further purified by treating with DCM: hexane (1:9 ratio), solid was filtered and dried under vacuum to obtain the title compound (0.090 g, 33.4% yield) as a white solid. $^1$H NMR (300 MHz, CDCl$_3$): δ ppm 4.67 (d, J=4.5 Hz, 1H), 4.51 (d, J=4.5 Hz, 1H), 4.46 (dd, J=11.1, 4.2 Hz, 1H), 3.23-3.0 (m, 9H), 2.84-2.75 (m, 3H), 2.64-2.56 (m, 4H), 2.09-0.78 (m, 24H), 1.37 (s, 3H), 1.07 (s, 3H), 1.01 (s, 3H), 0.96 (s, 3H), 0.91 (s, 3H), 0.87 (s, 6H), 0.85 (s, 3H), 0.38-0.29 (m, 4H); ES-MS: m/z 790.02 (M+H)$^+$.

Example 10: Preparation of (1R,3S)-3-((((1R,3aS,5aR,5bR,7aR,9S,11aR,11bR,13aR,13bR)-3a-(((R)-2-(1,1-dioxidothiomorpholino)-3-fluoropropyl)amino)-5a,5b,8,8,11a-pentamethyl-1-(1-methylcyclopropyl)icosahydro-1H-cyclopenta[a]chrysen-9-yl)oxy)carbonyl)-2,2-dimethyl cyclobutane-1-carboxylic acid

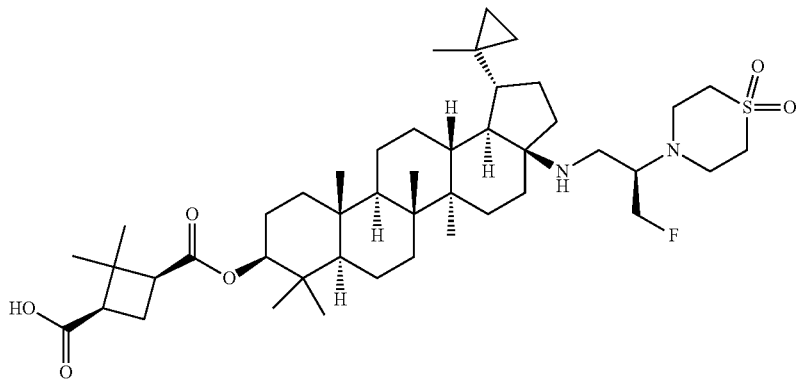

Step 1: Synthesis of 1-benzyl 3-((1R,3aS,5aR,5bR,
7aR,9S,11aR,11bR,13aR,13bR)-3a-(((R)-2-(1,1-
dioxidothiomorpholino)-3-fluoropropyl)amino)-5a,
5b,8,8,11a-pentamethyl-1-(1-methyl cyclopropyl)
icosahydro-1H-cyclopenta[a]chrysen-9-yl) (1R,3S)-
2,2-dimethylcyclobutane-1,3-dicarboxylate compound (0.200 g, 22.2% yield) as an off-white solid. $^1$H NMR (300 MHz, CDCl$_3$): δ ppm 7.36-7.35 (m, 5H), 5.15, 5.09 (ABq, J$_{AB}$=12.3 Hz, 2H), 4.64-4.62 (m, 1H), 4.48-4.36 (m, 2H), 3.27-3.22 (m, 2H), 3.18-3.02 (m, 7H), 2.85-2.72 (m, 3H), 2.59-2.50 (m, 1H), 2.42-2.32 (m, 1H), 2.10-0.78

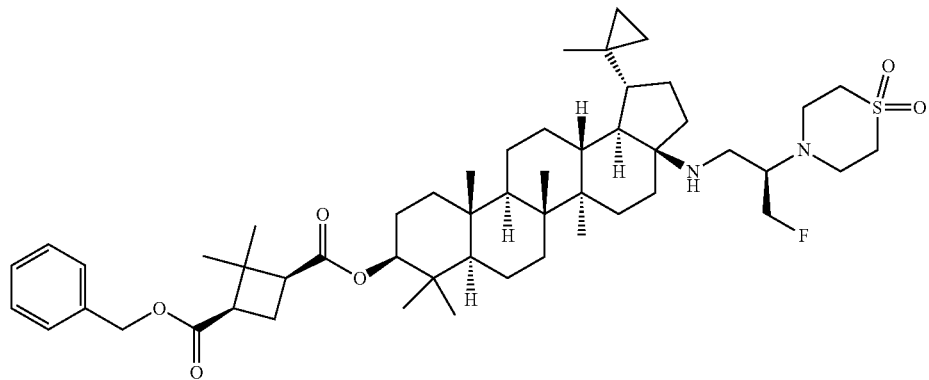

To a stirred solution of (R)-4-(1-fluoro-3-hydroxypropan-2-yl)thiomorpholine 1,1-dioxide (Intermediate 11, 0.645 g, 3.061 mmol, 3.0 eq) in DCM (14 ml) at 0° C. was added trifluoromethanesulfonic anhydride (0.548 ml, 3.265 mmol, 3.2 eq). After 10 minutes stirring at 0° C., 2,6-Lutidine (0.38 ml, 3.265 mmol, 3.2 eq) was added and stirred at same temperature for about 10 minutes. 1-((1R,3aS,5aR,5bR,7aR,9S,11aR,11bR,13aR,13bR)-3a-amino-5a,5b,8,8,11a-pentamethyl-1-(1-methylcyclopropyl)icosahydro-1H-cyclopenta[a]chrysen-9-yl) 3-benzyl (1S,3R)-2,2-dimethylcyclobutane-1,3-dicarboxylate (Intermediate 1, 0.700 g, 1.020 mmol, 1.0 eq) and triethylamine (0.45 ml, 3.265 mmol, 3.2 eq) were added to the reaction mixture and stirred at 0° C. for about 1 hour. The reaction mixture was allowed to stir at room temperature for overnight. TLC indicated starting material was completed and the desired product was observed. The reaction mixture was diluted with DCM (100 ml), washed with saturated sodium bicarbonate solution (100 ml), water and brine solution (100 ml). The organic layer was dried over sodium sulfate, filtered and concentrated under reduced pressure. The crude compound was purified by silica gel column chromatography using 0-20% ethyl acetate in hexanes gradient to obtain the title (m, 26H), 1.34 (s, 3H), 1.04 (s, 3H), 0.97 (s, 6H), 0.91 (s, 3H), 0.86 (s, 3H), 0.85 (s, 3H), 0.84 (s, 3H), 0.40-0.20 (m, 4H); ES-MS: m/z 880.01 (M+H)$^+$.

Step 2: Synthesis of (1R,3S)-3-((((1R,3aS,5aR,5bR,
7aR,9S,11aR,11bR,13aR,13bR)-3a-(((R)-2-(1,1-
dioxidothiomorpholino)-3-fluoropropyl)amino)-5a,
5b,8,8,11a-pentamethyl-1-(1-methylcyclopropyl)
icosahydro-1H-cyclopenta[a]chrysen-9-yl)oxy)
carbonyl)-2,2-dimethyl cyclobutane-1-carboxylic
acid

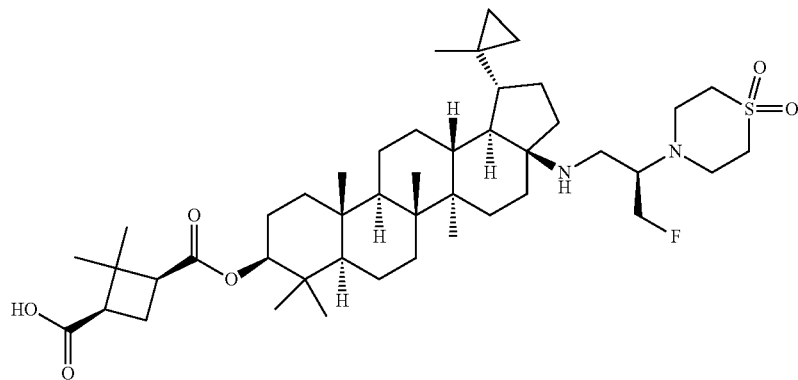

To a stirred solution of 1-benzyl 3-((1R,3aS,5aR,5bR,7aR,9S,11aR,11bR,13aR,13bR)-3a-(((R)-2-(1,1-dioxidothiomorpholino)-3-fluoropropyl)amino)-5a,5b,8,8,11a-pentamethyl-1-(1-methylcyclopropyl)icosahydro-1H-cyclopenta[a]chrysen-9-yl) (1R,3S)-2,2-dimethyl cyclobutane-1,3-dicarboxylate (step 1, 0.200 g, 0.227 mmol, 1.0 eq) in methanol (2 ml) and THF (2 ml) was added aqueous 2.5N KOH solution (0.68 ml, 1.706 mmol, 7.5 eq). The reaction mixture was stirred at room temperature for overnight. TLC indicated starting material was consumed and the desired product was observed. The reaction mixture was evaporated under reduced pressure, cooled to 0° C., pH adjusted to 4.0 with 1N HCl and extracted with DCM (2×100 ml). The combined organic layer was washed with water (100 ml), dried over sodium sulfate, filtered and concentrated under reduced pressure. The crude compound was purified by silica gel column chromatography using 0-5% methanol in dichloromethane gradient. The obtained compound was further purified by treating with DCM:hexane (1:9 ratio), precipitates formed were filtered and dried under vacuum to obtain the title compound (0.080 g, 44.6% yield) as a white solid. $^1$H NMR (300 MHz, CDCl$_3$): δ ppm 4.64-4.40 (m, 3H), 3.30-2.98 (m, 9H), 2.80-2.50 (m, 5H), 2.20-0.78 (m, 26H), 1.35 (s, 3H), 1.05 (s, 3H), 1.01 (s, 3H), 0.92 (s, 9H), 0.88 (s, 3H), 0.87 (s, 3H), 0.40-0.20 (m, 4H); ES-MS: m/z 790.02 (M+H)$^+$.

Example 11: Preparation of (1R,3S)-3-((((1R,3aS,5aR,5bR,7aR,9S,11aR,11bR,13aR,13bR)-3a-(((S)-2-(4-(isopropylsulfonyl)piperazin-1-yl)propyl)amino)-5a,5b,8,8,11a-pentamethyl-1-(1-methylcyclopropyl) icosahydro-1H-cyclopenta[a]chrysen-9-yl)oxy) carbonyl)-2,2-dimethyl cyclobutane-1-carboxylic acid mmol, 1.5 eq) in DCM (30 ml) at 0° C. was added trifluoromethanesulfonic anhydride (0.41 ml, 2.478 mmol, 1.7 eq). After 10 minutes stirring at 0° C., 2,6-Lutidine (0.28 ml, 2.478 mmol, 1.7 eq) was added and stirred at 0° C. for about 10 minutes. 1-(((1R,3aS,5aR,5bR,7aR,9S,11aR,11bR,13aR,13bR)-3a-amino-5a,5b,8,8,11a-pentamethyl-1-(1-methylcyclopropyl)icosahydro-1H-cyclopenta[a]chrysen-9-yl) 3-benzyl (1S,3R)-2,2-dimethylcyclobutane-1,3-dicarboxylate (Intermediate 1, 1.0 g, 1.457 mmol, 1.0 eq) dissolved in DCM (10 ml) followed by triethylamine (0.6 ml, 4.372 mmol, 3.0 eq) were added to the reaction mixture and stirred at 0° C. for about 1 hour. The reaction mixture was allowed to stir at room temperature for about 4 hours. TLC indicated starting material was consumed and the desired product was observed. The reaction mixture was diluted with water (150 ml) and extracted with DCM (3×200 ml). The combined organic layer was washed with water (100 ml) and brine solution (100 ml). The organic layer was dried over sodium sulfate, filtered and concentrated under reduced pressure. The crude compound was purified by silica gel column

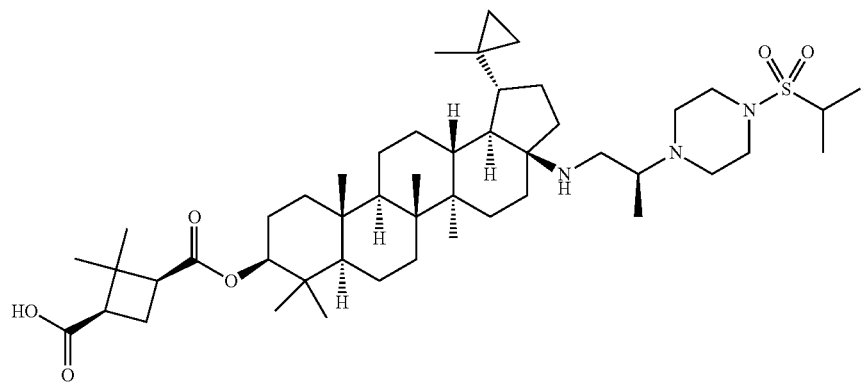

Step 1: Synthesis of 1-benzyl 3-((1R,3aS,5aR,5bR,7aR,9S,11aR,11bR,13aR,13bR)-3a-(((S)-2-(4-(isopropylsulfonyl)piperazin-1-yl)propyl)amino)-5a,5b,8,8,11a-pentamethyl-1-(1-methyl cyclopropyl) icosahydro-1H-cyclopenta[a]chrysen-9-yl) (1R,3S)-2,2-dimethylcyclobutane-1,3-dicarboxylate chromatography using 2% methanol in dichloromethane eluent. The fractions containing the expected product were combined and concentrated under reduced pressure to obtain the title compound (0.350 g, 26.3% yield) as a yellow semi solid. $^1$H NMR (300 MHz, CDCl$_3$): δ ppm 7.35 (m, 5H), 5.15, 5.09 (ABq, J$_{AB}$=12.3 Hz, 2H), 4.44 (dd, J=11.1, 4.8

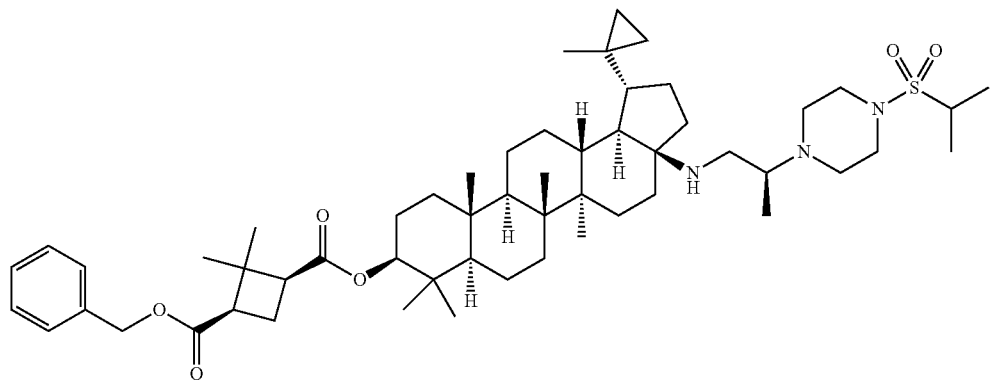

To a stirred solution of (S)-2-(4-(isopropylsulfonyl)piperazin-1-yl)propan-1-ol (Intermediate 12, 0.547 g, 2.186

Hz, 1H), 3.48-3.31 (m, 4H), 3.23-3.18 (m, 1H), 2.92-2.43 (m, 10H), 2.10-0.78 (m, 35H), 1.34 (s, 3H), 1.10 (s, 3H), 1.0

(s, 3H), 0.96 (s, 3H), 0.93 (s, 3H), 0.87 (s, 3H), 0.85 (s, 3H), 0.84 (s, 3H), 0.40-0.20 (m, 4H); ES-MS: m/z 919.03 (M+H)$^+$.

Step 2: Synthesis of (1R,3S)-3-(((((1R,3aS,5aR,5bR, 7aR,9S,11aR,11bR,13aR,13bR)-3a-(((S)-2-(4-(iso-propylsulfonyl)piperazin-1-yl)propyl)amino)-5a,5b, 8,8,11a-pentamethyl-1-(1-methyl cyclopropyl) icosahydro-1H-cyclopenta[a]chrysen-9-yl)oxy) carbonyl)-2,2-dimethyl cyclobutane-1-carboxylic acid

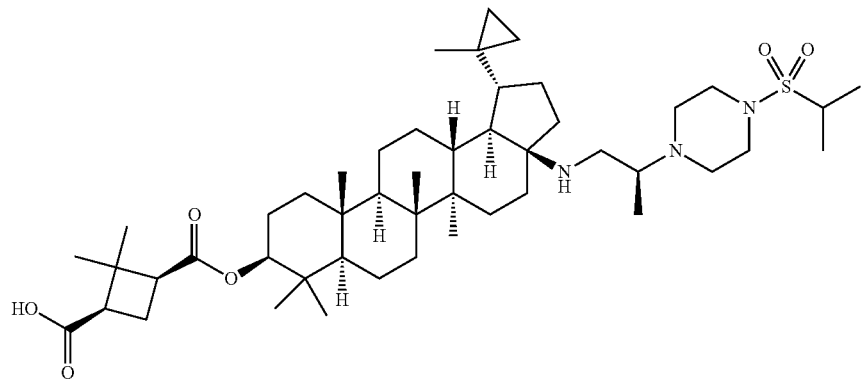

To a stirred solution of 1-benzyl 3-((1R,3aS,5aR,5bR, 7aR,9S,11aR,11bR,13aR,13bR)-3a-(((S)-2-(4-(isopropyl sulfonyl)piperazin-1-yl)propyl)amino)-5a,5b,8,8,11a-pentamethyl-1-(1-methylcyclopropyl)icosahydro-1H-cyclopenta[a]chrysen-9-yl) (1R,3S)-2,2-dimethyl cyclobutane-1, 3-dicarboxylate (step 1, 0.350 g, 0.381 mmol, 1.0 eq) in methanol (3.5 ml) and THF (3.5 ml) at 0° C. was added aqueous 2.5N KOH solution (1.14 ml, 2.858 mmol, 7.5 eq). The reaction mixture was stirred at room temperature for overnight. TLC indicated starting material was consumed and the desired product was observed. The reaction mixture was evaporated under reduced pressure, cooled to 0° C., pH adjusted to 4.0 with 1N HCl and extracted with DCM (3×150 ml). The combined organic layers were washed with water (150 ml), dried over sodium sulfate, filtered and evaporated under reduced pressure. The crude compound was purified by silica gel column chromatography using 6% methanol in dichloromethane eluent. The fractions containing the expected product were combined and concentrated under reduced pressure. The obtained compound was dissolved in DCM (2 ml), treated with hexane (10 ml), stirred at room temperature for about 15 minutes. The precipitates formed were collected by filtration and dried under vacuum to obtain the title compound (70 mg, 22.2% yield) as an off-white solid. $^1$H NMR (300 MHz, CDCl$_3$): δ ppm 4.47 (m, 1H), 3.50-3.30 (m, 4H), 3.25-3.15 (m, 1H), 2.93 (m, 1H), 2.83-2.73 (m, 2H), 2.68-2.50 (m, 7H), 2.10-0.78 (m, 35H), 1.34 (s, 3H), 1.17 (s, 3H), 1.07 (s, 3H), 1.03 (s, 3H), 0.93 (s, 3H), 0.90 (s, 3H), 0.86 (s, 6H), 0.52-0.22 (m, 4H); ES-MS: m/z 829.01 (M+H)$^+$.

Example 12: Preparation of (1R,3S)-3-(((((1R,3aS, 5aR,5bR,7aR,9S,11aR,11bR,13aR,13bR)-3a-(((2R,3 S)-2-(1,1-dioxidothiomorpholino)-3-fluorobutyl) amino)-5a,5b,8,8,11a-pentamethyl-1-(1-methylcyclopropyl)icosahydro-1H-cyclopenta chrysen-9-yl) oxy)carbonyl)-2,2-di methylcyclobutane-1-carboxylic acid

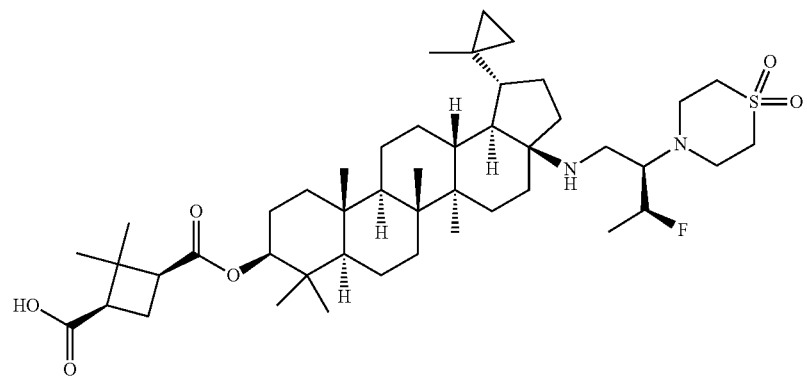

Step 1: Synthesis of 1-benzyl 3-((1R,3aS,5aR,5bR, 7aR,9S,11aR,11bR,13aR,13bR)-3a-(((2R,3S)-2-(1,1-dioxidothiomorpholino)-3-fluorobutyl)amino)-5a,5b, 8,8,11a-pentamethyl-1-(1-methylcyclopropyl) icosahydro-1H-cyclopenta[a]chrysen-9-yl) (1R,3 S)-2,2-dimethyl cyclobutane-1,3-dicarboxylate

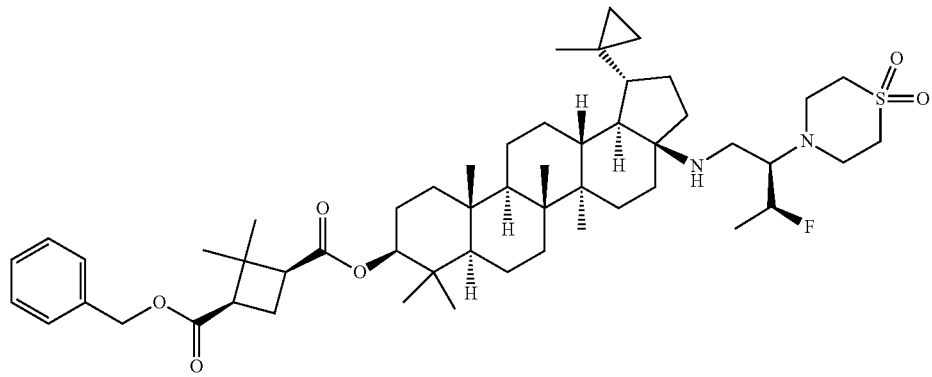

To a stirred solution of 4-((2R,3S)-3-fluoro-1-hydroxybutan-2-yl)thiomorpholine 1,1-dioxide (Intermediate 13, 0.590 g, 2.623 mmol, 2.0 eq) in DCM (20 ml) at 0° C. was added 2,6-Lutidine (0.45 ml, 3.933 mmol, 3.0 eq). The reaction mixture was stirred at 0° C. for about 10 minutes, then trifluoromethanesulfonic anhydride (0.567 ml, 3.277 mmol, 2.5 eq) was added and stirred at same temperature for about 15 minutes. 1-((1R,3aS,5aR,5bR,7aR, 9S,11aR,11bR,13aR, 13bR)-3a-amino-5a,5b,8,8,11a-pentamethyl-1-(1-methylcyclopropyl) icosahydro-1H-cyclopenta[a]chrysen-9-yl) 3-benzyl (1S,3R)-2,2-dimethylcyclobutane-1,3-dicarboxylate (Intermediate 1, 0.9 g, 1.311 mmol, 1.0 eq) and triethylamine (0.55 ml, 3.933 mmol, 3.0 eq) were added to the reaction mixture and stirred at 0° C. for about 4 hours. The reaction mixture was allowed to stir at room temperature for overnight. Saturated sodium bicarbonate solution was added to the reaction mixture and extracted with DCM (2×30 ml). The combined organic layer was washed with water, dried over sodium sulfate and concentrated under reduced pressure. The crude compound was purified by silica gel column chromatography using 20% ethyl acetate in hexanes as an eluent to obtain the title compound (0.3 g, 25.64% yield) as an off-white solid. $^1$H NMR (300 MHz, CDCl$_3$): δ ppm 7.36-7.34 (m, 5H), 5.15, 5.09 (ABq, J$_{AB}$=12.3 Hz, 2H), 4.44 (dd, J=11.1, 4.5 Hz, 1H), 4.50-4.48 (m, 0.5H), 4.33-4.31 (m, 0.5H), 3.22-3.13 (m, 2H), 3.10-3.0 (m, 7H), 2.85-2.58 (m, 4H), 2.55-2.43 (m, 1H), 2.08-0.78 (m, 29H), 1.34 (s, 3H), 0.99 (s, 3H), 0.96 (s, 6H), 0.90 (s, 3H), 0.85 (s, 6H), 0.84 (s, 3H), 0.40-0.20 (m, 4H); ES-MS: m/z 893.91 (M+H)$^+$.

Step 2: Synthesis of (1R,3 S)-3-((((1R,3aS,5aR, 5bR,7 aR,9S,11aR,11bR,13aR,13bR)-3a-(((2R,3 S)-2-(1,1-dioxidothiomorpholino)-3-fluorobutyl) amino)-5a,5b,8,8,11a-pentamethyl-1-(1-methylcyclopropyl)icosahydro-1H-cyclopenta[a]chrysen-9-yl) oxy)carbonyl)-2,2-dimethyl cyclobutane-1-carboxylic acid

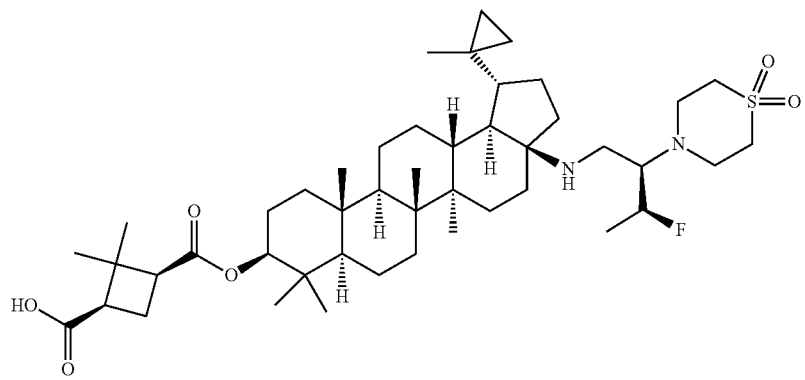

To a stirred solution of 1-benzyl 3-((1R,3aS,5aR,5bR, 7aR,9S,11aR,11bR,13aR,13bR)-3a-(((2R,3 S)-2-(1,1-dioxidothiomorpholino)amino)-5a,5b,8,8,11a-penta methyl-1-(1-methylcyclopropyl)icosahydro-1H-cyclopenta[a]chrysen-9-yl) (1R,3S)-2,2-dimethylcyclobutane-1,3-dicarboxylate (step 1, 0.3 g, 0.335 mmol, 1.0 eq) in methanol (3 ml) and THF (3 ml) was added aqueous 2.5N KOH solution (1.0 ml, 2.518 mmol, 7.5 eq). The reaction mixture was stirred at room temperature for overnight. TLC indicated starting material was consumed and the desired product was observed. The reaction mixture was evaporated, cooled to 0° C., pH adjusted to 5.0 with 1N HCl and extracted with DCM (2×25 ml). The combined organic layer was washed with water, dried over sodium sulfate and concentrated under reduced pressure. The crude compound was purified by silica gel column chromatography using 2% methanol in dichloromethane as an eluent to obtain the title compound (0.13 g, 48.32% yield) as an off-white solid. $^1$H NMR (300 MHz, CDCl$_3$): δ ppm 4.49-4.32 (m, 2H), 3.21-3.04 (m, 9H), 2.85-2.70 (m, 3H), 2.64-2.48 (m, 2H), 2.10-0.78 (m, 29H), 1.33 (s, 3H), 1.0 (s, 3H), 0.96 (s, 3H), 0.91 (s, 3H), 0.86 (s, 9H), 0.85 (s, 3H), 0.40-0.22 (m, 4H); ES-MS: m/z 803.82 (M+H)$^+$.

Example 13: Preparation of (1R,3S)-3-((((1R,3aS, 5aR,5bR,7aR,9S,11aR,11bR,13aR,13bR)-3a-(((2S, 3S)-2-(1,1-dioxidothiomorpholino)-3-hydroxybutyl) amino)-5a,5b,8,8,11a-penta methyl-1-(1-methylcyclopropyl)icosahydro-1H-cyclopenta[a] chrysen-9-yl)oxy)carbonyl)-2,2-dimethylcyclobutane-1-carboxylic acid

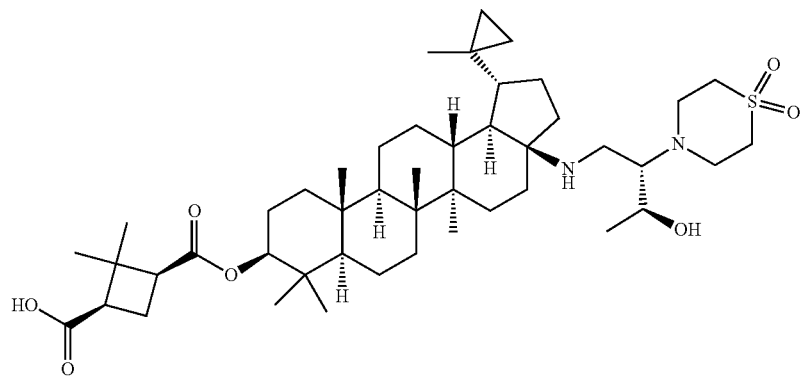

Step 1: Synthesis of 1-benzyl 3-((1R,3aS,5aR,5bR, 7aR,9S,11aR,11bR,13aR,13bR)-3a-(((2S,3S)-3-((tert-butyldimethylsilyl)oxy)-2-(1,1-dioxidothiomorpholino)butyl)amino)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate (0.21 ml, 1.86 mmol, 1.6 eq) was added to the reaction mixture, stirred for about 10 minutes. 1-((1R,3aS,5aR,5bR, 7aR,9S,11aR,11bR,13aR,13bR)-3a-amino-5a,5b,8,8,11a-pentamethyl-1-(1-methylcyclopropyl)icosahydro-1H-cyclopenta[a]chrysen-9-yl) 3-benzyl (1S,3R)-2,2-dimethylcyclobutane-1,3-dicarboxylate (Intermediate 1, 0.800 g, 1.166 mmol, 1.0 eq) followed by triethylamine (0.48 ml, 3.498 mmol, 3.0 eq) were added to the reaction mixture and stirred at 0° C. for about 1 hour. The reaction mixture was changed to room temperature and stirred for overnight. TLC indicated starting material was completed and the desired product was observed. The reaction mixture was quenched with aqueous sodium bicarbonate solution and extracted with DCM (3×100 ml). The combined organic layer was washed with water (100 ml), dried over sodium sulfate, filtered and concentrated under reduced pressure. The crude compound was purified by silica gel column chromatography using 20-30% ethyl acetate in hexanes gradient to obtain the title compound (0.400 g, 34% yield) as an off-white solid. $^1$H NMR (300 MHz, CDCl$_3$): δ ppm 7.36-7.30 (m, 5H), 5.15, 5.09 (ABq, J$_{AB}$=12.3 Hz, 2H), 4.45 (dd, J=11.1, 4.5 Hz, 1H), 3.95-3.92 (m, 1H), 3.44-3.39 (m,

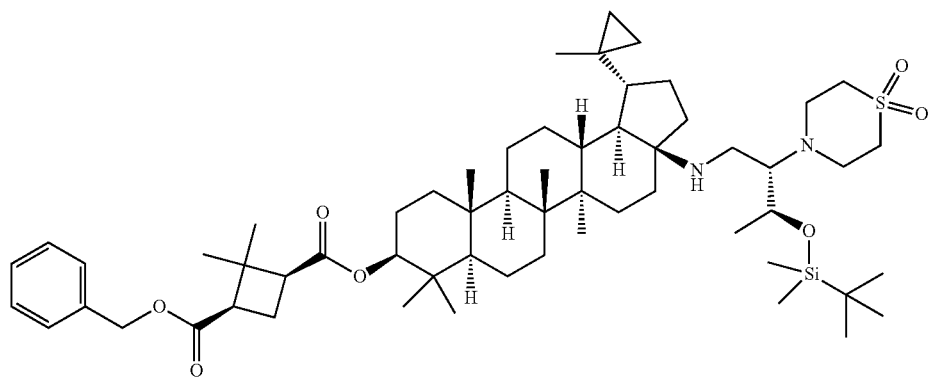

To a stirred solution of 4-((2S,3S)-3-((tert-butyldimethylsilyl)oxy)-1-hydroxybutan-2-yl)thiomorpholine 1,1-dioxide (Intermediate 14, 0.787 g, 2.33 mmol, 2.0 eq) in DCM (16 ml) at 0° C. was added trifluoromethanesulfonic anhydride (0.31 ml, 1.86 mmol, 1.6 eq). The reaction mixture was stirred at 0° C. for about 10 minutes. Next, 2,6-Lutidine 2H), 3.21-3.11 (m, 2H), 3.03-2.93 (m, 5H), 2.84-2.73 (m, 2H), 2.69-2.62 (m, 1H), 2.59-2.53 (m, 2H), 2.47-2.35 (m, 2H), 2.08-0.78 (m, 30H), 1.34 (s, 3H), 1.0 (s, 3H), 0.96 (s, 3H), 0.96 (s, 3H), 0.91 (s, 3H), 0.87 (s, 9H), 0.85 (s, 3H), 0.84 (s, 3H), 0.36-0.23 (m, 4H), 0.05 (s, 3H), 0.04 (s, 3H); ES-MS: m/z 1005.97 (M+H)$^+$.

Step 2: Synthesis of (1R,3S)-3-((a 1R,3aS,5aR,5bR, 7aR,9S,11aR,11bR,13aR,13bR)-3a-(((2S,3S)-3-((tert-butyldimethylsilyl)oxy)-2-(1,1-dioxidothiomorpholino)butyl)amino)-5a,5b,8,8,11a-pentamethyl-1-(1-methylcyclopropyl)icosahydro-1H-cyclopenta[a]chrysen-9-yl)oxy) carbonyl)-2,2-dimethylcyclobutane-1-carboxylic acid

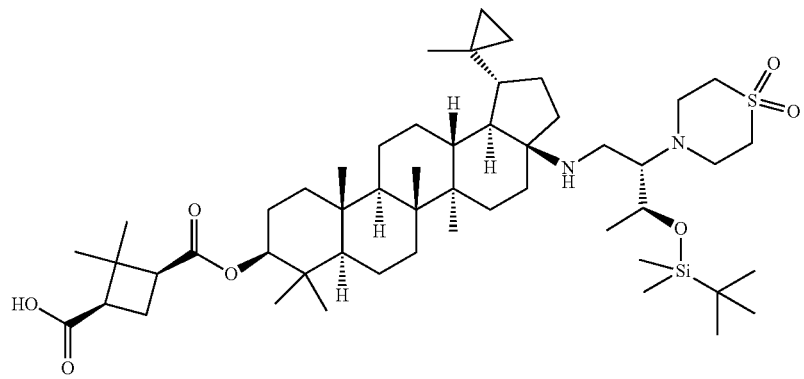

To a stirred solution of 1-benzyl 3-((1R,3aS,5aR,5bR, 7aR,9S,11aR,11bR,13aR,13bR)-3a-(((2S,3S)-3-((tert-butyldimethylsilyl)oxy)-2-(1,1-dioxidothiomorpholino)butyl)amino)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate (step 1, 0.400 g, 0.397 mmol, 1.0 eq) in methanol (4 ml) and THF (4 ml) was added aqueous 1.5N KOH solution (1.9 ml, 2.98 mmol, 7.5 eq). The reaction mixture was stirred at room temperature for about 5 hours. TLC indicated starting material was completed and the desired product was observed. The reaction mixture was evaporated under reduced pressure, cooled to 0° C., acidified with 1N HCl to pH 4.0 and extracted with DCM (3×50 ml). The combined organic layer was washed with water (50 ml), dried over sodium sulfate, filtered and evaporated under reduced pressure. The residue was purified by silica gel column chromatography using 0-6% methanol in dichloromethane gradient to obtain the title compound (0.200 g, 55% yield) as a solid. $^1$H NMR (300 MHz, CDCl$_3$): δ ppm 4.49-4.44 (m, 1H), 4.0-3.92 (m, 1H), 3.40-3.22 (m, 4H), 3.04-2.90 (m, 5H), 2.80-2.70 (m, 3H), 2.60-2.50 (m, 3H), 2.32 (m, 1H), 2.10-0.78 (m, 36H), 1.33 (s, 3H), 1.06 (s, 3H), 1.04 (s, 3H), 0.97 (s, 3H), 0.95 (s, 3H), 0.91 (s, 3H), 0.89 (s, 6H), 0.40-0.20 (m, 4H), 0.04 (s, 3H), 0.03 (s, 3H); ES-MS: m/z 915.74 (M+H)$^+$.

Step 3: Synthesis of (1R,3S)-3-((((1R,3aS,5aR,5bR, 7aR,9S,11aR,11bR,13aR,13bR)-3a-(((2S,3 S)-2-(1,1-dioxidothiomorpholino)-3-hydroxybutyl)amino)-5a,5b,8,8,11a-pentamethyl-1-(1-methylcyclopropyl)icosahydro-1H-cyclopenta[a]chrysen-9-yl)oxy)carbonyl)-2,2-dimethylcyclobutane-1-carboxylic acid

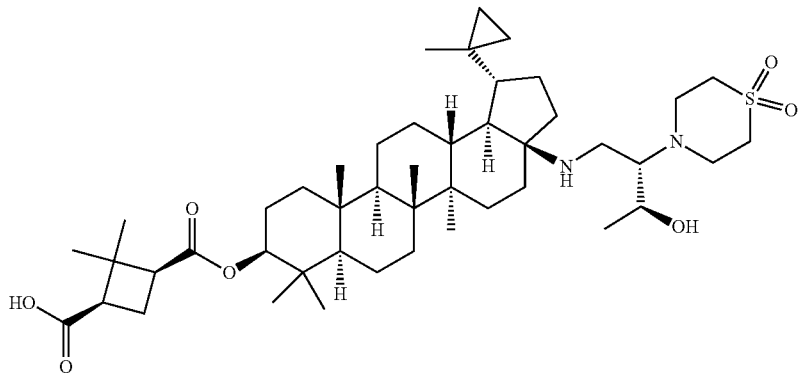

To a stirred solution of (1R,3S)-3-((((1R,3aS,5aR,5bR, 7aR,9S,11aR,11bR,13aR, 13bR)-3a-(((2S,3S)-3-((tert-butyldimethylsilyl)oxy)-2-(1,1-dioxidothiomorpholino)butyl) amino)-5a,5b,8,8,11a-pentamethyl-1-(1-methylcyclopropyl)icosahydro-1H-cyclopenta[a]chrysen-9-yl)oxy)carbonyl)-2,2-dimethylcyclobutane-1-carboxylic acid (step 2, 0.200 g, 0.218 mmol, 1.0 eq) in THF (2 ml) at 0° C. was added TBAF (0.654 ml, 0.654 mmol, 3.0 eq, 1.0M in THF). The reaction mixture was stirred at room temperature for overnight. TLC indicated starting material was not completed, again TBAF (1.526 ml, 1.526 mmol, 7.0 eq) was added at 0° C., changed to room temperature and stirred at room temperature for overnight. TLC indicated starting material was completed and the desired product was observed. The reaction mixture was diluted with water (50 ml) and extracted with DCM (3×30 ml). The combined organic layers were washed with water (50 ml), dried over sodium sulfate, filtered and evaporated under reduced pressure. The residue was purified by silica gel column chromatography using 0-5% methanol in dichloromethane gradient. The obtained compound was further purified by treating with ethyl acetate (1 ml) and hexane (10 ml), stirred at room temperature for about 10 minutes, filtered and dried under vacuum to obtain the title compound (0.080 g, 45.7% yield) as a solid. $^1$H NMR (300 MHz, CDCl$_3$): δ ppm 4.46 (dd, J=11.7, 4.8 Hz, 1H), 3.80 (m, 1H), 3.42-3.32 (m, 2H), 3.18-3.0 (m, 7H), 2.80-2.50 (m, 7H), 2.08-0.78 (m, 27H), 1.36 (s, 3H), 1.06 (s, 3H), 1.03 (s, 3H), 0.98 (s, 3H), 0.91 (s, 3H), 0.88 (s, 3H), 0.85 (s, 6H), 0.35-0.20 (m, 4H); ES-MS: m/z 801.73 (M+H)$^+$.

Example 14: Preparation of (1R,3S)-3-((((1R,3aS, 5aR,5bR,7aR,9S,11aR,11bR,13aR,13bR)-3a-(((2R, 3R)-3-hydroxy-2-(4-(isopropylsulfonyl)piperazin-1-yl)butyl)amino)-5a,5b,8,8,11a-pentamethyl-1-(1-methylcyclopropyl)icosahydro-1H-cyclopenta[a]chrysen-9-yl)oxy) carbonyl)-2,2-dimethylcyclobutane-1-carboxylic acid To a stirred solution of (2R,3R)-3-((tert-butyldimethylsilyl)oxy)-2-(4-(isopropyl sulfonyl)piperazin-1-yl)butan-1-ol (Intermediate 15, 3.21 g, 8.16 mmol, 1.6 eq) in DCM (50 ml) at 0° C. was added trifluoromethanesulfonic anhydride (1.45 ml, 8.67 mmol, 1.7 eq). The reaction mixture was stirred at 0° C. for about 10 minutes. 2,6-Lutidine (0.65 ml, 8.67 mmol, 1.7 eq) was added and stirred at 0° C. for 15 minutes. 1-((1R,3aS,5aR,5bR,7aR,9S,11aR, 11bR,13aR,13bR)-3a-amino-5a,5b,8,8,11a-pentamethyl-1-(1-methylcyclopropyl) icosahydro-1H-cyclopenta[a]chrysen-9-yl) 3-benzyl (1S, 3R)-2,2-dimethylcyclobutane-1,3-dicarboxylate (Intermediate 1, 3.5 g, 5.10 mmol, 1.0 eq) and triethylamine (2.13 ml, 15.3 mmol, 3.0 eq) were added to the reaction mixture and stirred at 0° C. for about 1 hour. Reaction mixture was changed to room temperature and stirred for overnight. TLC indicated starting material was completed and the desired product was observed. The reaction mixture was diluted with water (100 ml), basified with aqueous sodium bicarbonate solution and extracted with DCM (3×100 ml). The combined organic layer was washed with water (100 ml), dried over sodium sulfate, filtered and concentrated under reduced pressure. The residue was purified by silica gel column chromatography using 0-2%

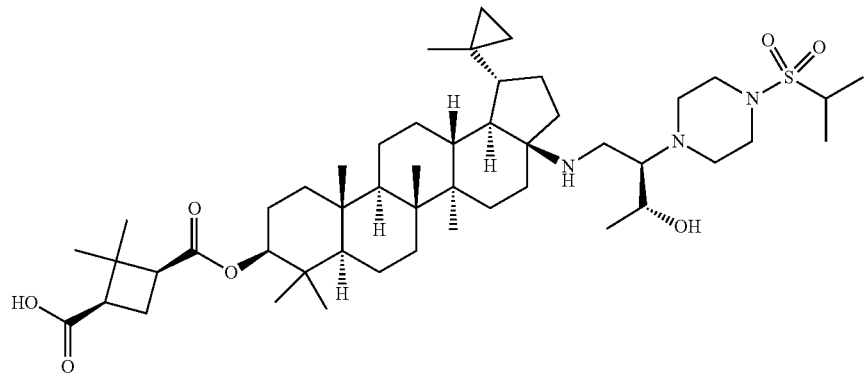

Step 1: Synthesis of 1-benzyl 3-((1R,3aS,5aR,5bR, 7aR,9S,11aR,11bR,13aR,13bR)-3a-(((2R,3R)-3-((tert-butyldimethylsilyl)oxy)-2-(4-(isopropylsulfonyl)piperazin-1-yl)butyl) amino)-5a,5b,8,8,11a-pentamethyl-1-(1-methylcyclopropyl)icosahydro-1H-cyclopenta[a]chrysen-9-yl) (1R,3 S)-2,2-dimethylcyclobutane-1,3-dicarboxylate methanol in dichloromethane gradient to obtain the title compound (2.0 g, 36.9% yield) as a solid. $^1$H NMR (300 MHz, CDCl$_3$): δ ppm 7.35 (m, 5H), 5.15, 5.09 (ABq, J$_{AB}$=12.6 Hz, 2H), 4.44 (dd, J=11.1, 4.5 Hz, 1H), 4.01-3.98 (m, 1H), 3.30-3.15 (m, 5H), 2.90-2.32 (m, 10H), 2.08-1.48 (m, 13H), 1.47-1.13 (m, 24H), 1.07-0.78 (m, 31H), 0.38-0.18 (m, 4H), 0.04 (s, 3H), 0.03 (s, 3H); ES-MS: m/z 1063.68 (M+H)$^+$.

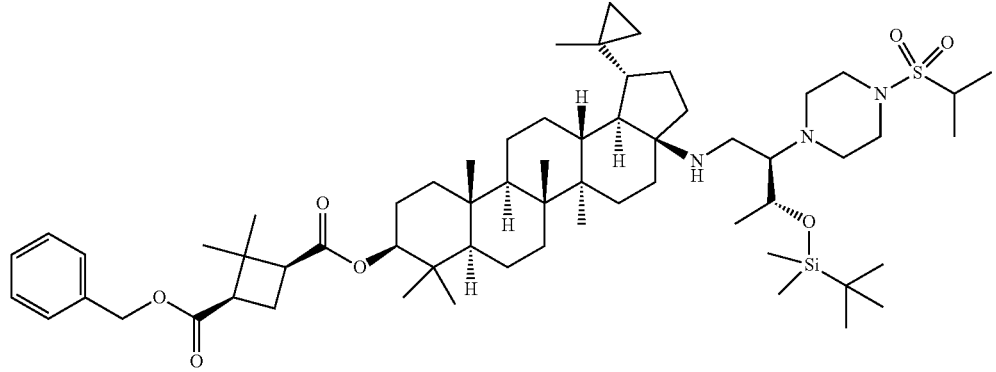

Step 2: Synthesis of 1-benzyl 3-((1R,3aS,5aR,5bR, 7aR,9S,11aR,11bR,13aR,13bR)-3a-(((2R,3R)-3-hydroxy-2-(4-(isopropylsulfonyl)piperazin-1-yl)butyl)amino)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate

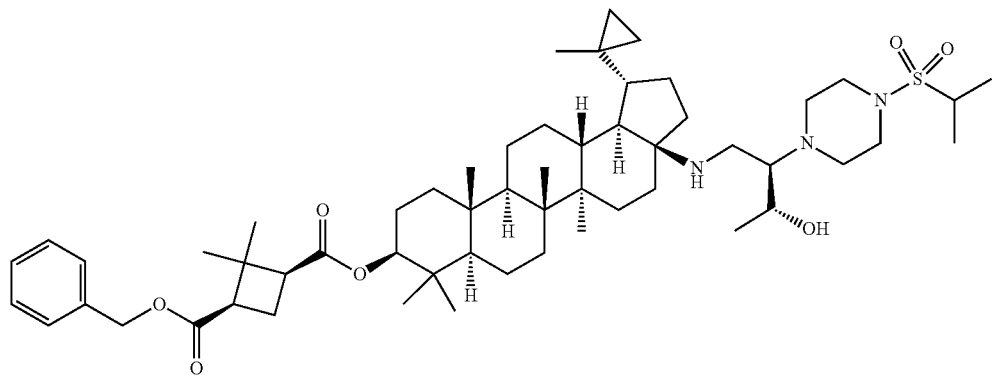

To a stirred solution of 1-benzyl 3-((1R,3aS,5aR,5bR, 7aR,9S,11aR,11bR,13aR,13bR)-3a-(((2R,3R)-3-((tert-butyldimethylsilyl)oxy)-2-(4-(isopropylsulfonyl)piperazin-1-yl)butyl) amino)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate (step 1, 2.0 g, 1.88 mmol, 1.0 eq) in THF (20 ml) at 0° C. was added TBAF (7.52 ml, 7.52 mmol, 4.0 eq, 1.0M in THF). The reaction mixture was stirred at room temperature for overnight. TLC indicated starting material was completed and the desired product was observed. The reaction mixture was diluted with water (100 ml) and extracted with DCM (3×100 ml). The combined organic layer was washed with water (100 ml), dried over sodium sulfate, filtered and concentrated under reduced pressure. The crude compound was purified by silica gel column chromatography using 0-4% methanol in dichloromethane gradient to obtain the title compound (0.500 g, 28% yield) as a solid. $^1$H NMR (300 MHz, CDCl$_3$): δ ppm 7.36-7.31 (m, 5H), 5.15, 5.09 (ABq, J$_{AB}$=12.3 Hz, 2H), 4.44 (dd, J=10.8, 4.5 Hz, 1H), 3.67-3.56 (m, 1H), 3.42-3.33 (m, 4H), 3.25-3.13 (m, 1H), 2.95-2.57 (m, 9H), 2.43-1.90 (m, 6H), 1.88-1.18 (m, 32H), 1.03-0.78 (m, 22H), 0.25-0.24 (m, 4H); ES-MS: m/z 948.93 (M+H)$^+$.

Step 3: Synthesis of (1R,3S)-3-((((1R,3aS,5aR,5bR, 7aR,9S,11aR,11bR,13aR,13bR)-3a-(((2R,3R)-3-hydroxy-2-(4-(isopropylsulfonyl)piperazin-1-yl)butyl)amino)-5a,5b,8,8,11a-pentamethyl-1-(1-methylcyclopropyl)icosahydro-1H-cyclopenta[a]chrysen-9-yl)oxy) carbonyl)-2,2-dimethylcyclobutane-1-carboxylic acid

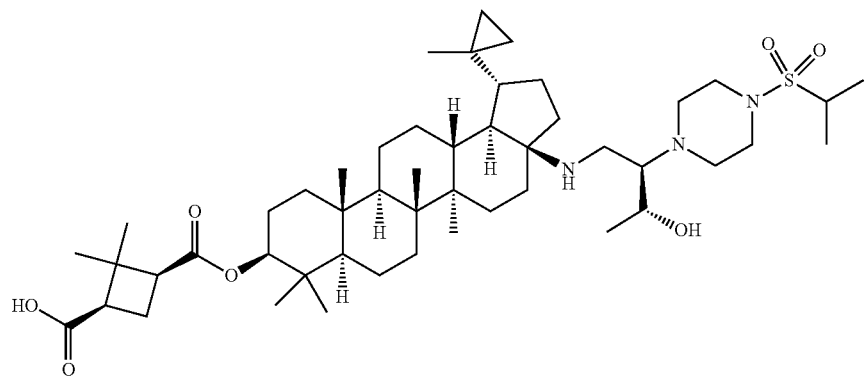

To a stirred solution of 1-benzyl 3-((1R,3aS,5aR,5bR, 7aR,9S,11aR,11bR,13aR,13bR)-3a-(((2R,3R)-3-hydroxy-2-(4-(isopropylsulfonyl)piperazin-1-yl)butyl)amino)-5a,5b,8, 8,11a-pentamethyl-1-(1-methylcyclopropyl)icosahydro-1H-cyclopenta[a]chrysen-9-yl) (1R,3S)-2,2-dimethylcyclobutane-1,3-dicarboxylate (step 2, 0.500 g, 0.527 mmol, 1.0 eq) in THF (5 ml) and methanol (5 ml) at 0° C. was added aqueous 1.5N KOH solution (2.63 ml, 3.954 mmol, 7.5 eq). The reaction mixture was changed to room temperature and stirred for overnight. TLC indicated starting material was completed and the desired product was observed. The reaction mixture was evaporated under reduced pressure. The residue was diluted with water (20 ml), cooled to 0° C., acidified with 1N HCl to pH 4.0 and extracted with DCM (3×50 ml). The combined organic layer was washed with water (50 ml), dried over sodium sulfate, filtered and concentrated under reduced pressure. The residue was purified by silica gel column chromatography using 0-10% methanol in dichloromethane gradient. The obtained compound was treated with DCM (5 ml) and hexane (40 ml), stirred at room temperature for about 15 minutes and solvent was decanted. Again, DCM (5 ml) and hexane (20 ml) were added, stirred at room temperature for about 15 minutes, precipitate formed was filtered and dried under vacuum for 2 hours to obtain the title compound (0.180 g, 40% yield) as a solid. $^1$H NMR (300 MHz, CDCl$_3$): δ ppm 4.46 (dd, J=11.7, 4.8 Hz, 1H), 3.75 (m, 1H), 3.35 (m, 4H), 3.23-3.14 (m, 1H), 2.92-2.88 (m, 2H), 2.79-2.74 (m, 4H), 2.61-2.51 (m, 4H), 2.10-1.2 (m, 35H), 1.10-0.78 (m, 24H), 0.34-0.25 (m, 4H); ES-MS: m/z 858.82 (M+H)$^+$.

Example 15: Preparation of (1R,3S)-3-(((((1R,3aS, 5aR,5bR,7aR,9S,11aR,11bR,13aR,13bR)-3a-(((2R, 3R)-2-(1,1-dioxidothiomorpholino)-3-hydroxybutyl) amino)-5a,5b,8,8,11a-penta methyl-1-(prop-1-en-2-yl)icosahydro-1H-cyclopenta[a]chrysen-9-yl)oxy) carbonyl)-2,2-dimethylcyclobutane-1-carboxylic acid

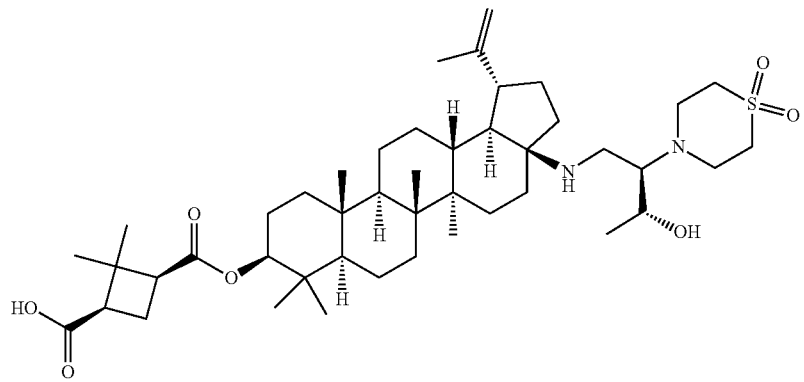

Step 1: Synthesis of 1-benzyl 3-((1R,3aS,5aR,5bR, 7aR,9S,11 aR,11bR,13aR,13bR)-3a-(((2R,3R)-3-((tert-butyldimethylsilyl)oxy)-2-(1,1-dioxidothiomorpholino)butyl)amino)-5a,5b, 8,8,11a-pentamethyl-1-(prop-1-en-2-yl)icosahydro-1H-cyclopenta[a]chrysen-9-yl) (1R,3 S)-2,2-dimethylcyclobutane-1,3-dicarboxylate

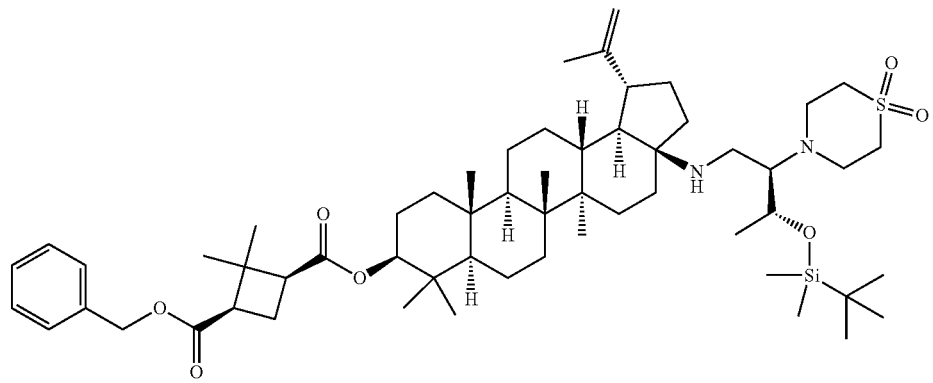

To a stirred solution of 4-((2R,3R)-3-((tert-butyldimethylsilyl)oxy)-1-hydroxybutan-2-yl)thiomorpholine 1,1-dioxide (Intermediate 8, 4.14 g, 12.27 mmol, 1.5 eq) in DCM (80 ml) at 0° C. was added trifluoromethanesulfonic anhydride (2.33 ml, 13.9 mmol, 1.7 eq) and stirred for about 10 minutes. 2,6-Lutidine (1.6 ml, 13.9 mmol, 1.7 eq) was added to the reaction mixture and stirred at 0° C. for about 15 minutes. 1-((1R,3aS,5aR,5bR,7aR,9S,11aR, 11bR,13aR,13bR)-3a-amino-5a,5b,8,8,11a-pentamethyl-1-(prop-1-en-2-yl)icosahydro-1H-cyclopenta[a]chrysen-9-yl) 3-benzyl (1S,3R)-2,2-dimethylcyclobutane-1,3-dicarboxylate (Intermediate 16, 5.5 g, 8.18 mmol, 1.0 eq) and triethylamine (3.42 ml, 24.54 mmol, 3.0 eq) were added to the reaction mixture, stirred at 0° C. for about 1 hour and allowed to stir at room temperature for overnight. TLC indicated starting material was completed and the desired product was observed. Aqueous sodium bicarbonate solution was added to the reaction mixture and extracted with DCM (3×100 ml). The combined organic layer was washed with water (100 ml), dried over sodium sulfate, filtered and concentrated under reduced pressure. The residue was purified by silica gel column chromatography using 0-5% methanol in dichloromethane gradient to obtain the title compound (4.0 g, 49.3% yield) as an off-white solid. $^1$HNMR (300 MHz, CDCl$_3$): δ ppm 7.36-7.30 (m, 5H), 5.14, 5.09 (ABq, $J_{AB}$=12.3 Hz, 2H), 4.69 (s, 1H), 4.58 (s, 1H), 4.43 (dd, J=11.7, 4.5 Hz, 1H), 4.03-3.98 (m, 1H), 3.47-3.37 (m, 2H), 3.30-3.18 (m, 2H), 3.10-2.94 (m, 5H), 2.85-2.40 (m, 7H), 2.07-1.98 (m, 2H), 1.93-0.75 (m, 25H), 1.68 (s, 3H), 1.33 (s, 3H), 1.05 (s, 3H), 0.96 (s, 3H), 0.95 (s, 3H), 0.88 (s, 9H), 0.85 (s, 3H), 0.84 (s, 3H), 0.83 (s, 3H), 0.07 (s, 6H); ES-MS: m/z 991.93 (M+H)$^+$.

Step 2: Synthesis of 1-benzyl 3-((1R,3aS,5aR,5bR,7aR,9S,11aR,11bR,13aR,13bR)-3a-(((2R,3R)-2-(1,1-dioxidothiomorpholino)-3-hydroxybutyl)amino)-5a,5b,8,8,11a-pentamethyl-1-(prop-1-en-2-yl)icosahydro-1H-cyclopenta[a]chrysen-9-yl) (1R,3S)-2,2-dimethyl cyclobutane-1,3-dicarboxylate

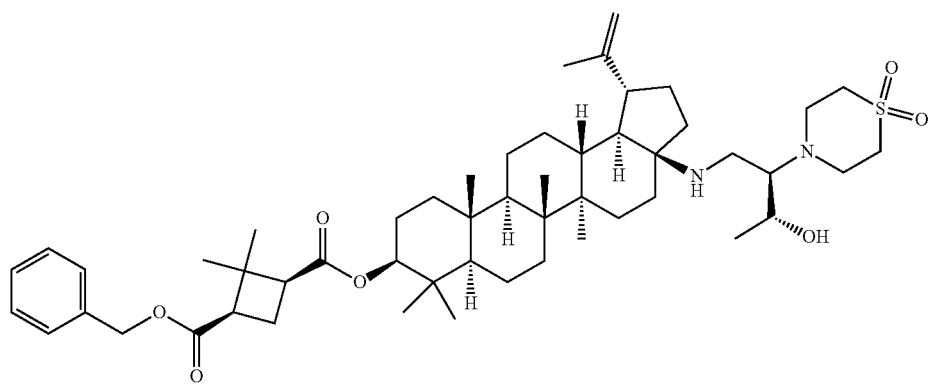

To a stirred solution of 1-benzyl 3-((1R,3aS,5aR,5bR,7aR,9S,11aR,11bR,13aR,13bR)-3a-(((2R,3R)-3-((tert-butyldimethylsilyl)oxy)-2-(1,1-dioxidothiomorpholino)butyl)amino)-5a,5b,8,8,11a-pentamethyl-1-(prop-1-en-2-yl)icosahydro-1H-cyclopenta[a]chrysen-9-yl) (1R,3S)-2,2-dimethylcyclobutane-1,3-dicarboxylate (step 1, 4.0 g, 4.034 mmol, 1.0 eq) in THF (60 ml) at 0° C. was added TBAF (20.17 ml, 20.17 mmol, 5.0 eq, 1.0M in THF). The reaction mixture was changed to room temperature and stirred for overnight. TLC indicated starting material was completed and the desired product was observed. The reaction mixture was diluted with water (50 ml) and extracted with DCM (3×50 ml). The combined organic layer was washed with water (2×50 ml), dried over sodium sulfate, filtered and concentrated under reduced pressure. The residue was purified by silica gel column chromatography using 0-5% methanol in DCM gradient to obtain the title compound (2.0 g, 56.6% yield) as a solid. $^1$H NMR (300 MHz, CDCl$_3$): δ ppm 7.35 (m, 5H), 5.14, 5.09 (ABq, $J_{AB}$=12.3 Hz, 2H), 4.69 (s, 1H), 4.60 (s, 1H), 4.45-4.40 (m, 1H), 3.72 (m, 1H), 3.45-3.35 (m, 2H), 3.13-3.03 (m, 7H), 2.85-2.73 (m, 2H), 2.70-2.58 (m, 2H), 2.57-2.42 (m, 3H), 2.07-1.98 (m, 2H), 1.90-0.75 (m, 25H), 1.68 (s, 3H), 1.34 (s, 3H), 1.05 (s, 3H), 0.96 (s, 6H), 0.85 (s, 3H), 0.84 (s, 3H), 0.83 (s, 3H); ES-MS: m/z 877.84 (M+H)$^+$.

Step 3: Synthesis of (1R,3 S)-3-((((1R,3aS,5aR, 5bR,7aR,9S,11aR,11bR,13aR,13bR)-3a-(((2R,3R)-2-(1,1-dioxidothiomorpholino)-3-hydroxybutyl) amino)-5a,5b,8,8,11a-pentamethyl-1-(prop-1-en-2-yl)icosahydro-1H-cyclopenta[a]chrysen-9-yl)oxy) carbonyl)-2,2-dimethyl cyclobutane-1-carboxylic acid

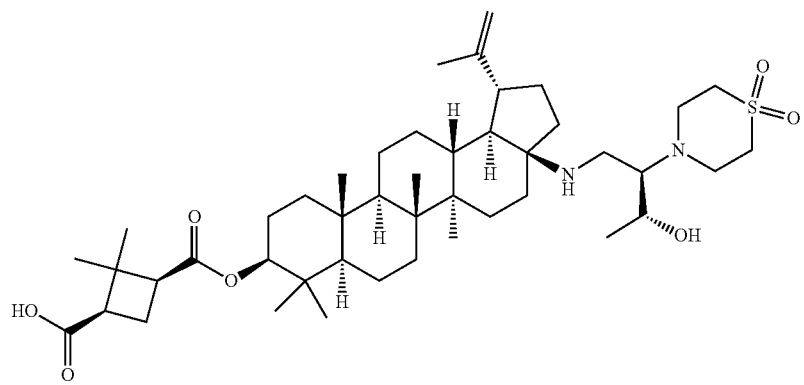

To a stirred solution of 1-benzyl 3-((1R,3aS,5aR,5bR, 7aR,9S,11aR,11bR,13aR,13bR)-3a-(((2R,3R)-2-(1,1-dioxidothiomorpholino)-3-hydroxybutyl)amino)-5a,5b,8,8,11a-penta methyl-1-(prop-1-en-2-yl)icosahydro-1H-cyclopenta[a]chrysen-9-yl) (1R,3S)-2,2-dimethyl cyclobutane-1,3-dicarboxylate (step 2, 2.0 g, 2.279 mmol, 1.0 eq) in THF (12 ml) and methanol (12 ml) at 0° C. was added aqueous 1.5N KOH solution (12 ml, 17.09 mmol, 7.5 eq). The reaction mixture was changed to room temperature and stirred for about 4 hours. TLC indicated starting material was completed and the desired product was observed. The reaction mixture was evaporated under reduced pressure, diluted with water (20 ml), acidified with 1N HCl to pH 4.0 and extracted with DCM (3×50 ml). The combined organic layer was washed with water (20 ml), dried over sodium sulfate, filtered and concentrated under reduced pressure. The residue was purified by silica gel column chromatography using 4-8% methanol in DCM gradient. The obtained compound was further purified by treating with Chloroform (5 ml) and hexane (20 ml), stirred for about 10 minutes and decanted. This procedure was repeated twice, finally filtered and dried under vacuum to obtain the title compound (0.800 g, 44.6% yield) as an off-white solid. $^1$H NMR (300 MHz, CDCl$_3$): δ ppm 4.69 (s, 1H), 4.60 (s, 1H), 4.50-4.45 (m, 1H), 3.83-3.74 (m, 1H), 3.40-3.07 (m, 9H), 2.80-2.49 (m, 7H), 2.07-0.77 (m, 27H), 1.68 (s, 3H), 1.36 (s, 3H), 1.10 (s, 3H), 1.06 (s, 3H), 0.97 (s, 3H), 0.89 (s, 3H), 0.85 (s, 6H); ES-MS: m/z 787.60 (M+H)$^+$.

Example 16: Preparation of (1R,3S)-3-((((1R,3aS, 5aR,5bR,7aR,9S,11aR,11bR,13aR,13bR)-3a-(((R)-2-carboxy-2-(1,1-dioxidothiomorpholino)ethyl) amino)-5a,5b,8,8,11a-pentamethyl-1-(1-methylcyclopropyl)icosahydro-1H-cyclopenta[a] chrysen-9-yl)oxy)carbonyl)-2,2-dimethylcyclobutane-1-carboxylic acid

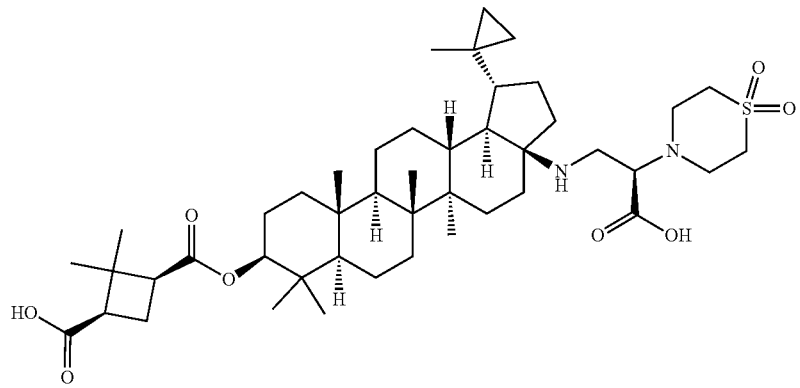

Step 1: Synthesis of 1-benzyl 3-((1R,3aS,5aR,5bR,7aR,9S,11aR,11bR,13aR,13bR)-3a-(((R)-2-(1,1-dioxidothiomorpholino)-3-methoxy-3-oxopropyl)amino)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate

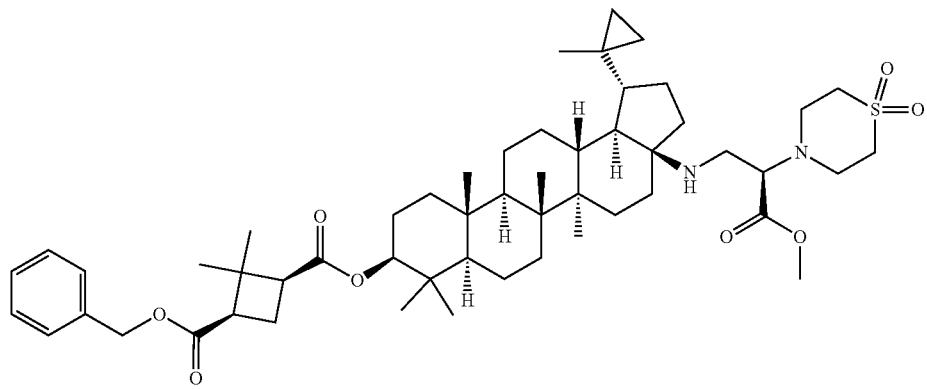

To a stirred solution of methyl (R)-2-(1,1-dioxidothiomorpholino)-3-hydroxypropanoate (Intermediate 5, 0.34 g, 1.457 mmol, 1.25 eq) in dichloromethane (16 ml) at 0° C. was added trifluoromethanesulfonic anhydride (0.27 ml, 1.632 mmol, 1.4 eq). The reaction mixture was stirred at 0° C. for 10 minutes, then 2,6-lutidine (0.19 ml, 1.667 mmol, 1.43 eq) was added and stirred at same temperature for 10 minutes. 1-((1R,3aS,5aR,5bR,7aR,9S,11aR,11bR,13aR,13bR)-3a-amino-5a,5b,8,8,11a-pentamethyl-1-(1-methylcyclopropyl) icosahydro-1H-cyclopenta[a]chrysen-9-yl) 3-benzyl (1S,3R)-2,2-dimethylcyclobutane-1,3-dicarboxylate (Intermediate 1, 0.8 g, 1.166 mmol, 1.0 eq) followed by triethylamine (0.23 ml, 1.667 mmol, 1.43 eq) were added to the reaction mixture and stirred at 0° C. for about 1 hour. The reaction mixture was changed to room temperature and stirred for about 4 hours. TLC indicated starting material was completed and the desired product was observed. The reaction mixture was basified with saturated sodium bicarbonate solution and extracted with dichloromethane (3×50 ml). The combined organic layer was washed with water (20 ml), dried over Na$_2$SO$_4$, filtered and concentrated under reduced pressure. The crude compound was purified by silica gel column chromatography using 0-3% methanol in dichloromethane gradient to obtain the title compound (0.680 g, 64.7% yield) as a solid. $^1$H NMR (300 MHz, CDCl$_3$): δ ppm 7.35 (m, 5H), 5.15, 5.09 (ABq, J$_{AB}$=12.3 Hz, 2H), 4.44 (dd, J=11.1, 4.5 Hz 1H), 3.70 (s, 3H), 3.42-3.35 (m, 1H), 3.35-3.25 (m, 1H), 3.15-2.94 (m, 7H), 2.85-2.57 (m, 5H), 2.08-1.0 (m, 28H), 1.0-0.78 (m, 22H), 0.38-0.20 (m, 4H).

Step 2: Synthesis of (1R,3 S)-3-((((1R,3aS,5aR,5bR,7aR,9S,11aR,11bR,13aR,13bR)-3a-(((R)-2-(1,1-dioxidothiomorpholino)-3-methoxy-3-oxopropyl)amino)-5a,5b,8,8,11a-pentamethyl-1-(1-methylcyclopropyl)icosahydro-1H-cyclopenta[a]chrysen-9-yl)oxy)carbonyl)-2,2-dimethyl cyclobutane-1-carboxylic acid

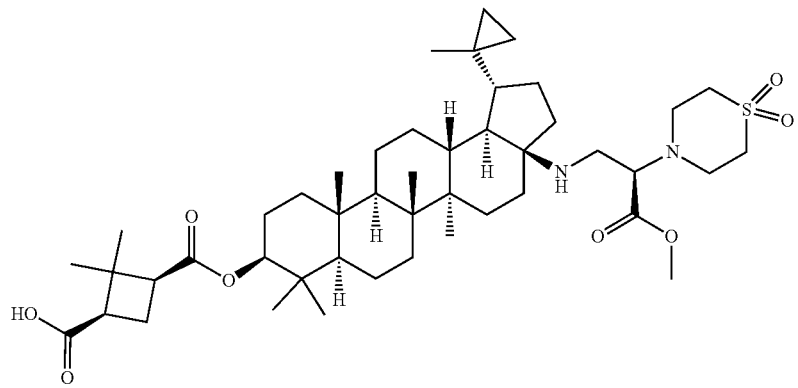

To a suspension of 10% Pd/C (500 mg) in ethyl acetate (7 ml) and methanol (7 ml) was added 1-benzyl 3-((1R,3aS,5aR,5bR,7aR,9S,11aR,11bR,13aR,13bR)-3a-(((R)-2-(1,1-dioxidothiomorpholino)-3-methoxy-3-oxopropyl)amino)-5a,5b,8,8,11a-pentamethyl-1-(1-methylcyclopropyl) icosahydro-1H-cyclopenta[a]chrysen-9-yl) (1R,3S)-2,2-dimethylcyclobutane-1,3-dicarboxylate (step 1, 0.35 g, 0.386 mmol, 1.0 eq) and ammonium formate (0.121 g, 1.933 mmol, 5.0 eq). The reaction mixture was stirred at room temperature for about 1 hour. TLC indicated starting material was completed and the desired product was observed. The reaction mixture was filtered through celite pad and washed with 5% methanol in DCM (100 ml). The filtrate was evaporated under reduced pressure and the residue was purified by silica gel column chromatography using 5 to 10% methanol in DCM with one drop acetic acid gradient. The obtained solid was treated with ethyl acetate (2 ml) and hexane (8 mL) and stirred at room temperature for 20 minutes. The precipitates formed were collected by filtration and dried under vacuum to obtain the title compound (40 mg, 12.69% yield) as an off-white solid. $^1$H NMR (300 MHz, CDCl$_3$): δ ppm 4.47-4.45 (m, 1H), 3.70 (s, 3H), 3.42-3.35 (m, 1H), 3.28 (m, 1H), 3.15-3.02 (m, 4H), 2.98 (m, 3H), 2.85-2.75 (m, 2H), 2.65-2.52 (m, 3H), 2.10-1.18 (m, 25H), 1.10-0.78 (m, 25H), 0.40-0.20 (m, 4H); ES-MS: m/z 815.88 (M+H)$^+$.

Step-3: Synthesis of (1R,3S)-3-(((((1R,3aS,5aR,5bR,7aR,9S,11aR,11bR,13aR,13bR)-3a-(((R)-2-carboxy-2-(1,1-dioxidothiomorpholino)ethyl)amino)-5a,5b,8,8,11a-pentamethyl-1-(1-methylcyclopropyl)icosahydro-1H-cyclopenta[a]chrysen-9-yl)oxy)carbonyl)-2,2-dimethylcyclobutane-1-carboxylic acid

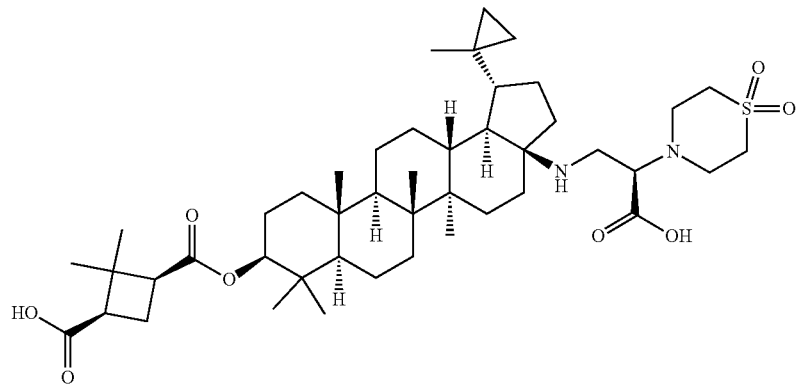

To a stirred solution of 1-benzyl 3-((1R,3aS,5aR,5bR,7aR,9S,11aR,11bR,13aR,13bR)-3a-(((R)-2-(1,1-dioxidothiomorpholino)-3-methoxy-3-oxopropyl)amino)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate (0.3 g, 0.33 mmol, 1.0 eq) in methanol (3 ml) and THF (3 ml) was added aqueous 2.5N KOH solution (1.0 ml, 2.48 mmol, 7.5 eq). The reaction mixture was stirred at room temperature for overnight. TLC indicated starting material was consumed and the desired product was observed. The reaction mixture was evaporated under reduced pressure, diluted with water (10 ml), cooled to 0° C., acidified with 1N HCl to pH 2.0 and extracted with DCM (3×25 ml). The combined organic layer was washed with water (20 ml), dried over Na$_2$SO$_4$, filtered and concentrated under reduced pressure. The residue was purified by silica gel column chromatography using one drop acetic acid in 10% methanol in DCM as an eluent. The obtained compound was further purified by treating with ethyl acetate (20 ml), heated to reflux for about 30 minutes. The reaction mixture was cooled to room temperature, solid was filtered, washed with ethyl acetate (5 ml) and dried under vacuum to obtain the title compound (50 mg, 18.8% yield) as a white solid. $^1$H NMR (300 MHz, DMSO-d$_6$): δ ppm 4.38-4.32 (m, 1H), 3.08-2.93 (m, 8H), 2.82-2.68 (m, 4H), 2.37-2.23 (m, 2H), 2.0-0.78 (m, 26H), 1.27 (s, 3H), 1.05 (s, 3H), 0.95 (s, 3H), 0.91 (s, 6H), 0.85 (s, 3H), 0.84 (s, 3H), 0.83 (s, 3H), 0.4-0.18 (m, 4H); ESI-MS: m/z 823.55 (M+Na)$^+$.

Example 17: Preparation of (1R,3S)-3-((((1R,3aS, 5aR,5bR,7aR,9S,11aR,11bR,13aR,13bR)-3a-(((2R, 3R)-2-(1,1-dioxidothiomorpholino)-3-(2-(2-methoxyethoxy)acetoxy)butyl)amino)-5a,5b,8,8,11a-pentamethyl-1-(1-methylcyclopropyl)icosahydro-1H-cyclopenta chrysen-9-yl)oxy)carbonyl)-2,2-dimethylcyclobutane-1-carboxylic acid

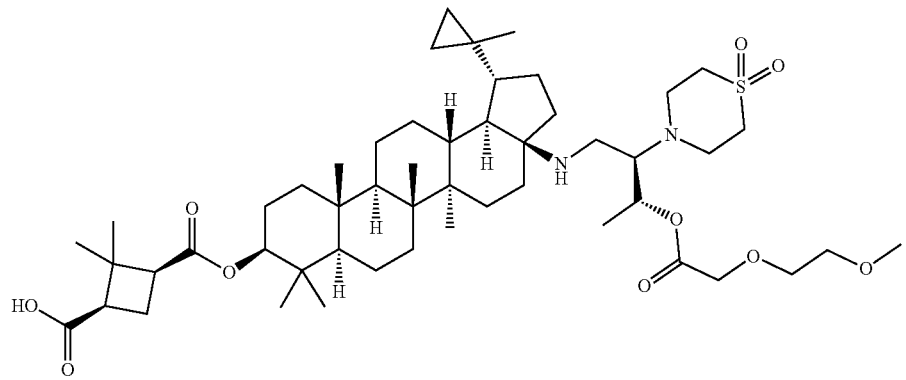

To a stirred solution of (1R,3S)-3-((((1R,3aS,5aR,5bR,7aR,9S,11aR,11bR,13aR,13bR)-3a-(((2R,3R)-2-(1,1-dioxidothiomorpholino)-3-hydroxybutyl)amino)-5a,5b,8,8,11a-pentamethyl-1-(1-methylcyclopropyl)icosahydro-1H-cyclopenta[a]chrysen-9-yl)oxy) carbonyl)-2,2-dimethylcyclobutane-1-carboxylic acid (Example 8, 0.400 g, 0.499 mmol, 1.0 eq) in DCM (10 ml) was added DMAP (0.030 g, 0.24 mmol, 0.5 eq), EDC.HCl (0.430 g, 2.24 mmol, 4.5 eq) and 2-(2-methoxyethoxy)acetic acid (Intermediate 17, 0.167 g, 1.24 mmol, 2.5 eq, Step-2). The reaction mixture was stirred at room temperature for overnight. TLC indicated starting material was completed and the desired product was observed. The reaction mixture was diluted with water (10 ml) and extracted with DCM (3×20 ml). The combined organic layer was washed with water (20 ml), dried over sodium sulfate, filtered and concentrated under reduced pressure. The crude compound was purified by silica gel column chromatography using 0-4% methanol in dichloromethane gradient. The obtained compound was further purified by treating with chloroform (2 ml) and hexane (8 ml), stirred at room temperature for about 30 minutes, filtered and dried under vacuum to obtain the title compound (0.100 g, 21.8% yield) as a solid. $^1$H NMR (300 MHz, CDCl$_3$): δ ppm 5.15-5.09 (m, 1H), 4.48 (m, 1H), 4.16 (s, 2H), 3.73-3.71 (m, 2H), 3.62-3.58 (m, 2H), 3.38 (s, 3H), 3.27-3.19 (m, 4H), 3.0-2.95 (m, 5H), 2.85-2.73 (m, 2H), 2.65-2.55 (m, 1H), 2.50-2.35 (m, 2H), 2.08-2.0 (m, 2H), 1.90-0.78 (m, 27H), 1.36 (s, 3H), 1.09 (s, 3H), 1.06 (s, 3H), 0.98 (s, 3H), 0.90 (s, 3H), 0.90 (s, 3H), 0.87 (s, 3H), 0.87 (s, 3H), 0.38-0.25 (m, 4H); ES-MS: m/z 917.95 (M+H)$^+$.

Example 18: Preparation of (1R,3S)-3-((((1R,3aS, 5aR,5bR,7aR,9S,11aR,11bR,13aR,13bR)-3a-(((12R, 13R)-13-(1,1-dioxidothiomorpholino)-12-methyl-2, 5,8,11-tetraoxatetradecan-14-yl)amino)-5a,5b,8,8, 11a-pentamethyl-1-(1-methylcyclopropyl) icosahydro-1H-cyclopenta[a]chrysen-9-yl)oxy) carbonyl)-2,2-dimethylcyclobutane-1-carboxylic acid

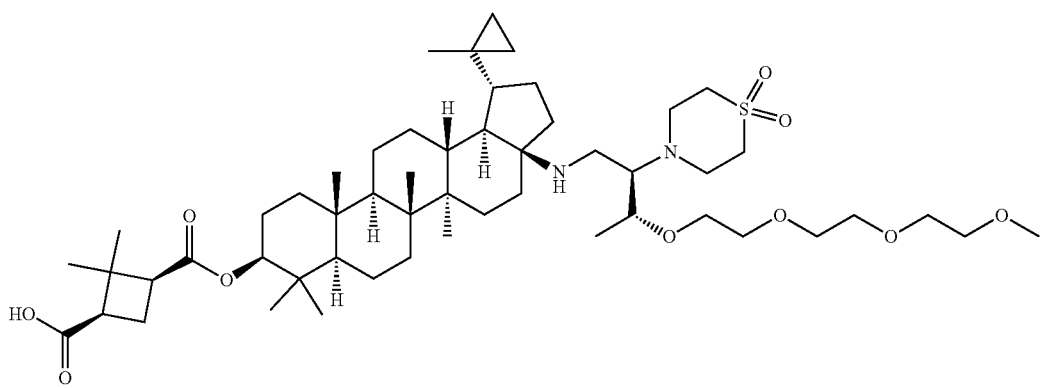

Step 1: Synthesis of 1-benzyl 3-((1R,3aS,5aR,5bR,7aR,9S,11aR,11bR,13aR,13bR)-3a-(((12R,13R)-13-(1,1-dioxidothiomorpholino)-12-methyl-2,5,8,11-tetraoxatetradecan-14-yl)amino)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate

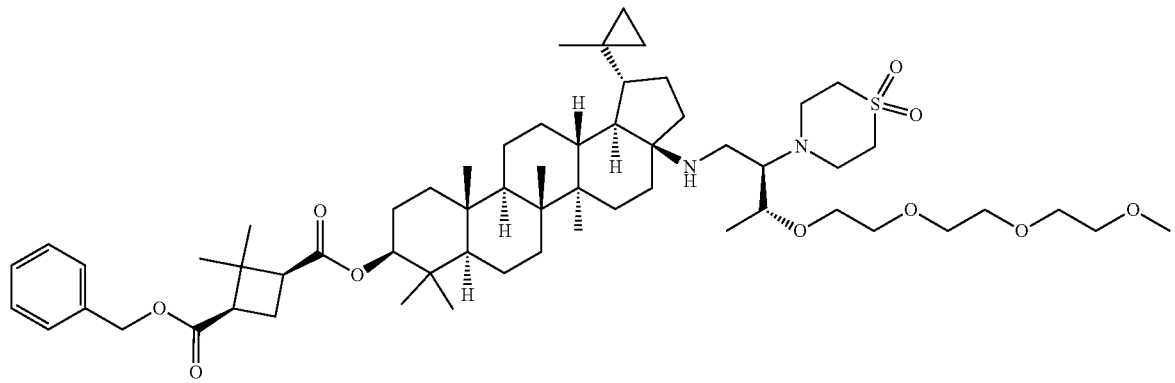

To a stirred solution of 4-((12R,13R)-14-hydroxy-12-methyl-2,5,8,11-tetraoxatetradecan-13-yl)thiomorpholine 1,1-dioxide (Intermediate 18, 0.775 g, 2.099 mmol, 1.6 eq) in DCM (20 ml) at 0° C. was added trifluoromethanesulfonic anhydride (0.39 ml, 2.361 mmol, 1.8 eq). After stirring for 10 minutes at 0° C., 2,6-Lutidine (0.3 ml, 2.623 mmol, 2.0 eq) was added and stirred at same temperature for about 10 minutes. 1-((1R,3aS,5aR,5bR,7aR,9S,11aR,11bR,13aR,13bR)-3a-amino-5a,5b,8,8,11a-pentamethyl-1-(1-methylcyclopropyl)icosahydro-1H-cyclopenta[a]chrysen-9-yl) 3-benzyl (1S,3R)-2,2-dimethylcyclobutane-1,3-dicarboxylate (Intermediate 1, 0.900 g, 1.311 mmol, 1.0 eq) and triethylamine (0.5 ml, 3.935 mmol, 3.0 eq) were added to the reaction mixture and stirred at 0° C. for about 1 hour. The reaction mixture was allowed to stir at room temperature for overnight. TLC indicated starting material was completed and the desired product was observed. The reaction mixture was diluted with DCM (100 ml), washed with saturated sodium bicarbonate solution (100 ml), water and brine solution. The organic layer was dried over sodium sulfate, filtered and concentrated under reduced pressure. The crude product was purified by silica gel column chromatography using 0-5% methanol in dichloromethane gradient to obtain the title compound (1.0 g, 73.5% yield) as an off-white solid. $^1$H NMR (300 MHz, CDCl$_3$): δ ppm 7.35 (m, 5H), 5.15, 5.09 (ABq, J$_{AB}$=12.6 Hz, 2H), 4.44 (dd, J=10.5, 4.2 Hz, 1H), 3.67-3.65 (m, 4H), 3.64-3.61 (m, 6H), 3.60-3.58 (m, 1H), 3.57-3.52 (m, 3H), 3.45-3.40 (m, 1H), 3.38 (s, 3H), 3.36-3.27 (m, 1H), 3.23-3.10 (m, 1H), 3.09-3.06 (m, 1H), 3.05-2.92 (m, 6H), 2.83-2.64 (m, 3H), 2.60-2.54 (m, 3H), 2.10-0.78 (m, 27H), 1.34 (s, 3H), 1.03 (s, 3H), 0.96 (s, 3H), 0.95 (s, 3H), 0.91 (s, 3H), 0.89 (s, 3H), 0.86 (s, 3H), 0.85 (s, 3H), 0.40-0.19 (m, 4H); ES-MS: m/z 1038.95 (M+H)$^+$.

Step 2: Synthesis of (1R,3S)-3-(((((1R,3aS,5aR,5bR,7aR,9S,11aR,11bR,13aR,13bR)-3a-(((12R,13R)-13-(1,1-dioxidothiomorpholino)-12-methyl-2,5,8,11-tetraoxatetradecan-14-yl)amino)-5a,5b,8,8,11a-pentamethyl-1-(1-methylcyclopropyl)icosahydro-1H-cyclopenta[a]chrysen-9-yl)oxy)carbonyl)-2,2-dimethylcyclobutane-1-carboxylic acid

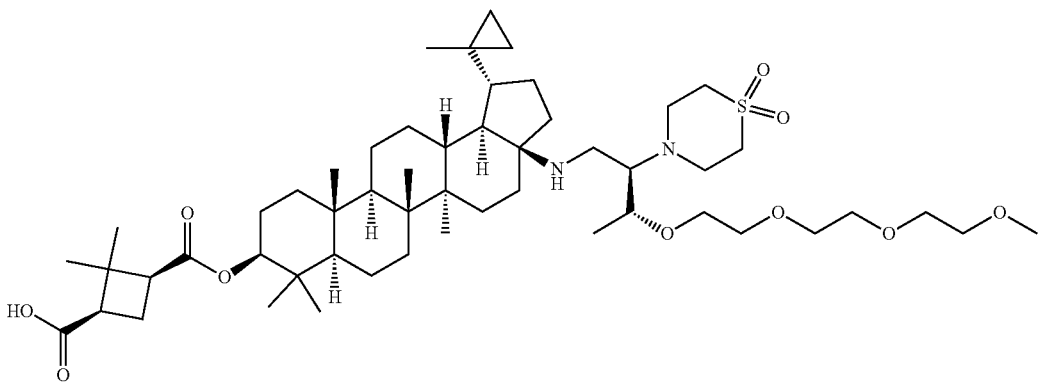

To a stirred solution of 1-benzyl 3-((1R,3aS,5aR,5bR,7aR,9S,11aR,11bR,13aR,13bR)-3a-(((12R,13R)-13-(1,1-dioxidothiomorpholino)-12-methyl-2,5,8,11-tetraoxatetradecan-14-yl)amino)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate (step 1, 1.0 g, 0.963 mmol, 1.0 eq) in THF (10 ml) and methanol (10 ml) at 0° C. was added aqueous 2.5N KOH solution (2.89 ml, 7.229 mmol, 7.5 eq). The reaction mixture was stirred at room temperature for overnight. TLC indicated starting material was consumed and the desired product was observed. The reaction mixture was evaporated under reduced pressure, cooled to 0° C., acidified with 1N HCl to pH 4.0 and extracted with DCM (2×100 ml). The combined organic layer was washed with water (100 ml), dried over $Na_2SO_4$, filtered and concentrated under reduced pressure. The crude product was purified by silica gel column chromatography using 0-7% methanol in DCM gradient to obtain the title compound (0.050 g, 5.47% yield) as an off-white solid. $^1$H NMR (300 MHz, CDCl$_3$): δ ppm 4.46 (dd, J=11.4, 4.8 Hz, 1H), 3.65-3.50 (m, 14H), 3.42-3.32 (m, 5H), 3.18-3.10 (m, 2H), 3.05-2.95 (m, 6H), 2.82-2.72 (m, 3H), 2.70-2.50 (m, 3H), 2.08-0.76 (m, 27H), 1.36 (s, 3H), 1.07 (s, 3H), 1.02 (s, 3H), 0.96 (s, 3H), 0.91 (s, 3H), 0.88 (s, 3H), 0.86 (s, 3H), 0.86 (s, 3H), 0.40-0.20 (m, 4H); ES-MS: m/z 947.99 (M+H)$^+$.

Example 19: Preparation of (1R,3S)-3-((((1R,3aS,5aR,5bR,7aR,9S,11aR,11bR,13aR,13bR)-3a-(((2R,3R)-2-(1,1-dioxidothiomorpholino)-3-(2-(2-methoxyethoxy)acetoxy)butyl)amino)-5a,5b,8,8,11a-pentamethyl-1-(prop-1-en-2-yl)icosahydro-1H-cyclopenta chrysen-9-yl)oxy)carbonyl)-2,2-dimethylcyclobutane-1-carboxylic acid

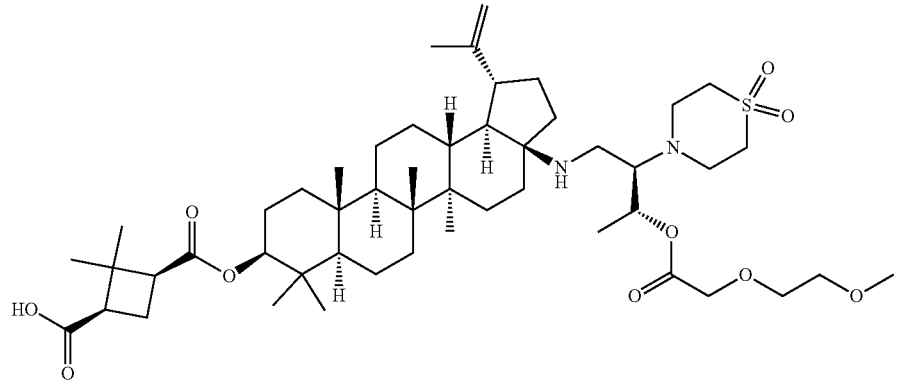

To a stirred solution of (1R,3S)-3-((((1R,3aS,5aR,5bR,7aR,9S,11aR,11bR,13aR,13bR)-3a-(((2R,3R)-2-(1,1-dioxidothiomorpholino)-3-hydroxybutyl)amino)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid (Example-15, 0.650 g, 0.825 mmol, 1.0 eq) in DCM (13 ml) was added 2-(2-methoxyethoxy)acetic acid (Intermediate 17, 0.276 g, 2.06 mmol, 2.5 eq), DMAP (0.050 g, 0.41 mmol, 0.5 eq) and EDC.HCl (0.711 g, 3.71 mmol, 4.5 eq). The reaction mixture was stirred at room temperature for overnight. TLC indicated starting material was completed and the desired product was observed. The reaction mixture was diluted with water (50 ml) and extracted with DCM (3×50 ml). The combined organic layer was washed with water (50 ml), dried over sodium sulfate, filtered and concentrated under reduced pressure. The residue was purified by silica gel column chromatography using 0-6% methanol in dichloromethane gradient. The obtained compound was further purified by treating with ethyl acetate (5 ml) and hexane (50 ml), stirred at room temperature for about 30 minutes, filtered and dried under vacuum to obtain the title compound (0.480 g, 64% yield) as a white solid. $^1$H NMR (300 MHz, CDCl$_3$): δ ppm 5.14-5.09 (m, 1H), 4.68 (s, 1H), 4.59 (s, 1H), 4.53-4.48 (m, 1H), 4.17 (s, 2H), 3.75-3.68 (m, 2H), 3.62-3.57 (m, 2H), 3.38 (s, 3H), 3.33-2.85 (m, 9H), 2.81-2.40 (m, 5H), 2.05-0.77 (m, 26H), 1.68 (s, 3H), 1.38 (s, 3H), 1.24 (d, J=6.6 Hz, 3H), 1.12 (s, 3H), 1.06 (s, 3H), 0.97 (s, 3H), 0.90 (s, 3H), 0.86 (s, 3H), 0.85 (s, 3H); ES-MS: m/z 904.04 (M+H)$^+$.

Example 20: Preparation of 4-(((1R,3aS,5aR,5bR, 7aR,9S,11aR,11bR,13aR,13bR)-3a-(((2R,3R)-2-(1, 1-dioxidothiomorpholino)-3-hydroxybutyl)amino)- 5a,5b,8,8,11a-pentamethyl-1-(prop-1-en-2-yl) icosahydro-1H-cyclopenta chrysen-9-yl)oxy)-2,2- dimethyl-4-oxobutanoic acid

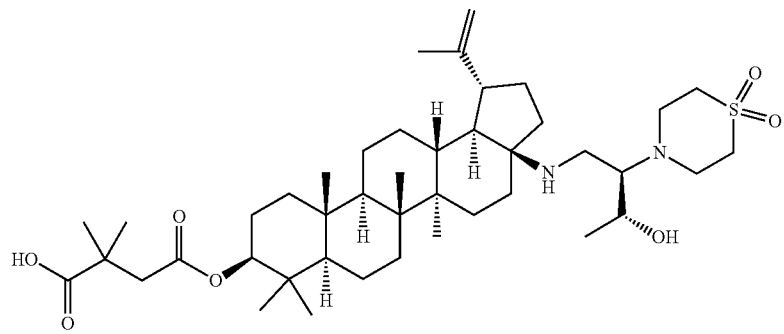

Step 1: Synthesis of (1R,3aS,5aR,5bR,7 aR,9S, 11aR,11bR,13aR,13bR)-3a-((tert-butoxycarbonyl) amino)-5a,5b,8,8,11a-pentamethyl-1-(prop-1-en-2- yl)icosahydro-1H-cyclopenta[a]chrysen-9-yl acetate Step 2: Synthesis of (1R,3aS,5aR,5bR,7aR,9S,11aR, 11bR,13aR,13bR)-3a-amino-5a,5b,8,8,11a-pentam- ethyl-1-(prop-1-en-2-yl)icosahydro-1H-cyclopenta [a]chrysen-9-yl acetate

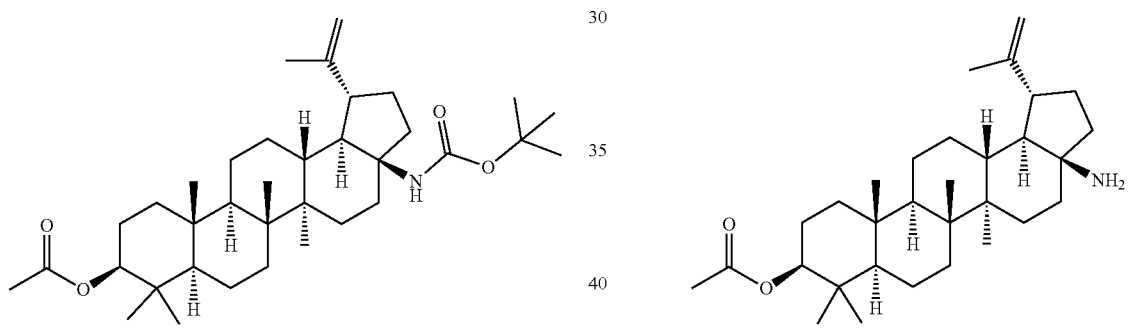

To a stirred solution of tert-butyl ((1R,3aS,5aR,5bR,7aR, 9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)carbamate (prepared as described in WO 2017/149518 A2, 12 g, 22.734 mmol, 1.0 eq) in THF (120 ml) at 0° C. was added triethylamine (9.5 ml, 68.203 mmol, 3.0 eq), DMAP (0.333 g, 2.728 mmol, 0.12 eq) and acetic anhydride (3 ml, 31.828 mmol, 1.4 eq). The reaction mixture was stirred at room temperature for overnight. TLC indicated starting material was consumed and the desired product was observed. The reaction mixture was diluted with ethyl acetate (200 ml) and washed with water (2×200 ml). The organic layer was dried over sodium sulfate, filtered and concentrated under reduced pressure. The crude compound was treated with n-hexane (100 ml), stirred at room temperature for about 1 hour, filtered and dried under vacuum to obtain the title compound (12 g, 93% yield) as an off-white solid. $^1$H NMR (300 MHz, CDCl$_3$): δ ppm 4.71 (s, 1H), 4.60 (s, 1H), 4.47 (dd, J=9.9, 4.5 Hz, 1H), 4.34 (s, 1H), 2.58-2.30 (m, 3H), 2.05 (s, 3H), 2.02-0.77 (m, 22H), 1.68 (s, 3H), 1.44 (s, 9H), 1.01 (s, 3H), 0.95 (s, 3H), 0.85 (s, 3H), 0.84 (s, 3H), 0.83 (s, 3H); ES-MS: m/z 570.39 (M+H)$^+$.

To a stirred solution of (1R,3aS,5aR,5bR,7aR,9S,11aR, 11bR,13aR,13bR)-3a-((tert-butoxycarbonyl)amino)-5a,5b, 8,8,11a-pentamethyl-1-(prop-1-en-2-yl)icosahydro-1H-cyclopenta[a]chrysen-9-yl acetate (step 1, 12 g, 21.057 mmol, 1.0 eq) in 1,4-dioxane (24 ml) was added 4N HCl in 1,4-dioxane (24 ml). The reaction mixture was stirred at room temperature for overnight. TLC indicated starting material was consumed and the desired product was observed. The reaction mixture was concentrated under reduced pressure and basified with saturated sodium bicarbonate solution. The obtained solid was filtered and washed with water. The solid was dissolved in DCM, dried over sodium sulfate, filtered and concentrated under reduced pressure. The solid was further purified by trituration with n-Hexane (100 ml), filtered, washed with hexane and dried under vacuum to obtain the title compound (7 g, 70.7% yield) as an off-white solid. $^1$H NMR (300 MHz, CDCl$_3$): δ ppm 4.71 (s, 1H), 4.59 (s, 1H), 4.47 (dd, J=9.0, 5.4 Hz, 1H), 2.57-2.48 (m, 1H), 2.04 (s, 3H), 1.68 (s, 3H), 1.66-0.77 (m, 24H), 1.04 (s, 3H), 0.95 (s, 3H), 0.85 (s, 3H), 0.84 (s, 3H), 0.83 (s, 3H); ES-MS: m/z 470.44 (M+H)$^+$.

127

Step 3: Synthesis of (1R,3aS,5aR,5bR,7aR,9S,11aR, 11bR,13aR,13bR)-3a-(((2R,3R)-3-((tert- butyldimethylsilyl)oxy)-2-(1,1-dioxidothiomorpholino)butyl) amino)-5a,5b,8,8,11a-pentamethyl-1-(prop-1-en-2-yl)icosahydro-1H-cyclopenta[a]chrysen-9-yl acetate

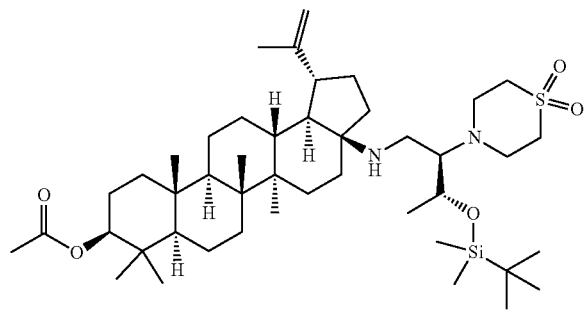

To a stirred solution of 4-((2R,3R)-3-((tert-butyldimethylsilyl)oxy)-1-hydroxybutan-2-yl)thiomorpholine 1,1-dioxide (Intermediate-8, 8.5 g, 25.326 mmol, 1.7 eq) in DCM (70 ml) at 0° C. was added 2,6-Lutidine (3.8 ml, 32.775 mmol, 2.2 eq). After 10 minutes stirring at 0° C., trifluoromethane sulfonic anhydride (5 ml, 29.795 mmol, 2.0 eq) was added and stirred at 0° C. for about 20 minutes. (1R,3aS,5aR,5bR,7aR,9S,11aR,11bR,13aR,13bR)-3a-amino-5a,5b,8,8,11a-pentamethyl-1-(prop-1-en-2-yl)icosahydro-1H-cyclopenta[a]chrysen-9-yl acetate (step 2, 7 g, 14.897 mmol, 1.0 eq) and triethylamine (7.27 ml, 52.142 mmol, 3.5 eq) were added to the reaction mixture and stirred at 0° C. for about 1 hour. The reaction mixture was stirred at room temperature for overnight. TLC indicated starting material was consumed and the desired product was observed. The reaction mixture was diluted with DCM (200 ml), washed with saturated sodium carbonate solution (100 ml) and water (100 ml). The organic layer was dried over sodium sulfate, filtered and concentrated under reduced pressure. The crude product was purified by silica gel column chromatography using 0-10% ethyl acetate in hexane gradient. The obtained compound was further purified by treating with n-hexane, filtered and dried under vacuum to obtain the title compound (7.0 g, 59% yield) as an off-white solid. $^1$H NMR (300 MHz, CDCl$_3$): δ ppm 4.68 (s, 1H), 4.58 (s, 1H), 4.49-4.44 (m, 1H), 4.08-4.0 (m, 1H), 3.44-3.39 (m, 2H), 3.28-3.22 (m, 2H), 3.06-3.01 (m, 4H), 2.60-2.40 (m, 4H), 2.04 (s, 3H), 1.93-0.76 (m, 27H), 1.68 (s, 3H), 1.04 (s, 3H), 0.94 (s, 3H), 0.87 (s, 9H), 0.85 (s, 3H), 0.84 (s, 3H), 0.83 (s, 3H), 0.07 (s, 6H); ES-MS: m/z 789.67 (M+H)$^+$.

128

Step 4: Synthesis of 4-((2R,3R)-3-((tert-butyldimethylsilyl)oxy)-1-(((1R,3aS,5aR,5bR,7aR,9S,11aR, 11bR,13aR,13bR)-9-hydroxy-5a,5b,8,8,11a-pentamethyl-1-(prop-1-en-2-yl)icosahydro-3aH-cyclopenta[a]chrysen-3a-yl)amino)butan-2-yl)thiomorpholine 1,1-dioxide

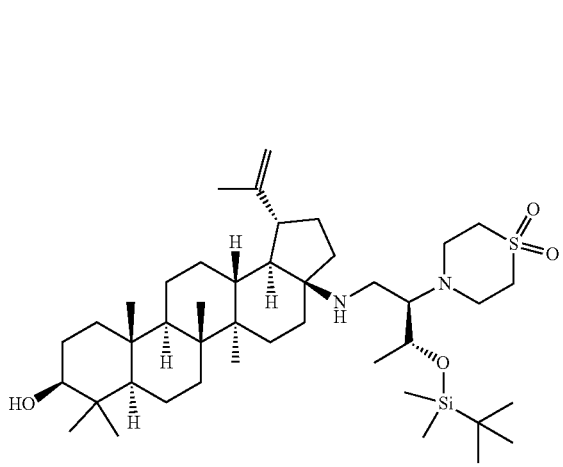

To a stirred solution of (1R,3aS,5aR,5bR,7aR,9S,11aR, 11bR,13aR,13bR)-3a-(((2R,3R)-3-((tert-butyldimethylsilyl)oxy)-2-(1,1-dioxidothiomorpholino)butyl)amino)-5a,5b,8, 8,11a-pentamethyl-1-(prop-1-en-2-yl)icosahydro-1H-cyclopenta[a]chrysen-9-yl acetate (step 3, 7.0 g, 8.868 mmol, 1.0 eq) in methanol (70 ml) and THF (70 ml) was added aqueous 1N KOH solution (53.2 ml, 53.212 mmol, 6.0 eq). The reaction mixture was stirred at room temperature for overnight. TLC indicated starting material was consumed and the desired product was observed. The reaction mixture was concentrated under reduced pressure, DCM (400 ml) was added and washed with water (200 ml). The organic layer was dried over sodium sulfate, filtered and concentrated under reduced pressure. The crude product was purified by silica gel column chromatography using 0-30% ethyl acetate in hexanes gradient to obtain the title compound (6.0 g, 91% yield) as an off-white solid. $^1$H NMR (300 MHz, CDCl$_3$): δ ppm 4.69 (s, 1H), 4.58 (s, 1H), 4.04-3.99 (m, 1H), 3.44-3.39 (m, 2H), 3.28-3.16 (m, 3H), 3.07-2.96 (m, 4H), 2.61-2.40 (m, 4H), 1.97-0.66 (m, 27H), 1.68 (s, 3H), 1.04 (s, 3H), 0.96 (s, 3H), 0.95 (s, 3H), 0.87 (s, 9H), 0.82 (s, 3H), 0.75 (s, 3H), 0.07 (s, 6H); ES-MS: m/z 747.74 (M+H)$^+$.

Step 5: Synthesis of 1-(tert-butyl) 4-((1R,3aS,5aR,5bR,7aR,9S,11aR,11bR,13aR,13bR)-3a-(((2R,3R)-3-((tert-butyldimethylsilyl)oxy)-2-(1,1-dioxidothiomorpholino)butyl)amino)-5a,5b,8,8,11a-pentamethyl-1-(prop-1-en-2-yl)icosahydro-1H-cyclopenta[a]chrysen-9-yl) 2,2-dimethylsuccinate

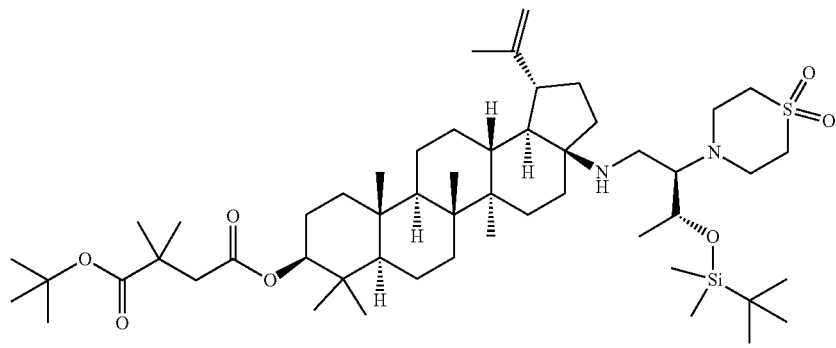

To a stirred solution of 4-((2R,3R)-3-((tert-butyldimethylsilyl)oxy)-1-(((1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)amino)butan-2-yl)thiomorpholine 1,1-dioxide (step 4, 1 g, 1.338 mmol, 1.0 eq) in DCM (20 ml) was added EDC.HCl (0.897 g, 4.683 mmol, 3.5 eq), DMAP (0.081 g, 0.669 mmol, 0.5 eq) and 4-(tert-butoxy)-3,3-dimethyl-4-oxobutanoic acid (prepared as described in WO 2013/020245, 0.676 g, 3.345 mmol, 2.5 eq). The reaction mixture was stirred at room temperature for overnight. TLC indicated starting material was consumed and the desired product was observed. The reaction mixture was diluted with DCM (100 ml) and washed with water (100 ml). The organic layer was dried over sodium sulfate, filtered and concentrated under reduced pressure. The crude product was purified by silica gel column chromatography using 0-30% ethyl acetate in hexanes gradient to obtain the title compound (1 g, 80.2% yield) as an off-white solid. $^1$H NMR (300 MHz, CDCl$_3$): δ ppm 4.68 (s, 1H), 4.58 (s, 1H), 4.48 (dd, J=10.5, 6.0 Hz, 1H), 4.02-3.99 (m, 1H), 3.47-3.39 (m, 2H), 3.27-3.22 (m, 2H), 3.0 (m, 4H), 2.62-2.40 (m, 4H), 2.53 (s, 2H), 1.97-0.75 (m, 33H), 1.68 (s, 3H), 1.43 (s, 9H), 1.04 (s, 3H), 0.94 (s, 3H), 0.87 (s, 9H), 0.84 (s, 6H), 0.82 (s, 3H), 0.07 (s, 6H); ES-MS: m/z 932.06 (M+H)$^+$.

Step 6: Synthesis of 1-(tert-butyl) 4-((1R,3aS,5aR,5bR,7aR,9S,11aR,11bR,13aR,13bR)-3a-(((2R,3R)-2-(1,1-dioxidothiomorpholino)-3-hydroxybutyl)amino)-5a,5b,8,8,11a-pentamethyl-1-(prop-1-en-2-yl)icosahydro-1H-cyclopenta[a]chrysen-9-yl) 2,2-dimethylsuccinate

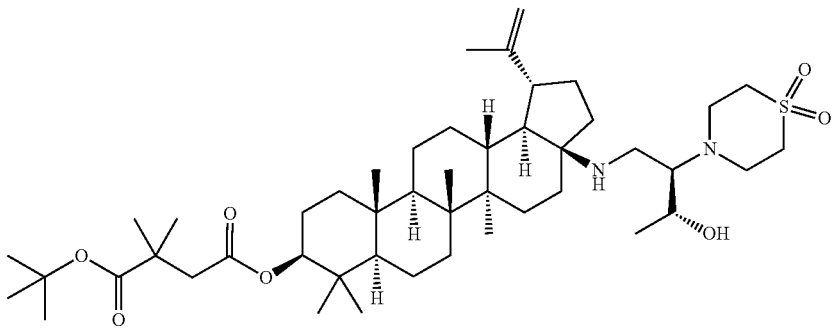

To a stirred solution of 1-(tert-butyl) 4-(((1R,3aS,5aR,5bR, 7aR,9S,11aR,11bR,13aR,13bR)-3a-(((2R,3R)-3-((tert-butyldimethylsilyl)oxy)-2-(1,1-dioxidothiomorpholino)butyl)amino)-5a,5b,8,8,11a-pentamethyl-1-(prop-1-en-2-yl)icosahydro-1H-cyclopenta[a]chrysen-9-yl) 2,2-dimethylsuccinate (step 1, 1 g, 1.073 mmol, 1.0 eq) in THF (10 ml) was added TBAF (4.29 ml, 4.294 mmol, 4.0 eq, 1.0M in THF). The reaction mixture was stirred at room temperature for overnight. TLC indicated starting material was consumed and the desired product was observed. The reaction mixture was diluted with ethyl acetate (100 ml) and washed with water (100 ml). The organic layer was dried over sodium sulfate, filtered and concentrated under reduced pressure. The crude product was purified by silica gel column chromatography using 0-4% methanol in dichloromethane gradient to obtain the title compound (0.800 g, 91.2% yield) as an off-white solid. $^1$H NMR (300 MHz, CDCl$_3$): δ ppm 4.68 (s, 1H), 4.59 (s, 1H), 4.48 (dd, J=10.2, 6.0 Hz, 1H), 3.73-3.68 (m, 1H), 3.42-3.37 (m, 2H), 3.18-3.05 (m, 6H), 2.65-2.45 (m, 6H), 1.96-0.76 (m, 24H), 1.68 (s, 3H), 1.43 (s, 9H), 1.26 (d, J=6.0 Hz, 3H), 1.23 (s, 3H), 1.22 (s, 3H), 1.04 (s, 3H), 0.94 (s, 3H), 0.84 (s, 6H), 0.82 (s, 3H); ES-MS: m/z 818.12 (M+H)$^+$.

Step 7: Synthesis of 4-(((1R,3aS,5aR,5bR,7aR,9S,11aR,11bR,13aR,13bR)-3a-(((2R,3R)-2-(1,1-dioxidothiomorpholino)-3-hydroxybutyl)amino)-5a,5b,8,8,11a-pentamethyl-1-(prop-1-en-2-yl)icosahydro-1H-cyclopenta[a]chrysen-9-yl)oxy)-2,2-dimethyl-4-oxobutanoic acid

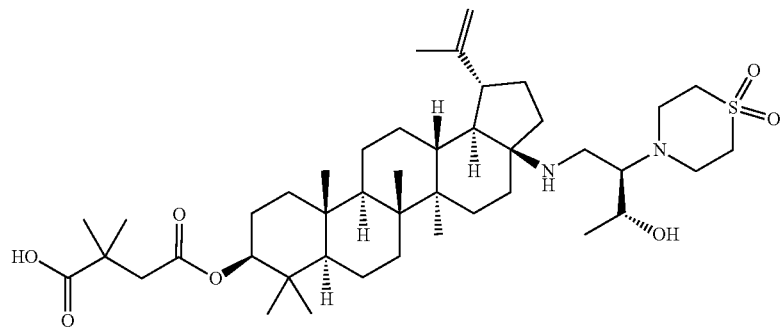

To a stirred solution of 1-(tert-butyl) 4-((1R,3aS,5aR,5bR,7aR,9S,11aR,11bR,13aR,13bR)-3a-(((2R,3R)-2-(1,1-dioxidothiomorpholino)-3-hydroxybutyl)amino)-5a,5b,8,8,11a-pentamethyl-1-(prop-1-en-2-yl)icosahydro-1H-cyclopenta[a]chrysen-9-yl) 2,2-dimethylsuccinate (step 2, 0.800 g, 0.978 mmol, 1.0 eq) in 1,4-dioxane (2 ml) was added 4N HCl in 1,4-dioxane (2 ml). The reaction mixture was stirred at room temperature for overnight. TLC indicated starting material was consumed and the desired product was observed. The reaction mixture was concentrated under reduced pressure. The crude compound was dissolved in DCM (100 ml) and washed with water (100 ml). The organic layer was dried over sodium sulfate, filtered and concentrated under reduced pressure. The crude compound was purified by silica gel column chromatography using 0-5% methanol in dichloromethane gradient. The obtained compound was further purified by recrystallization with DCM:hexane (1:5, 10 ml). The mixture was cooled, filtered, washed with hexane and dried under vacuum to obtain the title compound (0.500 g, 67% yield) as an off-white solid. $^1$H NMR (300 MHz, CDCl$_3$): δ ppm 4.69 (s, 1H), 4.59 (s, 1H), 4.49-4.44 (m, 1H), 3.73 (m, 1H), 3.42-3.37 (m, 2H), 3.20-3.05 (m, 6H), 2.70-2.48 (m, 6H), 1.95-0.75 (m, 33H), 1.67 (s, 3H), 1.05 (s, 3H), 0.96 (s, 3H), 0.84 (s, 3H), 0.83 (s, 3H), 0.80 (s, 3H); ES-MS: m/z 762.0 (M+H)$^+$.

Example 21: Preparation of (1R,3S)-3-((((1R,3aS, 5aR,5bR,7aR,9S,11aR,11bR,13aR,13bR)-3a-(((15R, 16R)-16-(1,1-dioxidothiomorpholino)-15-methyl-13-oxo-2,5,8,11,14-pentaoxaheptadecan-17-yl)amino)-5a,5b,8,8,11a-pentamethyl-1-(prop-1-en-2-yl) icosahydro-1H-cyclopenta[a]chrysen-9-yl)oxy) carbonyl)-2,2-dimethylcyclobutane-1-carboxylic acid

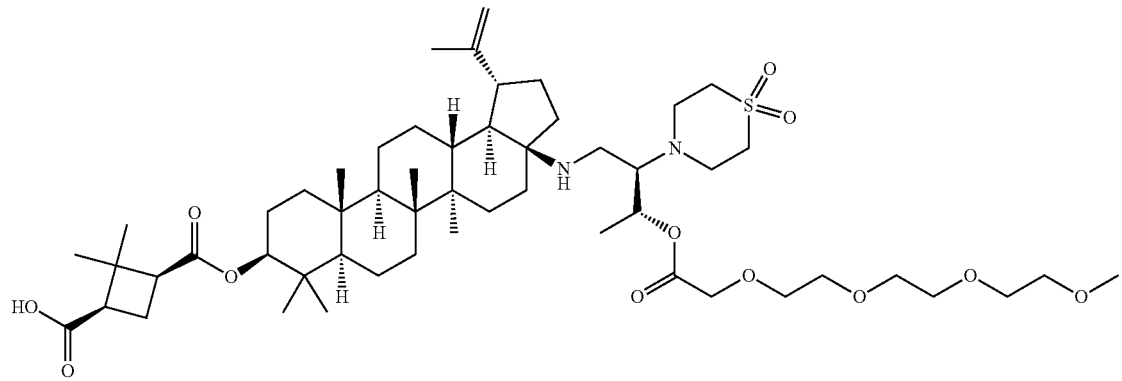

To a stirred solution of (1R,3S)-3-((((1R,3aS,5aR,5bR,7aR,9S,11aR,11bR,13aR,13bR)-3a-(((2R,3R)-2-(1,1-dioxidothiomorpholino)-3-hydroxybutyl)amino)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid (Example 15, 0.350 g, 0.444 mmol, 1.0 eq) in DCM (5 ml) was added EDC.HCl (0.383 g, 2.000 mmol, 4.5 eq), DMAP (0.027 g, 0.222 mmol, 0.5 eq) and 2,5,8,11-tetraoxatridecan-13-oic acid (0.247 g, 1.111 mmol, 2.5 eq). The reaction mixture was stirred at room temperature for overnight. TLC indicated starting material was consumed and the desired product was observed. The reaction mixture was diluted with DCM (100 ml), washed with 1N HCl (50 ml) and water (100 ml). The organic layer was dried over sodium sulfate, filtered and concentrated under reduced pressure. The crude compound was purified by silica gel column chromatography using 0-5% methanol in dichloromethane gradient. The obtained compound was further purified by treating with 1:8 (MTBE:Hexane; 18 ml), filtered, washed with n-Hexane and dried under vacuum to obtain the title compound (60 mg, 13.6% yield) as an off-white solid. $^1$H NMR (300 MHz, CDCl$_3$): δ ppm 5.13-5.08 (m, 1H), 4.68 (s, 1H), 4.59 (s, 1H), 4.53-4.48 (m, 1H), 4.23-4.17 (m, 2H), 3.78-3.63 (m, 10H), 3.57-3.54 (m, 2H), 3.38 (s, 3H), 3.30-2.86 (m, 8H), 2.82-2.73 (m, 2H), 2.63-2.32 (m, 6H), 2.10-0.78 (m, 27H), 1.68 (s, 3H), 1.38 (s, 3H), 1.11 (s, 3H), 1.06 (s, 3H), 0.97 (s, 3H), 0.89 (s, 3H), 0.86 (s, 3H), 0.85 (s, 3H).

Example 22: Preparation of (1R,3S)-3-((((1R,3aS, 5aR,5bR,7aR,9S,11aR,11bR,13aR,13bR)-3a-(((12R, 13R)-13-(1,1-dioxidothiomorpholino)-12-methyl-2, 5,8,11-tetraoxatetradecan-14-yl)amino)-5a,5b,8,8, 11a-pentamethyl-1-(prop-1-en-2-yl)icosahydro-1H-cyclopenta[a]chrysen-9-yl)oxy)carbonyl)-2,2-dimethylcyclobutane-1-carboxylic acid

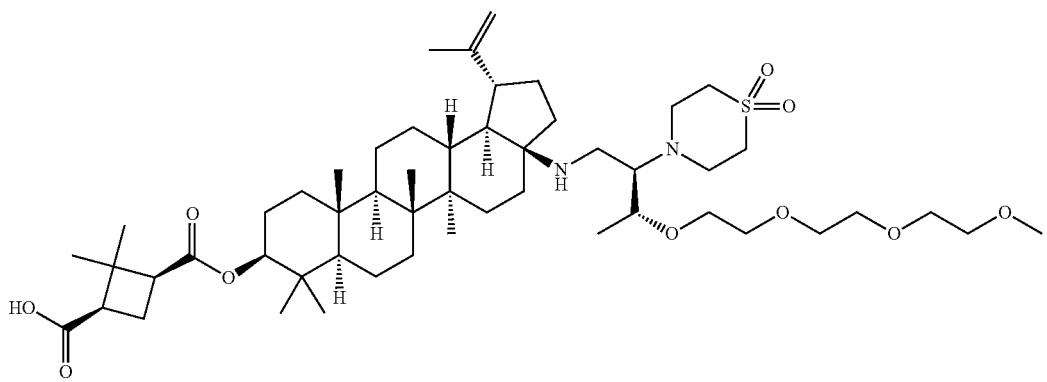

Step 1: Synthesis of (1R,3aS,5aR,5bR,7 aR,9S, 11aR,11bR,13aR,13bR)-3a-(((12R,13R)-13-(1,1-dioxidothiomorpholino)-12-methyl-2,5,8,11-tetraoxatetradecan-14-yl)amino)-5a,5b,8,8,11a-pentamethyl-1-(prop-1-en-2-yl)icosahydro-1H-cyclopenta[a]chrysen-9-yl acetate

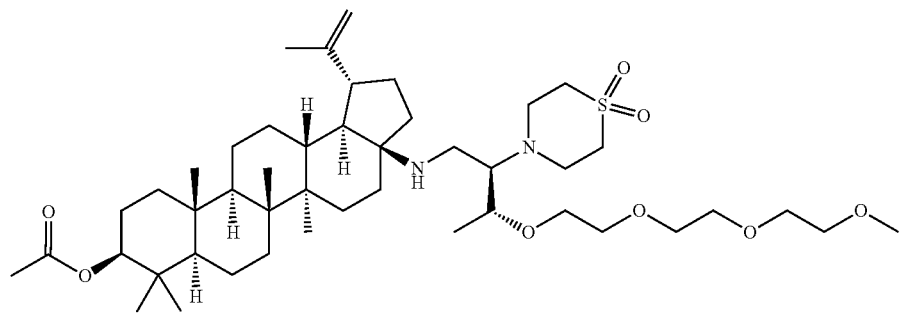

To a stirred solution of 4-((12R,13R)-14-hydroxy-12-methyl-2,5,8,11-tetraoxatetradecan-13-yl)thiomorpholine 1,1-dioxide (Intermediate 18, 0.849 g, 2.298 mmol, 1.8 eq) in DCM (20 ml) at 0° C. was added 2,6-Lutidine (0.32 ml, 2.79 mmol, 2.2 eq). The reaction mixture was stirred at same temperature for about 10 minutes, triflic anhydride (0.43 ml, 2.54 mmol, 2.0 eq) was added and stirred at 0° C. for about 15 minutes. (1R,3aS,5aR,5bR,7aR,9S,11aR,11bR,13aR,13bR)-3a-amino-5a,5b,8,8,11a-pentamethyl-1-(prop-1-en-2-yl)icosahydro-1H-cyclopenta[a]chrysen-9-yl acetate (Example 20-step 2, 0.600 g, 1.277 mmol, 1.0 eq) and triethylamine (0.56 ml, 4.06 mmol, 3.5 eq) were added to the reaction mixture, stirred at 0° C. for 1 hour and stirred at room temperature for overnight. TLC indicated starting material was consumed and the desired product was observed. The reaction mixture was basified with aqueous sodium bicarbonate solution and extracted with DCM (3×50 ml). The combined organic layer was washed with water (30 ml), dried over sodium sulfate, filtered and concentrated under reduced pressure. Another 500 mg batch with same experimental procedure was combined and purified by silica gel column chromatography using 40-50% ethyl acetate in hexanes gradient to obtain the title compound (1.0 g, 95.33% yield) as a solid. $^1$H NMR (300 MHz, CDCl$_3$): δ ppm 4.69 (s, 1H), 4.59 (s, 1H), 4.49-4.44 (m, 1H), 3.66-3.53 (m, 13H), 3.45-3.35 (m, 2H), 3.38 (s, 3H), 3.07-2.97 (m, 6H), 2.04 (s, 3H), 1.90-0.77 (m, 31H), 1.68 (s, 3H), 1.05 (s, 3H), 0.95 (s, 3H), 0.85 (s, 3H), 0.84 (s, 3H), 0.83 (s, 3H).

Step 2: Synthesis of 4-((12R,13R)-14-(((1R,3aS, 5aR,5bR,7aR,9S,11aR,11bR,13aR,13bR)-9-hydroxy-5a, 5b,8,8,11a-pentamethyl-1-(prop-1-en-2-yl)icosahydro-3aH-cyclopenta[a]chrysen-3a-yl) amino)-12-methyl-2,5,8,11-tetraoxatetradecan-13-yl) thiomorpholine 1,1-dioxide

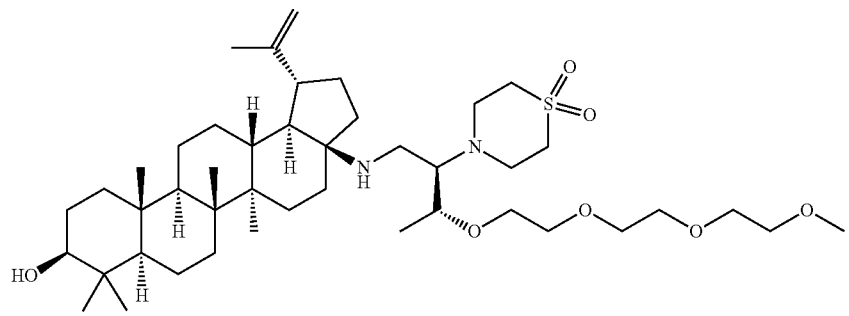

To a stirred solution of (1R,3aS,5aR,5bR,7aR,9S,11aR, 11bR,13aR,13bR)-3a-(((12R,13R)-13-(1,1-dioxidothiomorpholino)-12-methyl-2,5,8,11-tetraoxatetradecan-14-yl) amino)-5a,5b,8,8,11a-pentamethyl-1-(prop-1-en-2-yl) icosahydro-1H-cyclopenta[a]chrysen-9-yl acetate (step 1, 1.0 g, 1.217 mmol, 1.0 eq) in methanol (10 ml) and THF (10 ml) was added aqueous 2.5N KOH solution (3.57 ml, 9.13 mmol, 7.5 eq). The reaction mixture was stirred at room temperature for overnight. TLC indicated starting material was completed and the desired product was observed. The reaction mixture was evaporated under reduced pressure, diluted with water (40 ml) and neutralized with 1N HCl solution and extracted with DCM (3×50 ml). The combined organic layer was washed with water (30 ml), dried over sodium sulfate, filtered and concentrated under reduced pressure. The crude compound was purified by silica gel column chromatography using 0-3% methanol in dichloromethane gradient to obtain the title compound (0.500 g, 52.74% yield) as an off-white solid. $^1$H NMR (300 MHz, CDCl$_3$): δ ppm 4.69 (s, 1H), 4.58 (s, 1H), 3.66-3.53 (m, 14H), 3.38 (s, 3H), 3.30-3.0 (m, 8H), 2.58-2.56 (m, 1H), 2.41 (m, 1H), 2.0-0.75 (m, 44H), 1.67 (s, 3H).

Step 3: Synthesis of 1-benzyl 3-((1R,3aS,5aR,5bR,7 aR,9S,11 aR,11bR,13aR,13bR)-3a-(((12R,13R)-13- (1,1-dioxidothiomorpholino)-12-methyl-2,5,8,11- tetraoxatetradecan-14-yl)amino)-5a,5b,8,8,11a-pentamethyl-1-(prop-1-en-2-yl)icosahydro-1H-cyclopenta[a]chrysen-9-yl) (1R,3 S)-2,2-dimethylcyclobutane-1,3-dicarboxylate

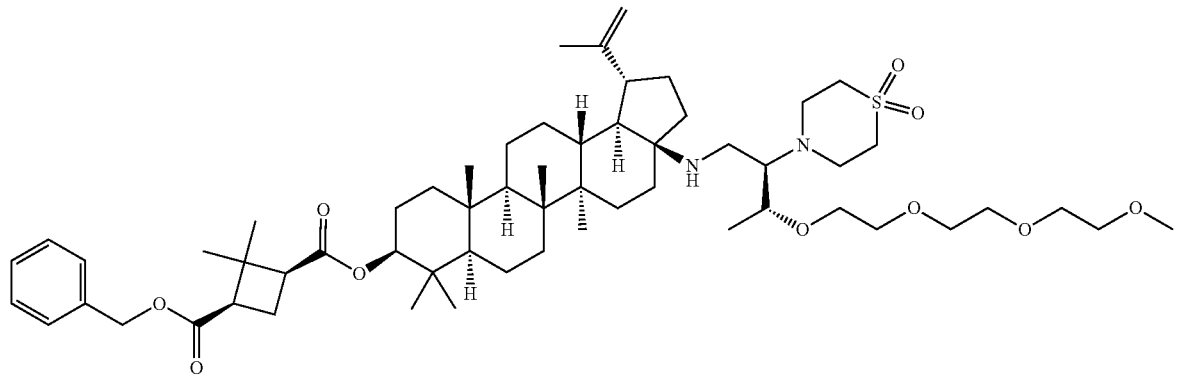

To a stirred solution of 4-((12R,13R)-14-(((1R,3aS,5aR, 5bR,7aR,9S,11aR,11bR,13aR,13bR)-9-hydroxy-5a,5b,8,8, 11a-pentamethyl-1-(prop-1-en-2-yl)icosahydro-3aH-cyclopenta[a]chrysen-3a-yl)amino)-12-methyl-2,5,8,11- tetraoxatetradecan-13-yl)thiomorpholine 1,1-dioxide (step 2, 0.500 g, 0.641 mmol, 1.0 eq) in DCM (20 ml) was added (1S,3R)-3-((benzyloxy)carbonyl)-2,2-dimethylcyclobutane-1-carboxylic acid (prepared according to the procedure described in WO2011/007230A2, 0.505 g, 1.925 mmol, 3.0 eq) followed by EDC.HCl (0.733 g, 3.846 mmol, 6.0 eq) and DMAP (0.070 g, 0.577 mmol, 0.9 eq). The reaction mixture was stirred at room temperature for overnight. TLC indicated starting material was completed and the desired product was observed. The reaction mixture was diluted with water (30 ml) and extracted with DCM (3×30 ml). The combined organic layer was washed with water (30 ml), dried over sodium sulfate, filtered and concentrated under reduced pressure. The residue was purified by silica gel column chromatography using 0-3% methanol in dichloromethane gradient to obtain the title compound (0.060 g, 22.8% yield) as a solid. $^1$H NMR (300 MHz, CDCl$_3$): δ ppm 7.34 (m, 5H), 5.14, 5.09 (ABq, J$_{AB}$=12.3 Hz, 2H), 4.69 (s, 1H), 4.58 (s, 1H), 4.46-4.40 (m, 1H), 4.06-4.0 (m, 1H), 3.78-3.52 (m, 13H), 3.37 (s, 5H), 3.07-2.97 (m, 6H), 2.84-2.52 (m, 5H), 2.42-2.38 (m, 1H), 2.08-0.77 (m, 31H), 1.68 (s, 3H), 1.33 (s, 3H), 1.04 (s, 3H), 0.96 (s, 3H), 0.95 (s, 3H), 0.84 (s, 3H), 0.83 (s, 3H).

Step 4: Synthesis of (1R,3S)-3-((((1R,3aS,5aR,5bR,
7aR,9S,11aR,11bR,13aR,13bR)-3a-(((12R,13R)-13-
(1,1-dioxidothiomorpholino)-12-methyl-2,5,8,11-
tetraoxatetradecan-14-yl)amino)-5a,5b,8,8,11a-
pentamethyl-1-(prop-1-en-2-yl)icosahydro-1H-
cyclopenta[a]chrysen-9-yl)oxy)carbonyl)-2,2-
dimethylcyclobutane-1-carboxylic acid concentration of ~30,000 cells per well in 96 well plate. Test compound was added to the micro plate in defined format with the final concentration of DMSO (vehicle) is not more than 1%. Incubation was carried out in $CO_2$ incubator for ~96 hours for viral infection. At the end of incubation period an aliquot from each well was taken for p24 estimation. The quantitation of p24 is an index for antiviral activity of the

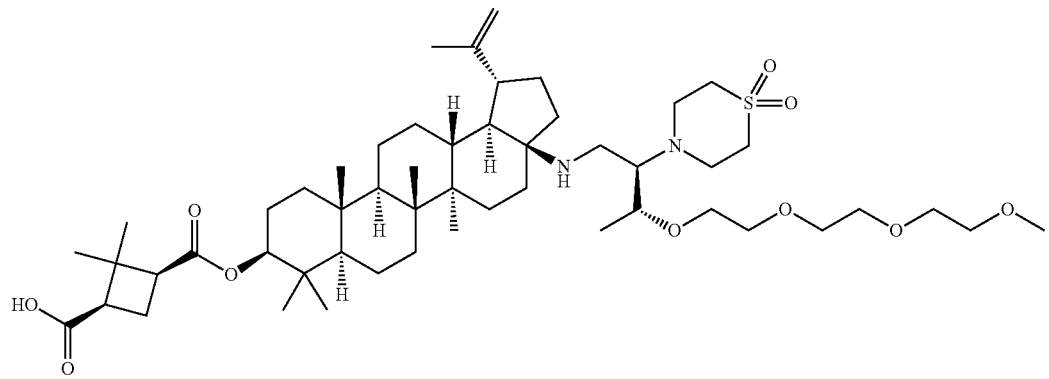

To a stirred solution of 1-benzyl 3-((1R,3aS,5aR,5bR,
7aR,9S,11aR,11bR,13aR,13bR)-3a-(((12R,13R)-13-(1,1-dioxidothiomorpholino)-12-methyl-2,5,8,11-tetraoxatetradecan-14-yl)amino)-5a,5b,8,8,11a-pentamethyl-1-(prop-1-en-2-yl)icosahydro-1H-cyclopenta[a]chrysen-9-yl) (1R,3S)-2,2-dimethylcyclobutane-1,3-dicarboxylate (step 3, 0.200 g, 0.195 mmol, 1.0 eq) in THF (2 ml) and methanol (2 ml) was added aqueous 1.5N KOH solution (0.97 ml, 1.46 mmol, 7.5 eq). The reaction mixture was stirred at room temperature for 2 days. TLC indicated starting material was completed and the desired product was observed. The reaction mixture was evaporated under reduced pressure, diluted with water (10 ml), acidified with 1N HCl to pH 4 to 5 and extracted with DCM (3×50 ml). The combined organic layer was washed with water (30 ml), dried over sodium sulfate, filtered and concentrated under reduced pressure. The crude compound was purified by silica gel column chromatography using 0-5% methanol in dichloromethane gradient. The obtained compound was treated with ethyl acetate (2 ml) and hexane (8 ml), stirred at room temperature for 20 minutes, solvent was decanted and this procedure was repeated twice, finally filtered, washed with hexane (2 ml) and dried under vacuum to obtain the title compound (0.060 g, 32.96% yield) as a solid. $^1$H NMR (300 MHz, $CDCl_3$): δ ppm 4.68 (s, 1H), 4.59 (s, 1H), 4.54 (m, 1H), 3.80-3.52 (m, 12H), 3.37 (s, 3H), 3.27-2.32 (m, 16H), 2.03-0.77 (m, 25H), 1.68 (s, 3H), 1.38 (s, 3H), 1.18 (s, 3H), 1.06 (s, 3H), 0.98 (s, 3H), 0.92 (s, 3H), 0.87 (s, 6H), 0.83 (s, 3H); ES-MS: m/z 933.94 $(M+H)^+$.

Biological Activity

The compounds described herein are tested for their antiviral activity following procedures known to a person of ordinary skill in the art. For example, the following protocols can be employed for testing the compounds. These protocols are illustrative and do not limit to the scope of the invention.

Example 23: Evaluation of Compounds Antiviral Activity Against HIV-1 Strain 92HT599 in MT2 cells MT2 cells were infected with HIV-1 strain 92HT599 (10 TCID 50/30000 cells). The infected cells were plated at the compound. Percent inhibition was calculated with reference to control values (vehicle controls). p24 estimation was carried out using Advance biosciences kit as per the procedure detailed by supplier.

For serum binding assay, wherein "A" refers to an $IC_{50}$ value of less than 10 nM, "B" refers to $IC_{50}$ value in range of 10.01-20 nM, and "C" refers to $IC_{50}$ values greater than 20 nM. The $IC_{50}$ (nM) values are set forth in below Table-1.

TABLE 1

| Ex. no | $IC_{50}$ (nM) |
|---|---|
| 1 | C |
| 2 | A |
| 3 | C |
| 4 | B |
| 5 | A |
| 6 | A |
| 7 | A |
| 8 | A |
| 9 | A |
| 10 | A |
| 11 | A |
| 12 | C |
| 13 | A |
| 14 | A |
| 15 | A |
| 16 | B |
| 17 | A |
| 18 | A |
| 19 | A |
| 20 | A |

Example 24: Evaluation of compounds antiviral activity against pNL4-3/WT & V7A strains in MT4 cells MT4 cells were Transfected with HIV-1 Plasmid (pNL4-3-WT & V7A) (Cells were incubating with required number of TCID50 of HIV-1 for 1.5 h at 37° C.). After infection, the infected cells were plated at the concentration of $3×10^4$ cells per well in 96 well plate. Test compound was added to the test plate in defined format with the final concentration of DMSO is not more than 1%. Incubation was carried out in $CO_2$ incubator for 4 days for viral infection. At the end of incubation period an aliquot from each well was taken for p24 estimation. p24 estimation was carried out using Advance biosciences kit as per the procedure detailed by supplier.

For pNL4-3 WT assay, the selected compounds exhibits $IC_{50}$ wherein "A" refers to an $IC_{50}$ value of less than 10 nM, "B" refers to $IC_{50}$ value in range of 10.01-50 nM, and "C" refers to $IC_{50}$ values greater than 50 nM;

For pNL4-3 V7A assay, the selected compounds exhibits $IC_{50}$ wherein "A" refers to an $IC_{50}$ value of less than 1-50 nM, "B" refers to $IC_{50}$ value in range of 50.01-100 nM, and "C" refers to $IC_{50}$ values greater than 100 nM. The $IC_{50}$ (nM) values are set forth in Table-2.

TABLE 2

| Example no | pNL4-3 WT $IC_{50}$ | pNL4-3 V7A $IC_{50}$ |
|---|---|---|
| 1 | C | C |
| 2 | A | A |
| 3 | C | C |
| 4 | C | C |
| 5 | A | A |
| 6 | B | A |
| 7 | A | A |
| 8 | A | A |
| 9 | B | B |
| 10 | A | A |
| 11 | A | A |
| 12 | B | C |
| 13 | A | A |
| 14 | A | A |
| 15 | A | A |
| 16 | C | C |
| 17 | A | A |
| 18 | A | A |
| 19 | A | A |
| 20 | A | A |

REFERENCES

1. Antiviral methods and protocols (Eds: D Kinchington and R. F. Schinazi) Humana Press Inc., 2000.
2. HIV protocols (Eds: N. L. Michael and J. H. Kim) Humana Press Inc, 1999.
3. DAIDS Virology manual from HIV laboratories, Publication NIH-97-3838, 1997.
4. HIV-1 p24 antigen capture assay, enzyme immunoassay for detection of Human immunodeficiency Virus Type 1 (HIV-1) p24 in tissue culture media—Advanced bio science laboratories, Inc kit procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

All publications and patent applications cited in this application are herein incorporated by reference to the same extent as if each individual publication or patent application was specifically and individually indicated to be incorporated herein by reference.

We claim:

1. A compound of the formula (I):

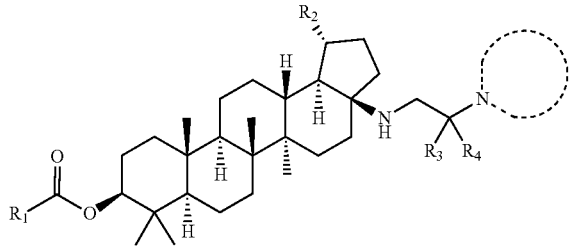

Formula (I)

wherein, $R_1$ is selected from

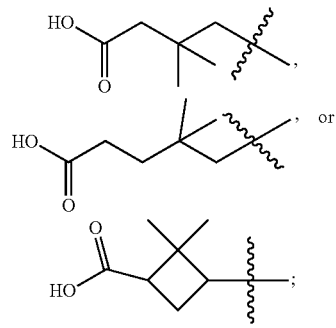

$R_2$ is selected from $C_1$-$C_6$ alkyl, optionally substituted $C_2$-$C_6$ alkenyl, or optionally substituted $C_3$-$C_8$ cycloalkyl; wherein the optional substituent is $C_1$-$C_6$ alkyl;

$R_3$ is hydrogen;

$R_4$ is selected from optionally substituted $C_1$-$C_6$ alkyl or —C(O)O$R_a$; wherein $C_1$-$C_6$ alkyl is ethyl and the optional substituent is selected from halo, hydroxy, alkoxy, or —OC(O)CH$_2$alkoxy;

ring

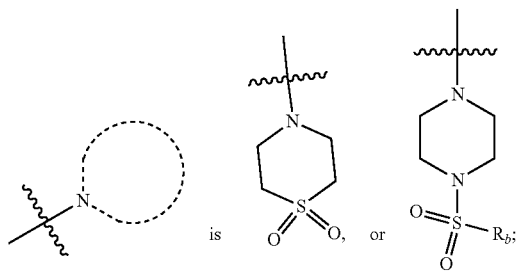

$R_a$ is hydrogen or $C_1$-$C_6$ alkyl; and $R_b$ is $C_1$-$C_6$ alkyl;

or pharmaceutically acceptable salts, pharmaceutically acceptable stereoisomers, or a combination thereof.

2. The compound according to claim 1, which is a compound of the formula (IA):

Formula (IA)

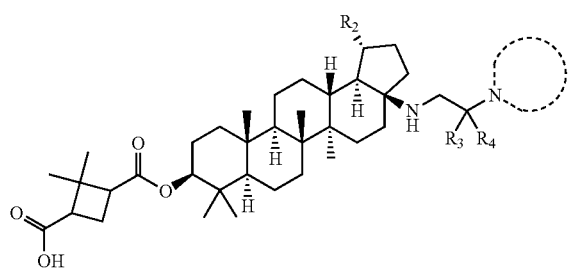

wherein,
R$_2$ is

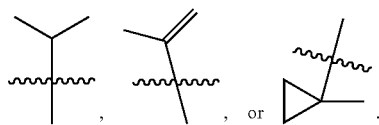

R$_3$ is hydrogen;
R$_4$ is selected from optionally substituted C$_1$-C$_6$ alkyl or —C(O)OR$_a$; wherein C$_1$-C$_6$ alkyl is ethyl and the optional substituent is selected from halo, hydroxy, alkoxy, or —OC(O)CH$_2$alkoxy;
ring

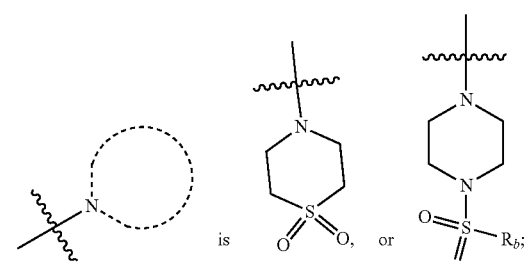

R$_a$ is hydrogen or C$_1$-C$_6$ alkyl; and
R$_b$ is C$_1$-C$_6$ alkyl; or
pharmaceutically acceptable salts, pharmaceutically acceptable stereoisomers, or combination thereof.

3. The compound according to claim 1, which is a compound of the formula (IB):

wherein,
R$_3$ is hydrogen;
R$_4$ is selected from optionally substituted C$_1$-C$_6$ alkyl, or —C(O)OR$_a$; wherein C$_1$-C$_6$ alkyl is ethyl and the optional substituent is selected from halo, hydroxy, alkoxy, or —OC(O)CH$_2$alkoxy;
R$_a$ is hydrogen or C$_1$-C$_6$ alkyl; or
pharmaceutically acceptable salts, pharmaceutically acceptable stereoisomers, or combination thereof.

4. A compound selected from the group consisting of:
(1R,3S)-3-((((1R,3aS,5aR,5bR,7aR,9S,11aR,11bR,13aR,13bR)-3a-(((2R,3R)-2-(1,1-dioxidothiomorpholino)-3-hydroxybutyl)amino)-5a,5b,8,8,11a-pentamethyl-1-(1-methylcyclopropyl)icosahydro-1H-cyclopenta[a]chrysen-9-yl)oxy) carbonyl)-2,2-dimethylcyclobutane-1-carboxylic acid, (1R,3S)-3-((((1R,3aS,5aR,5bR,7aR,9S,11aR,11bR,13aR,13bR)-3a-(((2R,3S)-2-(1,1-dioxidothiomorpholino)-3-fluorobutyl)amino)-5a,5b,8,8,11a-pentamethyl-1-(1-methylcyclopropyl)icosahydro-1H-cyclopenta[a]chrysen-9-yl)oxy)carbonyl)-2,2-di methylcyclobutane-1-carboxylic acid, (1R,3S)-3-((((1R,3aS,5aR,5bR,7aR,9S,11aR,11bR,13aR,13bR)-3a-(((2S,3S)-2-(1,1-dioxidothiomorpholino)-3-hydroxybutyl)amino)-5a,5b,8,8,11a-pentamethyl-1-(1-methylcyclopropyl)icosahydro-1H-cyclopenta[a]chrysen-9-yl)oxy)carbonyl)-2,2-dimethylcyclobutane-1-carboxylic acid, (1R,3S)-3-((((1R,3aS,5aR,5bR,7aR,9S,11aR,11bR,13aR,13bR)-3a-(((2R,3R)-3-hydroxy-2-(4-(isopropylsulfonyl) piperazin-1-yl)butyl)amino)-5a,5b,8,8,11a-pentamethyl-1-(1-methylcyclopropyl)icosahydro-1H-cyclopenta[a]chrysen-9-yl)oxy)carbonyl)-2,2-dimethylcyclobutane-1-carboxylic acid, (1R,3S)-3-((((1R,3aS,5aR,5bR,7aR,9S,11aR,11bR,13aR,13bR)-3a-(((2R,3R)-2-(1,1-dioxidothiomorpholino)-3-hydroxybutyl)amino)-5a,5b,8,8,11a-penta methyl-1-(prop-1-en-2-yl)icosahydro-1H-cyclopenta[a]chrysen-9-yl)oxy)carbonyl)-2,2-dimethylcyclobutane-1-carboxylic acid, (1R,3S)-3-((((1R,3aS,5aR,5bR,7aR,9S,11aR,11bR,13aR,13bR)-3a-(((R)-2-carboxy-2-(1,1-dioxidothiomorpholino)ethyl)amino)-5a,5b,8,8,11a-pentamethyl-1-(1-methylcyclopropyl)icosahydro-1H-cyclopenta[a]chrysen-9-yl)oxy)carbonyl)-2,2-dimethylcyclobutane-1-carboxylic acid, Formula (IB)

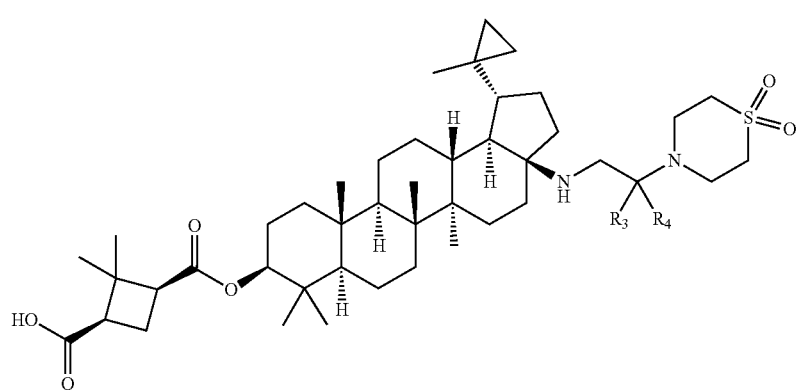

(1R,3S)-3-((((1R,3aS,5aR,5bR,7aR,9S,11aR,11bR,13aR,13bR)-3a-(((2R,3R)-2-(1,1-dioxidothiomorpholino)-3-(2-(2-methoxyethoxy) acetoxy)butyl)amino)-5a,5b,8,8,11a-pentamethyl-1-(1-methylcyclopropyl)icosahydro-1H-cyclopenta[a]chrysen-9-yl)oxy)carbonyl)-2,2-dimethylcyclobutane-1-carboxylic acid, (1R,3S)-3-((((1R,3aS,5aR,5bR,7aR,9S,11aR,11bR,13aR,13bR)-3a-(((12R,13R)-13-(1,1-dioxidothiomorpholino)-12-methyl-2,5,8,11-tetraoxatetradecan-14-yl)amino)-5a,5b,8,8,11a-pentamethyl-1-(1-methylcyclopropyl)icosahydro-1H-cyclopenta[a]chrysen-9-yl)oxy)carbonyl)-2,2-dimethylcyclobutane-1-carboxylic acid, (1R,3S)-3-((((1R,3aS,5aR,5bR,7aR,9S,11aR,11bR,13aR,13bR)-3a-(((2R,3R)-2-(1,1-dioxidothiomorpholino)-3-(2-(2-methoxyethoxy) acetoxy)butyl)amino)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid, 4-(((1R,3aS,5aR,5bR,7aR,9S,11aR,11bR,13aR,13bR)-3a-(((2R,3R)-2-(1,1-dioxidothiomorpholino)-3-hydroxybutyl)amino)-5a,5b,8,8,11a-pentamethyl-1-(prop-1-en-2-yl)icosahydro-1H-cyclopenta[a]chrysen-9-yl)oxy)-2,2-dimethyl-4-oxobutanoic acid, (1R,3S)-3-((((1R,3aS,5aR,5bR,7aR,9S,11aR,11bR,13aR,13bR)-3a-(((15R,16R)-16-(1,1-dioxidothiomorpholino)-15-methyl-13-oxo-2,5,8,11,14-pentaoxaheptadecan-17-yl)amino)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid, and (1R,3S)-3-((((1R,3aS,5aR,5bR,7aR,9S,11aR,11bR,13aR,13bR)-3a-(((12R,13R)-13-(1,1-dioxidothiomorpholino)-12-methyl-2,5,8,11-tetraoxatetradecan-14-yl)amino)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid, or pharmaceutically acceptable salts, pharmaceutically acceptable stereoisomers, or combination thereof.

5. A pharmaceutical composition comprising a compound according to claim 1 and at least one pharmaceutically acceptable excipient.

6. The pharmaceutical composition according to claim 5, wherein the pharmaceutically acceptable excipient is a carrier or diluent.

7. A method of treating HIV in a subject in need thereof comprising administering to the subject a therapeutically effective amount of a compound according to claim 1.

8. A pharmaceutical composition comprising a compound according to claim 4, and at least one pharmaceutically acceptable excipient.

9. The pharmaceutical composition according to claim 8, wherein the pharmaceutically acceptable excipient is a carrier or diluent.

10. A method of treating HIV in a subject in need thereof comprising administering to the subject a therapeutically effective amount of a compound according to claim 4.

* * * * *